United States Patent
Mabry, III et al.

(10) Patent No.: US 11,384,147 B2
(45) Date of Patent: Jul. 12, 2022

(54) ANTI-PD-1 ANTIBODIES AND USES THEREOF

(71) Applicant: Jounce Therapeutics, Inc., Cambridge, MA (US)

(72) Inventors: George Robert Mabry, III, Needham, MA (US); Stephen Sazinsky, Melrose, MA (US)

(73) Assignee: Jounce Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/845,805

(22) Filed: Apr. 10, 2020

(65) Prior Publication Data
US 2020/0399374 A1   Dec. 24, 2020

Related U.S. Application Data

(62) Division of application No. 15/800,346, filed on Nov. 1, 2017, now Pat. No. 10,654,929.

(60) Provisional application No. 62/416,602, filed on Nov. 2, 2016.

(51) Int. Cl.
| | |
|---|---|
| C07K 16/28 | (2006.01) |
| A61K 39/395 | (2006.01) |
| A61P 35/00 | (2006.01) |
| C07K 16/30 | (2006.01) |
| A61K 39/00 | (2006.01) |

(52) U.S. Cl.
CPC ........ *C07K 16/2818* (2013.01); *A61K 39/395* (2013.01); *A61P 35/00* (2018.01); *C07K 16/30* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/52* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,595,048 B2 | 9/2009 | Honjo et al. |
| 8,008,449 B2 | 8/2011 | Korman et al. |
| 8,354,509 B2 | 1/2013 | Carven et al. |
| 8,709,416 B2 | 4/2014 | Langermann et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,952,136 B2 | 2/2015 | Carven et al. |
| 9,067,999 B1 | 6/2015 | Honjo et al. |
| 9,073,994 B2 | 7/2015 | Honjo et al. |
| 2015/0087581 A1 | 3/2015 | Sasikumar et al. |
| 2015/0125463 A1 | 5/2015 | Cogswell et al. |
| 2015/0210769 A1 | 7/2015 | Freeman et al. |
| 2015/0232555 A1 | 8/2015 | Carven et al. |
| 2016/0039903 A1 | 2/2016 | Ring et al. |
| 2016/0052990 A1 | 2/2016 | Ring et al. |
| 2016/0075783 A1 | 3/2016 | King et al. |
| 2017/0166642 A1 | 6/2017 | Pantaleo et al. |

FOREIGN PATENT DOCUMENTS

| | | |
|---|---|---|
| EP | 1537878 | 11/2006 |
| WO | 2010105256 A1 | 9/2010 |
| WO | 2014124217 A1 | 8/2014 |
| WO | 2014151006 A2 | 9/2014 |
| WO | 2014179664 A2 | 11/2014 |
| WO | 2015112800 A1 | 7/2015 |
| WO | 2015112805 A1 | 7/2015 |
| WO | 2015112900 A | 7/2015 |
| WO | 2016079076 A1 | 5/2016 |
| WO | 2016106159 A1 | 6/2016 |
| WO | 2016106159 | 3/2017 |
| WO | 2017055547 A1 | 4/2017 |
| WO | 2017125815 A2 | 7/2017 |
| WO | 2018053709 A1 | 3/2018 |

OTHER PUBLICATIONS

Saxena et al. 'Therapeutic cancer vaccines.' Nature Reviews Cancer vol. 21, pp. 360-378 (2021).*
Agrawal et al., "Nivolumab dose selection: challenges, opportunities, and lessons learned for cancer immunotherapy," Journal for ImmunoTherapy of Cancer, 4:72, 2016 (12 pages).
Ahamadi et al., "Model-Based Characterization of the Pharmacokinetics of Pembrolizumab: A Humanized Anti-PD-1 Monoclonal Antibody in Advanced Solid Tumors," CPT Pharmacometrics Syst. Pharmacol. 6, 49-57, 2017.
Bajaj et al., "Exposure-Response Analysis of Nivolumab in Patients With Previously Treated or Untreated Advanced Melanoma," The Journal of Clinical Pharmacology, 2017, 57(12) 1527-1533.
Bajaj et al., "Model-Based Population Pharmacokinetic Analysis of Nivolumab in Patients With Solid Tumors," CPT Pharmacometrics Syst. Pharmcol. 6:58-66, 2017.
Brahmer et al., "Management of Immune-Related Adverse Events in Patients Treated With Immune Checkpoint nhibitor Therapy: American Society of Clinical Oncology Clinical Practice Guideline," Journal of Clinical Oncology, Feb. 14, 2018 (60 pages).
Chatterjee et al., "Population Pharmacokinetic/Pharmacodynamic Modeling of Tumor Size Dynamics in Pembrolizumab-Treated Advanced Melanoma," CPT Pharmacometrics Syst. Pharmacol. 6:29-39, 2017.
Common Terminology Criteria for Adverse Events (CTCAE), US Department of Health and Human Services, Version 5.0, Nov. 27, 2017 (147 pags).

(Continued)

*Primary Examiner* — Nora M Rooney
(74) *Attorney, Agent, or Firm* — McNeill Baur PLLC

(57) ABSTRACT

Provided herein are various embodiments relating to antibodies. Some of the embodiments include antagonist antibodies that bind PD-1. Such antibodies can be used in methods to treat, for example, cancer.

72 Claims, 10 Drawing Sheets
Specification includes a Sequence Listing.

(56) References Cited

OTHER PUBLICATIONS

Deng, et al., "Projecting human pharmacokinetics of therapeutic antibodies from nonclinical data," mAbs3:1, 61-66 Jan./Feb. 2011.
Driessens et al., "Costimulatory and coinhibitory receptors in anti-tumor immunity," Immunol Rev.; 229(1): 126-144; May 2009.
Eisenhauer et al., "New response evaluation criteria in solid tumours: Revised RECIST guideline (version 1.1)," European Journal of Cancer, 45: 228-247, 2009.
Elassaiss-Schaap et al., "Using Model-Based "Learn and Confirm" to Reveal the Pharmacokinetics-Pharmacodynamics Relationship of Pembrolizumab in the KEYNOTE-001 Trial," CPT Pharmacometrics Syst. Pharmacol. 6, 21-28, 2017.
EMA Keytruda Assessment Report 2016, Procedure No. EMEA/H/C/003820/II/0007 (116 pages).
EMA Keytruda Assessment Report 2017, Procedure No. EMEA/H/C/003820/II/0027 (138 pages).
EMA OPDIVO Assessment Report 2015, Procedure No. EMEA/H/C/003985/0000 (130 pages).
EMA OPDIVO Assessment Report 2016, Procedure No. EMEA/H/C/003985/II/0003 (104 pages).
Everds et al., "Unexpected Hematologic Effects of Biotherapeutics in Nonclinical Species and in Humans," Toxicologic Pathology, 41: 280-302, 2013.
Freeman et al., "Reinvigorating exhausted HIV-specific T cells via PD-1-PD-1 ligand blockade," JEM, vol. 203, No. 10, 2223-2227; Oct. 2, 2006.
Freshwater et al., "Evaluation of dosing strategy for pembrolizumab for oncology indications," Journal for mmunoTherapy of Cancer 5:43, 2017 (9 pages).
Generate Functional Antibodies cross-reacting to both human and murine PD-1, Wuxi Biologies poster, Dec. 9, 2015 (1 page).
Gong et al., "Development of PD-1 and PD-L1 inhibitors as a form of cancer immunotherapy: a comprehensive review of registration trialsand future considerations," Journal for ImmunoTherapy of Cancer (2018) 6:8, 18 pages.
Guleria et al., "A critical role for the programmed death ligand 1 in fetomaternal tolerance," JEM, vol. 202, No. 2, 231-237, Jul. 18, 2005.
Hargadon et al., "Immune checkpoint blockade therapy for cancer: An overview of FDA approved immune checkpoint inhibitors," International Immunopharmacology 62: 29-39, 2018.
Harvey et al., "Cancer, Inflammation, and Therapy: Effects on Cytochrome P450-Mediated Drug Metabolism and mplications for Novel Immunotherapeutic Agents," Clinical Pharmacology & Therapeutics, vol. 96, No. 4, Oct. 2014 (9 pages).
International Search Report and Written Opinion of International Application No. PCT/US2017/059481, dated Feb. 5, 2018 (17 pages).
Kavecansky et al., "Beyond Checkpoint Inhibitors: The Next Generation of Immunotherapy in Oncology," The American Journal of Hematology/Oncology, vol. 13: 9-20; 2017.
Keir et al. "PD-1 and Its Ligands in Tolerance and Immunity," Annu. Rev. Immunol. 26:677-704, 2008.
Lee et al., "Structural basis of checkpoint blockade by monoclonal antibodies in cancer immunotherapy," Nature Communications, vol. 7, p. 13354, Oct. 31, 2016.
Maing et al.,"A first-in-human phase I study of the anti-PD-1 antibody PDR001 in patients with advanced solid tumors," 2016 ASCO Annual Meeting, J Clin Oncol 34, 2016 (suppl; abstr 3060).
Nivolumab, Therapeutic Antibody Database, http://tabs.craic.com/antibodies/265, retrieved Jul. 31, 2015 (3 pages).
Pembrolizumab, Therapeutic Antibody Database, http://tabs.craic.com/antibodies/1004, retrieved Jul. 31, 2015 (3 pages).
Puzanov et al., "Managing toxicities associated with immune checkpoint inhibitors: consensus recommendations from the Society for Immunotherapy of Cancer (SITC) Toxicity Management Working Group," Journal for ImmunoTherapy of Cancer 5:95, 2017 (28 pages).
Tang et al., "Comprehensive analysis of the clinical immuno-oncology landscape," Annals of Oncology 29: 84-91, 2018.
Wang et al., Nivolumab Exposure-Response Analyses of Efficacy and Safety in Previously Treated Squamous or Nonsquamous Non-SmallCell Lung Cancer, Clin Cancer Res; 23(18) Sep. 15, 2017 (12 pages).
Emens et al., "Cancer vaccines: on the threshold of success," Expert Opin Emerg Drugs. Jun. 2008 ; 13(2): 295-308.
Chaplin, D. "Overview of the Immune Response," Allergy Clin Immunol. Feb. 2010 ; 125(2 Suppl 2): S3-23 (41 pages).
Agata et al., "Expression of the PD-1 antigen on the surface of stimulated mouse T and B lymphocytes," International Immunology, vol. 8, No. 5, pp. 765-772, 1996 (8 pages).

* cited by examiner

ANTI-PD-1 ANTIBODIES AND USES THEREOF

CROSS-REFERENCE TO RELATED APPLICATIONS

This application is a divisional of U.S. application Ser. No. 15/800,346, filed Nov. 1, 2017, which claims the benefit of priority of U.S. Provisional Application No. 62/416,602, filed Nov. 2, 2016, which is incorporated by reference herein in its entirety for any purpose.

FIELD OF THE INVENTION

Antibodies that bind to Programmed Death-1 protein (PD-1) are provided. Methods of treatment comprising administering anti-PD-1 antibodies are also provided.

BACKGROUND

The Programmed Death 1 (PD-1) protein is an inhibitory member of the CD28 family of receptors, which also includes CD28, CTLA-4, ICOS and BTLA. PD-1 is expressed on the surface of activated B cells, T cells, and myeloid cells. PD-1 contains a membrane proximal immunoreceptor tyrosine inhibitory motif (ITIM) and a membrane distal tyrosine-based switch motif (ITSM). Although structurally similar to CTLA-4, PD-1 lacks the MYPPY motif that is critical for B7-1 and B7-2 binding. In addition, although CD28, ICOS and CTLA-4 (other members of the CD28 family) all have an unpaired cysteine residue allowing for homodimerization, PD-1 is believed to exist as a monomer, lacking the unpaired cysteine residue characteristic in other CD28 family members. The PD-1 receptor has two ligands, PD-ligand-1 (PD-L1) and PD-L2. The term "PD-L1" refers to the ligand of the PD-1 receptor also known as CD274 and B7H 1. PD-L1 is a 290 amino acid protein with an extracellular IgV-like domain, an extracellular IgC-like domain, a transmembrane domain and a highly conserved intracellular domain of approximately 30 amino acids. PD-L1 is constitutively expressed on many cells such as antigen presenting cells (e.g., dendritic cells, macrophages, and B-cells) and on hematopoietic and non-hematopoietic cells (e.g., vascular endothelial cells, pancreatic islets, and sites of immune privilege). The term "PD-L2" refers to the ligand of the PD-1 receptor also known as CD273 and B7-DC. PD-L2 has an extracellular IgV-like domain, an extracellular IgC-like domain, a transmembrane domain and an intracellular domain of approximately 30 amino acids in humans. PD-L2 has a more restricted expression than PD-L1, with its expression largely confined to hematopoietic cells including macrophages, dendritic cells, some B cell subsets and bone marrow-derived mast cells.

PD-1 functions as an immune checkpoint and works to prevent the activation of T-cells. PD-1 antagonists activate the immune system to attack tumors and have shown success in treating cancers, and in some instances, with less toxicity than other chemotherapeutic treatments. PD-1 antagonists can also be used in combination regimens with other chemotherapeutic agents. Currently approved PD-1 antagonists include anti-PD-1 antibodies, Opdivo® and Keytruda®, and anti-PD-L1 antibody, Tecentriq™.

There remains a need for additional antagonists of PD-1 for treatment of cancer and other diseases and disorders.

SUMMARY

Antibodies that bind Programmed Death 1 (PD-1) are provided, wherein the antibodies bind human PD-1 and mouse PD-1, and wherein the antibodies block binding of PD-L1 and/or PD-L2 to PD-1.

In some embodiments, an isolated antibody that binds to Programmed Death 1 (PD-1) is provided, wherein the antibody binds to an epitope comprising amino acids 126 to 136 of human PD-1. In some embodiments, amino acids 126 to 136 are numbered according to SEQ ID NO: 1. In some embodiments, the antibody binds to human PD-1 of SEQ ID NO: 382 with at least 10-fold greater affinity than the antibody binds to one or more PD-1 variants selected from I126A, L128A, A132L, I134A, and E136A.

In some embodiments, the antibody:
a) binds to human PD-1 ECD-Fc of SEQ ID NO: 401 with at least 10-fold greater affinity than the antibody binds to PD-1 variant I126A ECD-Fc (SEQ ID NO: 389); and/or
b) binds to human PD-1 ECD-Fc of SEQ ID NO: 401 with at least 10-fold greater affinity than the antibody binds to PD-1 variant L128A ECD-Fc (SEQ ID NO: 390); and/or
c) binds to human PD-1 ECD-Fc of SEQ ID NO: 401 with at least 10-fold greater affinity than the antibody binds to PD-1 variant A132L ECD-Fc (SEQ ID NO: 391); and/or
d) binds to human PD-1 ECD-Fc of SEQ ID NO: 401 with at least 10-fold greater affinity than the antibody binds to PD-1 variant I134A ECD-Fc (SEQ ID NO: 392); and/or
e) binds to human PD-1 ECD-Fc of SEQ ID NO: 401 with at least 10-fold greater affinity than the antibody binds to PD-1 variant E136A ECD-Fc (SEQ ID NO: 393).

In some embodiments, the antibody binds to mouse PD-1 ECD-Fc of SEQ ID NO: 403. In some embodiments, the antibody binds to mouse PD-1 ECD-Fc of SEQ ID NO: 403 with at least 10-fold greater affinity than the antibody binds to mouse PD-1 variant H129P ECD-Fc (SEQ I NO: 394). In some embodiments, the antibody binds to rat PD-1 variant P129H ECD-Fc (SEQ ID NO: 397) with at least 10-fold greater affinity than the antibody binds to rat PD-1 ECD-Fc (SEQ ID NO: 405).

In various embodiments, affinity is determined by biolayer interferometry.

In some embodiments, the antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27. In some embodiments, the antibody comprises a heavy chain variable region ($V_H$) that is at least 90%, 91%, 92%, 93%, 94%, 95%, 96%, 97%, 98%, 99%, or 100% identical to the amino acid sequence of SEQ ID NO: 20 and a light chain variable region ($V_L$) that is at least 90%, 91%, 92%, 93%, 94%, 95%, 96%, 97%, 98%, 99%, or 100% identical to the amino acid sequence of SEQ ID NO: 24. In some embodiments, the antibody comprises a $V_H$ comprising the amino acid sequence of SEQ ID NO: 20 and a $V_L$ comprising the amino acid sequence of SEQ ID NO: 24.

In some embodiments, an antibody that binds to Programmed Death 1 (PD-1) is provided, wherein the antibody comprises:
i) (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 9; (e) LCDR2 comprising the amino acid sequence of SEQ ID NO: 10; and (f) LCDR3 comprising the amino acid sequence of SEQ ID NO: 11; or ii) (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15; (d) LCDR1 comprising the amino acid sequence of SEQ ID NO: 17; (e) LCDR2 comprising the amino acid sequence of SEQ ID NO: 18; and (f) LCDR3 comprising the amino acid sequence of SEQ ID NO: 19; or iii) (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27; or iv) (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31; (d) LCDR1 comprising the amino acid sequence of SEQ ID NO: 33; (e) LCDR2 comprising the amino acid sequence of SEQ ID NO: 34; and (f) LCDR3 comprising the amino acid sequence of SEQ ID NO: 35; or v) (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39; (d) LCDR1 comprising the amino acid sequence of SEQ ID NO: 41; (e) LCDR2 comprising the amino acid sequence of SEQ ID NO: 42; and (f) LCDR3 comprising the amino acid sequence of SEQ ID NO: 43; or vi) (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119; (d) LCDR1 comprising an amino acid sequence selected from SEQ ID NOs: 49, 57, 65, 73, 81, 89, 97, 105, 113, and 121; (e) LCDR2 comprising an amino acid sequence selected from SEQ ID NOs: 50, 58, 66, 74, 82, 90, 98, 106, 114, and 122; and (f) LCDR3 comprising an amino acid sequence selected from SEQ ID NOs: 51, 59, 67, 75, 83, 91, 99, 107, 115, and 123; or vii)(a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287; (d) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (e) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (f) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291; or viii) (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319; (d) LCDR1 comprising an amino acid sequence selected from SEQ ID NOs: 297, 305, 313, and 321; (e) LCDR2 comprising an amino acid sequence selected from SEQ ID NOs: 298, 306, 314 and 322; and (f) LCDR3 comprising an amino acid sequence selected from SEQ ID NOs: 299, 307, 315, and 323.

In some embodiments, an antibody that binds PD-1 is provided, which comprises a heavy chain variable region ($V_H$) and a light chain variable region ($V_L$), wherein:

i) the $V_H$ is at least 90%, 91%, 92%, 93%, 94%, 95%, 96%, 97%, 98%, 99%, or 100% identical to the amino acid sequence of SEQ ID NO: 4 and the $V_L$ is at least 90%, 91%, 92%, 93%, 94%, 95%, 96%, 97%, 98%, 99%, or 100% identical to the amino acid sequence of SEQ ID NO: 8; or ii) the $V_H$ is at least 90%, 91%, 92%, 93%, 94%, 95%, 96%, 97%, 98%, 99%, or 100% identical to the amino acid sequence of SEQ ID NO: 12 and the $V_L$ is at least 90%, 91%, 92%, 93%, 94%, 95%, 96%, 97%, 98%, 99%, or 100% identical to the amino acid sequence of SEQ ID NO: 16; or iii) the $V_H$ is at least 90%, 91%, 92%, 93%, 94%, 95%, 96%, 97%, 98%, 99%, or 100% identical to the amino acid sequence of SEQ ID NO: 20 and the $V_L$ is at least 90%, 91%, 92%, 93%, 94%, 95%, 96%, 97%, 98%, 99%, or 100% identical to the amino acid sequence of SEQ ID NO: 24; or iv) the $V_H$ is at least 90%, 91%, 92%, 93%, 94%, 95%, 96%, 97%, 98%, 99%, or 100% identical to the amino acid sequence of SEQ ID NO: 28 and the $V_L$ is at least 90%, 91%, 92%, 93%, 94%, 95%, 96%, 97%, 98%, 99%, or 100% identical to the amino acid sequence of SEQ ID NO: 32; or v) the $V_H$ is at least 90%, 91%, 92%, 93%, 94%, 95%, 96%, 97%, 98%, 99%, or 100% identical to the amino acid sequence of SEQ ID NO: 36 and the $V_L$ is at least 90%, 91%, 92%, 93%, 94%, 95%, 96%, 97%, 98%, 99%, or 100% identical to the amino acid sequence of SEQ ID NO: 40; or vi) the $V_H$ is at least 90%, 91%, 92%, 93%, 94%, 95%, 96%, 97%, 98%, 99%, or 100% identical to an amino acid sequence selected from SEQ ID NOs: 44, 52, 60, 68, 76, 84, 92, 100, 108 and 116; and the $V_L$ is at least 90%, 91%, 92%, 93%, 94%, 95%, 96%, 97%, 98%, 99%, or 100% identical to an amino acid sequence selected from SEQ ID NOs: 48, 56, 64, 72, 80, 88, 96, 104, 112, and 120; or vii) the $V_H$ is at least 90%, 91%, 92%, 93%, 94%, 95%, 96%, 97%, 98%, 99%, or 100% identical to an amino acid sequence selected from SEQ ID NOs: 124, 132, 140, 148, 156, 164, 172, 180, 188, 196, 204, 212, 220, 228, 236, 244, 252, 260, 268, 276, and 284; and the $V_L$ is at least 90%, 91%, 92%, 93%, 94%, 95%, 96%, 97%, 98%, 99%, or 100% identical to an amino acid sequence selected from SEQ ID NOs: 128, 136, 144, 152, 160, 168, 176, 184, 192, 200, 208, 216, 224, 232, 240, 248, 256, 264, 272, 280 and 288; or viii) the $V_H$ is at least 90%, 91%, 92%, 93%, 94%, 95%, 96%, 97%, 98%, 99%, or 100% identical to an amino acid sequence selected from SEQ ID NOs: 292, 300, 308 and 316; and the $V_L$ is at least 90%, 91%, 92%, 93%, 94%, 95%, 96%, 97%, 98%, 99%, or 100% identical to an amino acid sequence selected from SEQ ID NOs: 296, 304, 312, and 320.

In some embodiments, an antibody that binds PD-1 is provided, which comprises a heavy chain variable region ($V_H$) and a light chain variable region ($V_L$), wherein:

i) the $V_H$ comprises the amino acid sequence of SEQ ID NO: 4 and the $V_L$ comprises the amino acid sequence of SEQ ID NO: 8; or ii) the $V_H$ comprises the amino acid sequence of SEQ ID NO: 12 and the $V_L$ comprises the amino acid sequence of SEQ ID NO: 16; or iii) the $V_H$ comprises the amino acid sequence of SEQ ID NO: 20 and the $V_L$ comprises the amino acid sequence of SEQ ID NO: 24; or iv) the $V_H$ comprises the amino acid sequence of SEQ ID NO: 28 and the $V_L$ comprises the amino acid sequence of SEQ ID NO: 32; or v) the $V_H$ comprises the amino acid sequence of SEQ ID NO: 36 and the $V_L$ comprises the amino acid sequence of SEQ ID NO: 40; or vi) the $V_H$ comprises the amino acid sequence of SEQ ID NO: 44 and the $V_L$ comprises the amino acid sequence of SEQ ID NO: 48; or vii) the $V_H$ comprises the amino acid sequence of SEQ ID NO: 52 and the $V_L$ comprises the amino acid sequence of SEQ ID NO: 56; or viii) the $V_H$ comprises the amino acid sequence of SEQ ID NO: 60 and the $V_L$ comprises the amino acid sequence of SEQ ID NO: 64; or ix) the $V_H$ comprises the amino acid sequence of SEQ ID NO: 68 and the $V_L$ comprises the amino acid sequence of SEQ ID NO: 72; or x) the $V_H$ comprises the amino acid sequence of SEQ ID NO: 76 and the $V_L$ comprises the amino acid sequence of SEQ ID NO: 80; or xi) the $V_H$ comprises the amino acid sequence of SEQ ID NO: 84 and the $V_L$ comprises the amino acid sequence of SEQ ID NO: 88; or xii) the $V_H$ comprises the amino acid sequence of SEQ ID NO: 92 and the $V_L$ comprises the amino acid sequence of SEQ ID NO: 96; or xiii) the $V_H$ comprises the amino acid sequence of SEQ ID NO: 100 and the $V_L$ comprises the amino acid sequence of SEQ ID NO: 104; or xiv) the $V_H$ comprises the amino acid sequence of SEQ ID NO: 108 and the $V_L$ comprises the amino acid sequence of SEQ ID NO: 112; or xv) the $V_H$ comprises the amino acid sequence of SEQ ID NO: 116 and the $V_L$ comprises the amino acid sequence of SEQ ID NO: 120; or xvi) the $V_H$ comprises the amino acid sequence of SEQ ID NO: 124 and the $V_L$ comprises the amino acid sequence of SEQ ID NO: 128; or xvii) the $V_H$ comprises the amino acid sequence of SEQ ID NO: 132 and the $V_L$ comprises the amino acid sequence of SEQ ID NO: 136; or xviii) the $V_H$ comprises the amino acid sequence of SEQ ID NO: 140 and the $V_L$ comprises the amino acid sequence of SEQ ID NO: 144; or xix) the $V_H$ comprises the amino acid sequence of SEQ ID NO: 148 and the $V_L$ comprises the amino acid sequence of SEQ ID NO: 152; or xx) the $V_H$ comprises the amino acid sequence of SEQ ID NO: 156 and the $V_L$ comprises the amino acid sequence of SEQ ID NO: 160; or xxi) the $V_H$ comprises the amino acid sequence of SEQ ID NO: 164 and the $V_L$ comprises the amino acid sequence of SEQ ID NO: 168; or xxii) the $V_H$ comprises the amino acid sequence of SEQ ID NO: 172 and the $V_L$ comprises the amino acid sequence of SEQ ID NO: 176; or xxiii) the $V_H$ comprises the amino acid sequence of SEQ ID NO: 180 and the $V_L$ comprises the amino acid sequence of SEQ ID NO: 184; or xxiv) the $V_H$ comprises the amino acid sequence of SEQ ID NO: 188 and the $V_L$ comprises the amino acid sequence of SEQ ID NO: 192; or xxv) the $V_H$ comprises the amino acid sequence of SEQ ID NO: 196 and the $V_L$ comprises the amino acid sequence of SEQ ID NO: 200; or xxvi) the $V_H$ comprises the amino acid sequence of SEQ ID NO: 204 and the $V_L$ comprises the amino acid sequence of SEQ ID NO: 208; or xxvii) the $V_H$ comprises the amino acid sequence of SEQ ID NO: 212 and the $V_L$ comprises the amino acid sequence of SEQ ID NO: 216; or xxviii) the $V_H$ comprises the amino acid sequence of SEQ ID NO: 220 and the $V_L$ comprises the amino acid sequence of SEQ ID NO: 224; or xxix) the $V_H$ comprises the amino acid sequence of SEQ ID NO: 228 and the $V_L$ comprises the amino acid sequence of SEQ ID NO: 232; or xxx) the $V_H$ comprises the amino acid sequence of SEQ ID NO: 236 and the $V_L$ comprises the amino acid sequence of SEQ ID NO: 240; or xxxi) the $V_H$ comprises the amino acid sequence of SEQ ID NO: 244 and the $V_L$ comprises the amino acid sequence of SEQ ID NO: 248; or xxxii) the $V_H$ comprises the amino acid sequence of SEQ ID NO: 252 and the $V_L$ comprises the amino acid sequence of SEQ ID NO: 256; or xxxiii) the $V_H$ comprises the amino acid sequence of SEQ ID NO: 260 and the $V_L$ comprises the amino acid sequence of SEQ ID NO: 264; or xxxiv) the $V_H$ comprises the amino acid sequence of SEQ ID NO: 268 and the $V_L$ comprises the amino acid sequence of SEQ ID NO: 272; or xxxv) the $V_H$ comprises the amino acid sequence of SEQ ID NO: 276 and the $V_L$ comprises the amino acid sequence of SEQ ID NO: 280; or xxxvi) the $V_H$ comprises the amino acid sequence of SEQ ID NO: 284 and the $V_L$ comprises the amino acid sequence of SEQ ID NO: 288; or xxxvii) the $V_H$ comprises the amino acid sequence of SEQ ID NO: 292 and the $V_L$ comprises the amino acid sequence of SEQ ID NO: 296; or xxxviii) the $V_H$ comprises the amino acid sequence of SEQ ID NO: 300 and the $V_L$ comprises the amino acid sequence of SEQ ID NO: 304; or xxxix) the $V_H$ comprises the amino acid sequence of SEQ ID NO: 308 and the $V_L$ comprises the amino acid sequence of SEQ ID NO: 312; or xl) the $V_H$ comprises the amino acid sequence of SEQ ID NO: 316 and the $V_L$ comprises the amino acid sequence of SEQ ID NO: 320.

In some embodiments, an antibody that competes with an antibody provided herein for binding to human PD-1 is provided, wherein the antibody binds to human PD-1 and mouse PD-1, and where in the antibody inhibits binding of human PD-1 to human PD-L1, inhibits binding of human PD-1 to human PD-L2, inhibits binding of mouse PD-1 to mouse PD-L1, and inhibits binding of mouse PD-1 to mouse PD-L2.

In some embodiments, an antibody provided herein binds to human PD-1 with an affinity ($K_D$) of less than 5 nM. In some embodiments, an antibody provided herein binds to mouse PD-1 with an affinity ($K_D$) of less than 10 nM. In some embodiments, affinity is determined using biolayer interferometry.

In some embodiments, an antibody provided herein is a monoclonal antibody. In some embodiments, an antibody provided herein is a human antibody, chimeric antibody, or a humanized antibody. In some embodiments, an antibody provided herein is an antibody fragment selected from a Fab, Fab', Fv, scFv or (Fab')$_2$ fragment. In some embodiments, an antibody provided herein is a full length antibody. In some embodiments, an antibody provided herein is an IgG1 or IgG4 antibody.

In some embodiments, an antibody provided herein binds human PD-1. In some embodiments, human PD-1 comprises the amino acid sequence of SEQ ID NO: 382. In some embodiments, an antibody provided herein binds mouse PD-1. In some embodiments, mouse PD-1 comprises the amino acid sequence of SEQ ID NO: 383. In some embodiments, an antibody provided herein binds cynomolgus monkey PD-1. In some embodiments, cynomolgus monkey PD-1 comprises the amino acid sequence of SEQ ID NO: 384.

In some embodiments, an antibody provided herein inhibits binding of PD-1 to PD-L1. In some embodiments, an antibody provided herein inhibits binding of PD-1 to PD-L2. In some embodiments, an antibody provided herein inhibits binding of PD-1 to PD-L1 and inhibits the binding of PD-1 to PD-L2.

In some embodiments, administration of an antibody provided herein to a mammal increases the level of at least one cytokine selected from IFNγ and IL-2. In some embodiments, an antibody provided herein increases the level of at least one cytokine selected from IFNγ and IL-2 by at least 2-fold. In some embodiments, the level of the cytokine is measured 1 hour, 2 hours, 3 hours, 4 hours, 5 hours, 6 hours, 8 hours, 10 hours, 12 hours, 14 hours, 16 hours, 18 hours, 20 hours, 22 hours, 24 hours, 36 hours, or 48 hours after administration of the antibody. In some embodiments, at least one cytokine is IFNγ. In some embodiments, at least one cytokine is IL-2. In some embodiments, the level of the chemokine is measured 24 hours after administration of the antibody.

In some embodiments, administration of an antibody provided herein to a mammal enhances an immune response in the mammal. In some embodiments, administration of an antibody provided herein to a mammal results in activation of T cells in the mammal. In some embodiments, administration of an antibody provided herein to a mammal reduces tumor size in a mammal with cancer. In some embodiments, the mammal is a human. In some embodiments, the human has cancer. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, an isolated nucleic acid is provided, which encodes an antibody provided herein. In some embodiments, a vector is provided, which comprises the nucleic acid. In some embodiments, a host cell is provided, which comprises the vector. In some embodiments, a host cell is provided, which produces an antibody provided herein. In some embodiments, a method for making an anti-PD-1 antibody is provided, comprising culturing the host cell under conditions suitable for expression of the antibody. In some embodiments, the method further comprises recovering the antibody produced by the host cell.

In some embodiments, a pharmaceutical composition is provided, comprising an anti-PD-1 antibody provided herein and a pharmaceutically acceptable carrier.

In some embodiments, a method of treating cancer in a mammal is provided, comprising administering an effective amount of an anti-PD-1 antibody provided herein, or a pharmaceutical composition comprising an anti-PD-1 antibody provided herein and a pharmaceutically acceptable carrier. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, a method of enhancing an immune response in a mammal is provided, comprising administering an effective amount of an anti-PD-1 antibody provided herein, or a pharmaceutical composition comprising an anti-PD-1 antibody provided herein and a pharmaceutically acceptable carrier.

In some embodiments, a method of increasing activation of a T cell in a mammal is provided, comprising administering an effective amount of an anti-PD-1 antibody provided herein, or a pharmaceutical composition comprising an anti-PD-1 antibody provided herein and a pharmaceutically acceptable carrier.

In some embodiments, a method of reducing tumor size in a in a mammal with cancer is provided, comprising administering an effective amount of an anti-PD-1 antibody provided herein, or a pharmaceutical composition comprising an anti-PD-1 antibody provided herein and a pharmaceutically acceptable carrier.

In any of the embodiments provided herein, the mammal may be a human.

In some embodiments, the mammal is administered at least one additional therapeutic agent. In some such embodiments, the additional therapeutic agent is administered concurrently or sequentially with the anti-PD-1 antibody. In some embodiments, the additional therapeutic agent is selected from an anti-ICOS antibody and an anti-CTLA4 antibody. In some embodiments, the additional therapeutic agent is an anti-ICOS antibody. In some embodiments, the additional therapeutic agent is a cancer vaccine. In some embodiments, the cancer vaccine is selected from a DNA vaccine, an engineered virus vaccine, an engineered tumor cell vaccine, and a cancer vaccine developed using neoantigens.

In some embodiments, use of an antibody provided herein is provided for the manufacture of a medicament to treat cancer. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC). In some embodiments, the medicament is for administration with at least one additional therapeutic agent. In some embodiments, the additional therapeutic agent is selected from an anti-ICOS antibody and an anti-CTLA4 antibody. In some embodiments, the additional therapeutic agent is an anti-ICOS antibody. In some embodiments, the additional therapeutic agent is a cancer vaccine. In some embodiments, the cancer vaccine is selected from a DNA vaccine, an engineered virus vaccine, an engineered tumor cell vaccine, and a cancer vaccine developed using neoantigens.

In some embodiments, the present disclosure provides uses of an antibody provided herein or a pharmaceutical composition comprising an antibody provided herein and a pharmaceutically acceptable carrier for treating cancer. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, the present disclosure provides uses of an antibody provided herein or a pharmaceutical composition comprising an antibody provided herein and a pharmaceutically acceptable carrier, and at least one additional therapeutic agent, for treating cancer. In some embodiments, the additional therapeutic agent is selected from an anti-ICOS antibody and an anti-CTLA4 antibody. In some embodiments, the additional therapeutic agent is an anti-ICOS antibody. In some embodiments, the additional therapeutic agent is a cancer vaccine. In some embodiments, the cancer vaccine is selected from a DNA vaccine, an engineered virus vaccine, an engineered tumor cell vaccine, and a cancer vaccine developed using neoantigens. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, an antibody provided herein or a pharmaceutical composition comprising an antibody provided herein and a pharmaceutically acceptable carrier for use in treating cancer is provided. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, a method of increasing the level of at least one cytokine selected from IFNγ and IL-2 in a mammal is provided, comprising administering to the mammal an antibody provided herein. In some embodiments, the level of the cytokine is measured 1 hour, 2 hours, 3 hours, 4 hours, 5 hours, 6 hours, 8 hours, 10 hours, 12 hours, 14 hours, 16 hours, 18 hours, 20 hours, 22 hours, 24 hours, 36 hours, or 48 hours after administration of the antibody. In some embodiments, at least one cytokine is IFNγ. In some embodiments, at least one cytokine is IL-2. In some embodiments, the level of the cytokine is measured 24 hours after administration of the antibody. In some embodiments, the mammal is a human. In some embodiments, the human has cancer. In some embodiments, the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC). In some embodiments, the cancer is selected from melanoma, gastric cancer, head & neck squamous cell cancer (HNSCC), non-small cell lung cancer (NSCLC), and triple negative breast cancer (TNBC).

In some embodiments, an immune response is enhanced following administration of the anti-PD-1 antibody. In some embodiments, activation of T cells is increased following administration of the anti-PD-1 antibody. In some embodiments, tumor size is decreased following administration of the anti-PD-1 antibody.

In some embodiments, the mammal is administered at least one additional therapeutic agent. In some embodiments, the additional therapeutic agent is administered concurrently or sequentially with the anti-PD-1 antibody. In some embodiments, the additional therapeutic agent is selected from an anti-ICOS antibody and an anti-CTLA4 antibody. In some embodiments, the additional therapeutic is an anti-ICOS antibody. In some embodiments, the additional therapeutic agent is a cancer vaccine. In some embodiments, the cancer vaccine is selected from a DNA vaccine, an engineered virus vaccine, an engineered tumor cell vaccine, and a cancer vaccine developed using neoantigens.

In some embodiments, a sample of the cancer from the mammal has been determined to express PD-1. In some embodiments, the sample shows 1+, 2+, or 3+ staining of PD-1 by immunohistochemistry (IHC). In some embodiments, the sample has been determined to have an elevated level of PD-L1. In some embodiments, PD-L1 levels are determined using IHC.

BRIEF DESCRIPTION OF THE DRAWINGS

FIGS. 4A-1, 4A-2, 4B-1, 4B-2, and 4C show the ability of anti-PD-1 antibodies disclosed herein to block the binding of human ligands to human PD-1. Octet analysis on a Forte-Bio instrument was used to assess the effect of the antibodies on the interaction between human PD-L1 and human PD-L2 with human PD-1.

DETAILED DESCRIPTION OF SOME EMBODIMENTS

Figure 1:
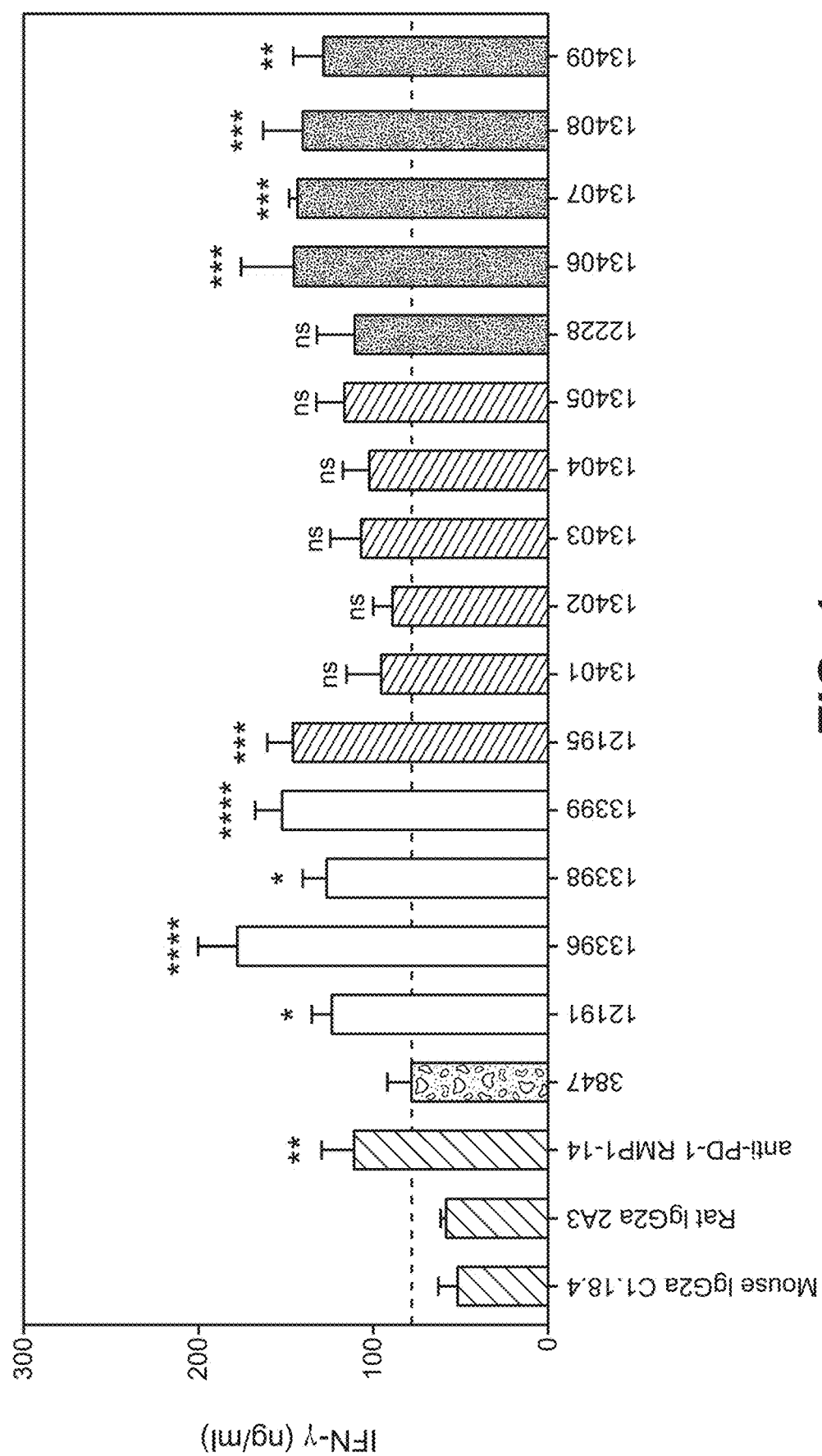
FIG. 1 shows IFNγ concentrations after mouse splenocyte T cells activated with anti-CD3 and anti-CD28 antibodies are contacted with anti-PD-1 antibodies. Mouse IgG1 and rat IgG2a were used as controls. RMP1-14 was used as a positive control anti-PD-1 antibody.

Antibodies that bind PD-1 are provided. Antibody heavy chains and light chains that are capable of forming antibodies that bind PD-1 are also provided. In addition, antibodies, heavy chains, and light chains comprising one or more particular complementarity determining regions (CDRs) are provided. Polynucleotides encoding antibodies to PD-1 are provided. Polynucleotides encoding antibody heavy chains or lights chains are also provided. Methods of producing and/or purifying antibodies to PD-1 are provided. Methods of treatment using antibodies to PD-1 are provided. Such methods include, but are not limited to, methods of treating cancer. Methods of detecting PD-1 are provided. Such methods include methods to identify an individual who may benefit from treatment with an anti-PD-1 antibody, to monitor treatment of an individual with an anti-PD-1 antibody and to improve therapeutic efficacy of an anti-PD-1 antibody in an individual.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

As is understood by one skilled in the art, reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"PD-1" and "programmed death 1" as used herein refer to any native PD-1 that results from expression and processing of PD-1 in a cell. The term includes PD-1 from any vertebrate source, including mammals such as primates (e.g., humans and cynomolgus monkeys) and rodents (e.g., mice and rats), unless otherwise indicated. The term also includes naturally occurring variants of PD-1, e.g., splice variants or allelic variants. The amino acid sequence of an exemplary human PD-1 precursor protein (with signal sequence, amino acids 1-20) is shown in SEQ ID NO: 1. The amino acid sequence of an exemplary mature human PD-1 is shown in SEQ ID NO: 382. The amino acid sequence of an exemplary mouse PD-1 precursor protein (with signal sequence, amino acids 1-20) is shown in SEQ ID NO: 2. The amino acid sequence of an exemplary mature mouse PD-1 is shown in SEQ ID NO: 383. The amino acid sequence of an exemplary cynomolgus monkey PD-1 precursor protein (with signal sequence, amino acids 1-20) is shown in SEQ ID NO: 3. The amino acid sequence of an exemplary mature cynomolgus monkey PD-1 is shown in SEQ ID NO: 384.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an PD-1 epitope is an antibody that binds this epitope with greater affinity, avidity, more readily, and/or with greater duration than it binds to other PD-1 epitopes or non-PD-1 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), more preferably, at least 90% pure, more preferably, at least 95% pure, yet more preferably, at least 98% pure, and most preferably, at least 99% pure.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antibody specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antibody specific to the epitope binds. It is noted that, in some embodiments, not every one of the residues within the linear epitope need be directly bound (or involved in a bond) with the antibody. In some embodiments, linear epitopes can be from immunizations with a peptide that effectively consisted of the sequence of the linear epitope, or from structural sections of a protein that are relatively isolated from the remainder of the protein (such that the antibody can interact, at least primarily), just with that sequence section.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and $(Fab')_2$ (including a chemically linked $F(ab')_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, and/or a combination of the Kabat, Chothia, AbM, and/or contact definitions. Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The AbM definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, H26-H35B of H1, 50-58 of H2, and 95-102 of H3. The Contact definition can include, for example, CDRs (CDR-L1, CDR-L2, CDR-L3, CDR-H1, CDR-H2, and CDR-H3) at amino acid residues 30-36 of L1, 46-55 of L2, 89-96 of L3, 30-35 of H1, 47-58 of H2, and 93-101 of H3. The Chothia definition can include, for example, CDRs (CDR-L1, CDR-L2, CDR-L3, CDR-H1, CDR-H2, and CDR-H3) at amino acid residues 24-34 of L1, 50-56 of L2, 89-97 of L3, 26-32 . . . 34 of H1, 52-56 of H2, and 95-102 of H3. CDRs can also be provided as shown in any one or more of the accompanying figures. With the exception of CDR1 in $V_H$, CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hyper variable region", including hypervariable loops. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).)

The term "heavy chain variable region" as used herein refers to a region comprising at least three heavy chain CDRs. In some embodiments, the heavy chain variable region includes the three CDRs and at least FR2 and FR3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, $C_H1$, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" as used herein refers to a region comprising at least three light chain CDRs. In some embodiments, the light chain variable region includes the three CDRs and at least FR2 and FR3. In some embodiments, the light chain variable region includes at least light chain LCDR1, framework (FR) 2, LCDR2, FR3, and LCDR3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Nonlimiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art (such as, for example, ELISA $K_D$, KinExA, bio-layer interferometry (BLI), and/or surface plasmon resonance devices (such as a BIAcore® device), including those described herein).

The term "$K_D$", as used herein, refers to the equilibrium dissociation constant of an antibody-antigen interaction.

In some embodiments, the "$K_D$," "$K_d$," "Kd" or "Kd value" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, serial dilutions of polypeptide, for example, full length antibody, are injected in PBS with 0.05% TWEEN-20' surfactant (PBST) at 25° C. at a flow rate of approximately 25 µL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_d$) is calculated as the ratio $k_{off}/k_{on}$. See, for example, Chen et al., *J. Mol. Biol.* 293:865-881 (1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In some embodiments, the difference between said two values (for example, $K_d$ values) is substantially the same, for example, less than about 50%, less than about 40%, less than about 30%, less than about 20%, and/or less than about 10% as a function of the reference/comparator value.

In some embodiments, the difference between said two values (for example, $K_d$ values) is substantially different, for example, greater than about 10%, greater than about 20%, greater than about 30%, greater than about 40%, and/or greater than about 50% as a function of the value for the reference/comparator molecule.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51:19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is ForteBio Octet® RED96 system (Pall Corporation). See, e.g., Abdiche et al., 2008, *Anal. Biochem.* 377: 209-277.

The term "$k_{on}$", as used herein, refers to the rate constant for association of an antibody to an antigen. Specifically, the rate constants ($k_{on}$ and $k_{off}$) and equilibrium dissociation constants are measured using IgGs (bivalent) with monovalent PD-1 antigen. "$K_{on}$", "$k_{on}$", "association rate constant", or "ka", are used interchangeably herein. The value indicates the binding rate of a binding protein to its target antigen or the rate of complex formation between an antibody and antigen, shown by the equation: Antibody("Ab")+Antigen ("Ag")→Ab-Ag.

The term "$k_{off}$", as used herein, refers to the rate constant for dissociation of an antibody from the antibody/antigen complex. $k_{off}$ is also denoted as "$K_{off}$" or the "dissociation rate constant". This value indicates the dissociation rate of an antibody from its target antigen or separation of Ab-Ag complex over time into free antibody and antigen as shown by the equation:

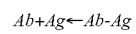

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing other cytokines, inducing apoptosis, and enzymatic activity. In some embodiments, biological activity of a PD-1 protein includes, for example, promoting apoptosis in antigen-specific T cells, reducing apoptosis in regulatory T (Treg) cells, inhibiting activation of T cells, inhibiting proliferation of T cells, and facilitating T cell anergy or exhaustion.

An "affinity matured" antibody refers to an antibody with one or more alterations in one or more CDRs compared to a parent antibody which does not possess such alterations, such alterations resulting in an improvement in the affinity of the antibody for antigen.

A "chimeric antibody" as used herein refers to an antibody in which a portion of the heavy and/or light chain is derived from a particular source or species, while at least a part of the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species. The chimeric construct can also be a functional fragment, as noted above.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an antibody fragment, such as Fab, an scFv, a (Fab')$_2$, etc. The term humanized also denotes forms of non-human (for example, murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence of non-human immunoglobulin. Humanized antibodies can include human immunoglobulins (recipient antibody) in which residues from a complementary determining region (CDR) of the recipient are substituted by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody can comprise residues that are found neither in the recipient antibody nor in the imported CDR or framework sequences, but are included to further refine and optimize antibody performance. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments, the humanized antibody can also comprise at least a portion of an immunoglobulin constant region or domain (Fc), typically that of a human immunoglobulin. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody. As will be appreciated, a humanized sequence can be identified by its primary sequence and does not necessarily denote the process by which the antibody was created.

An "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein encompasses antibodies produced in humans, antibodies produced in non-human animals that comprise human immunoglobulin genes, such as XenoMouse® mice, and antibodies selected using in vitro methods, such as phage display (Vaughan et al., 1996, Nature Biotechnology, 14:309-314; Sheets et al., 1998, Proc. Natl. Acad. Sci. (USA) 95:6157-6162; Hoogenboom and Winter, 1991, J. Mol. Biol., 227:381; Marks et al., 1991, J. Mol. Biol., 222:581), wherein the antibody repertoire is based on a human immunoglobulin sequence. The term "human antibody" denotes the genus of sequences that are human sequences. Thus, the term is not designating the process by which the antibody was created, but the genus of sequences that are relevant.

A "functional Fc region" possesses an "effector function" of a native sequence Fc region. Exemplary "effector functions" include Fc receptor binding; Clq binding; CDC; ADCC; phagocytosis; down regulation of cell surface receptors (for example B cell receptor; BCR), etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, for example, Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (for example B cell receptor); and B cell activation.

"Human effector cells" are leukocytes which express one or more FcRs and perform effector functions. In some embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, for example, from blood.

"Antibody-dependent cell-mediated cytotoxicity" or "ADCC" refers to a form of cytotoxicity in which secreted Ig bound onto Fc receptors (FcRs) present on certain cytotoxic cells (for example NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 or 6,737,056 (Presta), may be performed. Useful effector cells for such assays include PBMC and NK cells. Alternatively, or additionally, ADCC activity of the molecule of interest may be assessed in vivo, for example, in an animal model such as that disclosed in Clynes et al. *Proc. Natl. Acad. Sci. (USA)* 95:652-656 (1998). Additional polypeptide variants with altered Fc region amino acid sequences (polypeptides with a variant Fc region) and increased or decreased ADCC activity are described, for example, in U.S. Pat. Nos. 7,923, 538, and 7,994,290.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, for example, as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, for example, in U.S. Pat. No. 6,194,551 B1, U.S. Pat. Nos. 7,923,538, 7,994,290 and WO 1999/51642. See also, for example, Idusogie et al., *J. Immunol.* 164: 4178-4184 (2000).

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. Such variants which display decreased binding to an FcR may possess little or no appreciable binding to an FcR, for example, 0-20% binding to the FcR compared to a native sequence IgG Fc region.

The polypeptide variant which "mediates antibody-dependent cell-mediated cytotoxicity (ADCC) in the presence of human effector cells more effectively" than a parent antibody is one which in vitro or in vivo is more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (for example, an extracellular domain sequence), naturally occurring variant forms (for example, alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |

TABLE 1-continued

| Original Residue | Exemplary Substitutions |
| --- | --- |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" or "subject" are used interchangeably herein to refer to an animal; for example, a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, mesothelioma, and various types of head and neck cancer.

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering an anti-PD-1 antibody. "Ameliorating" also includes shortening or reduction in duration of a symptom.

In the context of cancer, the term "treating" includes any or all of: inhibiting growth of cancer cells, inhibiting replication of cancer cells, lessening of overall tumor burden and ameliorating one or more symptoms associated with the disease.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

A sample that has an "elevated level of PD-1" or "expresses PD-1 at an elevated level" or is means that the level of PD-1 is such that one of skill in the art would conclude that the cancer may be treatable with an anti-PD-1 therapy, such as an antibody provided herein. In some embodiments, an "elevated level of PD-1" is one in which 1% of the cells within a tumor sample show staining for PD-1. In some embodiments a "high level" in regard to PD-1 is 1% or more staining, for example, 1, 5, 10, 20, 30, 40, 50, 60, 70, 80, 90, or 100% of the cells within the tumor sample show staining. In some embodiments, the PD-1 levels can be measured by chromogenic IHC or immunofluorescence IHC (Aqua scoring).

A sample that "expresses PD-1" or has "positive staining for PD-1" or is "PD-1 positive" means that 1% or more of the cells in a sample show staining for PD-1. In some embodiments, a sample that is PD-1 positive displays at least weak, moderate, and/or strong cell staining (based on membrane expression of PD-1). A sample with moderate or strong cell staining for PD-1 is also considered to be "PD-1$^{HIGH}$."

A sample that has a "low level of PD-L1" or expresses "PD-L1 at a low level" or is "PD-L1$^{LOW}$" means that the level of PD-L1 is below the threshold level of expression for a cancer that is normally indicated for treatment with a PD-1 therapy. In some embodiments, a "low level of PD-L1" is one in which less than 5% of the cells in the tumor show membrane staining for PD-L1. In some embodiments a "low level" in regard to PD-L1 is less than 5% staining, for example, 4%, 3%, 2%, 1%, or 0% of the cells of the tumor show staining. In some embodiments, the PD-L1 levels can be measured by chromogenic IHC or immunofluorescence IHC (Aqua scoring). A sample that expresses no detectable PD-L1 can also be said to "express a low level of PD-L1." Thus, no detectable PD-L1 is encompassed within the term "low."

A sample that has an "elevated level of PD-L1" or "expresses PD-L1 at an elevated level" or is "PD-L1$^{HIGH}$" means that the level of PD-L1 that is such that one of skill in the art would conclude that the cancer may be treatable with a PD-1 therapy. In some embodiments, an "elevated level of PD-L1" is one in which 50% of the cells in the tumor or more have membrane staining of PD-L1, for example, 50, 60, 70, 80, 90, or 100% of the cells of the tumor show membrane staining. In some embodiments, the PD-L1 levels can be measured by chromogenic IHC or immunofluorescence IHC (AQUA scoring).

A sample that "expresses PD-L1" or has "positive staining for PD-L1" or is "PD-L1 positive" means that 1% or more of the cells have membrane staining for PD-L1. In some embodiments, a sample that is PD-L1 positive displays at least weak, moderate, and/or strong cell staining (based on membrane expression of PD-L1).

A sample that "lacks PD-L1 expression" or has "negative staining for PD-L1" or is "PD-L1 negative" means that PD-L1 expression on the surface of cells of the sample is undetectable by IHC, such as chromogenic IHC or immunofluorescence IHC (Aqua scoring). A PD-L1 negative sample is also be considered to be "PD-L1$^{ww}$."

In some embodiments, any method for measuring the level of PD-L1 can be employed. In some embodiments, this can include using the PD-L1 IHC 22C3 pharmDx test (Dako, Inc., Carpinteria, Calif.), which is a clinically validated and FDA approved test for evaluation of PD-L1 expression in NSCLC. PD-L1 IHC 22C3 pharmDx is a qualitative immunohistochemical assay using monoclonal mouse anti-PD-L1 antibody, (clone 22C3), that can be used in the detection of PD-L1 protein in formalin-fixed paraffin-embedded (FFPE) Non-Small Cell Lung Cancer (NSCLC) tissues. The assay can be performed on Autostainer Link 48 system and visualized using the EnVision FLEX system. PD-L1 protein expression is qualified using Tumor Proportion Score (TPS), which is the percentage of viable tumor cells showing partial or complete membrane staining. In some embodiments, the specimen is considered PD-L1 positive if TPS≥1% of the viable tumor cells exhibit membrane staining at any intensity. In some embodiments, the specimen is considered PD-L1$^{HIGH}$ if TPS≥50% of the viable tumor cells exhibit membrane staining at any intensity. PD-L1 IHC 22C3 pharmDx is indicated as an aid in identifying NSCLC patients for treatment with KEYTRUDA® (pembrolizumab). Additional details on the scoring system and response to pembrolizumab are described in the article by Garon et al. (N Engl J Med 2015; 372:2018-28).

The term "control" refers to a composition known to not contain an analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (for example, analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression/nonprogression/improvement, etc.). While the present disclosure may provide exemplary predetermined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. A "reversible IDO inhibitor" is a compound that reversibly inhibits IDO enzyme activity either at the catalytic site or at a non-catalytic site and an "irreversible IDO inhibitor" is a compound that irreversibly inhibits IDO enzyme activity by forming a covalent bond with the enzyme. Nonlimiting exemplary IDO inhibitors include Indoximod (New Link Genetics), INCB024360 (Incyte Corp.), 1-methyl-D-tryptophan (New Link Genetics), and GDC-0919 (Genentech, Inc.).

A "chimeric antigen receptor T cell therapy" or "CAR-T therapy" refers to a therapeutic agent comprising a T cell genetically modified to express a receptor that recognizes an antigen expressed by tumor cell. The antigen may be an antigen specifically expressed by the tumor or an antigen expressed by both cancerous cells and healthy tissue. In some embodiments CAR-T therapy is adoptive CAR-T therapy, in which a patients T cells are removed and modified to express the chimeric antigen receptor, and then returned to the patient. See, e.g., Dai et al., 2016, *J Natl Cancer Inst*, 108 (7): djv439, doi: 10.1093/jnci/djv439; Gill et al., 2015, *Blood Rev, pii: S0268-960X(15)00080-6*, doi: 10.1016/j.blre.2015.10.003; Gill et al., 2015, *Immunol Rev*, 263(1):68-89. doi: 10.1111/imr.12243.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

II. Anti-PD-1 Antibodies

Novel antibodies directed against PD-1 are provided. Anti-PD-1 antibodies include, but are not limited to, humanized antibodies, chimeric antibodies, mouse antibodies, human antibodies, and antibodies comprising the heavy chain and/or light chain CDRs discussed herein. In some embodiments, an isolated antibody that binds to PD-1 is provided. In some embodiments, a monoclonal antibody that binds to PD-1 is provided. In some embodiments, an anti- PD-1 antibody is an antagonist anti-PD-1 antibody. In some embodiments, an anti-PD-1 antibody provided herein inhibits binding of PD-1 to PD-L1 and/or PD-L2. In some embodiments, an anti-PD-1 antibody provided herein inhibits binding of PD-1 to PD-L1. In some embodiments, an anti-PD-1 antibody provided herein inhibits binding of PD-1 to PD-L1 and PD-L2. In some embodiments, administration of the anti-PD-1 antibodies described herein enhances an immune response in a subject, and/or increases activation of T cells in a subject.

In some embodiments, an anti-PD-1 antibody comprises at least one, two, three, four, five, or six CDRs selected from (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 9; (e) LCDR2 comprising the amino acid sequence of SEQ ID NO: 10; and (f) LCDR3 comprising the amino acid sequence of SEQ ID NO: 11.

In some embodiments, an anti-PD-1 antibody comprises at least one, two, three, four, five, or six CDRs selected from (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15; (d) LCDR1 comprising the amino acid sequence of SEQ ID NO: 17; (e) LCDR2 comprising the amino acid sequence of SEQ ID NO: 18; and (f) LCDR3 comprising the amino acid sequence of SEQ ID NO: 19.

In some embodiments, an anti-PD-1 antibody comprises at least one, two, three, four, five, or six CDRs selected from (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, an anti-PD-1 antibody comprises at least one, two, three, four, five, or six CDRs selected from (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31; (d) LCDR1 comprising the amino acid sequence of SEQ ID NO: 33; (e) LCDR2 comprising the amino acid sequence of SEQ ID NO: 34; and (f) LCDR3 comprising the amino acid sequence of SEQ ID NO: 35.

In some embodiments, an anti-PD-1 antibody comprises at least one, two, three, four, five, or six CDRs selected from (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39; (d) LCDR1 comprising the amino acid sequence of SEQ ID NO: 41; (e) LCDR2 comprising the amino acid sequence of SEQ ID NO: 42; and (f) LCDR3 comprising the amino acid sequence of SEQ ID NO: 43.

In some embodiments, an anti-PD-1 antibody comprises at least one, two, three, four, five, or six CDRs selected from (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119; (d) LCDR1 comprising an amino acid sequence selected from SEQ ID NOs: 49, 57, 65, 73, 81, 89, 97, 105, 113, and 121; (e) LCDR2 comprising an amino acid sequence selected from SEQ ID NOs: 50, 58, 66, 74, 82, 90, 98, 106, 114, and 122; and (f) LCDR3 comprising an amino acid sequence selected from SEQ ID NOs: 51, 59, 67, 75, 83, 91, 99, 107, 115, and 123.

In some embodiments, an anti-PD-1 antibody comprises at least one, two, three, four, five, or six CDRs selected from (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287; (d) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (e) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (f) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, an anti-PD-1 antibody comprises at least one, two, three, four, five, or six CDRs selected from (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271; (d) LCDR1 comprising an amino acid sequence selected from SEQ ID NOs: 289, 241, 249, 257, 265, and 273; (e) LCDR2 comprising an amino acid sequence selected from SEQ ID NOs: 290, 242, 250, 258, 266, and 274; and (f) LCDR3 comprising an amino acid sequence selected from SEQ ID NOs: 291, 243, 251, 259, 267, and 275.

In some embodiments, an anti-PD-1 antibody comprises at least one, two, three, four, five, or six CDRs selected from (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231; (d) LCDR1 comprising an amino acid sequence selected from SEQ ID NOs: 193, 201, 209, 217, 225, and 233; (e) LCDR2 comprising an amino acid sequence selected from SEQ ID NOs: 194, 202, 210, 218, 226, and 234; and (f) LCDR3 comprising an amino acid sequence selected from SEQ ID NOs: 195, 203, 211, 219, 227, and 235.

In some embodiments, an anti-PD-1 antibody comprises at least one, two, three, four, five, or six CDRs selected from (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183; (d) LCDR1 comprising an amino acid sequence selected from SEQ ID NOs: 281, 129, 137, 145, 153, 161, 169, 177, and 185; (e) LCDR2 comprising an amino acid sequence selected from SEQ ID NOs: 282, 130, 138, 146, 154, 162, 170, 178, and 286; and (f) LCDR3 comprising an amino acid sequence selected from SEQ ID NOs: 283, 131, 139, 147, 155, 163, 171, 179, and 187.

In some embodiments, an anti-PD-1 antibody comprises at least one, two, three, four, five, or six CDRs selected from (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319; (d) LCDR1 comprising an amino acid sequence selected from SEQ ID NOs: 297, 305, 313, and 321; (e) LCDR2 comprising an amino acid sequence selected from SEQ ID NOs: 298, 306, 314 and 322; and (f) LCDR3 comprising an amino acid sequence selected from SEQ ID NOs: 299, 307, 315, and 323.

In some embodiments, an anti-PD-1 antibody comprises a heavy chain variable region and a light chain variable region. In some embodiments, an anti-PD-1 antibody comprises at least one heavy chain comprising a heavy chain variable region and at least a portion of a heavy chain constant region, and at least one light chain comprising a light chain variable region and at least a portion of a light chain constant region. In some embodiments, an anti-PD-1 antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the anti-PD-1 antibody that comprises the three heavy chain CDRs. In some embodiments, the light chain is the region of the anti-PD-1 antibody that comprises the three light chain CDRs.

In some embodiments, the anti-PD-1 antibody comprises six CDRs including (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 9; (e) LCDR2 comprising the amino acid sequence of SEQ ID NO: 10; and (f) LCDR3 comprising the amino acid sequence of SEQ ID NO: 11.

In some embodiments, the anti-PD-1 antibody comprises six CDRs including (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15; (d) LCDR1 comprising the amino acid sequence of SEQ ID NO: 17; (e) LCDR2 comprising the amino acid sequence of SEQ ID NO: 18; and (f) LCDR3 comprising the amino acid sequence of SEQ ID NO: 19.

In some embodiments, the anti-PD-1 antibody comprises six CDRs including (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-PD-1 antibody comprises six CDRs including (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31; (d) LCDR1 comprising the amino acid sequence of SEQ ID NO: 33; (e) LCDR2 comprising the amino acid sequence of SEQ ID NO: 34; and (f) LCDR3 comprising the amino acid sequence of SEQ ID NO: 35.

In some embodiments, the anti-PD-1 antibody comprises six CDRs including (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39; (d) LCDR1 comprising the amino acid sequence of SEQ ID NO: 41; (e) LCDR2 comprising the amino acid sequence of SEQ ID NO: 42; and (f) LCDR3 comprising the amino acid sequence of SEQ ID NO: 43.

In some embodiments, the anti-PD-1 antibody comprises six CDRs including (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119; (d) LCDR1 comprising an amino acid sequence selected from SEQ ID NOs: 49, 57, 65, 73, 81, 89, 97, 105, 113, and 121; (e) LCDR2 comprising an amino acid sequence selected from SEQ ID NOs: 50, 58, 66, 74, 82, 90, 98, 106, 114, and 122; and (f) LCDR3 comprising an amino acid sequence selected from SEQ ID NOs: 51, 59, 67, 75, 83, 91, 99, 107, 115, and 123.

In some embodiments, the anti-PD-1 antibody comprises six CDRs including (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287; (d) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (e) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (f) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, the anti-PD-1 antibody comprises six CDRs including (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271; (d) LCDR1 comprising an amino acid sequence selected from SEQ ID NOs: 289, 241, 249, 257, 265, and 273; (e) LCDR2 comprising an amino acid sequence selected from SEQ ID NOs: 290, 242, 250, 258, 266, and 274; and (f) LCDR3 comprising an amino acid sequence selected from SEQ ID NOs: 291, 243, 251, 259, 267, and 275.

In some embodiments, the anti-PD-1 antibody comprises six CDRs including (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231; (d) LCDR1 comprising an amino acid sequence selected from SEQ ID NOs: 193, 201, 209, 217, 225, and 233; (e) LCDR2 comprising an amino acid sequence selected from SEQ ID NOs: 194, 202, 210, 218, 226, and 234; and (f) LCDR3 comprising an amino acid sequence selected from SEQ ID NOs: 195, 203, 211, 219, 227, and 235.

In some embodiments, the anti-PD-1 antibody comprises six CDRs including (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183; (d) LCDR1 comprising an amino acid sequence selected from SEQ ID NOs: 281, 129, 137, 145, 153, 161, 169, 177, and 185; (e) LCDR2 comprising an amino acid sequence selected from SEQ ID NOs: 282, 130, 138, 146, 154, 162, 170, 178, and 286; and (f) LCDR3 comprising an amino acid sequence selected from SEQ ID NOs: 283, 131, 139, 147, 155, 163, 171, 179, and 187.

In some embodiments, the anti-PD-1 antibody comprises six CDRs including (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319; (d) LCDR1 comprising an amino acid sequence selected from SEQ ID NOs: 297, 305, 313, and 321; (e) LCDR2 comprising an amino acid sequence selected from SEQ ID NOs: 298, 306, 314 and 322; and (f) LCDR3 comprising an amino acid sequence selected from SEQ ID NOs: 299, 307, 315, and 323.

In some embodiments, the anti-PD-1 antibody comprises the six CDRs as described above and binds to PD-1. In some embodiments, the anti-PD-1 antibody comprises the six CDRs as described above, binds to PD-1 and inhibits binding of PD-1 to PD-L1 and/or PD-L2. In some embodiments, the anti-PD-1 antibody comprises the six CDRs as described above, binds to PD-1 and inhibits binding of PD-1 to PD-L1. In some embodiments, the anti-PD-1 antibody comprises the six CDRs as described above, binds to PD-1 and inhibits binding of PD-1 to PD-L1 and PD-L2. In some embodiments, the anti-PD-1 antibody comprises the six CDRs as described above, binds to PD-1 and enhances an immune response in a subject, and/or increases activation of T cells in a subject following administration of the antibody to the subject.

In some embodiments, an anti-PD-1 antibody is provided that competes with an anti-PD-1 antibody described herein for binding to PD-1. In some embodiments, an antibody that competes for binding with any of the antibodies provided herein can be made and/or used.

In some embodiments, the anti-PD-1 antibody comprises at least one, at least two, or all three VH CDR sequences selected from (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7.

In some embodiments, the anti-PD-1 antibody comprises at least one, at least two, or all three VH CDR sequences selected from (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15.

In some embodiments, the anti-PD-1 antibody comprises at least one, at least two, or all three VH CDR sequences selected from (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23.

In some embodiments, the anti-PD-1 antibody comprises at least one, at least two, or all three VH CDR sequences selected from (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO:31.

In some embodiments, the anti-PD-1 antibody comprises at least one, at least two, or all three VH CDR sequences selected from (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39.

In some embodiments, the anti-PD-1 antibody comprises at least one, at least two, or all three VH CDR sequences selected from (a) HCDR1 comprising the amino acid sequence of SEQ ID NO: 61; (b) HCDR2 comprising the amino acid sequence of SEQ ID NO: 62; and (c) HCDR3 comprising the amino acid sequence of SEQ ID NO: 63.

In some embodiments, the anti-PD-1 antibody comprises at least one, at least two, or all three VH CDR sequences selected from (a) HCDR1 comprising the amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119.

In some embodiments, the anti-PD-1 antibody comprises at least one, at least two, or all three VH CDR sequences selected from (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287.

In some embodiments, the anti-PD-1 antibody comprises at least one, at least two, or all three VH CDR sequences selected from (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271.

In some embodiments, the anti-PD-1 antibody comprises at least one, at least two, or all three VH CDR sequences selected from (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231.

In some embodiments, the anti-PD-1 antibody comprises at least one, at least two, or all three VH CDR sequences selected from (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183.

In some embodiments, the anti-PD-1 antibody comprises at least one, at least two, or all three VH CDR sequences selected from (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319.

In some embodiments, the antibody comprises at least one, at least two, or all three VL CDR sequences selected from (a) LCDR1 comprising the amino acid sequence of SEQ ID NO: 9; (b) LCDR2 comprising the amino acid sequence of SEQ ID NO: 10; and (c) LCDR3 comprising the amino acid sequence of SEQ ID NO: 11.

In some embodiments, the antibody comprises at least one, at least two, or all three VL CDR sequences selected from (a) LCDR1 comprising the amino acid sequence of SEQ ID NO: 17; (b) LCDR2 comprising the amino acid sequence of SEQ ID NO: 18; and (c) LCDR3 comprising the amino acid sequence of SEQ ID NO: 19.

In some embodiments, the antibody comprises at least one, at least two, or all three VL CDR sequences selected from (a) LCDR1 comprising the amino acid sequence of SEQ ID NO: 25; (b) LCDR2 comprising the amino acid sequence of SEQ ID NO: 26; and (c) LCDR3 comprising the amino acid sequence of SEQ ID NO: 27.

In some embodiments, the antibody comprises at least one, at least two, or all three VL CDR sequences selected from (a) LCDR1 comprising the amino acid sequence of SEQ ID NO: 33; (b) LCDR2 comprising the amino acid sequence of SEQ ID NO: 34; and (c) LCDR3 comprising the amino acid sequence of SEQ ID NO: 35.

In some embodiments, the antibody comprises at least one, at least two, or all three VL CDR sequences selected from (a) LCDR1 comprising the amino acid sequence of SEQ ID NO: 41; (b) LCDR2 comprising the amino acid sequence of SEQ ID NO: 42; and (c) LCDR3 comprising the amino acid sequence of SEQ ID NO: 43.

In some embodiments, the antibody comprises at least one, at least two, or all three VL CDR sequences selected from (a) LCDR1 comprising an amino acid sequence selected from SEQ ID NOs: 49, 57, 65, 73, 81, 89, 97, 105, 113, and 121; (b) LCDR2 comprising an amino acid sequence selected from SEQ ID NOs: 50, 58, 66, 74, 82, 90, 98, 106, 114, and 122; and (c) LCDR3 comprising an amino acid sequence selected from SEQ ID NOs: 51, 59, 67, 75, 83, 91, 99, 107, 115, and 123.

In some embodiments, the antibody comprises at least one, at least two, or all three VL CDR sequences selected from (a) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (b) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (c) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, the antibody comprises at least one, at least two, or all three VL CDR sequences selected from (a) LCDR1 comprising an amino acid sequence selected from SEQ ID NOs: 289, 241, 249, 257, 265, and 273; (b) LCDR2 comprising an amino acid sequence selected from SEQ ID NOs: 290, 242, 250, 258, 266, and 274; and (c) LCDR3 comprising an amino acid sequence selected from SEQ ID NOs: 291, 243, 251, 259, 267, and 275.

In some embodiments, the antibody comprises at least one, at least two, or all three VL CDR sequences selected (a) LCDR1 comprising an amino acid sequence selected from SEQ ID NOs: 193, 201, 209, 217, 225, and 233; (b) LCDR2 comprising an amino acid sequence selected from SEQ ID NOs: 194, 202, 210, 218, 226, and 234; and (c) LCDR3 comprising an amino acid sequence selected from SEQ ID NOs: 195, 203, 211, 219, 227, and 235.

In some embodiments, the antibody comprises at least one, at least two, or all three VL CDR sequences selected from (a) LCDR1 comprising an amino acid sequence selected from SEQ ID NOs: 281, 129, 137, 145, 153, 161, 169, 177, and 185; (b) LCDR2 comprising an amino acid sequence selected from SEQ ID NOs: 282, 130, 138, 146, 154, 162, 170, 178, and 286; and (c) LCDR3 comprising an amino acid sequence selected from SEQ ID NOs: 283, 131, 139, 147, 155, 163, 171, 179, and 187.

In some embodiments, the antibody comprises at least one, at least two, or all three VL CDR sequences selected from (a) LCDR1 comprising an amino acid sequence selected from SEQ ID NOs: 297, 305, 313, and 321; (b) LCDR2 comprising an amino acid sequence selected from SEQ ID NOs: 298, 306, 314 and 322; and (c) LCDR3 comprising an amino acid sequence selected from SEQ ID NOs: 299, 307, 315, and 323.

In some embodiments, any of the six CDRs provided herein can be combined as subparts with any of the other CDRs provided herein, for a total of six CDRs in a construct. Thus, in some embodiments, two CDRs from a first antibody (for example, HCDR1 and HCDR2) can be combined with four CDRs from a second antibody (HCDR3, LCDR1, LCDR2, and LCDR3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In some embodiments, the anti-PD-1 antibody comprises (I) a VH domain comprising at least one, at least two, or all three VH CDR sequences selected from (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; and (II) a VL domain comprising at least one, at least two, or all three VL CDR sequences selected from (d) LCDR1 comprising the amino acid sequence of SEQ ID NO: 9; (e) LCDR2 comprising the amino acid sequence of SEQ ID NO: 10; and (f) LCDR3 comprising the amino acid sequence of SEQ ID NO: 11.

In some embodiments, the anti-PD-1 antibody comprises (I) a VH domain comprising at least one, at least two, or all three VH CDR sequences selected from (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15; and (II) a VL domain comprising at least one, at least two, or all three VL CDR sequences selected from (d) LCDR1 comprising the amino acid sequence of SEQ ID NO: 17; (e) LCDR2 comprising the amino acid sequence of SEQ ID NO: 18; and (f) LCDR3 comprising the amino acid sequence of SEQ ID NO: 19.

In some embodiments, the anti-PD-1 antibody comprises (I) a VH domain comprising at least one, at least two, or all three VH CDR sequences selected from (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; and (II) a VL domain comprising at least one, at least two, or all three VL CDR sequences selected from (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-PD-1 antibody comprises (I) a VH domain comprising at least one, at least two, or all three VH CDR sequences selected from (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31; and (II) a VL domain comprising at least one, at least two, or all three VL CDR sequences selected from (d) LCDR1 comprising the amino acid sequence of SEQ ID NO: 33; (e) LCDR2 comprising the amino acid sequence of SEQ ID NO: 34; and (f) LCDR3 comprising the amino acid sequence of SEQ ID NO: 35.

In some embodiments, the anti-PD-1 antibody comprises (I) a VH domain comprising at least one, at least two, or all three VH CDR sequences selected from (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39; and (II) a VL domain comprising at least one, at least two, or all three VL CDR sequences selected from (d) LCDR1 comprising the amino acid sequence of SEQ ID NO: 41; (e) LCDR2 comprising the amino acid sequence of SEQ ID NO: 42; and (f) LCDR3 comprising the amino acid sequence of SEQ ID NO: 43.

In some embodiments, the anti-PD-1 antibody comprises (I) a VH domain comprising at least one, at least two, or all three VH CDR sequences selected from (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119; and (II) a VL domain comprising at least one, at least two, or all three VL CDR sequences selected from (d) LCDR1 comprising an amino acid sequence selected from SEQ ID NOs: 49, 57, 65, 73, 81, 89, 97, 105, 113, and 121; (e) LCDR2 comprising an amino acid sequence selected from SEQ ID NOs: 50, 58, 66, 74, 82, 90, 98, 106, 114, and 122; and (f) LCDR3 comprising an amino acid sequence selected from SEQ ID NOs: 51, 59, 67, 75, 83, 91, 99, 107, 115, and 123.

In some embodiments, the anti-PD-1 antibody comprises (I) a VH domain comprising at least one, at least two, or all three VH CDR sequences selected from (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287; and (II) a VL domain comprising at least one, at least two, or all three VL CDR sequences selected from (d) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (e) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (f) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, the anti-PD-1 antibody comprises (I) a VH domain comprising at least one, at least two, or all three VH CDR sequences selected from (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271; and (II) a VL domain comprising at least one, at least two, or all three VL CDR sequences selected from (d) LCDR1 comprising an amino acid sequence selected from SEQ ID NOs: 289, 241, 249, 257, 265, and 273; (e) LCDR2 comprising an amino acid sequence selected from SEQ ID NOs: 290, 242, 250, 258, 266, and 274; and (f) LCDR3 comprising an amino acid sequence selected from SEQ ID NOs: 291, 243, 251, 259, 267, and 275.

In some embodiments, the anti-PD-1 antibody comprises (I) a VH domain comprising at least one, at least two, or all three VH CDR sequences selected from (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231; and (II) a VL domain comprising at least one, at least two, or all three VL CDR sequences selected from (d) LCDR1 comprising an amino acid sequence selected from SEQ ID NOs: 193, 201, 209, 217, 225, and 233; (e) LCDR2 comprising an amino acid sequence selected from SEQ ID NOs: 194, 202, 210, 218, 226, and 234; and (f) LCDR3 comprising an amino acid sequence selected from SEQ ID NOs: 195, 203, 211, 219, 227, and 235.

In some embodiments, the anti-PD-1 antibody comprises (I) a VH domain comprising at least one, at least two, or all three VH CDR sequences selected from (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183; and (II) a VL domain comprising at least one, at least two, or all three VL CDR sequences selected from (d) LCDR1 comprising an amino acid sequence selected from SEQ ID NOs: 281, 129, 137, 145, 153, 161, 169, 177, and 185; (e) LCDR2 comprising an amino acid sequence selected from SEQ ID NOs: 282, 130, 138, 146, 154, 162, 170, 178, and 286; and (f) LCDR3 comprising an amino acid sequence selected from SEQ ID NOs: 283, 131, 139, 147, 155, 163, 171, 179, and 187.

In some embodiments, the anti-PD-1 antibody comprises (I) a VH domain comprising at least one, at least two, or all three VH CDR sequences selected from (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319; and (II) a VL domain comprising at least one, at least two, or all three VL CDR sequences selected from (d) LCDR1 comprising an amino acid sequence selected from SEQ ID NOs: 297, 305, 313, and 321; (e) LCDR2 comprising an amino acid sequence selected from SEQ ID NOs: 298, 306, 314 and 322; and (f) LCDR3 comprising an amino acid sequence selected from SEQ ID NOs: 299, 307, 315, and 323.

In some embodiments, an anti-PD-1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, but an anti-PD-1 antibody comprising that sequence retains the ability to bind to PD-1. In some embodiments, a total of 1 to 10 amino acids have been substituted, inserted and/or deleted in SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316. In some embodiments, substitutions, insertions, or deletions occur in regions outside the CDRs (that is, in the FRs). Optionally, the anti-PD-1 antibody comprises the VH sequence in SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316, including post-translational modifications of that sequence.

In some embodiments, the VH comprises: (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7.

In some embodiments, the VH comprises: (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15.

In some embodiments, the VH comprises: (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23.

In some embodiments, the VH comprises: (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31.

In some embodiments, the VH comprises: (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39.

In some embodiments, the VH comprises: (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119.

In some embodiments, the VH comprises: (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287.

In some embodiments, the VH comprises: (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271.

In some embodiments, the VH comprises: (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231.

In some embodiments, the VH comprises: (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183.

In some embodiments, the VH comprises: (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319.

In some embodiments, an anti-PD-1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320. In some embodiments, a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-PD-1 antibody comprising that sequence retains the ability to bind to PD-1. In some embodiments, a total of 1 to 10 amino acids have been substituted, inserted and/or deleted in SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320. In some embodiments, the substitutions, insertions, or deletions occur in regions outside the CDRs (that is, in the FRs). Optionally, the anti-PD-1 antibody comprises the VL sequence in SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320, including post-translational modifications of that sequence.

In some embodiments, the VL comprises: (a) LCDR1 comprising the amino acid sequence of SEQ ID NO: 9; (b) LCDR2 comprising the amino acid sequence of SEQ ID NO: 10; and (c) LCDR3 comprising the amino acid sequence of SEQ ID NO: 11.

In some embodiments, the VL comprises: (a) LCDR1 comprising the amino acid sequence of SEQ ID NO: 17; (b) LCDR2 comprising the amino acid sequence of SEQ ID NO: 18; and (c) LCDR3 comprising the amino acid sequence of SEQ ID NO: 19.

In some embodiments, the VL comprises: (a) LCDR1 comprising the amino acid sequence of SEQ ID NO: 25; (b) LCDR2 comprising the amino acid sequence of SEQ ID NO: 26; and (c) LCDR3 comprising the amino acid sequence of SEQ ID NO: 27.

In some embodiments, the VL comprises: (a) LCDR1 comprising the amino acid sequence of SEQ ID NO: 33; (b) LCDR2 comprising the amino acid sequence of SEQ ID NO: 34; and (c) LCDR3 comprising the amino acid sequence of SEQ ID NO: 35.

In some embodiments, the VL comprises: (a) LCDR1 comprising the amino acid sequence of SEQ ID NO: 41; (b) LCDR2 comprising the amino acid sequence of SEQ ID NO: 42; and (c) LCDR3 comprising the amino acid sequence of SEQ ID NO: 43.

In some embodiments, the VL comprises: (a) LCDR1 comprising an amino acid sequence selected from SEQ ID NOs: 49, 57, 65, 73, 81, 89, 97, 105, 113, and 121; (b) LCDR2 comprising an amino acid sequence selected from SEQ ID NOs: 50, 58, 66, 74, 82, 90, 98, 106, 114, and 122; and (c) LCDR3 comprising an amino acid sequence selected from SEQ ID NOs: 51, 59, 67, 75, 83, 91, 99, 107, 115, and 123.

In some embodiments, the VL comprises: (a) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (b) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (c) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, the VL comprises: (a) LCDR1 comprising an amino acid sequence selected from SEQ ID NOs: 289, 241, 249, 257, 265, and 273; (b) LCDR2 comprising an amino acid sequence selected from SEQ ID NOs: 290, 242, 250, 258, 266, and 274; and (c) LCDR3 comprising an amino acid sequence selected from SEQ ID NOs: 291, 243, 251, 259, 267, and 275.

In some embodiments, the VL comprises: (a) LCDR1 comprising an amino acid sequence selected from SEQ ID NOs: 193, 201, 209, 217, 225, and 233; (b) LCDR2 comprising an amino acid sequence selected from SEQ ID NOs: 194, 202, 210, 218, 226, and 234; and (c) LCDR3 comprising an amino acid sequence selected from SEQ ID NOs: 195, 203, 211, 219, 227, and 235.

In some embodiments, the VL comprises: (a) LCDR1 comprising an amino acid sequence selected from SEQ ID NOs: 281, 129, 137, 145, 153, 161, 169, 177, and 185; (b) LCDR2 comprising an amino acid sequence selected from SEQ ID NOs: 282, 130, 138, 146, 154, 162, 170, 178, and 286; and (c) LCDR3 comprising an amino acid sequence selected from SEQ ID NOs: 283, 131, 139, 147, 155, 163, 171, 179, and 187.

In some embodiments, the VL comprises: (a) LCDR1 comprising an amino acid sequence selected from SEQ ID NOs: 297, 305, 313, and 321; (b) LCDR2 comprising an amino acid sequence selected from SEQ ID NOs: 298, 306, 314 and 322; and (c) LCDR3 comprising an amino acid sequence selected from SEQ ID NOs: 299, 307, 315, and 323.

In some embodiments, an anti-PD-1 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316 and a light chain variable domain (VL) having at least 90%, 91%, 92%, 93%, 94%, 95%, 96%, 97%, 98%, 99%, or 100% sequence identity to the amino acid sequence of SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320. In some embodiments, a VH sequence having at least 90%, 91%, 92%, 93%, 94%, 95%, 96%, 97%, 98%, or 99% identity contains substitutions (for example, conservative substitutions), insertions, or deletions relative to the reference sequence, and a VL sequence having at least 90%, 91%, 92%, 93%, 94%, 95%, 96%, 97%, 98%, or 99% identity contains substitutions (for example, conservative substitutions), insertions, or deletions relative to the reference sequence, but an anti-PD-1 antibody comprising that sequence retains the ability to bind to PD-1. In some embodiments, a total of 1 to 10 amino acids have been substituted, inserted and/or deleted in SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316. In some embodiments, a total of 1 to 10 amino acids have been substituted, inserted and/or deleted in SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320. In some embodiments, substitutions, insertions, or deletions occur in regions outside the CDRs (that is, in the FRs). Optionally, the anti-PD-1 antibody comprises the VH sequence in SEQ ID NO: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316 and the VL sequence of SEQ ID NO: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320, including post-translational modifications of one or both sequence.

In some embodiments, the anti-PD-1 antibody comprises (a) HCDR1 comprising the amino acid sequence of SEQ ID NO: 5; (b) HCDR2 comprising the amino acid sequence of SEQ ID NO: 6; (c) HCDR3 comprising the amino acid sequence of SEQ ID NO: 7; (d) LCDR1 comprising the amino acid sequence of SEQ ID NO: 9; (e) LCDR2 comprising the amino acid sequence of SEQ ID NO: 10; and (f) LCDR3 comprising the amino acid sequence of SEQ ID NO: 11.

In some embodiments, the anti-PD-1 antibody comprises (a) HCDR1 comprising the amino acid sequence of SEQ ID NO: 13; (b) HCDR2 comprising the amino acid sequence of SEQ ID NO: 14; (c) HCDR3 comprising the amino acid sequence of SEQ ID NO: 15; (d) LCDR1 comprising the amino acid sequence of SEQ ID NO: 17; (e) LCDR2 comprising the amino acid sequence of SEQ ID NO: 18; and (f) LCDR3 comprising the amino acid sequence of SEQ ID NO: 19.

In some embodiments, the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

In some embodiments, the anti-PD-1 antibody comprises (a) HCDR1 comprising the amino acid sequence of SEQ ID NO: 29; (b) HCDR2 comprising the amino acid sequence of SEQ ID NO: 30; (c) HCDR3 comprising the amino acid sequence of SEQ ID NO: 31; (d) LCDR1 comprising the amino acid sequence of SEQ ID NO: 33; (e) LCDR2 comprising the amino acid sequence of SEQ ID NO: 34; and (f) LCDR3 comprising the amino acid sequence of SEQ ID NO: 35.

In some embodiments, the anti-PD-1 antibody comprises (a) HCDR1 comprising the amino acid sequence of SEQ ID NO: 37; (b) HCDR2 comprising the amino acid sequence of SEQ ID NO: 38; (c) HCDR3 comprising the amino acid sequence of SEQ ID NO: 39; (d) LCDR1 comprising the amino acid sequence of SEQ ID NO: 41; (e) LCDR2 comprising the amino acid sequence of SEQ ID NO: 42; and (f) LCDR3 comprising the amino acid sequence of SEQ ID NO: 43.

In some embodiments, the anti-PD-1 antibody comprises (a) HCDR1 comprising an amino acid sequence selected from SEQ ID NOs: 45, 53, 61, 69, 77, 85, 93, 101, 109 and 117; (b) HCDR2 comprising an amino acid sequence selected from SEQ ID NOs: 46, 54, 62, 70, 78, 86, 94, 102, 110 and 118; (c) HCDR3 comprising an amino acid sequence selected from SEQ ID NOs: 47, 55, 63, 71, 79, 87, 95, 103, 111, and 119; (d) LCDR1 comprising an amino acid sequence selected from SEQ ID NOs: 49, 57, 65, 73, 81, 89, 97, 105, 113, and 121; (e) LCDR2 comprising an amino acid sequence selected from SEQ ID NOs: 50, 58, 66, 74, 82, 90, 98, 106, 114, and 122; and (f) LCDR3 comprising an amino acid sequence selected from SEQ ID NOs: 51, 59, 67, 75, 83, 91, 99, 107, 115, and 123.

In some embodiments, the anti-PD-1 antibody comprises (a) HCDR1 comprising an amino acid sequence selected from SEQ ID NOs: 125, 133, 141, 149, 157, 165, 173, 181, 189, 197, 205, 213, 221, 229, 237, 245, 253, 261, 269, 277 and 285; (b) HCDR2 comprising an amino acid sequence selected from SEQ ID NOs: 126, 134, 142, 150, 158, 166, 174, 182, 190, 198, 206, 214, 222, 230, 238, 246, 254, 262, 270, 278 and 286; (c) HCDR3 comprising an amino acid sequence selected from SEQ ID NOs: 127, 135, 143, 151, 159, 167, 175, 183, 191, 199, 207, 215, 223, 231, 239, 247, 255, 263, 271, 279 and 287; (d) LCDR1 comprising an amino acid sequence selected from SEQ ID NOs: 129, 137, 145, 153, 161, 169, 177, 185, 193, 201, 209, 217, 225, 233, 241, 249, 257, 265, 273, 281 and 289; (e) LCDR2 comprising an amino acid sequence selected from SEQ ID NOs: 130, 138, 146, 154, 162, 170, 178, 186, 194, 202, 210, 218, 226, 234, 242, 250, 258, 266, 274, 282, and 290; and (f) LCDR3 comprising an amino acid sequence selected from SEQ ID NOs: 131, 139, 147, 155, 163, 171, 179, 187, 195, 203, 211, 219, 227, 235, 243, 251, 259, 267, 275, 283 and 291.

In some embodiments, the anti-PD-1 antibody comprises (a) HCDR1 comprising an amino acid sequence selected from SEQ ID NOs: 285, 237, 245, 253, 261 and 269; (b) HCDR2 comprising an amino acid sequence selected from SEQ ID NOs: 286, 238, 246, 254, 262, and 270; (c) HCDR3 comprising an amino acid sequence selected from SEQ ID NOs: 287, 239, 247, 255, 263, and 271; (d) LCDR1 comprising an amino acid sequence selected from SEQ ID NOs: 289, 241, 249, 257, 265, and 273; (e) LCDR2 comprising an amino acid sequence selected from SEQ ID NOs: 290, 242, 250, 258, 266, and 274; and (f) LCDR3 comprising an amino acid sequence selected from SEQ ID NOs: 291, 243, 251, 259, 267, and 275.

In some embodiments, the anti-PD-1 antibody comprises (a) HCDR1 comprising an amino acid sequence selected from SEQ ID NOs: 189, 197, 205, 213, 221, and 229; (b) HCDR2 comprising an amino acid sequence selected from SEQ ID NOs: 190, 198, 206, 214, 222, and 230; (c) HCDR3 comprising an amino acid sequence selected from SEQ ID NOs: 191, 199, 207, 215, 223, and 231; (d) LCDR1 comprising an amino acid sequence selected from SEQ ID NOs: 193, 201, 209, 217, 225, and 233; (e) LCDR2 comprising an amino acid sequence selected from SEQ ID NOs: 194, 202, 210, 218, 226, and 234; and (f) LCDR3 comprising an amino acid sequence selected from SEQ ID NOs: 195, 203, 211, 219, 227, and 235.

In some embodiments, the anti-PD-1 antibody comprises (a) HCR1 comprising an amino acid sequence selected from SEQ ID NOs: 277, 125, 133, 141, 149, 157, 165, 173, and 181; (b) HCDR2 comprising an amino acid sequence selected from SEQ ID NOs: 278, 126, 134, 142, 150, 158, 166, 174, and 182; (c) HCDR3 comprising an amino acid sequence selected from SEQ ID NOs: 279, 127, 135, 143, 151, 159, 167, 175, and 183; (d) LCDR1 comprising an amino acid sequence selected from SEQ ID NOs: 281, 129, 137, 145, 153, 161, 169, 177, and 185; (e) LCDR2 comprising an amino acid sequence selected from SEQ ID NOs: 282, 130, 138, 146, 154, 162, 170, 178, and 286; and (f) LCDR3 comprising an amino acid sequence selected from SEQ ID NOs: 283, 131, 139, 147, 155, 163, 171, 179, and 187.

In some embodiments, the anti-PD-1 antibody comprises (a) HCDR1 comprising an amino acid sequence selected from SEQ ID NOs: 293, 301, 309 and 317; (b) HCDR2 comprising an amino acid sequence selected from SEQ ID NOs: 294, 302, 310 and 318; (c) HCDR3 comprising an amino acid sequence selected from SEQ ID NOs: 295, 303, 311 and 319; (d) LCDR1 comprising an amino acid sequence selected from SEQ ID NOs: 297, 305, 313, and 321; (e) LCDR2 comprising an amino acid sequence selected from SEQ ID NOs: 298, 306, 314 and 322; and (f) LCDR3 comprising an amino acid sequence selected from SEQ ID NOs: 299, 307, 315, and 323.

In some embodiments, an anti-PD-1 antibody comprises a VH as in any of the embodiments provided herein, and a VL as in any of the embodiments provided herein. In some embodiments, the antibody comprises the VH and VL sequences in SEQ ID NO: 4 and SEQ ID NO: 8, respectively, including post-translational modifications of those sequences. In some embodiments, the antibody comprises the VH and VL sequences in SEQ ID NO: 12 and SEQ ID NO: 16, respectively, including post-translational modifications of those sequences. In some embodiments, the antibody comprises the VH and VL sequences in SEQ ID NO: 20 and SEQ ID NO: 24, respectively, including post-translational modifications of those sequences. In some embodiments, the antibody comprises the VH and VL sequences in SEQ ID NO: 28 and SEQ ID NO: 32, respectively, including post-translational modifications of those sequences. In some embodiments, the antibody comprises the VH and VL sequences in SEQ ID NO: 36 and SEQ ID NO: 40, respectively, including post-translational modifications of those sequences. In some embodiments, the antibody comprises the VH and VL sequences in SEQ ID NO: 44 and SEQ ID NO: 48, respectively, including post-translational modifications of those sequences. In some embodiments, the antibody comprises the VH and VL sequences in SEQ ID NO: 52 and SEQ ID NO: 56, respectively, including post-translational modifications of those sequences. In some embodiments, the antibody comprises the VH and VL sequences in SEQ ID NO: 60 and SEQ ID NO: 64, respectively, including post-translational modifications of those sequences. In some embodiments, the antibody comprises the VH and VL sequences in SEQ ID NO: 68 and SEQ ID NO: 72, respectively, including post-translational modifications of those sequences. In some embodiments, the antibody comprises the VH and VL sequences in SEQ ID NO: 76 and SEQ ID NO: 80, respectively, including post-translational modifications of those sequences. In some embodiments, the antibody comprises the VH and VL sequences in SEQ ID NO: 84 and SEQ ID NO: 88, respectively, including post-translational modifications of those sequences. In some embodiments, the antibody comprises the VH and VL sequences in SEQ ID NO: 92 and SEQ ID NO: 96, respectively, including post-translational modifications of those sequences. In some embodiments, the antibody comprises the VH and VL sequences in SEQ ID NO: 100 and SEQ ID NO: 104, respectively, including post-translational modifications of those sequences. In some embodiments, the antibody comprises the VH and VL sequences in SEQ ID NO: 108 and SEQ ID NO: 112, respectively, including post-translational modifications of those sequences. In some embodiments, the antibody comprises the VH and VL sequences in SEQ ID NO: 116 and SEQ ID NO: 120, respectively, including post-translational modifications of those sequences. In some embodiments, the antibody comprises the VH and VL sequences in SEQ ID NO: 124 and SEQ ID NO: 128, respectively, including post-translational modifications of those sequences. In some embodiments, the antibody comprises the VH and VL sequences in SEQ ID NO: 132 and SEQ ID NO: 136, respectively, including post-translational modifications of those sequences. In some embodiments, the antibody comprises the VH and VL sequences in SEQ ID NO: 140 and SEQ ID NO: 144, respectively, including post-translational modifications of those sequences. In some embodiments, the antibody comprises the VH and VL sequences in SEQ ID NO: 148 and SEQ ID NO: 152, respectively, including post-translational modifications of those sequences. In some embodiments, the antibody comprises the VH and VL sequences in SEQ ID NO: 156 and SEQ ID NO: 160, respectively, including post-translational modifications of those sequences. In some embodiments, the antibody comprises the VH and VL sequences in SEQ ID NO: 164 and SEQ ID NO: 168, respectively, including post-translational modifications of those sequences. In some embodiments, the antibody comprises the VH and VL sequences in SEQ ID NO: 172 and SEQ ID NO: 176, respectively, including post-translational modifications of those sequences. In some embodiments, the antibody comprises the VH and VL sequences in SEQ ID NO: 180 and SEQ ID NO: 184, respectively, including post-translational modifications of those sequences. In some embodiments, the antibody comprises the VH and VL sequences in SEQ ID NO: 188 and SEQ ID NO: 192, respectively, including post-translational modifications of those sequences. In some embodiments, the antibody comprises the VH and VL sequences in SEQ ID NO: 196 and SEQ ID NO: 200, respectively, including post-translational modifications of those sequences. In some embodiments, the antibody comprises the VH and VL sequences in SEQ ID NO: 204 and SEQ ID NO: 208, respectively, including post-translational modifications of those sequences. In some embodiments, the antibody comprises the VH and VL sequences in SEQ ID NO: 212 and SEQ ID NO: 216, respectively, including post-translational modifications of those sequences. In some embodiments, the antibody comprises the VH and VL sequences in SEQ ID NO: 220 and SEQ ID NO: 224, respectively, including post-translational modifications of those sequences. In some embodiments, the antibody comprises the VH and VL sequences in SEQ ID NO: 228 and SEQ ID NO: 232, respectively, including post-translational modifications of those sequences. In some embodiments, the antibody comprises the VH and VL sequences in SEQ ID NO: 236 and SEQ ID NO: 240, respectively, including post-translational modifications of those sequences. In some embodiments, the antibody comprises the VH and VL sequences in SEQ ID NO: 244 and SEQ ID NO: 248, respectively, including post-translational modifications of those sequences. In some embodiments, the antibody comprises the VH and VL sequences in SEQ ID NO: 252 and SEQ ID NO: 256, respectively, including post-translational modifications of those sequences. In some embodiments, the antibody comprises the VH and VL sequences in SEQ ID NO: 260 and SEQ ID NO: 264, respectively, including post-translational modifications of those sequences. In some embodiments, the antibody comprises the VH and VL sequences in SEQ ID NO: 268 and SEQ ID NO: 272, respectively, including post-translational modifications of those sequences. In some embodiments, the antibody comprises the VH and VL sequences in SEQ ID NO: 276 and SEQ ID NO: 280, respectively, including post-translational modifications of those sequences. In some embodiments, the antibody comprises the VH and VL sequences in SEQ ID NO: 284 and SEQ ID NO: 288, respectively, including post-translational modifications of those sequences. In some embodiments, the antibody comprises the VH and VL sequences in SEQ ID NO: 292 and SEQ ID NO: 296, respectively, including post-translational modifications of those sequences. In some embodiments, the antibody comprises the VH and VL sequences in SEQ ID NO: 300 and SEQ ID NO: 304, respectively, including post-translational modifications of those sequences. In some embodiments, the antibody comprises the VH and VL sequences in SEQ ID NO: 308 and SEQ ID NO: 312, respectively, including post-translational modifications of those sequences. In some embodiments, the antibody comprises the VH and VL sequences in SEQ ID NO: 316 and SEQ ID NO: 320, respectively, including post-translational modifications of those sequences.

In some embodiments, antibodies which compete with the anti-PD-1 antibodies provided herein for binding to PD-1 are provided. In some embodiments, antibodies compete with the anti-PD-1 antibodies provided herein for binding to an epitope on PD-1.

In some embodiments, competition assays may be used to identify a monoclonal antibody that competes with an anti-PD-1 antibody described herein (such as 12228, 13406, 13407, 13408, and 13409) for binding to PD-1. Competition assays can be used to determine whether two antibodies bind the same epitope by recognizing identical or sterically overlapping epitopes or one antibody competitively inhibits binding of another antibody to the antigen. In some embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch.14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-PD-1 antibody described herein is a chimeric, humanized or human antibody. In some embodiments, an antibody that competes with a chimeric, humanized, or human anti-PD-1 antibody as described herein is provided.

In some embodiments, antibodies that bind to any one or more of the epitopes that the antibodies provided herein are provided. In some embodiments, antibodies that bind and overlap an epitope to which the present antibodies bind to are provided. In some embodiments, an antibody is provided that competes with at least one of the antibodies provided herein. In some embodiments, an antibody is provided that competes with at least two of the antibodies provided herein. In some embodiments, an antibody is provided that competes with at least three of the antibodies provided herein. In some embodiments, the antibody binds to an overlapping epitope as an antibody described in the examples herein. In some embodiments, the entire epitope is bound and/or obstructed by the competing antibody. In some embodiments, a part of the epitope is bound and/or obstructed by the competing antibody. In some embodiments, the competing antibody's paratope binds to at least a part of the epitope of an antibody provided herein. In some embodiments, the competing antibody's paratope binds the target, and a different section of the competing antibody's structure obstruct at least a part of the epitope of an antibody provided herein.

Exemplary Chimeric Antibodies

In some embodiments, an antibody provided herein is a chimeric antibody. Certain chimeric antibodies are described, for example, in U.S. Pat. No. 4,816,567; and Morrison et al., (1984) Proc. Natl. Acad. Sci. USA, 81:6851-6855 (1984)). In one example, a chimeric antibody comprises a non-human variable region (for example, a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies comprising the heavy and/or light chain variable regions of an antibody selected from, e.g., antibody 11606; antibody 11613; antibody 11645; antibody 12191; antibody 12195; antibody 12220; antibody 12228; antibody 12535; antibody 12536; antibody 12541; antibody 12543; antibody 12544; antibody 12545; antibody 12549; antibody 12550; antibody 12553; antibody 12554; antibody 12562; antibody 12563; antibody 12564; antibody 12565; antibody 12571; antibody 12572; antibody 12576; antibody 12583; antibody 12584; antibody 13396; antibody 13398; antibody 13399; antibody 13401; antibody 13402; antibody 13403; antibody 13404; antibody 13405; antibody 13406; antibody 13407; antibody 13408; antibody 13409; antibody 11624; and antibody 12190, as disclosed herein. Additional nonlimiting exemplary chimeric antibodies include chimeric antibodies comprising heavy chain CDR1, CDR2, and CDR3, and/or light chain CDR1, CDR2, and CDR3 of an antibody selected from antibody 11606; antibody 11613; antibody 11645; antibody 12191; antibody 12195; antibody 12220; antibody 12228; antibody 12535; antibody 12536; antibody 12541; antibody 12543; antibody 12544; antibody 12545; antibody 12549; antibody 12550; antibody 12553; antibody 12554; antibody 12562; antibody 12563; antibody 12564; antibody 12565; antibody 12571; antibody 12572; antibody 12576; antibody 12583; antibody 12584; antibody 13396; antibody 13398; antibody 13399; antibody 13401; antibody 13402; antibody 13403; antibody 13404; antibody 13405; antibody 13406; antibody 13407; antibody 13408; antibody 13409; antibody 11624; and antibody 12190, as disclosed herein. In some embodiments, the chimeric anti-PD-1 antibody comprises the variable regions described above and binds to PD-1. In some embodiments, the chimeric anti-PD-1 antibody comprises the variable regions described above, binds to PD-1 and inhibits binding of PD-1 to PD-L1 and/or PD-L2. In some embodiments, the anti-PD-1 antibody comprises the variable regions described above, binds to PD-1 and inhibits binding of PD-1 to PD-L1. In some embodiments, the anti-PD-1 antibody comprises the variable regions described above, binds to PD-1 and inhibits binding of PD-1 to PD-L1 and PD-L2. In some embodiments, the anti-PD-1 antibody comprises the variable regions described above, binds to PD-1 and enhances an immune response in a subject, and/or increases activation of T cells in a subject following administration of the antibody to the subject. In some embodiments, administration of the anti-PD-1 antibodies described herein stimulates the activity of an immune cell, reduces the downmodulation of an immune cell, or increases a T cell response in a subject.

In some embodiments, a chimeric anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316, wherein the antibody binds PD-1. In some embodiments, a chimeric anti-PD-1 antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320, wherein the antibody binds PD-1. In some embodiments, a chimeric anti-PD-1 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 4, 12, 20, 28, 36, 44, 52, 60, 68, 76, 84, 92, 100, 108, 116, 124, 132, 140, 148, 156, 164, 172, 180, 188, 196, 204, 212, 220, 228, 236, 244, 252, 260, 268, 276, 284, 292, 300, 308, or 316; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 8, 16, 24, 32, 40, 48, 56, 64, 72, 80, 88, 96, 104, 112, 120, 128, 136, 144, 152, 160, 168, 176, 184, 192, 200, 208, 216, 224, 232, 240, 248, 256, 264, 272, 280, 288, 296, 304, 312 or 320; wherein the antibody binds PD-1.

Exemplary chimeric anti-PD-1 antibodies also include chimeric antibodies that compete for binding to PD-1 with an antibody or fragment thereof described herein. Thus, in some embodiments, a chimeric anti-PD-1 antibody is provided that competes for binding to PD-1 with an antibody selected from antibody 11606; antibody 11613; antibody 11645; antibody 12191; antibody 12195; antibody 12220; antibody 12228; antibody 12535; antibody 12536; antibody 12541; antibody 12543; antibody 12544; antibody 12545; antibody 12549; antibody 12550; antibody 12553; antibody 12554; antibody 12562; antibody 12563; antibody 12564; antibody 12565; antibody 12571; antibody 12572; antibody 12576; antibody 12583; antibody 12584; antibody 13396; antibody 13398; antibody 13399; antibody 13401; antibody 13402; antibody 13403; antibody 13404; antibody 13405; antibody 13406; antibody 13407; antibody 13408; antibody 13409; antibody 11624; and antibody 12190, or a fragment thereof. In some embodiments, the chimeric anti-PD-1 antibody competes for binding to PD-1 with an antibody described herein and inhibits binding of PD-1 to PD-L1 and/or PD-L2. In some embodiments, the chimeric anti-PD-1 antibody competes for binding to PD-1 with an antibody described herein and inhibits binding of PD-1 to PD-L1. In some embodiments, the chimeric anti-PD-1 antibody competes for binding to PD-1 with an antibody described herein and inhibits binding of PD-1 to PD-L1 and PD-L2. In some embodiments, the chimeric anti-PD-1 antibody competes for binding to PD-1 with an antibody described herein and enhances an immune response in a subject, and/or increases activation of T cells in a subject following administration of the antibody to the subject.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-PD-1 antibody comprising a human IgG1 heavy chain constant region or a human IgG3 heavy chain constant region is selected. In some embodiments, when effector function is not desirable, a chimeric anti-PD-1 antibody comprising a human IgG4 or IgG2 heavy chain constant region is selected.

Exemplary Humanized Antibodies

In some embodiments, humanized antibodies that bind PD-1 are provided. Humanized antibodies are useful as therapeutic molecules because humanized antibodies reduce or eliminate the human immune response as compared to non-human antibodies, which can result in an immune response to an antibody therapeutic (such as the human anti-mouse antibody (HAMA) response), and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) *Front. Biosci.* 13: 1619-1633, and are further described, for example, in Riechmann et al., (1988) *Nature* 332:323-329; Queen et al., (1989) *Proc. Natl Acad. Sci. USA* 86: 10029-10033; U.S. Pat. Nos. 5,821,337, 7,527,791, 6,982,321, and 7,087,409; Kashmiri et al., (2005) *Methods* 36:25-34; Padlan, (1991)*Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260 (describing the "guided selection" approach to FR shuffling)

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of light or heavy chain variable regions (see, for example, Carter et al. (1992) *Proc. Natl. Acad. Sci. USA,* 89:4285; and Presta et al. (1993) *J. Immunol,* 151:2623); human mature (somatically mutated) framework regions or human germline framework regions (see, for example, Almagro and Fransson, (2008) *Front. Biosci.* 13:1619-1633); and framework regions derived from screening FR libraries (see, for example, Baca et al., (1997) *J. Biol. Chem.* 272: 10678-10684 and Rosok et al., (1996) *J. Biol. Chem.* 271 :22611-22618).

Exemplary humanized anti-PD-1 antibodies include antibodies that compete for binding to PD-1 with an antibody or fragment thereof described herein. Thus, in some embodiments, a humanized anti-PD-1 antibody is provided that competes for binding to PD-1 with an antibody or fragment thereof selected from antibody 11606; antibody 11613; antibody 11645; antibody 12191; antibody 12195; antibody 12220; antibody 12228; antibody 12535; antibody 12536; antibody 12541; antibody 12543; antibody 12544; antibody 12545; antibody 12549; antibody 12550; antibody 12553; antibody 12554; antibody 12562; antibody 12563; antibody 12564; antibody 12565; antibody 12571; antibody 12572; antibody 12576; antibody 12583; antibody 12584; antibody 13396; antibody 13398; antibody 13399; antibody 13401; antibody 13402; antibody 13403; antibody 13404; antibody 13405; antibody 13406; antibody 13407; antibody 13408; antibody 13409; antibody 11624; and antibody 12190. In some embodiments, the humanized anti-PD-1 antibody competes for binding to PD-1 with an antibody described herein and inhibits binding of PD-1 to PD-L1 and/or PD-L2. In some embodiments, the humanized anti-PD-1 antibody competes for binding to PD-1 with an antibody described herein and inhibits binding of PD-1 to PD-L1. In some embodiments, the humanized anti-PD-1 antibody competes for binding to PD-1 with an antibody described herein and inhibits binding of PD-1 to PD-L1 and PD-L2. In some embodiments, the humanized anti-PD-1 antibody competes for binding to PD-1 with an antibody described herein and enhances an immune response in a subject, and/or increases activation of T cells in a subject following administration of the antibody to the subject.

Exemplary Human Antibodies

In some embodiments, an anti-PD-1 antibody provided herein is a human antibody. Human antibodies can be produced using various techniques known in the art. Human antibodies are described generally in van Dijk and van de Winkel, (2001) Curr. Opin. Pharmacol. 5:368-374 and Lonberg, (2008) Curr. Opin. Immunol. 20:450-459. In some embodiments, the human antibody is not a naturally occurring antibody. In some embodiments, the human antibody is a monoclonal antibody; thus, in some embodiments, each of the human antibodies in a set can bind to the same epitope on the antigen.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, (2005) Nat. Biotech. 23: 1117-1125. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, for example, Kozbor (1984) J. Immunol, 133: 3001; Brodeur et al., Monoclonal Antibody Production Techniques and Applications, pp. 51-63 (Marcel Dekker, Inc., New York, 1987); and Boerner et al, (1991) J. Immunol., 147:86). Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, (2006) Xiandai Mianyixue, 26(4):265-268 (describing human-human hybridomas). Human hybridoma technology (Trioma technology) is also described in Vollmers and Brandlein, (2005) Histology and Histopathology, 20(3):927-937 (2005) and Vollmers and Brandlein, (2005) Methods and Findings in Experimental and Clinical Pharmacology, 27(3): 185-191.

Human antibodies can also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in Methods in Molecular Biology 178: 1-37 (O'Brien et al., ed., Human Press, Totowa, N.J., 2001) and further described, for example, in the McCafferty et al, (1990) Nature 348:552-554; Clackson et al, (1991) Nature 352: 624-628; Marks et al, (1992)J Mol. Biol 222: 581-597; Marks and Bradbury, in Methods in Molecular Biology 248: 161-175 (Lo, ed., Human Press, Totowa, N.J., 2003); Sidhu et al, (2004)J Mol. Biol. 338(2): 299-310; Lee et al., (2004) J Mol. Biol. 340(5): 1073-1093; Fellouse, (2004) Proc. Natl. Acad. Sci. USA 101(34): 12467-12472; and Lee et al, (2004) 1 Immunol. Methods 284(1-2): 119-132 and PCT publication WO 99/10494.

In certain phage display methods, repertoires of VH and VL genes are separately cloned by polymerase chain reaction (PCR) and recombined randomly in phage libraries, which can then be screened for antigen-binding phage as described in Winter et al., (1994) Ann. Rev. Immunol., 12:433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (for example, from human) to provide a single source of antibodies to a wide range of non-self and also self-antigens without any immunization as described by Griffiths et al., (1993) EMBO J 12:725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992), J. Mol. Biol, 227:381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

In some embodiments, a human anti-PD-1 antibody binds to a polypeptide having the sequence of SEQ ID NO: 1, 2, 3, 382, 383, or 384. In some embodiments, the human anti-PD-1 antibody binds to PD-1 and inhibits binding of PD-1 to PD-L1 and/or PD-L2. In some embodiments, the human anti-PD-1 antibody binds to PD-1 and inhibits binding of PD-1 to PD-L1. In some embodiments, the human anti-PD-1 antibody binds to PD-1 and inhibits binding of PD-1 to PD-L1 and PD-L2. In some embodiments, the human anti-PD-1 antibody binds to PD-1 and enhances an immune response in a subject, and/or increases activation of T cells in a subject following administration of the antibody to the subject.

Exemplary human anti-PD-1 antibodies also include antibodies that compete for binding to PD-1 with a human antibody or fragment thereof described herein. Thus, in some embodiments, a human anti-PD-1 antibody is provided that competes for binding to PD-1 with an antibody or fragment thereof selected from antibody 11606; antibody 11613; antibody 11645; antibody 12191; antibody 12195; antibody 12220; antibody 12228; antibody 12535; antibody 12536; antibody 12541; antibody 12543; antibody 12544; antibody 12545; antibody 12549; antibody 12550; antibody 12553; antibody 12554; antibody 12562; antibody 12563; antibody 12564; antibody 12565; antibody 12571; antibody 12572; antibody 12576; antibody 12583; antibody 12584; antibody 13396; antibody 13398; antibody 13399; antibody 13401; antibody 13402; antibody 13403; antibody 13404; antibody 13405; antibody 13406; antibody 13407; antibody 13408; antibody 13409; antibody 11624; and antibody 12190. In some embodiments, the human anti-PD-1 antibody competes for binding to PD-1 with an antibody described herein and inhibits binding of PD-1 to PD-L1 and/or PD-L2. In some embodiments, the human anti-PD-1 antibody competes for binding to PD-1 with an antibody described herein and inhibits binding of PD-1 to PD-L1. In some embodiments, the human anti-PD-1 antibody competes for binding to PD-1 with an antibody described herein and inhibits binding of PD-1 to PD-L1 and PD-L2. In some embodiments, the human anti-PD-1 antibody competes for binding to PD-1 with an antibody described herein and enhances an immune response in a subject, and/or increases activation of T cells in a subject following administration of the antibody to the subject.

In some embodiments, a chimeric human anti-PD-1 antibody is provided, where the antibody comprises the variable region from a human antibody that binds PD-1 and the constant region from a different human antibody. In some embodiments, a chimeric human anti-PD-1 antibody, where the antibody comprises the CDRs from a human antibody that binds PD-1 and a framework from a different human antibody is provided. In some embodiments, the antibody is not a naturally occurring human antibody.

In some embodiments, a human anti-PD-1 antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human anti-PD-1 antibody comprising a human IgG1 heavy chain constant region or a human IgG3 heavy chain constant region is selected. In some embodiments, when effector function is not desirable, a human anti-PD-1 antibody comprising a human IgG4 or IgG2 heavy chain constant region is selected.

As noted herein, the term "human antibody" denotes the genus of possible sequences for the antibody construct, rather than a source of the antibody.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, an antibody described herein comprises a human IgG constant region. In some embodiments, when effector function is desirable, an anti-PD-1 antibody comprising a human IgG1 heavy chain constant region or a human IgG3 heavy chain constant region is selected. In some embodiments, when effector function is not desirable, an anti-PD-1 antibody comprising a human IgG4 or IgG2 heavy chain constant region is selected. In some embodiments, the human light chain constant region is of an isotype selected from κ and λ. In some embodiments, an antibody described herein comprises a human IgG4 heavy chain constant region. In some embodiments, an antibody described herein comprises a human IgG4 constant region and a human κ light chain.

Throughout the present specification and claims unless explicitly stated or known to one skilled in the art, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

As noted above, whether or not effector function is desirable may depend on the particular method of treatment intended for an antibody. Thus, in some embodiments, when effector function is desirable, an anti-PD-1 antibody comprising a human IgG1 heavy chain constant region or a human IgG3 heavy chain constant region is selected. In some embodiments, when effector function is not desirable, an anti-PD-1 antibody comprising a human IgG4 or IgG2 heavy chain constant region is selected.

In some embodiments, an antibody comprises a variant Fc region has at least one amino acid substitution compared to the Fc region of a wild-type IgG or a wild-type antibody. In some embodiments, the variant Fc region has two or more amino acid substitutions in the Fc region of the wild-type antibody. In some embodiments, the variant Fc region has three or more amino acid substitutions in the Fc region of the wild-type antibody. In some embodiments, the variant Fc region has at least one, two or three or more Fc region amino acid substitutions described herein. In some embodiments, the variant Fc region herein will possess at least about 80% homology with a native sequence Fc region and/or with an Fc region of a parent polypeptide. In some embodiments, the variant Fc region herein will possess at least about 90% homology with a native sequence Fc region and/or with an Fc region of a parent polypeptide. In some embodiments, the variant Fc region herein will possess at least about 95% homology with a native sequence Fc region and/or with an Fc region of a parent polypeptide. In some embodiments, a heavy chain constant region lacks the C-terminal lysine (K) residue. In some such embodiments, the heavy chain or heavy chain constant region may be referred to as "desK." In some embodiments, the heavy chain constant region lacking the C-terminal lysine is an IgG, such as an IgG1, IgG2, IgG3, or IgG4.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. TIBTECH 15:26-32 (1997). The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (for example, complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, that is, between positions 294 and 300, due to minor sequence variations in antibodies. Such fucosylation variants may have improved ADCC function. See, for example, US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, for example, Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, for example, in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087 (Patel et al.); WO 1998/58964 (Raju, S.); and WO 1999/22764 (Raju, S.).

Antibody variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

The in vivo or serum half-life of human FcRn high affinity binding polypeptides can be assayed, for example, in transgenic mice, in humans, or in non-human primates to which the polypeptides with a variant Fc region are administered. See also, for example, Petkova et al. *International Immunology* 18(12):1759-1769 (2006).

In some embodiments, the antibody variant mediates ADCC in the presence of human effector cells more effectively than a parent antibody. In some embodiments, the antibody variant is substantially more effective at mediating ADCC in vitro, when the amounts of polypeptide variant and parent antibody used in the assay are essentially the same. In some embodiments, the antibody variant is substantially more effective at mediating ADCC in vivo, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

Exemplary Antibody Conjugates

In some embodiments, an anti-PD-1 antibody is conjugated to another molecule. In some embodiments, the additional molecule can be a detectable marker, such as a label. In some embodiments, the additional molecule can be a therapeutic molecule, such as a cytotoxic agent. In some embodiments, a label and/or a cytotoxic agent can be conjugated to the antibody. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the specific application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application. In some embodiments, the cytotoxic agent is at least one of an anti-metabolite, an alkylating agent, an antibiotic, a growth factor, a cytokine, an anti-angiogenic agent, an anti-mitotic agent, an anthracycline, toxin, or an apoptotic agent In some embodiments, a label and/or a cytotoxic agent is conjugated to an antibody using chemical methods in vitro. Nonlimiting exemplary chemical methods of conjugation are known in the art, and include services, methods and/or reagents commercially available from, for example, Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

In some embodiments, conjugation can be covalent. In some embodiments, conjugation can be non-covalent. In some embodiments, conjugation can be via a specific binding interaction, for example, through the binding of a secondary antibody.

Exemplary Leader Sequences

In order for some secreted proteins to express and secrete in large quantities, a leader sequence from a heterologous protein may be desirable. In some embodiments, employing heterologous leader sequences can be advantageous in that a resulting mature polypeptide can remain unaltered as the leader sequence is removed in the ER during the secretion process. The addition of a heterologous leader sequence can be useful to express and secrete some proteins.

Certain exemplary leader sequence sequences are described, for example, in the online Leader sequence Database maintained by the Department of Biochemistry, National University of Singapore. See Choo et al., *BMC Bioinformatics,* 6: 249 (2005); and PCT Publication No. WO 2006/081430.

III. Antibody Expression and Production

Nucleic Acid Molecules Encoding Anti-PD-1 Antibodies

Nucleic acid molecules comprising polynucleotides that encode one or more chains of an anti-PD-1 antibody are provided herein. In some embodiments, a nucleic acid molecule comprises a polynucleotide that encodes a heavy chain or a light chain of an anti-PD-1 antibody. In some embodiments, a nucleic acid molecule comprises both a polynucleotide that encodes a heavy chain and a polynucleotide that encodes a light chain, of an anti-PD-1 antibody. In some embodiments, a first nucleic acid molecule comprises a first polynucleotide that encodes a heavy chain and a second nucleic acid molecule comprises a second polynucleotide that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-PD-1 antibody comprises a nucleotide sequence that encodes at least one of the CDRs provided herein. In some embodiments, a polynucleotide encoding a heavy chain or light chain of an anti-PD-1 antibody comprises a nucleotide sequence that encodes at least 3 of the CDRs provided herein. In some embodiments, a polynucleotide encoding a heavy chain or light chain of an anti-PD-1 antibody comprises a nucleotide sequence that encodes at least 6 of the CDRs provided herein. In some embodiments, a polynucleotide encoding a heavy chain or light chain of an anti-PD-1 antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the nucleic acid is one that encodes for any of the amino acid sequences for the antibodies in the Sequence Table herein. In some embodiments, the nucleic acid is one that is at least 80% identical to a nucleic acid encoding any of the amino acid sequences for the antibodies in the Sequence Table herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein.

In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is an expression vector that is suitable for expression in a selected host cell.

Vectors comprising polynucleotides that encode anti-PD-1 heavy chains and/or anti-PD-1 light chains are provided. Vectors comprising polynucleotides that encode anti-PD-1 heavy chains and/or anti-PD-1 light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, for example, in Running Deer et al., *Biotechnol. Prog.* 20:880-889 (2004).

Host Cells

In some embodiments, anti-PD-1 antibody heavy chains and/or anti-PD-1 antibody light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, anti-PD-1 antibody heavy chains and/or anti-PD-1 antibody light chains may be expressed in yeast. See, for example, U.S. Publication No. US 2006/0270045 A1. In some embodiments, a particular eukaryotic host cell is selected based on its ability to make desired post-translational modifications to the anti-PD-1 antibody heavy chains and/or anti-PD-1 antibody light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the polynucleotides or vectors described herein are also provided. In some embodiments, a host cell comprising an anti-PD-1 antibody is provided. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Purification of Antibodies

Anti-PD-1 antibodies can be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-PD-1 antibody. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

Cell-Free Production of Antibodies

In some embodiments, an anti-PD-1 antibody is produced in a cell-free system. Nonlimiting exemplary cell-free systems are described, for example, in Sitaraman et al., *Meth ods Mol. Biol.* 498: 229-44 (2009); Spirin, *Trends Biotechnol.* 22: 538-45 (2004); Endo et al., *Biotechnol. Adv.* 21: 695-713 (2003).

Compositions

In some embodiments, antibodies prepared by the methods described above are provided. In some embodiments, the antibody is prepared in a host cell. In some embodiments, the antibody is prepared in a cell-free system. In some embodiments, the antibody is purified. In some embodiments, the antibody prepared in a host cell or a cell-free system is a chimeric antibody. In some embodiments, the antibody prepared in a host cell or a cell-free system is a humanized antibody. In some embodiments, the antibody prepared in a host cell or a cell-free system is a human antibody. In some embodiments, a cell culture media comprising an anti-PD-1 antibody is provided. In some embodiments, a host cell culture fluid comprising an anti-PD-1 antibody is provided.

In some embodiments, compositions comprising antibodies prepared by the methods described above are provided. In some embodiments, the composition comprises an antibody prepared in a host cell. In some embodiments, the composition comprises an antibody prepared in a cell-free system. In some embodiments, the composition comprises a purified antibody. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

In some embodiments, a composition comprising anti-PD-1 antibody at a concentration of more than about any one of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL is provided. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

IV. Therapeutic Compositions and Methods

Methods of Treating Diseases Using Anti-PD-1 Antibodies

Antibodies and compositions comprising antibodies are provided for use in methods of treatment for humans or animals. Methods of treating disease comprising administering anti-PD-1 antibodies are also provided. Nonlimiting exemplary diseases that can be treated with anti-PD-1 antibodies include, but are not limited to, cancer.

In some embodiments, a method of treating cancer is provided, wherein cells within a sample of the tumor express PD-L1. In some such embodiments, the tumor may be considered to be PD-L1-positive, or to express PD-L1. Expression of PD-L1 may be determined by IHC, e.g., as discussed herein. In some embodiments, a tumor is considered to express PD-L1 when a sample from the tumor shows 1+, 2+, or 3+ staining of PD-L1 by IHC. In some embodiments, the sample from the tumor shows 2+ or 3+ staining of PD-L1 by IHC. In some embodiments, a tumor sample from a subject is analyzed for PD-L1 expression and the subject is selected for treatment with an antibody described herein if the tumor sample shows PD-L1 expression. In some embodiments, the subject is selected if the tumor sample shows elevated expression of PD-L1.

In some embodiments, a subject is selected for treatment with an anti-PD-1 antibody provided herein if the subject's tumor is PD-L1$^{HIGH}$. In some embodiments, a subject is selected for treatment with an anti-PD-1 antibody provided herein if the subject's tumor is PD-L1$^{LOW}$. In some embodiments, a subject is selected for treatment with an anti-PD-1 antibody provided herein if the subject's tumor is PD-1$^{HIGH}$/PD-L1$^{LOW}$. In some embodiments, a subject is selected for treatment with an anti-PD-1 antibody provided herein if the subject's tumor is PD-1$^{HIGH}$/PD-L1$^{HIGH}$.

The anti-PD-1 antibody can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an anti-PD-1 antibody is administered to a subject one or more times. In some embodiments, an effective dose of an anti-PD-1 antibody is administered to the subject once a month, less than once a month, such as, for example, every two months or every three months. In some embodiments, an effective dose of an anti-PD-1 antibody is administered less than once a month, such as, for example, once every three weeks, once every two weeks, or once every week. An effective dose of an anti-PD-1 antibody is administered to the subject at least once. In some embodiments, the effective dose of an anti-PD-1 antibody may be administered multiple times, including for periods of at least a month, at least six months, or at least a year.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-PD-1 antibodies may be administered in an amount in the range of about 10 µg/kg body weight to about 100 mg/kg body weight per dose. In some embodiments, anti-PD-1 antibodies may be administered in an amount in the range of about 50 µg/kg body weight to about 5 mg/kg body weight per dose. In some embodiments, anti-PD-1 antibodies may be administered in an amount in the range of about 100 µg/kg body weight to about 10 mg/kg body weight per dose. In some embodiments, anti-PD-1 antibodies may be administered in an amount in the range of about 100 µg/kg body weight to about 20 mg/kg body weight per dose. In some embodiments, anti-PD-1 antibodies may be administered in an amount in the range of about 0.5 mg/kg body weight to about 20 mg/kg body weight per dose.

Pharmaceutical compositions are administered in an amount effective for enhancing an immune response and/or increasing T cell activation in a subject.

The therapeutically effective amount is typically dependent on the weight of the subject being treated, his or her physical or health condition, the extensiveness of the condition to be treated, or the age of the subject being treated. In general, anti-PD-1 antibodies may be administered in an amount in the range of about 10 µg/kg body weight to about 100 mg/kg body weight per dose. In some embodiments, anti-PD-1 antibodies may be administered in an amount in the range of about 50 µg/kg body weight to about 5 mg/kg body weight per dose. In some embodiments, anti-PD-1 antibodies may be administered in an amount in the range of about 100 µg/kg body weight to about 10 mg/kg body weight per dose. In some embodiments, anti-PD-1 antibodies may be administered in an amount in the range of about 100 µg/kg body weight to about 20 mg/kg body weight per dose. In some embodiments, anti-PD-1 antibodies may be administered in an amount in the range of about 0.5 mg/kg body weight to about 20 mg/kg body weight per dose.

Pharmaceutical Compositions

In some embodiments, compositions comprising anti-PD-1 antibodies are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, $7^{th}$ ed., Lippencott Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprising an anti-PD-1 antibody is provided. In some embodiments, the pharmaceutical composition comprises a chimeric antibody. In some embodiments, the pharmaceutical composition comprises a humanized antibody. In some embodiments, the pharmaceutical composition comprises an antibody prepared in a host cell or cell-free system as described herein. In some embodiments, the pharmaceutical composition comprises pharmaceutically acceptable carrier.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-PD-1 antibodies may be administered in an amount in the range of about 0.05 mg/kg body weight to about 100 mg/kg body weight per dose. In some embodiments, anti-PD-1 antibodies may be administered in an amount in the range of about 10 µg/kg body weight to about 100 mg/kg body weight per dose. In some embodiments, anti-PD-1 antibodies may be administered in an amount in the range of about 50 µg/kg body weight to about 5 mg/kg body weight per dose. In some embodiments, anti-PD-1 antibodies may be administered in an amount in the range of about 100 µg/kg body weight to about 10 mg/kg body weight per dose. In some embodiments, anti-PD-1 antibodies may be administered in an amount in the range of about 100 µg/kg body weight to about 20 mg/kg body weight per dose. In some embodiments, anti-PD-1 antibodies may be administered in an amount in the range of about 0.5 mg/kg body weight to about 20 mg/kg body weight per dose. In some embodiments, anti-PD-1 antibodies may be administered in an amount in the range of about 0.5 mg/kg body weight to about 10 mg/kg body weight per dose. In some embodiments, anti-PD-1 antibodies may be administered in an amount in the range of about 0.05 mg/kg body weight to about 20 mg/kg body weight per dose. In some embodiments, anti-PD-1 antibodies may be administered in an amount in the range of about 0.05 mg/kg body weight to about 10 mg/kg body weight per dose. In some embodiments, anti-PD-1 antibodies may be administered in an amount in the range of about 5 mg/kg body weight or lower, for example less than 4, less than 3, less than 2, or less than 1 mg/kg of the antibody.

In some embodiments, anti-PD-1 antibodies can be present in an amount in the range of about 50 µg/kg body weight to about 5 mg/kg body weight per dose. For example, in some embodiments, a dose for a 20 kg person can be within a range of about 1 mg to about 100 mg. In some embodiments, the dose can be within a range of 2 mg to 200 mg of the anti-PD-1 antibody. In some embodiments, the dose can be within a range of 10 mg to 400 mg of the anti-PD-1 antibody.

Routes of Administration

In some embodiments, anti-PD-1 antibodies can be administered in vivo by various routes, including, but not limited to, intravenous, intra-arterial, parenteral, intratumoral, intraperitoneal or subcutaneous. The appropriate formulation and route of administration may be selected according to the intended application.

Combination Therapy

Anti-PD-1 antibodies can be administered alone or with other modes of treatment. They can be provided before, substantially contemporaneous with, and/or after other modes of treatment, for example, surgery, chemotherapy, radiation therapy, or the administration of a biologic, such as another therapeutic antibody. In some embodiments, an anti-PD-1 antibody is administered in conjunction with another anti-cancer agent.

In some embodiments, the anti-PD-1 antibody is given concurrently with a second therapeutic agent. For example, the two or more therapeutic agents are administered with a time separation of no more than about 60 minutes, such as no more than about any of 30, 15, 10, 5, or 1 minutes. In some embodiments, the anti-PD-1 antibody is administered sequentially with a second therapeutic agent. For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month, or longer.

In some embodiments, the anti-PD-1 antibody is administered with a second therapeutic method for treatment. Thus, the administration of an antibody provided herein can be in combination with another system of treatment.

In some embodiments, an anti-PD-1 antibody provided herein is administered with an anti-ICOS therapy. In some embodiments, an anti-PD-1 antibody provided herein is administered with an antibody that binds Inducible T-Cell Costimulator (ICOS). In some embodiments, the anti-PD-1 antibody provided herein is administered with an isolated antibody that binds ICOS, wherein the anti-ICOS antibody is an agonist of CD4+ T cells (such as CD4+T effector (Teff) cells). In some embodiments, the antibody that binds ICOS is an agonist of CD4+ T cells (such as CD4+ Teff cells) and depletes T regulatory (Treg) cells. In some embodiments, the antibody that binds ICOS depletes Treg cells, but does not deplete Teff cells. In some embodiments, the antibody that binds ICOS induces pAKT signaling on CD4+ T cells. In some embodiments, the isolated antibody that binds ICOS induces pAKT signaling on CD4+ T cells and depletes Treg cells. In some embodiments, the isolated antibody that binds ICOS comprises:

i) (a) HCDR1 comprising the amino acid sequence of SEQ ID NO: 326; (b) HCDR2 comprising the amino acid sequence of SEQ ID NO: 327; (c) HCDR3 comprising the amino acid sequence of SEQ ID NO: 328; (d) LCDR1 comprising the amino acid sequence of SEQ ID NO: 329; (e) LCDR2 comprising the amino acid sequence of SEQ ID NO: 330; and (f) LCDR3 comprising the amino acid sequence of SEQ ID NO: 331; or ii) (a) HCDR1 comprising the amino acid sequence of SEQ ID NO: 334; (b) HCDR2 comprising the amino acid sequence of SEQ ID NO: 335; (c) HCDR3 comprising the amino acid sequence of SEQ ID NO: 336; (d) LCDR1 comprising the amino acid sequence of SEQ ID NO: 337; (e) LCDR2 comprising the amino acid sequence of SEQ ID NO: 338; and (f) LCDR3 comprising the amino acid sequence of SEQ ID NO: 339; or iii) (a) HCDR1 comprising the amino acid sequence of SEQ ID NO: 342; (b) HCDR2 comprising the amino acid sequence of SEQ ID NO: 343; (c) HCDR3 comprising the amino acid sequence of SEQ ID NO: 344; (d) LCDR1 comprising the amino acid sequence of SEQ ID NO: 345; (e) LCDR2 comprising the amino acid sequence of SEQ ID NO: 346; and (f) LCDR3 comprising the amino acid sequence of SEQ ID NO: 347; or iv) (a) HCDR1 comprising the amino acid sequence of SEQ ID NO: 350; (b) HCDR2 comprising the amino acid sequence of SEQ ID NO: 351; (c) HCDR3 comprising the amino acid sequence of SEQ ID NO: 352; (d) LCDR1 comprising the amino acid sequence of SEQ ID NO: 353 (e) LCDR2 comprising the amino acid sequence of SEQ ID NO: 354; and (f) LCDR3 comprising the amino acid sequence of SEQ ID NO: 355; or v) (a) HCDR1 comprising the amino acid sequence of SEQ ID NO: 358; (b) HCDR2 comprising the amino acid sequence of SEQ ID NO: 359; (c) HCDR3 comprising the amino acid sequence of SEQ ID NO: 360; (d) LCDR1 comprising the amino acid sequence of SEQ ID NO: 361; (e) LCDR2 comprising the amino acid sequence of SEQ ID NO: 362; and (f) LCDR3 comprising the amino acid sequence of SEQ ID NO: 363; or vi) (a) HCDR1 comprising the amino acid sequence of SEQ ID NO: 366; (b) HCDR2 comprising the amino acid sequence of SEQ ID NO: 367; (c) HCDR3 comprising the amino acid sequence of SEQ ID NO: 368; (d) LCDR1 comprising the amino acid sequence of SEQ ID NO: 369; (e) LCDR2 comprising the amino acid sequence of SEQ ID NO: 370; and (f) LCDR3 comprising the amino acid sequence of SEQ ID NO: 371; or vii)(a) HCDR1 comprising the amino acid sequence of SEQ ID NO: 374; (b) HCDR2 comprising the amino acid sequence of SEQ ID NO: 375; (c) HCDR3 comprising the amino acid sequence of SEQ ID NO: 376; (d) LCDR1 comprising the amino acid sequence of SEQ ID NO: 377; (e) LCDR2 comprising the amino acid sequence of SEQ ID NO: 378; and (f) LCDR3 comprising the amino acid sequence of SEQ ID NO: 379.

In some embodiments, an antibody that binds to ICOS is provided, wherein the antibody comprises a heavy chain variable region ($V_H$) and a light chain variable region ($V_L$), wherein:

i) the $V_H$ is at least 90%, 91%, 92%, 93%, 94%, 95%, 96%, 97%, 98%, 99%, or 100% identical to the amino acid sequence of SEQ ID NO: 324 and the $V_L$ is at least 90%, 91%, 92%, 93%, 94%, 95%, 96%, 97%, 98%, 99%, or 100% identical to the amino acid sequence of SEQ ID NO: 325; or ii) the $V_H$ is at least 90%, 91%, 92%, 93%, 94%, 95%, 96%, 97%, 98%, 99%, or 100% identical to the amino acid sequence of SEQ ID NO: 332 and the $V_L$ is at least 90%, 91%, 92%, 93%, 94%, 95%, 96%, 97%, 98%, 99%, or 100% identical to the amino acid sequence of SEQ ID NO: 333; or iii) the $V_H$ is at least 90%, 91%, 92%, 93%, 94%, 95%, 96%, 97%, 98%, 99%, or 100% identical to the amino acid sequence of SEQ ID NO: 340 and the $V_L$ is at least 90%, 91%, 92%, 93%, 94%, 95%, 96%, 97%, 98%, 99%, or 100% identical to the amino acid sequence of SEQ ID NO: 341; or iv) the $V_H$ is at least 90%, 91%, 92%, 93%, 94%, 95%, 96%, 97%, 98%, 99%, or 100% identical to the amino acid sequence of SEQ ID NO: 348 and the $V_L$ is at least 90%, 91%, 92%, 93%, 94%, 95%, 96%, 97%, 98%, 99%, or 100% identical to the amino acid sequence of SEQ ID NO: 349; or v) the $V_H$ is at least 90%, 91%, 92%, 93%, 94%, 95%, 96%, 97%, 98%, 99%, or 100% identical to the amino acid sequence of SEQ ID NO: 356 and the $V_L$ is at least 90%, 91%, 92%, 93%, 94%, 95%, 96%, 97%, 98%, 99%, or 100% identical to the amino acid sequence of SEQ ID NO: 357; or vi) the $V_H$ is at least 90%, 91%, 92%, 93%, 94%, 95%, 96%, 97%, 98%, 99%, or 100% identical to the amino acid sequence of SEQ ID NO: 364 and the $V_L$ is at least 90%, 91%, 92%, 93%, 94%, 95%, 96%, 97%, 98%, 99%, or 100% identical to the amino acid sequence of SEQ ID NO: 365; or vii) the $V_H$ is at least 90%, 91%, 92%, 93%, 94%, 95%, 96%, 97%, 98%, 99%, or 100% identical to the amino acid sequence of SEQ ID NO: 372 and the $V_L$ is at least 90%, 91%, 92%, 93%, 94%, 95%, 96%, 97%, 98%, 99%, or 100% identical to the amino acid sequence of SEQ ID NO: 373.

In general, anti-ICOS antibodies may be administered in an amount in the range of about 10 µg/kg body weight to about 100 mg/kg body weight per dose. In some embodiments, anti-ICOS antibodies may be administered in an amount in the range of about 50 µg/kg body weight to about 5 mg/kg body weight per dose. In some embodiments, anti-ICOS antibodies may be administered in an amount in the range of about 100 µg/kg body weight to about 10 mg/kg body weight per dose. In some embodiments, anti-ICOS antibodies may be administered in an amount in the range of about 100 µg/kg body weight to about 20 mg/kg body weight per dose. In some embodiments, anti-ICOS antibodies may be administered in an amount in the range of about 0.5 mg/kg body weight to about 20 mg/kg body weight per dose.

In some embodiments, the anti-PD-1 antibody provided herein is administered with an agonist anti-OX40 antibody (such as Medi6469, MedImmune; MOXR0916/RG7888, Roche). In some embodiments, the anti-PD-1 antibody provided herein is administered with an anti-CTLA4 antibody (such as ipilimumab, YERVOY®, BMS).

In some embodiments, an additional therapeutic agent is a chemotherapeutic agent. Exemplary chemotherapeutic agents that may be combined with the anti-PD-1 antibodies provided herein include, but are not limited to, capectiabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, and vincristine. In some embodiments, an anti-PD-1 antibody provided herein is administered with at least one kinase inhibitor. Nonlimiting exemplary kinase inhibitors include erlotinib, afatinib, gefitinib, crizotinib, dabrafenib, trametinib, vemurafenib, and cobimetanib.

In some embodiments, the additional therapeutic agent is an IDO inhibitor. Nonlimiting exemplary IDO inhibitors are described, e.g., in US 2016/0060237; and US 2015/0352206. Nonlimiting exemplary IDO inhibitors include Indoximod (New Link Genetics), INCB024360 (Incyte Corp), 1-methyl-D-tryptophan (New Link Genetics), and GDC-0919 (Genentech).

In some embodiments, an anti-PD-1 antibody provided herein is administered in combination with an immune-modifying drug (IMiD). Nonlimiting exemplary IMiDs include thalidomide, lenalidomide, and pomalidomide.

In some embodiments, an additional therapeutic agent is a cancer vaccine. Cancer vaccines have been investigated as a potential approach for antigen transfer and activation of dendritic cells. In particular, vaccination in combination with immunologic checkpoints or agonists for co-stimulatory pathways have shown evidence of overcoming tolerance and generating increased anti-tumor response. A range of cancer vaccines have been tested that employ different approaches to promoting an immune response against the tumor (see, e.g., Emens L A, Expert Opin Emerg Drugs 13(2): 295-308 (2008)). Approaches have been designed to enhance the response of B cells, T cells, or professional antigen-presenting cells against tumors. Exemplary types of cancer vaccines include, but are not limited to, peptide-based vaccines that employ targeting distinct tumor antigens, which may be delivered as peptides/proteins or as genetically-engineered DNA vectors, viruses, bacteria, or the like; and cell biology approaches, for example, for cancer vaccine development against less well-defined targets, including, but not limited to, vaccines developed from patient-derived dendritic cells, autologous tumor cells or tumor cell lysates, allogeneic tumor cells, and the like.

Thus, in certain embodiments, the anti-PD-1 antibodies provided herein may be used in combination with a cancer vaccine. Exemplary cancer vaccines include, but are not limited to, dendritic cell vaccines, oncolytic viruses, tumor cell vaccines, etc. In some embodiments, such vaccines augment the anti-tumor response. Examples of cancer vaccines that can be used in combination with anti-PD-1 antibodies provided herein include, but are not limited to, MAGE3 vaccine (e.g., for melanoma and bladder cancer), MUC1 vaccine (e.g., for breast cancer), EGFRv3 (such as Rindopepimut, e.g., for brain cancer, including glioblastoma multiforme), or ALVAC-CEA (e.g., for CEA+ cancers).

Nonlimiting exemplary cancer vaccines also include Sipuleucel-T, which is derived from autologous peripheral-blood mononuclear cells (PBMCs) that include antigen-presenting cells (see, e.g., Kantoff P W et al., N Engl J Med 363:411-22 (2010)). In Sipuleucel-T generation, the patient's PBMCs are activated ex vivo with PA2024, a recombinant fusion protein of prostatic acid phosphatase (a prostate antigen) and granulocyte-macrophage colony-stimulating factor (an immune-cell activator). Another approach to a candidate cancer vaccine is to generate an immune response against specific peptides mutated in tumor tissue, such as melanoma (see, e.g., Carreno B M et al., Science 348:6236 (2015)). Such mutated peptides may, in some embodiments, be referred to as neoantigens. As a nonlimiting example of the use of neoantigens in tumor vaccines, neoantigens in the tumor predicted to bind the major histocompatibility complex protein HLA-A*02:01 are identified for individual patients with a cancer, such as melanoma. Dendritic cells from the patient are matured ex vivo, then incubated with neoantigens. The activated dendritic cells are then administered to the patient. In some embodiments, following administration of the cancer vaccine, robust T-cell immunity against the neoantigen is detectable.

In some such embodiments, the cancer vaccine is developed using a neoantigen. In some embodiments, the cancer vaccine is a DNA vaccine. In some embodiments, the cancer vaccine is an engineered virus comprising a cancer antigen, such as PROSTVAC (rilimogene galvacirepvec/rilimogene glafolivec). In some embodiments, the cancer vaccine comprises engineered tumor cells, such as GVAX, which is a granulocyte-macrophage colony-stimulating factor (GM-CSF) gene-transfected tumor cell vaccine (see, e.g., Nemunaitis, 2005, Expert Rev Vaccines, 4: 259-74).

In some embodiments, an anti-PD-1 antibody described herein is administered before, concurrently, and/or after a cancer vaccine. In some embodiments, cancer vaccines developed using neoantigens are used in combination with the anti-PD-1 antibodies described herein. In some such embodiments, the combination is used to treat a cancer with a high mutational burden, such as melanoma, lung, bladder, or colorectal cancer.

In some embodiments, an anti-PD-1 antibody provided herein is administered in combination with a chimeric antigen receptor T cell therapy (CAR-T therapy).

Diagnostic Uses

Provided herein are methods of using the anti-PD-1 antibodies, polypeptides and polynucleotides for detection, diagnosis and monitoring of a disease, disorder or condition associated with the anti-PD-1 antibody epitope expression (either increased or decreased relative to a normal sample, and/or inappropriate expression, such as presence of expression in tissues(s) and/or cell(s) that normally lack the epitope expression). Provided herein are methods of determining whether a patient will respond to anti-PD-1 antibody therapy.

In some embodiments, the method comprises detecting whether the patient has cells that express PD-1 using an anti-PD-1 antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject.

In some embodiments, the cells or cell/tissue lysate are contacted with an anti-PD-1 antibody and the binding between the antibody and the cell is determined. When the test cells show binding activity as compared to a reference cell of the same tissue type, it may indicate that the subject would benefit from treatment with an anti-PD-1 antibody. In some embodiments, the test cells are from human tissues. In some embodiments, the test cells are from human blood.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{125}I$, $^{131}I$, $^{35}S$, $^{3}H$, or $^{32}P$), enzymes (for example, alkaline phosphatase, horseradish peroxidase, luciferase, or β-glactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art.

In some embodiments, the anti-PD-1 antibodies need not be labeled, and the presence thereof can be detected using a second labeled antibody which binds to the first anti-PD-1 antibody.

In some embodiments, the anti-PD-1 antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The anti-PD-1 antibodies and polypeptides can also be used for in vivo diagnostic assays, such as in vivo imaging. Generally, the antibody or the polypeptide is labeled with a radionuclide (such as $^{111}In$, $^{99}Tc$, $^{14}C$, $^{131}I$, $^{125}I$, $^{3}H$, or any other radionuclide label, including those outlined herein) so that the cells or tissue of interest can be localized using immunoscintigraphy.

The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first antibody is from a non-human, while the therapeutic is from a human. In some embodiments, the first and second antibodies can both bind to the antigen at the same time, by binding to separate epitopes.

Kits/Articles of Manufacture

Provided herein are also kits, medicines, compositions, and unit dosage forms for use in any of the methods described herein.

Kits can include one or more containers comprising an anti-PD-1 antibody (or unit dosage forms and/or articles of manufacture). In some embodiments, a unit dosage is provided wherein the unit dosage contains a predetermined amount of a composition comprising an anti-PD-1 antibody, with or without one or more additional agents. In some embodiments, such a unit dosage is supplied in single-use prefilled syringe for injection. In some embodiments, the composition contained in the unit dosage can comprise saline, sucrose, or the like; a buffer, such as phosphate, or the like; and/or be formulated within a stable and effective pH range. In some embodiments, the composition can be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition comprises heparin and/or a proteoglycan.

In some embodiments, the amount of the anti-PD-1 antibody used in the unit dose can be any of the amounts provided herein for the various methods and/or compositions described.

In some embodiments, kits further comprise instructions for use in the treatment of cancer in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises another therapeutic agent. In some embodiments, the additional therapeutic agent is an anti-ICOS antibody, e.g., as described herein, or an anti-CTLA4 antibody.

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Generation of Anti-PD-1 Antibodies

Eight naive human synthetic yeast libraries each of ~$10^9$ diversity were designed, generated, and propagated as described previously (see, e.g., WO2009036379; WO2010105256 WO2012009.568: Xu et al., Protein Eng Des Sel. 2013 October; 26(10):663-70). For the first 2 rounds of selection, a magnetic bead sorting technique utilizing the Miltenyi MACs system was performed, essentially as described (Siegel et al., J Immunol Methods. 2004 March; 286 (1-2):141-53). Briefly, yeast cells (~$10^{10}$ cells/library) were incubated with 3 ml of 10 nM biotinylated human PD-1-Fc fusion antigen for 15 min at room temperature in FACS wash buffer PBS with 0.1% BSA (biotinylations were done using the EZ-Link Sulfo-NHS-Biotinylation Kit, Thermo Scientific, Cat. #21425). After washing once with 50 ml ice-cold wash buffer, the cell pellet was resuspended in 40 mL wash buffer, and 500 µl Streptavidin MicroBeads (Miltenyi Biotec, Bergisch Gladbach, Germany, Cat. #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany, Cat. #130-042-401). After the 5 mL was loaded, the column was washed 3 times with 3 ml FACS wash buffer. The column was then removed from the magnetic field, and the yeast were eluted with 5 mL of growth media and then grown overnight. The following three rounds of sorting were performed using flow cytometry. Approximately $1\times10^8$ yeast were pelleted, washed three times with wash buffer, and incubated with 200, 100 or 10 nM biotinylated human PD-1 or 10 nM or 1 nM biotinylated human PD-1-Fc fusion antigen from 10 minutes up to 2 hours at room temperature. Incubation time varies with antigen concentration. Yeast were then washed twice and stained with goat anti-human F(ab')2 kappa-FITC diluted 1:100 (Southern Biotech, Birmingham, Ala., Cat. #2062-02) and either streptavidin-Alexa Fluor 633 (Life Technologies, Grand Island, N.Y., Cat. #S21375) diluted 1:500, or Extravidin-phycoerthyrin (Sigma-Aldrich, St Louis, Cat. #E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences) and sort gates were determined to select only PD-1 binding clones for two rounds. Depending on the populations, the third round was a negative sort to decrease reagent binders or further positive enrichment. After the final round of sorting, yeast were plated and individual colonies were picked for characterization.

The round 5 or round 6 binding population was used for a light chain diversification. Heavy chain plasmids were extracted and transformed into a light chain library with a diversity of $1\times10^6$. Selections were performed as described above with one round of MACS sorting and three rounds of FACS sorting using various concentrations of biotinylated antigen.

Affinity Maturation

Binding optimization of naïve and light chain batch shuffle clones was carried out utilizing diversification of CDRH1 and CDRH2.

CDRH1 and CDRH2 selection: The CDRH3s from clones selected from the light chain diversification procedure (light chain batch shuffle clones) were recombined into a premade library with CDRH1 and CDRH2 variants of a diversity of $1\times10^8$ and selections were performed using PD-1 antigen, as described above. Affinity pressures were applied by titrating the biotinylated antigen to sub-nanomolar concentrations and incubating with antibody-presenting yeast.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences, Cat. #17-5458-01).

Affinity Measurements of PD-1 Antibodies

The affinity of the PD-1 antibodies was determined by measuring their $K_D$ by ForteBio or MSD-SET. ForteBio affinity measurements were performed generally as previously described (Estep et al., MAbs. 2013 March-April; 5(2):270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 5 minutes, afterwards they were transferred to assay buffer for 5 min for off-rate measurement. Kinetics were analyzed using the 1:1 binding model.

Equilibrium affinity measurements performed as previously described (Estep et al., 2013). Solution equilibrium titrations (SET) were performed in PBS+0.1% IgG-Free BSA (PB SF) with antigen held constant at 50 pM and incubated with 3-to 5-fold serial dilutions of antibody starting at 10 nM. Antibodies (20 nM in PBS) were coated onto standard bind MSD-ECL plates overnight at 4° C. or at room temperature for 30 min. Plates were then blocked for 30 min with shaking at 700 rpm, followed by three washes with wash buffer (PBSF+0.05% Tween 20). SET samples were applied and incubated on the plates for 150 seconds with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation. Table 1 shows the results for the ForteBio affinity measurements.

TABLE 1

| Antibody | Human PD-1 Monovalent Affinity ($K_D$) | Mouse PD-1 Monovalent Affinity ($K_D$) |
| --- | --- | --- |
| mAb 1 (12228) | 49 nM | 6.3 nM |
| mAb 2 (13405) | 73 nM | 7.2 nM |
| mAb 3 (13406) | 3.2 nM | 3.5 nM |
| mAb 4 (13407) | 3.9 nM | 3.2 nM |
| mAb 5 (13408) | 1.2 nM | 5.3 nM |

Example 2: Mouse Activated Splenocytes Response to Anti-PD-1 Antibodies

When mouse T cells derived from splenocytes are activated with anti-CD3 and anti-CD28 antibodies, they express the cell-surface molecule and secrete the soluble molecule interferon-gamma (IFNγ). Blocking antibodies to PD-1 cause the production of IFNγ to be increased. Mouse splenocytes were obtained and incubated with soluble anti-CD3 and anti-CD28 antibodies. After 5 days, they were mixed with equal numbers of T cells purified from freshly prepared splenocytes and anti-PD-1 antibodies in different concentrations. Positive and negative control antibodies RMP1-14, 2A3, and C1.18.4 were purchased from BioXCell. After 24 hours, supernatants were collected and IFNγ concentrations measured by cytokine bead array. Anti-PD-1 antibodies disclosed herein were able to increase the production of IFNγ in a similar way to reference antibodies. See FIG. 1. At least antibodies 12191, 13396, 13398, 13399, 12195, 13406, 13407, 13408, and 13409 significantly increased IFNγ expression. Antibodies 13396, 13399, 12195, 13406, 13407, and 13408 caused the greatest increase in IFNγ expression.

Figure 2:
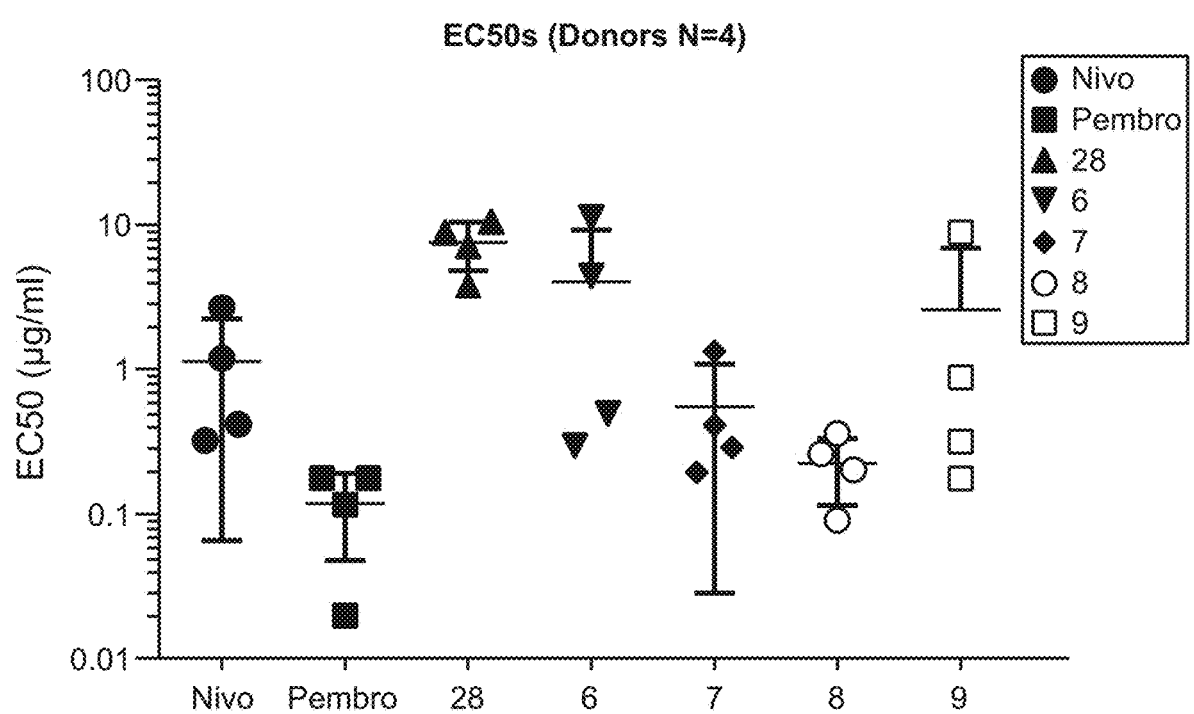
FIG. 2 shows the $EC_{50}$ of increase in IL-2 in whole blood samples activated with Staphylococcal enterotoxin B(SEB) after being incubated with anti-PD1 antibodies. nivolumab (Nivo) and pembrolizumab (Pembro) were used as control anti-PD1 antibodies. Effects from antibodies 12228 (28), 13406 (6), 13407 (7), 13408 (8), and 13409 (9) are shown.

Example 3: Human Activated Peripheral Mononuclear Blood Cells Respond to Anti-PD-1 Antibodies Whole blood samples activated with Staphylococcal enterotoxin B(SEB) have been shown to respond to an immune checkpoint blockade using an anti-PD-1 antibody, measured by increases of IL-2 secretion (see, e.g., EP2170959B1). Anti-PD-1 antibodies were prepared in a range of concentrations and added to wells of 96 well plates. Whole blood from four donors was diluted 1:10 in complete RPMI, and added to the same wells. Plates were incubated at room temperature for 30 minutes before addition of 50 µl SEB per well at a concentration of 40 µg/ml for a final concentration of 10 µg/ml. Plates were incubated at 37° C. for 4 days and supernatants were collected for measurement of secreted IL-2 by cytokine bead array (CBA) assay. Anti-PD-1 antibodies disclosed herein were able to increase the production of IL-2 from these cultures to the same level as reference anti-PD-1 antibodies. FIG. 2 shows the $EC_{50}$ of this increase for each antibody tested, in four healthy human donor samples.

Example 4: Antibody Blocking of Binding of Mouse PD-L1 and Mouse PD-L2 to Mouse PD-1

Figure 3A:
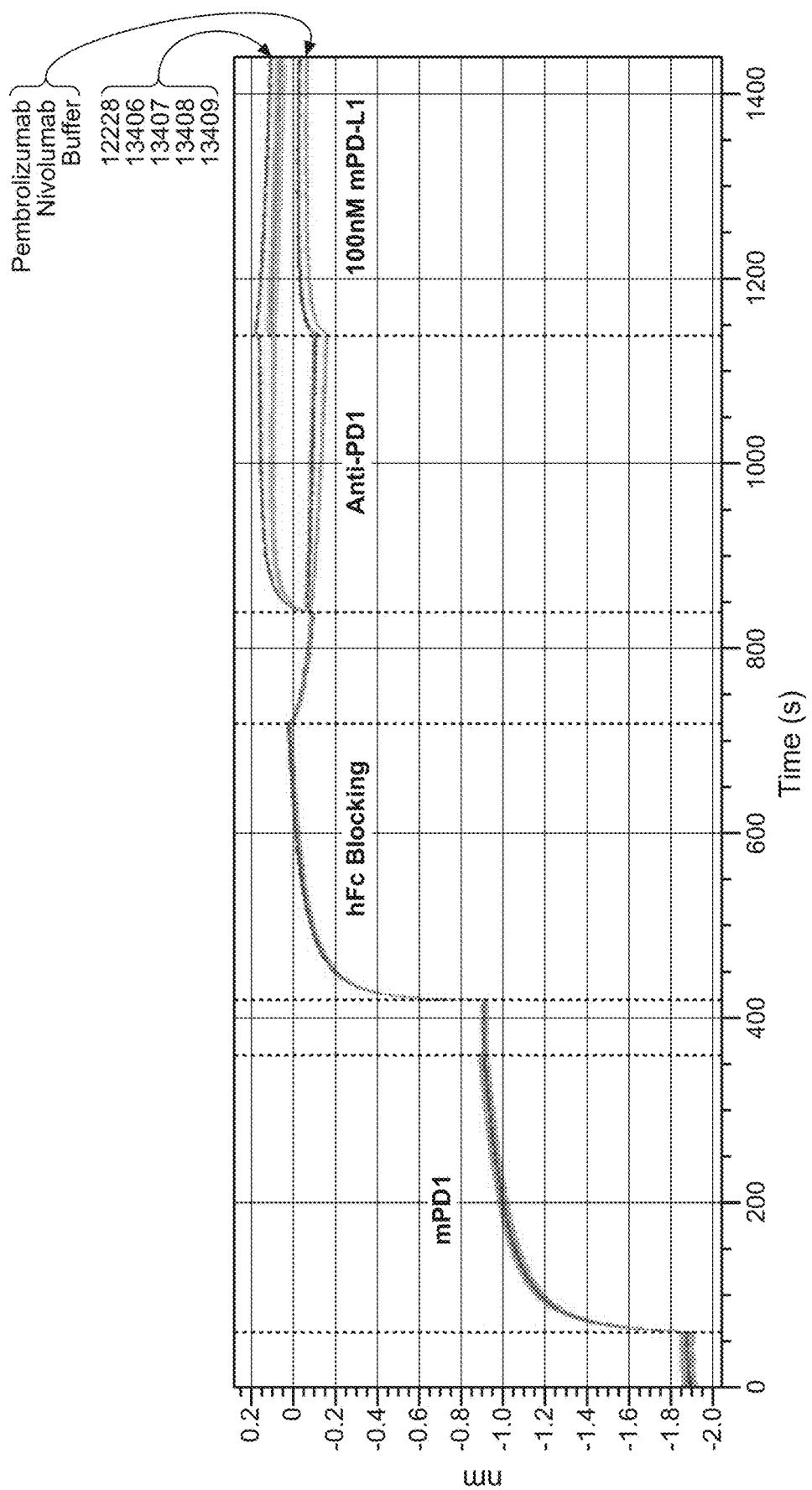
FIG. 3A-3B show the ability of anti-PD-1 antibodies disclosed herein to block binding of mouse ligands to mouse PD-1. Octet analysis on a Forte-Bio instrument was used to assess the effect of the antibodies on the interaction between mouse PD-L1 and mouse PD-L2 with mouse PD-1.
Figure 3B:
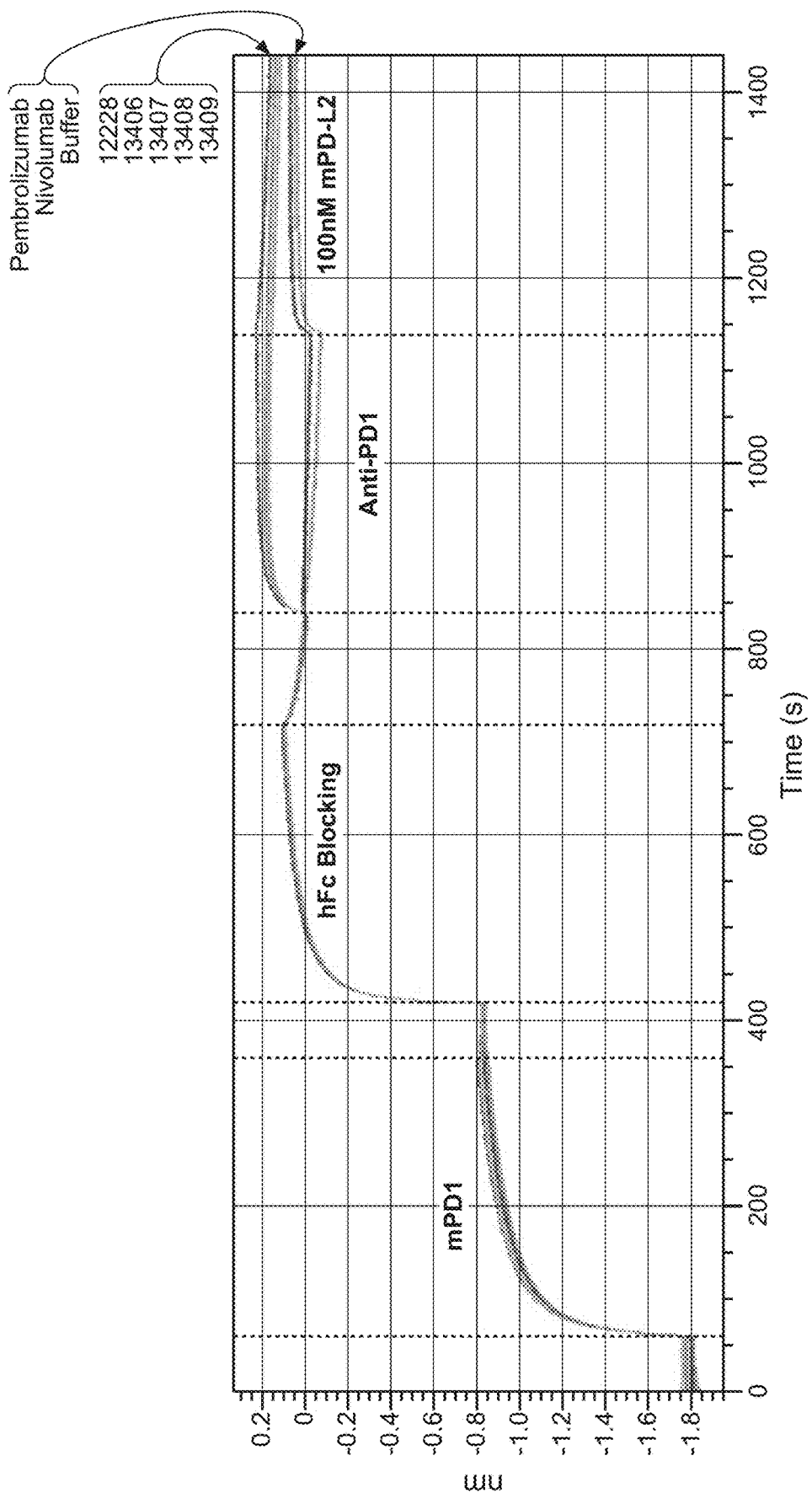
Figures 1, 4A:
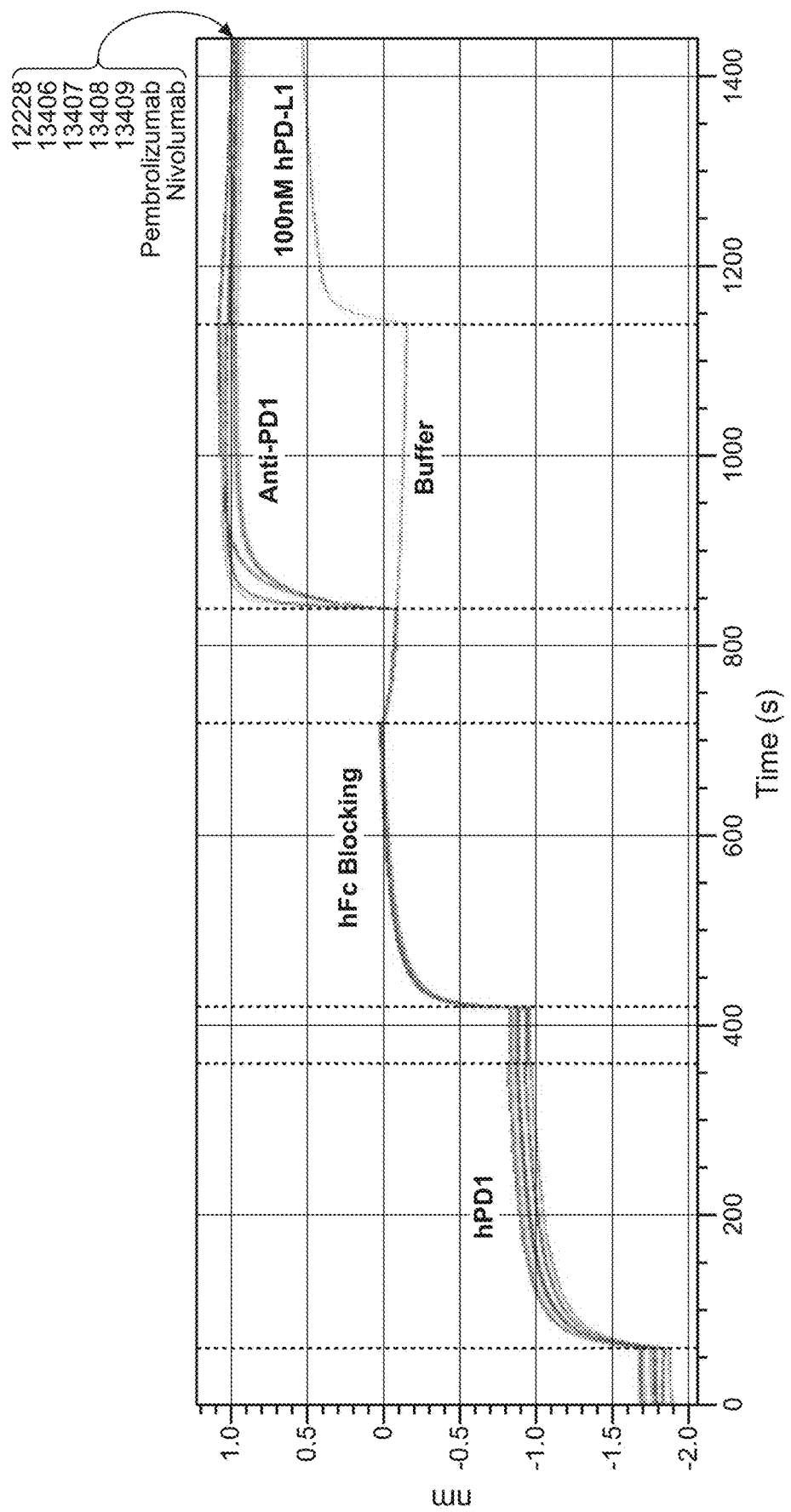
Figures 2, 4A:
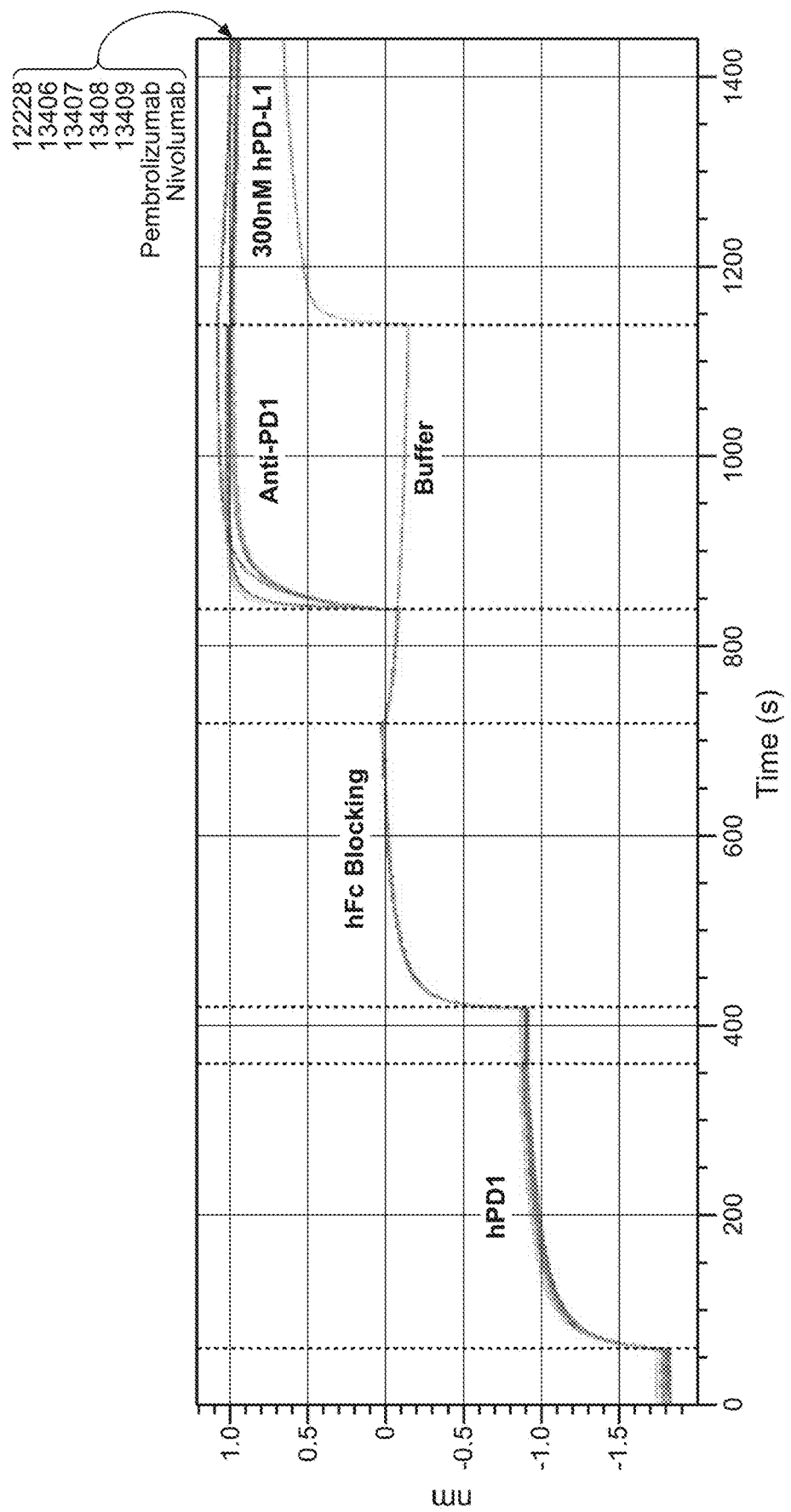
Figures 1, 4B:
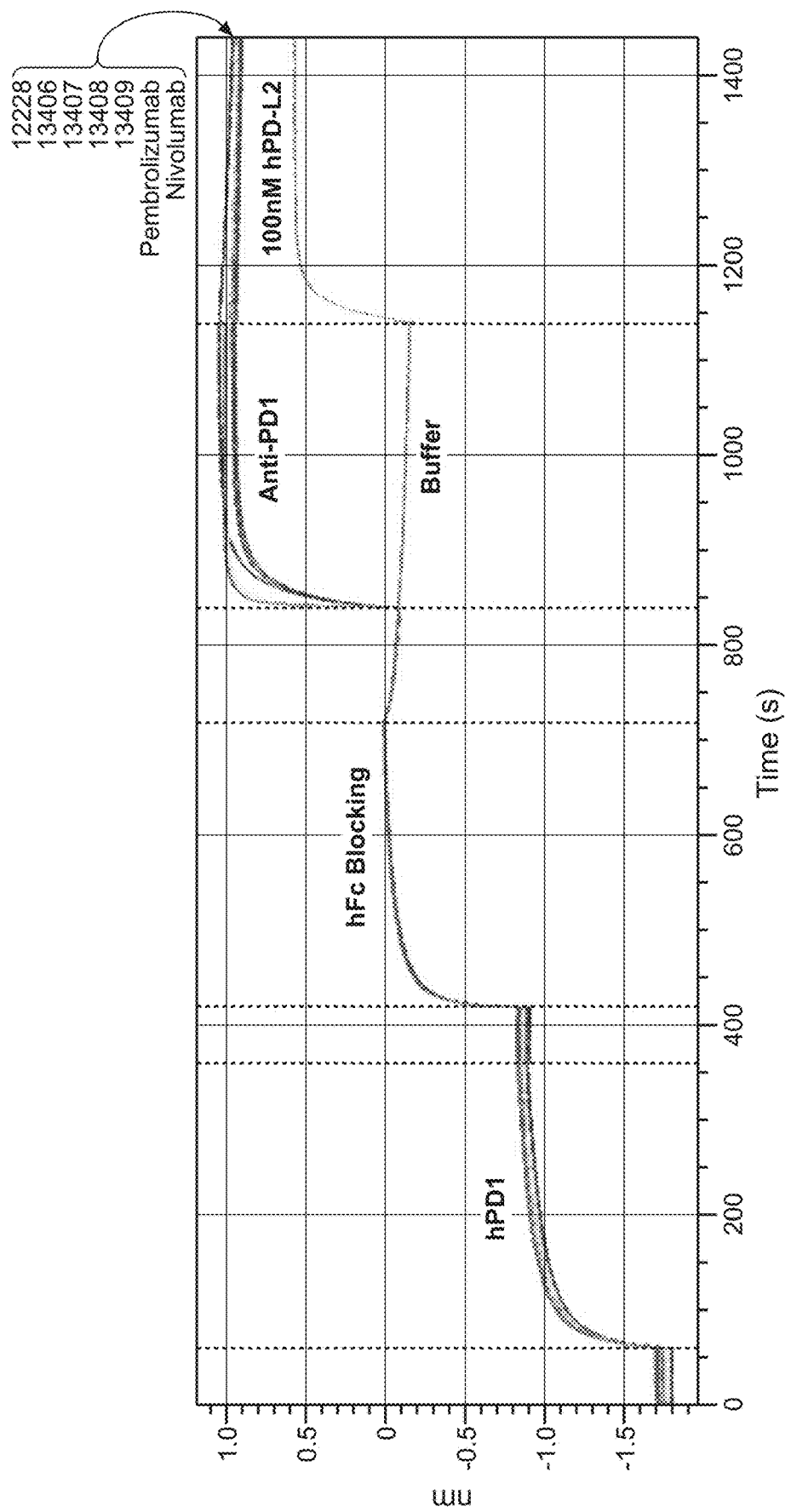
Figures 2, 4B:
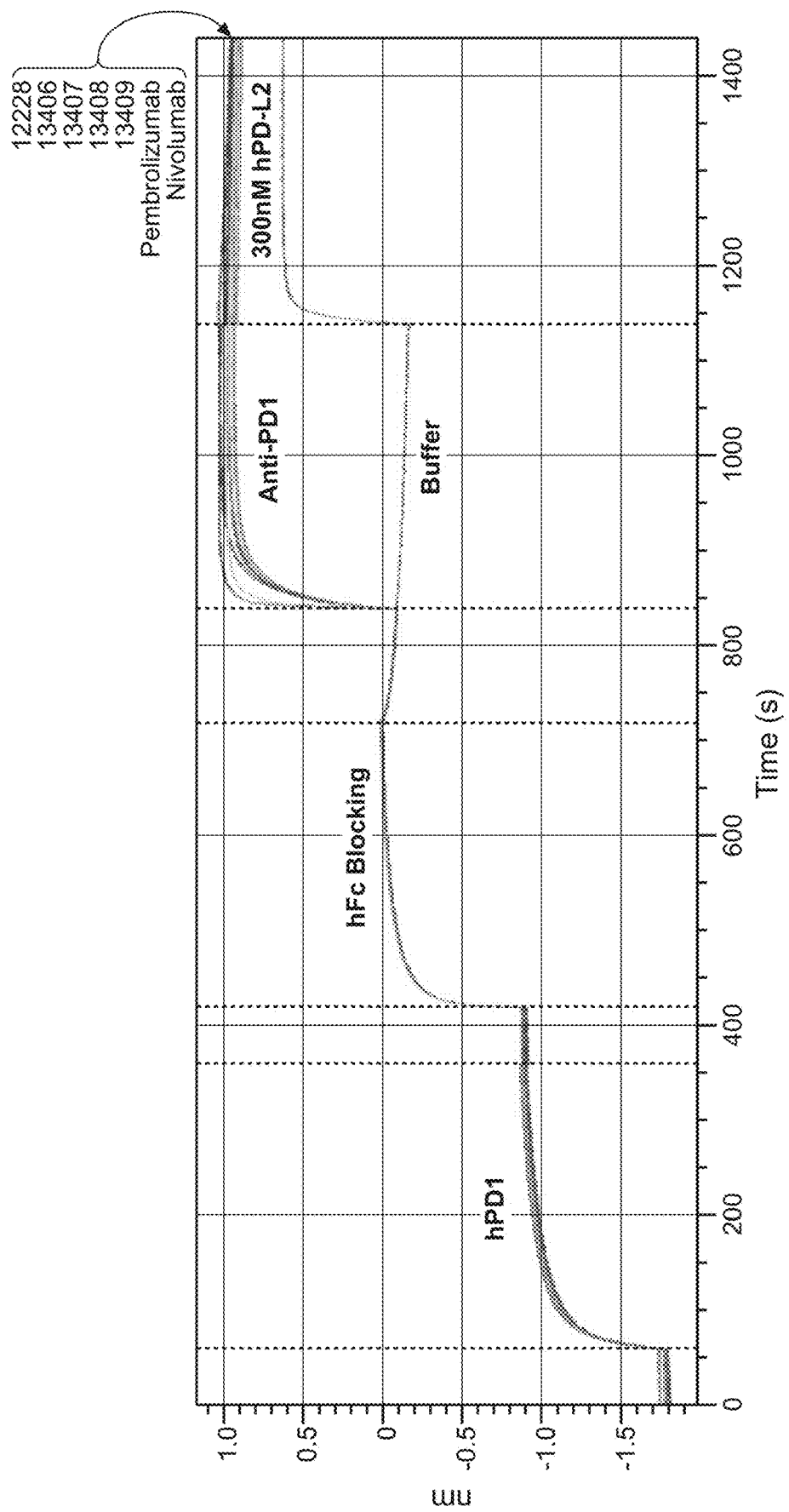
Figure 4C:
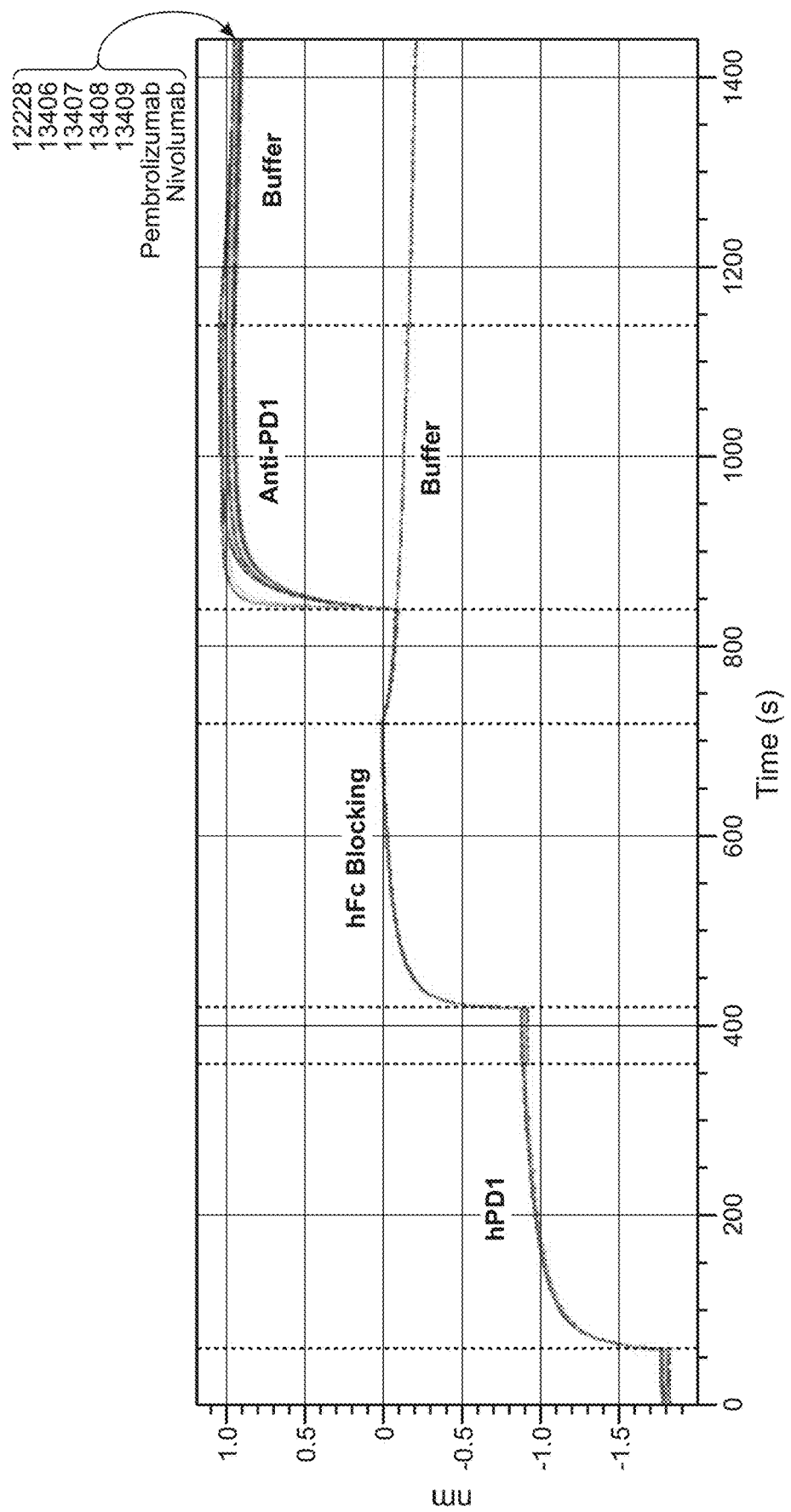

PD-L1 and PD-L2 are two natural ligands for PD-1 and the interaction of either ligand with PD-1 can downregulate an activating response in T cells. Approved therapeutic antibodies such as nivolumab and pembrolizumab have been shown to block this interaction and downregulate human T cell responses, although neither antibody binds to mouse PD-1 nor blocks the interaction of mouse PD-1 with mouse PD-L1 or mouse PD-L2. Octet analysis on a Forte-Bio instrument was used to assess the effect of anti-PD-1 antibodies disclosed herein on the interaction between mouse PD-L1 and mouse PD-1 and between mouse PD-L2 and mouse PD-1. Antibodies were diluted to 10 µg/mL, including an isotype control antibody for use in background subtraction. Mouse PD-1-Fc fusion was diluted to the desired concentrations (e.g., 100 nM). Soluble mouse isotype antibody, to be used as a blocking reagent, was diluted to 250 µg/mL. Mouse-PD-1 was coated on to sensors, followed by human Fc. Anti-PD-1 antibodies were added and finally the binding of either mouse PD-L1 or mouse PD-L2 was measured. FIG. 3 shows that the anti-PD-1 antibodies tested were capable of blocking the binding of both mouse ligands to mouse PD-1. In contrast, neither pembrolizumab or nivolumab bound to mouse PD-1 or blocked mouse ligand binding to mouse PD-1.

Example 5: Antibody Blocking of Binding of Human PD-L1 and Human PD-L2 to Human PD-1

PD-L1 and PD-L2 are two natural ligands for PD-1 and the interaction of either ligand with PD-1 can downregulate an activating response in T cells. Approved therapeutic antibodies such as nivolumab and pembrolizumab have been shown to block this interaction and downregulate human T cell responses. Octet analysis, on a Forte-Bio instrument was used to assess the effect of anti-PD-1 antibodies disclosed herein on the interaction between human PD-L1 and human PD-1 and human PD-L2 and human PD-1. Antibodies were diluted to 10 µg/mL, including an isotype control antibody for use in background subtraction. Human PD-1-Fc fusion was diluted to the desired concentrations (e.g., 100 nM). Soluble human Fc, to be used as a blocking reagent, was diluted to 250 µg/mL. Human-PD-1 was coated on to sensors, followed by human Fc. Anti-PD-1 antibodies were added and finally the binding of either human PD-L1 or human PD-L2 was measured. FIG. 4 shows that the anti-PD-1 antibodies tested were capable of blocking the binding of both human ligands to human PD-1, similar to pembrolizumab and nivolumab.

Example 6: In Vivo Tumor Challenge

Figure 5:
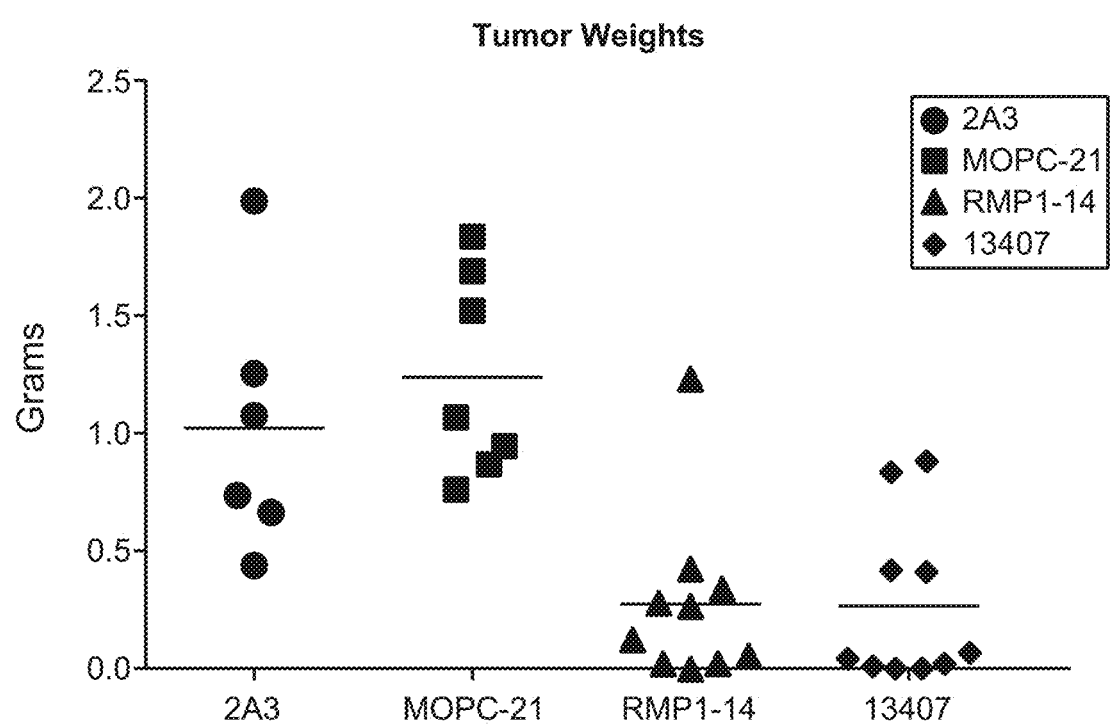
FIG. 5 shows the reduction in tumor sizes in mouse tumor models upon administration of an anti-PD-1 antibody disclosed herein. C57BL6/J mice were injected subcutaneously in their flanks with MC38 cells. Mouse IgG1 (MOPC-21) and rat IgG2a (2A3) were used as controls. RMP1-14 was used as a positive control anti-PD1 antibody.

The ability of anti-PD-1 antibodies to reduce tumor growth in mouse models was examined by injecting MC38 cells subcutaneously into the flanks of C57BL6/J mice. Mice were randomized into groups with an approximate 100 mm³ average tumor size on day 11 and injected intraperitoneally with 200 µg of anti-PD-1 antibody 13407. Repeat doses were administered on days 14, 18 and 21. Control antibodies, mouse IgG1 (MOPC-21), rat IgG2a (2A3), and positive control rat anti-mouse PD-1 (RMP1-14) were purchased from BioXcell. Tumor sizes were measured twice weekly and the experiment was terminated after 24 days. Tumor weights at the end of the experiment are shown in FIG. 5 and indicate that anti-PD-1 antibody 13407 reduced tumor growth in mice to a similar extent as the reference anti-PD-1 antibody.

Example 7: Antibody Epitope Mapping

Genes encoding various PD-1 variants, PD-L1, PD-L2 and antibody Fab fragments were synthesized and codon optimized by Atum inc. The human kappa light signal sequence (MGTPAQLLFLLLLWLPDTTG; SEQ ID NO:

400) was included at the 5' terminus of all genes. Genes were cloned into a mammalian expression vector and sequence verified prior to protein expression.

Recombinant proteins were expressed in Expi293™ Expression System (Thermo Fisher Scientific) utilizing the manufacturer's kit for media, transfection reagent, feeds and cells. The cells were transfected at 1 µg/mL of plasmid DNA to media ratio using Expifectamine™ following the manufacturer's protocol. The cells were cultured in shake flasks in an incubator kept at 37° C. and 5% $CO_2$. After 5 days the cultures were harvested by centrifugation at 3000 rcf for 15 minutes followed by filtration using a 0.2 µm filter.

Harvested supernatants were subjected to affinity purification. The proteins either contained a hexa-histidine tag or a Fc tag, which enabled either Ni-affinity purification or Protein A affinity purification.

Ni-affinity purifications were carried out on HisTrap™ Excel IMAC columns (GE Healthcare Life Sciences) using 43 mM sodium phosphate, 0.5 M sodium chloride, pH 7.4 as binding buffer. Bound protein was washed with binding buffer followed by binding buffer containing 20 mM imidazole. Step elutions were performed with binding buffer containing 90 mM, 150 mM, and 250 mM imidazole. Protein A affinity purifications were carried out on HiTrap MabSelect Sure columns (GE Healthcare Life Sciences) using PBS, pH 7.4 as binding buffer. Step elutions were performed to elute bound protein using 0.1 M citrate buffer at pH 4.0, pH 3.5 and pH 2.0. All acidic elution fractions were neutralized with 1M Tris, pH 9.0 using 20% v/v ratio. All elution fractions were analyzed by SEC-HPLC to determine fractions above target purity (>90% monomeric). For purifications that did not yield fractions above target purity, preparative size exclusion chromatography was performed using a Superdex200 chromatography column to achieve target purity. Prior to freezing, purified proteins were buffer exchanged into final buffer (either 20 mM histidine, 150 mM NaCl, pH6.0, or 20 mM HEPES, 150 mM NaCl, pH7.5), keeping them at a pH at least 1 unit away from the predicted pI of the target protein.

All protein interactions were assessed on a ForteBio OctetRED96 instrument. Proteins were diluted in kinetics buffer formulation (PBS+0.1% BSA, 0.02% Tween20, 0.05% sodium azide) with a sample volume was 220 µl/well. Ligand concentrations were normalized at 10 µg/ml and analyte concentrations at 100 nM. The blocking reagent was employed at a concentration of 250 µg/ml. Sensor equilibration time was set for 60 sec, and sample loading time established at 300 sec. Human Fc blocking time was set for 300 sec. Analysis of association time was set for 300 sec and dissociation time for 600 sec.

For this method, antibodies of interest are oriented and captured on biosensors derivatized with anti-human (or anti-mouse) Fc antibodies. Binding of target proteins of interest, in solution, to the antibody-loaded sensors is then assayed.

For interactions in which the proteins contain similar species Fc domains, an additional blocking step is included to minimize direct binding of the target protein to the biosensor independent of the captured antibody.

Binding events were confirmed with a Y (yes) if the affinity for a PD-1 variant or PD-1 of another species were within approximately 5-fold compared to affinity for wild-type human PD-1. Affinities that were reduced by >10-fold and <100-fold are indicated as Reduced. Affinities reduced by >100-fold are indicated as N (no). Interactions that were not assessed are listed as ND (not determined).

Variants of human PD-1 were produced as extracellular domain (ECD)-Fc fusions with C-terminal $His_6$ tags and used for binding analysis of PD-1 ligands as well as Fab fragments of nivolumab, pembrolizumab, and 13407. The results are shown in Table 2.

TABLE 2

Summary of PD-1 binding data

| PD-1 Species | PD-1 Variant (ECD-Fc fusions) | PD-L1 Fc Fusion | PD-L2 Fc Fusion | Nivo Fab | Pembro Fab | 13407 Fab |
|---|---|---|---|---|---|---|
| Human | WT | Y | Y | Y | Y | Y |
|  | D85G | ND | ND | Y | N | Y |
|  | R86L | ND | ND | Y | Y | Y |
|  | D85G/R86L | ND | ND | Y | N | Y |
|  | N33-Q167 | Y | Y | N | Y | Y |
|  | K78A | N | N | Y | Y | Y |
|  | I126A | N | Y | Y | Y | Reduced |
|  | L128A | Reduced | Y | Y | Y | Reduced |
|  | A132L | Y | Y | Y | Y | N |
|  | I134A | N | Y | Y | Y | N |
|  | E136A | N | Y | Y | Y | Reduced |
| Mouse | WT | Y | Y | N | N | Y |
|  | H129P | ND | ND | N | N | N |
| Rat | WT | ND | ND | N | N | N |
|  | P129H | ND | ND | N | N | Y |
| Dog | WT | ND | ND | N | N | N |
| Cyno | WT | Y | Y | Y | Y | Y |

Amino acid substitutions reported to affect binding of pembrolizumab were assessed for binding to the panel of molecules (Na et al., 2017, Cell Res., 27: 147-150). Pembrolizumab binding to PD-1 is ablated with the D85G substitution, whereas the binding of nivolumab and 13407 were not affected. The binding of nivolumab to PD-1 is also diminished when assessed against the N-terminal truncated variant N33-Q167. These results indicate that 13407 contacts amino acids that are significantly different than those contacted by pembrolizumab and nivolumab.

Additional variants were generated that were previously assessed for PD-L1 and PD-L2 ligands (Lazar-Molnar et al., 2008, PNAS, 105: 10483-10488). Binding of nivolumab and pembrolizumab was largely unaffected by these amino acid substitutions, whereas the binding affinity of 13407 was significantly reduced with the I126A, L128A, and E136A substitutions, and eliminated with the A132L and I134A substitutions. The data reveal a similar binding profile for 13407 to that of PD-L1.

The panel of Fab fragments was also assessed for binding to additional species of PD-1. Pembrolizumab and nivolumab fail to bind to mouse, rat, or dog PD-1. In contrast, 13407 binds to mouse PD-1. Surprisingly, 13407 fails to bind to rat PD-1 despite the high homology between rat and mouse PD-1. A variant of mouse PD-1 in which residue 129 is replaced with the corresponding residue from the rat sequence (H129P) was generated and found to ablate binding of 13407. When the reciprocal mutation, P129H, was introduced into the rat sequence, 13407 bound to the variant. Notable, the dog PD-1 sequence, to which 13407 does not bind, lacks a proline at this position.

In summary, 13407 binds an epitope of PD-1 distinct from the epitopes bound by nivolumab and pembrolizumab.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

| | | Table of Sequences |
|---|---|---|
| SEQ ID NO | Description | Sequence |
| 1 | Human PD-1 amino acid sequence; UniProtKB/ Swiss-Prot: Q15116; 1 Aug. 2016 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 382 | Mature human PD-1 amino acid sequence (without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 401 | Human PD-1 extracellular domain (ECD)-Fc-His$_6$ | ldspdrpwnp ptfspallvv tegdnatftc sfsntsesfv lnwyrmspsn qtdklaafpe drsqpgqdcr frvtqlpngr dfhmsvvrar rndsgtylcg aislapkaqi keslraelry terraevpta hpspsprpag qfqggsggDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSGHH HHHH |
| 385 | Human PD-1 D85G ECD-Fc-His$_6$ | dspdrpwnpp tfspallvvt egdnatftcs fsntsesfvl nwyrmspsnq tdklaafpeG rsqpgqdcrf rvtqlpngrd fhmsvvrarr ndsgtylcga islapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 386 | Human PD-1 R86L ECD-Fc-His$_6$ | dspdrpwnpp tfspallvvt egdnatftcs fsntsesfvl nwyrmspsnq tdklaafped Lsqpgqdcrf rvtqlpngrd fhmsvvrarr ndsgtylcga islapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 402 | Human PD-1 D85G/R86L ECD-Fc-His$_6$ | dspdrpwnpp tfspallvvt egdnatftcs fsntsesfvl nwyrmspsnq tdklaafpeG Lsqpgqdcrf rvtqlpngrd fhmsvvrarr ndsgtylcga islapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 387 | Human PD-1 N33-Q167 ECD-Fc-His$_6$ | npptfspall vvtegdnatf tcsfsntses fvlnwyrmsp snqtdklaaf pedrsqpgqd crfrvtqlpn grdfhmsvvr arrndsgtyl cgaislapka qikeslrael rvterraevp tahpspsprp agqfqggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 388 | Human PD-1 K78A ECD-Fc-His$_6$ | dspdrpwnpp tfspallvvt egdnatftcs fsntsesfvl nwyrmspsnq tdAlaafped rsqpgqdcrf rvtqlpngrd fhmsvvrarr ndsgtylcga islapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 389 | Human PD-1 I126A ECD-Fc-His$_6$ | dspdrpwnpp tfspallvvt egdnatftcs fsntsesfvl nwyrmspsnq tdklaafped rsqpgqdcrf rvtqlpngrd fhmsvvrarr ndsgtylcga Aslapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |

Table of Sequences

| SEQ ID NO | Description | Sequence |
|---|---|---|
| 390 | Human PD-1 L128A ECD-Fc-His$_6$ | dspdrpwnpp tfspallvvt egdnatftcs fsntsesfvl nwyrmspsnq tdklaafped rsqpgqdcrf rvtqlpngrd fhmsvvrarr ndsgtylcga isAapkaqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 391 | Human PD-1 A132L ECD-Fc-His$_6$ | dspdrpwnpp tfspallvvt egdnatftcs fsntsesfvl nwyrmspsnq tdklaafped rsqpgqdcrf rvtqlpngrd fhmsvvrarr ndsgtylcga islapkLqik eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 392 | Human PD-1 I134A ECD-Fc-His$_6$ | dspdrpwnpp tfspallvvt egdnatftcs fsntsesfvl nwyrmspsnq tdklaafped rsqpgqdcrf rvtqlpngrd fhmsvvrarr ndsgtylcga islapkaqAk eslraelrvt erraevptah pspsprpagq fqtlvggsgg DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGKGSG HHHHHH |
| 393 | Human PD-1 E136A ECD-Fc-His$_6$ | dttgdspdrp wnpptfspal lvvtegdnat ftcsfsntse sfvinwyrms psnqtdklaa fpedrsqpgq dcrfrvtqlp ngrdfhmsvv rarrndsgty lcgaislapk aqikAslrae lrvterraev ptahpspspr pagqfqtivg gsggDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG KGSGHHHHHH |
| 2 | Mouse PD-1; UniProtKB/ Swiss-Prot: Q02242; 1 Aug. 2016 | MWVRQVPWSF TWAVLQLSWQ SGWLLEVPNG PWRSLTFYPA WLTVSEGANA TFTCSLSNWS EDLMLNWNRL SPSNQTEKQA AFCNGLSQPV QDARFQIIQL PNRHDFHMNI LDTRRNDSGI YLCGAISLHP KAKIEESPGA ELVVTERILE TSTRYPSPSP KPEGRFQGMV IGIMSALVGI PVLLLLAWAL AVFCSTSMSE ARGAGSKDDT LKEEPSAAPV PSVAYEELDF QGREKTPELP TACVHTEYAT IVFTEGLGAS AMGRRGSADG LQGPRPPRHE DGHCSWPL |
| 383 | Mature mouse PD-1 amino acid sequence (without signal sequence) | SGWLLEVPNG PWRSLTFYPA WLTVSEGANA TFTCSLSNWS EDLMLNWNRL SPSNQTEKQA AFCNGLSQPV QDARFQIIQL PNRHDFHMNI LDTRRNDSGI YLCGAISLHP KAKIEESPGA ELVVTERILE TSTRYPSPSP KPEGRFQGMV IGIMSALVGI PVLLLLAWAL AVFCSTSMSE ARGAGSKDDT LKEEPSAAPV PSVAYEELDF QGREKTPELP TACVHTEYAT IVFTEGLGAS AMGRRGSADG LQGPRPPRHE DGHCSWPL |
| 403 | Mouse PD-1 ECD-Fc-His$_6$ | levpngpwrs ltfypawltv seganatftc slsnwsedlm lnwnrlspsn qtekgaafcn glsgpvgdar fqiiqlpnrh dfhmnildtr rndsgiylcg aislhpkaki eespgaelvv teriletstr ypspspkpeg rfqggsggDK THTCPPCPAP ELLGGPSVFL PPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSGHH HHHH |
| 394 | Mouse H129P PD-1 ECD-Fc-His$_6$ | levpngpwrs ltfypawltv seganatftc slsnwsedlm lnwnrlspsn qtekgaafcn glsgpvgdar fqiiqlpnrh dfhmnildtr rndsgiylcg aislPpkaki eespgaelvv teriletstr ypspspkpeg rfqggsggDK THTCPPCPAP ELLGGPSVFL PPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSGHH HHHH |
| 3 | Cynomolgus Monkey PD-1; UniProtKB/ Swiss-Prot: B0LAJ3; 1 Aug. 2016 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |

-continued

| SEQ ID NO | Description | Sequence |
|---|---|---|
| 384 | Mature cynomolgus monkey PD-1 (without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 404 | Cynomolgus monkey PD-1 ECD-Fc-His 6 | LESPDR PWNAPTFSPA LLLVTEGDNA TFTCSFSNAS ESFVLNWYRM SPSNQTDKLA AFPEDRSQPG QDCRFRVTRL PNGRDFHMSV VRARRNDSGT YLCGAISLAP KAQIKESLRA ELRVTERRAE VPTAHPSPSP RPAGQFQGGS GGDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGKG SGHHHHHH |
| 395 | Rat PD-1; NCBI Ref NP_0011003971.; 2 Oct. 2017 | MWVQQVPWSF TWAVLQLSWQ SGWLLEVLNK PWRPLTFSPT WLTVSEGANA TFTCSFSNWS EDLKLNWYRL SPSNQTEKQA AFCNGYSQPV RDARFQIVQL PNGHDFHMNI LDARRNDSGI YLCGAISLPP KAQIKESPGA ELVVTERILE TPTRYPRPSP KPEGQFQGLV IVIMSVLVGI PVLLLLAWAL AAFCSTGMSE AREAGRKEDP PKEAHAAAPV PSVAYEELDF QGREKTPEPA PCVHTEYATI VFTEGLDASA IGRRGSADGP QGPRPPRHED GHCSWPL |
| 396 | Mature rat PD-1 amino acid sequence (without signal sequence) | LEVLNKPWRP LTFSPTWLTV SEGANATFTC SFSNWSEDLK LNWYRLSPSN QTEKQAAFCN GYSQPVRDAR FQIVQLPNGH DFHMNILDAR RNDSGIYLCG AISLPPKAQI KESPGAELVV TERILETPTR YPRPSPKPEG QFQGLVIVIM SVLVGIPVLL LLAWALAAFC STGMSEAREA GRKEDPPKEA HAAAPVPSVA YEELDFQGRE KTPEPAPCVH TEYATIVFTE GLDASAIGRR GSADGPQGPR PPRHEDGHCS WPL |
| 405 | Rat PD-1 ECD-Fc-His₆ | levinkpwrp ltfsptwltv seganatftc sfsnwsedlk lnwyrlspsn qtekgaafcn gysqpvrdar fqivqlpngh dfhmnildar rndsgiylcg aislppkaqi kespgaelvv teriletptr yprpspkpeg qfqggsggDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSGHH HHHH |
| 397 | Rat P129H PD-1 ECD-Fc-His₆ | levinkpwrp ltfsptwltv seganatftc sfsnwsedlk lnwyrlspsn qtekgaafcn gysqpvrdar fqivqlpngh dfhmnildar rndsgiylcg aislHpkaqi kespgaelvv teriletptr yprpspkpeg qfqggsggDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGKGSGHH HHHH |
| 398 | Dog PD-1 amino acid sequence; NCBI Ref. NP_001301026.1 | MGSRRGPWPL VWAVLQLGWW PGWLLDSPDR PWSPLTFSPA QLTVQEGENA TFTCSLADIP DSFVLNWYRL SPRNQTDKLA AFQEDRIEPG RDRRFRVTRL PNGRDFHMSI VAARLNDSGI YLCGAIYLPP NTQINESPRA ELSVTERTLE PPTQSPSPPP RLSGQLQGLV IGVTSVLVGV LLLLLLTWVL AAVFPRATRG ACVCGSEDEP LKEGPDAAPV FTLDYGELDF QWREKTPEPP APCAPEQTEY ATIVFPGRPA SPGRRASASS LQGAQPPSPE DGPGLWPP |
| 399 | Mature dog PD-1 amino acid sequence (without signal sequence) | LDSPDRPWSP LTFSPAQLTV QEGENATFTC SLADIPDSFV LNWYRLSPRN QTDKLAAFQE DRIEPGRDRR FRVTRLPNGR DFHMSIVAAR LNDSGIYLCG AIYLPPNTQI NESPRAELSV TERTLEPPTQ SPSPPPRLSG QLQGLVIGVT SVLVGVLLLL LLTWVLAAVF PRATRGACVC GSEDEPLKEG PDAAPVFTLD YGELDFQWRE KTPEPPAPCA PEQTEYATIV FPGRPASPGR RASASSLQGA QPPSPEDGPG LWPP |
| 406 | Dog PD-1 ECD-Fc-His₆ | LDSPDR PWSPLTFSPA QLTVQEGENATFTCSLADIP DSFVLNWYRL SPRNQTDKLA AFQEDRIEPG RDRRFRVTRL PNGRDFHMSI VAARLNDSGI YLCGAIYLPP NTQINESPRA ELSVTERTLE PPTQSPSPPP RLSGQLQGGS GGDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGKG SGHHHHHH |
| 4 | 12228 VH Sequence | QVQLVQSGAE VKKPGASVKV SCKASGYTFT SYYMHWVRQA PGQGLEWMGI INPSGGSTSY AQKFQGRVTM TRDTSTSTVY MELSSLRSED TAVYYCARGG TYYDYTYWGQ GTLVTVSS |

Table of Sequences

| SEQ ID NO | Description | Sequence |
|---|---|---|
| 5 | 12228 HCDR1 | YTFTSYYMH |
| 6 | 12228 HCDR2 | IINPSGGSTSYAQKFQG |
| 7 | 12228 HCDR3 | ARGGTYYDYTY |
| 8 | 12228 VL Sequence | DIQMTQSPST LSASVGDRVT ITCRASQSIS SWLAWYQQKP GKAPKLLIYE ASSLESGVPS RFSGSGSGTE FTLTISSLQP DDFATYYCQQ YNSFPPTFGG GTKVEIK |
| 9 | 12228 LCDR1 | RASQSISSWLA |
| 10 | 12228 LCDR2 | EASSLES |
| 11 | 12228 LCDR3 | QQYNSFPPT |
| 12 | 13406 VH Sequence | QVQLVQSGAEVKKPGASVKVSCKASGYTFDQYYMHWVRQAPGQGLEWMGIINPSGGSTAYAQKFQGRVTMTRDTSTSTVYMELSSLRSEDTAVYYCARGGTYYDYTYWGQGTLVTVSS |
| 13 | 13406 HCDR1 | YTFDQYYMH |
| 14 | 13406 HCDR2 | IINPSGGSTAYAQKFQG |
| 15 | 13406 HCDR3 | ARGGTYYDYTY |
| 16 | 13406 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSEPPTEGGGTKVEIK |
| 17 | 13406 LCDR1 | RASQSISSWLA |
| 18 | 13406 LCDR2 | EASSLES |
| 19 | 13406 LCDR3 | QQYNSFPPT |
| 20 | 13407 VH Sequence | QVQLVQSGAEVKKPGASVKVSCKASGYTFPSYYMHWVRQAPGQGLEWMGIINPEGGSTAYAQKFQGRVTMTRDTSTSTVYMELSSLRSEDTAVYYCARGGTYYDYTYWGQGTLVTVSS |
| 21 | 13407 HCDR1 | YTFPSYYMH |
| 22 | 13407 HCDR2 | IINPEGGSTAYAQKFQG |
| 23 | 13407 HCDR3 | ARGGTYYDYTY |
| 24 | 13407 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSEPPTEGGGTKVEIK |
| 25 | 13407 LCDR1 | RASQSISSWLA |
| 26 | 13407 LCDR2 | EASSLES |
| 27 | 13407 LCDR3 | QQYNSFPPT |
| 28 | 13408 VH Sequence | QVQLVQSGAEVKKPGASVKVSCKASGYTFSDYYMHWVRQAPGQGLEWMGIINPSGGVTAYAQKFQGRVTMTRDTSTSTVYMELSSLRSEDTAVYYCARGGTYYDYTYWGQGTLVTVSS |
| 29 | 13408 HCDR1 | YTFSDYYMH |
| 30 | 13408 HCDR2 | IINPSGGVTAYAQKFQG |
| 31 | 13408 HCDR3 | ARGGTYYDYTY |
| 32 | 13408 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSEPPTEGGGTKVEIK |
| 33 | 13408 LCDR1 | RASQSISSWLA |
| 34 | 13408 LCDR2 | EASSLES |
| 35 | 13408 LCDR3 | QQYNSFPPT |

-continued

Table of Sequences

| SEQ ID NO | Description | Sequence |
|---|---|---|
| 36 | 13409 VH Sequence | QVQLVQSGAEVKKPGASVKVSCKASGYTFESYYMHWVRQAPGQGLEWMGIINPSGGVTAYAQKFQGRVTMTRDTSTSTVYMELSSLRSEDTAVYYCARGGTYYDYTYWGQGTLVTVSS |
| 37 | 13409 HCDR1 | YTFESYYMH |
| 38 | 13409 HCDR2 | IINPSGGVTAYAQKFQG |
| 39 | 13409 HCDR3 | ARGGTYYDYTY |
| 40 | 13409 VL Sequence | DIQMTQSPSTLSASVGDRVTITCRASQSISSWLAWYQQKPGKAPKLLIYEASSLESGVPSRFSGSGSGTEFTLTISS |
| 41 | 13409 LCDR1 | RASQSISSWLA |
| 42 | 13409 LCDR2 | EASSLES |
| 43 | 13409 LCDR3 | QQYNSFPPT |
| 44 | 13396 VH Sequence | QVQLVQSGAEVKKPGASVKVSCKASGYTFTSYYMHWVRQAPGQGLEWMGIINPDAGSTAYAQKFQGRVTMTRDTSTSTVYMELSSLRSEDTAVYYCARDQGHYYGMVWGQGTTVTVSS |
| 45 | 13396 HCDR1 | YTFTSYYMH |
| 46 | 13396 HCDR2 | IINPDAGSTAYAQKFQG |
| 47 | 13396 HCDR3 | ARDQGHYYGMGV |
| 48 | 13396 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQHNSYPPTFGGGTKVEIK |
| 49 | 13396 LCDR1 | RASQSISSWLA |
| 50 | 13396 LCDR2 | EASSLES |
| 51 | 13396 LCDR3 | QQHNSYPPT |
| 52 | 13398 VH Sequence | QVQLVQSGAEVKKPGASVKVSCKASGYTFGEYYMHWVRQAPGQGLEWMGIINPSEGSTGYAQKFQGRVTMTRDTSTSTVYMELSSLRSEDTAVYYCARDQGHYYGMGVWGQGTTVTVSS |
| 53 | 13398 HCDR1 | YTFGEYYMH |
| 54 | 13398 HCDR2 | IINPSEGSTGYAQKFQG |
| 55 | 13398 HCDR3 | ARDQGHYYGMGV |
| 56 | 13398 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQHNSYPPTFGGGTKVEIK |
| 57 | 13398 LCDR1 | RASQSISSWLA |
| 58 | 13398 LCDR2 | EASSLES |
| 59 | 13398 LCDR3 | QQHNSYPPT |
| 60 | 13399 VH Sequence | QVQLVQSGAEVKKPGASVKVSCKASGYTFSDYYMHWVRQAPGQGLEWMGIINPSAGSTGYAQKFQGRVIMIRDTSTSTVYMELSSLRSEDTAVYYCARDQGHYYGMGVWGQGTTVTVSS |
| 61 | 13399 HCDR1 | YTFSDYYMH |
| 62 | 13399 HCDR2 | IINPSAGSTGYAQKFQG |
| 63 | 13399 HCDR3 | ARDQGHYYGMGV |
| 64 | 13399 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQHNSYPPTFGGGTKVEIK |
| 65 | 13399 LCDR1 | RASQSISSWLA |
| 66 | 13399 LCDR2 | EASSLES |
| 67 | 13399 LCDR3 | QQHNSYPPT |

Table of Sequences

| SEQ ID NO | Description | Sequence |
|---|---|---|
| 68 | 13401 VH Sequence | QVQLVQSGAEVKKPGASVKVSCKASGYTFNSYYMSWVRQAPGQGLEWMGIIDPSKGSTAYAQKFQGRVIMIRDTSTSTVYMELSSLRSEDTAVYYCARHEYGMDVWGQGTTVTVSS |
| 69 | 13401 HCDR1 | YTFNSYYMS |
| 70 | 13401 HCDR2 | IIDPSKGSTAYAQKFQG |
| 71 | 13401 HCDR3 | ARHEYGMDV |
| 72 | 13401 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSFPPTFGGGTKVEIK |
| 73 | 13401 LCDR1 | RASQSISSWLA |
| 74 | 13401 LCDR2 | EASSLES |
| 75 | 13401 LCDR3 | QQYNSFPPT |
| 76 | 13402 VH Sequence | QVQLVQSGAEVKKPGASVKVSCKASGYTFTHYYMSWVRQAPGQGLEWMGMINPEGGSTAYAQKFQGRVIMIRDTSTSTVYMELSSLRSEDTAVYYCARHEYGMDVWGQGTTVTVSS |
| 77 | 13402 HCDR1 | YTFTHYYMS |
| 78 | 13402 HCDR2 | MINPEGGSTAYAQKFQG |
| 79 | 13402 HCDR3 | ARHEYGMDV |
| 80 | 13402 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSFPPTFGGGTKVEIK |
| 81 | 13402 LCDR1 | RASQSISSWLA |
| 82 | 13402 LCDR2 | EASSLES |
| 83 | 13402 LCDR3 | QQYNSFPPT |
| 84 | 13403 VH Sequence | QVQLVQSGAEVKKPGASVKVSCKASGYTFDSYYMSWVRQAPGQGLEWMGMINPSVGSTAYAQKFQGRVIMIRDTSTSTVYMELSSLRSEDTAVYYCARHEYGMDVWGQGTTVTVSS |
| 85 | 13403 HCDR1 | YTFDSYYMS |
| 86 | 13403 HCDR2 | MINPSVGSTAYAQKFQG |
| 87 | 13403 HCDR3 | ARHEYGMDV |
| 88 | 13403 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSFPPTFGGGTKVEIK |
| 89 | 13403 LCDR1 | RASQSISSWLA |
| 90 | 13403 LCDR2 | EASSLES |
| 91 | 13403 LCDR3 | QQYNSFPPT |
| 92 | 13404 VH Sequence | QVQLVQSGAEVKKPGASVKVSCKASGYTFASYAMSWVRQAPGQGLEWMGIIFPGGGSTSYAQKFQGRVIMIRDTSTSTVYMELSSLRSEDTAVYYCARHEYGMDVWGQGTTVTVSS |
| 93 | 13404 HCDR1 | YTFASYAMS |
| 94 | 13404 HCDR2 | IIFPGGGSTSYAQKFQG |
| 95 | 13404 HCDR3 | ARHEYGMDV |
| 96 | 13404 VL Sequence | DIQMTQSPSTLSASVGDRVTITCRASQSISSWLAWYQQKPGKAPKLLIYEASSLESGVPSRFSGSGSGTEFTLTISSLQPDDFATYYCQQYNSFPPTFGGGTKVEIK |
| 97 | 13404 LCDR1 | RASQSISSWLA |
| 98 | 13404 LCDR2 | EASSLES |

Table of Sequences

| SEQ ID NO | Description | Sequence |
|---|---|---|
| 99 | 13404 LCDR3 | QQYNSFPPT |
| 100 | 13405 VH Sequence | QVQLVQSGAEVKKPGASVKVSCKASGYTFASYYMGWVRQAPGQGLEWMGIINPA GGSTAYAQKFQGRVTMTRDTSTSTVYMELSSLRSEDTAVYYCARHEYGMDVWGQ GTTVTVSS |
| 101 | 13405 HCDR1 | YTFASYYMG |
| 102 | 13405 HCDR2 | IINPAGGSTAYAQKFQG |
| 103 | 13405 HCDR3 | ARHEYGMDV |
| 104 | 13405 VL Sequence | DIQMTQSPSTLSASVGDRVTITCRASQSISSWLAWYQQKPGKAPKLLIYEASSL ESGVPSRFSGSGSGTEFTLTISSLQPDDFATYYCQQYNSFPPTFGGGTKVEIK |
| 105 | 13405 LCDR1 | RASQSISSWLA |
| 106 | 13405 LCDR2 | EASSLES |
| 107 | 13405 LCDR3 | QQYNSFPPT |
| 108 | 12191 VH Sequence | QVQLVQSGAEVKKPGASVKVSCKASGYTFTSYYMHWVRQAPGQGLEWMGIINPG GGSTSYAQKFQGRVIMIRDTSTSTVYMELSSLRSEDTAVYYCARDQGHYYGMGV WGQGTTVTVSS |
| 109 | 12191 HCDR1 | YTFTSYYMH |
| 110 | 12191 HCDR2 | IINPGGGSTSYAQKFQG |
| 111 | 12191 HCDR3 | ARDQGHYYGMGV |
| 112 | 12191 VL Sequence | DIQMTQSPSTLSASVGDRVTITCRASQSISSWLAWYQQKPGKAPKLLIYEASSL ESGVPSRFSGSGSGTEFTLTISSLQPDDFATYYCQQHNSYPPTFGGGTKVEIK |
| 113 | 12191 LCDR1 | RASQSISSWLA |
| 114 | 12191 LCDR2 | EASSLES |
| 115 | 12191 LCDR3 | QQHNSYPPT |
| 116 | 12195 VH Sequence | QVQLVQSGAEVKKPGASVKVSCKASGYTFTSYYMSWVRQAPGQGLEWMGIINPS GGSTSYAQKFQGRVIMIRDTSTSTVYMELSSLRSEDTAVYYCARHEYGMDVWGQ GTTVTVSS |
| 117 | 12195 HCDR1 | YTFTSYYMS |
| 118 | 12195 HCDR2 | IINPSGGSTSYAQKFQG |
| 119 | 12195 HCDR3 | ARHEYGMDV |
| 120 | 12195 VL Sequence | DIQMTQSPSTLSASVGDRVTITCRASQSISSWLAWYQQKPGKAPKLLIYEASSL EASSLESGVPSRFSGSGSGTEFTLTISSLQPDDFATYYCQQYNSFPPTFGGGTK VEIK |
| 121 | 12195 LCDR1 | RASQSISSWLA |
| 122 | 12195 LCDR2 | EASSLES |
| 123 | 12195 LCDR3 | QQYNSFPPT |
| 124 | 12535 VH Sequence | EVQLLESGGGLVQPGGSLRLSCAASGFTFSHYLMSWVRQAPGKGLEWVSAISGS GKSTYYADSVKGRFTISRDNSKNTLYLQMNSLRAEDTAVYYCAKVYYGMPYWGQ GTLVTVSS |
| 125 | 12535 HCDR1 | FTFSHYLMS |
| 126 | 12535 HCDR2 | AISGSGKSTYYADSVKG |
| 127 | 12535 HCDR3 | AKVYYGMPY |
| 128 | 12535 VL Sequence | DIQMTQSPSSVSASVGDRVTITCRASQGIDSWLAWYQQKPGKAPKLLIYAASSL QSGVPSRFSGSGSGTDFILTISSLQPEDFATYYCQQASDVPWTFGGGTKVEIK |
| 129 | 12535 LCDR1 | RASQGIDSWLA |

| SEQ ID NO | Description | Sequence |
|---|---|---|
| 130 | 12535 LCDR2 | AASSLQS |
| 131 | 12535 LCDR3 | QQASDVPWT |
| 132 | 12536 VH Sequence | EVQLLESGGGLVQPGGSLRLSCAASGFTFSQYLMSWVRQAPGKGLEWVSAIGGS GASTYYADSVKGRFTISRDNSKNTLYLQMNSLRAEDTAVYYCAKVYYGMPYWGQ GTLVTVSS |
| 133 | 12536 HCDR1 | FTFSQYLMS |
| 134 | 12536 HCDR2 | AIGGSGASTYYADSVKG |
| 135 | 12536 HCDR3 | AKVYYGMPY |
| 136 | 12536 VL Sequence | DIQMTQSPSSVSASVGDRVTITCRASQGIDSWLAWYQQKPGKAPKLLIYAASSL QSGVPSRFSGSGSGTDFILTISSLQPEDFATYYCQQASDVPWTFGGGTKVEIK |
| 137 | 12536 LCDR1 | RASQGIDSWLA |
| 138 | 12536 LCDR2 | AASSLQS |
| 139 | 12536 LCDR3 | QQASDVPWT |
| 140 | 12541 VH Sequence | EVQLLESGGGLVQPGGSLRLSCAASGFTFRSYMMSWVRQAPGKGLEWVSAISGS GRDTYYADSVKGRFTISRDNSKNTLYLQMNSLRAEDTAVYYCAKVYYGMPYWGQ GTLVTVSS |
| 141 | 12541 HCDR1 | FTFRSYMMS |
| 142 | 12541 HCDR2 | AISGSGRDTYYADSVKG |
| 143 | 12541 HCDR3 | AKVYYGMPY |
| 144 | 12541 VL Sequence | DIQMTQSPSSVSASVGDRVTITCRASQGIDSWLAWYQQKPGKAPKLLIYAASSL QSGVPSRFSGSGSGTDFILTISSLQPEDFATYYCQQASDVPWTFGGGTKVEIK |
| 145 | 12541 LCDR1 | RASQGIDSWLA |
| 146 | 12541 LCDR2 | AASSLQS |
| 147 | 12541 LCDR3 | QQASDVPWT |
| 148 | 12543 VH Sequence | EVQLLE SGGGLVQPGGSLRLSCAASGFTFSQYMMSWVRQAPGKGLEWVSGISG SGGETYYADSVKGRFTISRDNSKNTLYLQMNSLRAEDTAVYYCAKVYYGMPYWG QGTLVTVSS |
| 149 | 12543 HCDR1 | FTFSQYMMS |
| 150 | 12543 HCDR2 | GISGSGGETYYADSVKG |
| 151 | 12543 HCDR3 | AKVYYGMPY |
| 152 | 12543 VL Sequence | DIQMTQSPSSVSASVGDRVTITCRASQGIDSWLAWYQQKPGKAPKLLIYAASSL QSGVPSRFSGSGSGTDFTLTISSLQPEDFATYYCQQASDVPWTFGGGTKVEIK |
| 153 | 12543 LCDR1 | RASQGIDSWLA |
| 154 | 12543 LCDR2 | AASSLQS |
| 155 | 12543 LCDR3 | QQASDVPWT |
| 156 | 12544 VH Sequence | EVQLLESGGGLVQPGGSLRLSCAASGFTFSSYLMSWVRQAPGKGLEWVSAISGS GSSTYYADSVKGRFTISRDNSKNTLYLQMNSLRAEDTAVYYCAKVYYGMPYWGQ GTLVTVSS |
| 157 | 12544 HCDR1 | FTFSSYLMS |
| 158 | 12544 HCDR2 | AISGSGSSTYYADSVKG |
| 159 | 12544 HCDR3 | AKVYYGMPY |
| 160 | 12544 VL Sequence | DIQMTQSPSSVSASVGDRVTITCRASQGIDSWLAWYQQKPGKAPKLLIYAASSL QSGVPSRFSGSGSGTDFTLTISSLQPEDFATYYCQQASDVPWTFGGGTKVEIK |
| 161 | 12544 LCDR1 | RASQGIDSWLA |

Table of Sequences

| SEQ ID NO | Description | Sequence |
|---|---|---|
| 162 | 12544 LCDR2 | AASSLQS |
| 163 | 12544 LCDR3 | QQASDVPWT |
| 164 | 12545 VH Sequence | EVQLLESGGGLVQPGGSLRLSCAASGFTFSHYLMSWVRQAPGKGLEWVSAISGSGGQTYYADSVKGRFTISRDNSKNTLYLQMNSLRAEDTAVYYCAKVYYGMPYWGQGTLVTVSS |
| 165 | 12545 HCDR1 | FTFSHYLMS |
| 166 | 12545 HCDR2 | AISGSGGQTYYADSVKG |
| 167 | 12545 HCDR3 | AKVYYGMPY |
| 168 | 12545 VL Sequence | DIQMTQSPSSVSASVGDRVTITCRASQGIDSWLAWYQQKPGKAPKLLIYAASSLQSGVPSRFSGSGSGTDFTLTISSLQPEDFATYYCQQASDVPWTFGGGTKVEIK |
| 169 | 12545 LCDR1 | RASQGIDSWLA |
| 170 | 12545 LCDR2 | AASSLQS |
| 171 | 12545 LCDR3 | QQASDVPWT |
| 172 | 12549 VH Sequence | EVQLLESGGGLVQPGGSLRLSCAASGFTFSQYSMSWVRQAPGKGLEWVSAISGGGGQTYYADSVKGRFTISRDNSKNTLYLQMNSLRAEDTAVYYCAKVYYGMPYWGQGTLVTVSS |
| 173 | 12549 HCDR1 | FTFSQYSMS |
| 174 | 12549 HCDR2 | AISGGGGQTYYADSVKG |
| 175 | 12549 HCDR3 | AKVYYGMPY |
| 176 | 12549 VL Sequence | DIQMTQSPSSVSASVGDRVTITCRASQGIDSWLAWYQQKPGKAPKLLIYAASSLQSGVPSRFSGSGSGTDFTLTISSLQPEDFATYYCQQASDVPWTFGGGTKVEIK |
| 177 | 12549 LCDR1 | RASQGIDSWLA |
| 178 | 12549 LCDR2 | AASSLQS |
| 179 | 12549 LCDR3 | QQASDVPWT |
| 180 | 12550 VH Sequence | EVQLLESGGGLVQPGGSLRLSCAASGFTFSLYAMSWVRQAPGKGLEWVSAISGSGGQTYYADSVKGRFTISRDNSKNTLYLQMNSLRAEDTAVYYCAKVYYGMPYWGQGTLVTVSS |
| 181 | 12550 HCDR1 | FTFSLYAMS |
| 182 | 12550 HCDR2 | AISGSGGQTYYADSVKG |
| 183 | 12550 HCDR3 | AKVYYGMPY |
| 184 | 12550 VL Sequence | DIQMTQSPSSVSASVGDRVTITCRASQGIDSWLAWYQQKPGKAPKLLIYAASSLQSGVPSRFSGSGSGTDFTLTISSLQPEDFATYYCQQASDVPWTFGGGTKVEIK |
| 185 | 12550 LCDR1 | RASQGIDSWLA |
| 186 | 12550 LCDR2 | AASSLQS |
| 187 | 12550 LCDR3 | QQASDVPWT |
| 188 | 12553 VH Sequence | QVQLVQSGAEVKKPGSSVKVSCKASGGTFGEYAISWVRQAPGQGLEWMGLIIPIFGTAQYAQKFQGRVTITADESTSTAYMELSSLRSEDTAVYYCARGASDGETGRLDLWGRGTLVTVSS |
| 189 | 12553 HCDR1 | GTFGEYAIS |
| 190 | 12553 HCDR2 | LIIPIFGTAQYAQKFQG |
| 191 | 12553 HCDR3 | ARGASDGETGRLDL |
| 192 | 12553 VL Sequence | DIVMTQSPDSLAVSLGERATINCKSSQSVLYSSNNKNYLATNYQQKPGQPPKLLIYTNASTRESGVPDRFSGSGSGTDFTLTISSLQAEDVAVYYCQQSYSLPFTFGGGTKVEIK |

| SEQ ID NO | Description | Sequence |
|---|---|---|
| 193 | 12553 LCDR1 | KSSQSVLYSSNNKNYLA |
| 194 | 12553 LCDR2 | MASTRES |
| 195 | 12553 LCDR3 | QQSYSLPFT |
| 196 | 12554 VH Sequence | QVQLVQSGAEVKKPGSSVKVSCKASGGTFSSYAISTAWRQAPGQGLEWMGLIIP AFGTANYAQKFQGRVTITADESTSTAYMELSSLRSEDTAVYYCARGASDGETGR LDLWGRGTLVTVSS |
| 197 | 12554 HCDR1 | GTFSSYAIS |
| 198 | 12554 HCDR2 | LIIPAFGTANYAQKFQG |
| 199 | 12554 HCDR3 | ARGASDGETGRLDL |
| 200 | 12554 VL Sequence | DIVMTQSPDSLAVSLGERATINCKSSQSVLYSSNNKNYLATNYQQKPGQPPKLL IYTNASTRESGVPDRFSGSGSGTDFTLTISSLQAEDVAVYYCQQSYSLPFTFGG GTKVEIK |
| 201 | 12554 LCDR1 | KSSQSVLYSSNNKNYLA |
| 202 | 12554 LCDR2 | MASTRES |
| 203 | 12554 LCDR3 | QQSYSLPFT |
| 204 | 12562 VH Sequence | QVQLVQSGAEVKKPGSSVKVSCKASGGTFSSYAISTAWRQAPGQGLEWMGVIIP IFGEANYAQKFQGRVTITADESTSTAYMELSSLRSEDTAVYYCARGASDGETGR LDLWGRGTLVTVSS |
| 205 | 12562 HCDR1 | GTFSSYAIS |
| 206 | 12562 HCDR2 | VIIPIFGEANYAQKFQG |
| 207 | 12562 HCDR3 | ARGASDGETGRLDL |
| 208 | 12562 VL Sequence | DIVMTQSPDSLAVSLGERATINCKSSQSVLYSSNNKNYLATNYQQKPGQPPKLL IYTNASTRESGVPDRFSGSGSGTDFTLTISSLQAEDVAVYYCQQSYSLPFTFGG GTKVEIK |
| 209 | 12562 LCDR1 | KSSQSVLYSSNNKNYLA |
| 210 | 12562 LCDR2 | MASTRES |
| 211 | 12562 LCDR3 | QQSYSLPFT |
| 212 | 12563 VH Sequence | QVQLVQSGAEVKKPGSSVKVSCKASGGTFGSYAISTAWRQAPGQGLEWMGVIIP IFGTANYAQKFQGRVTITADESTSTAYMELSSLRSEDTAVYYCARGASDGETGR LDLWGRGTLVTVSS |
| 213 | 12563 HCDR1 | GTFGSYAIS |
| 214 | 12563 HCDR2 | VIIPIFGTANYAQKFQG |
| 215 | 12563 HCDR3 | ARGASDGETGRLDL |
| 216 | 12563 VL Sequence | DIVMTQSPDSLAVSLGERATINCKSSQSVLYSSNNKNYLATNYQQKPGQPPKLL IYTNASTRESGVPDRFSGSGSGTDFTLTISSLQAEDVAVYYCQQSYSLPFTFGG GTKVEIK |
| 217 | 12563 LCDR1 | KSSQSVLYSSNNKNYLA |
| 218 | 12563 LCDR2 | MASTRES |
| 219 | 12563 LCDR3 | QQSYSLPFT |
| 220 | 12564 VH Sequence | QVQLVQSGAEVKKPGSSVKVSCKASGGTFSQYAISTAWRQAPGQGLEWMGVIIP SFGTANYAQKFQGRVTITADESTSTAYMELSSLRSEDTAVYYCARGASDGETGR LDLWGRGTLVTVSS |
| 221 | 12564 HCDR1 | GTFSQYAIS |
| 222 | 12564 HCDR2 | VIIPSFGTANYAQKFQG |

Table of Sequences

| SEQ ID NO | Description | Sequence |
|---|---|---|
| 223 | 12564 HCDR3 | ARGASDGETGRLDL |
| 224 | 12564 VL Sequence | DIVMTQSPDSLAVSLGERATINCKSSQSVLYSSNNKNYLATNYQQKPGQPPKLL IYTNASTRESGVPDRFSGSGSGTDFTLTISSLQAEDVAVYYCQQSYSLPFTFGG GTKVEIK |
| 225 | 12564 LCDR1 | KSSQSVLYSSNNKNYLA |
| 226 | 12564 LCDR2 | MASTRES |
| 227 | 12564 LCDR3 | QQSYSLPFT |
| 228 | 12565 VH Sequence | QVQLVQSGAEVKKPGSSVKVSCKASGGTFGEYAISTAWRQAPGQGLEWMGLIIP IFGTAQYAQKFQGRVTITADESTSTAYMELSSLRSEDTAVYYCARGASDGETGR LDLWGRGTLVTVSS |
| 229 | 12565 HCDR1 | GTFGEYAIS |
| 230 | 12565 HCDR2 | LIIPIFGTAQYAQKFQG |
| 231 | 12565 HCDR3 | ARGASDGETGRLDL |
| 232 | 12565 VL Sequence | DIVMTQSPDSLAVSLGERATINCKSSQSVLYSSNNKNYLAWYQQKPGQPPKLLI YWASTRESGVPDRFSGSGSGTDFTLTISSLQAEDVAVYYCQQSYSLPFTFGGGT KVEIK |
| 233 | 12565 LCDR1 | KSSQSVLYSSNNKNYLA |
| 234 | 12565 LCDR2 | MASTRES |
| 235 | 12565 LCDR3 | QQSYSLPFT |
| 236 | 12571 VH Sequence | QVQLVQSGAEVKKPGSSVKVSCKASGGTFGSSAISWVRQAPGQGLEWMGGIIPL FGTAAYAQKFQGRVTITADESTSTAYMELSSLRSEDTAVYYCARDGPGYSSSWY LDVWGQGTMVTVSS |
| 237 | 12571 HCDR1 | GTFGSSAIS |
| 238 | 12571 HCDR2 | GIIPLFGTAAYAQKFQG |
| 239 | 12571 HCDR3 | ARDGPGYSSSWYLDV |
| 240 | 12571 VL Sequence | EIVLTQSPATLSLSPGERATLSCRASQSVSSYLAWYQQKPGQAPRLLIYDASNR ATGIPARFSGSGSGTDFTLTISSLEPEDFAVYYCQQGYALPITFGGGTKVEIK |
| 241 | 12571 LCDR1 | RASQSVSSYLA |
| 242 | 12571 LCDR2 | DASNRAT |
| 243 | 12571 LCDR3 | QQGYALPIT |
| 244 | 12572 VH Sequence | QVQLVQSGAEVKKPGSSVKVSCKASGGTFSEYAISWVRQAPGQGLEWMGGIIPI FGTAVYAQKFQGRVTITADESTSTAYMELSSLRSEDTAVYYCARDGPGYSSSWY LDVWGQGTMVTVSS |
| 245 | 12572 HCDR1 | GTFSEYAIS |
| 246 | 12572 HCDR2 | GIIPIFGTAVYAQKFQG |
| 247 | 12572 HCDR3 | ARDGPGYSSSWYLDV |
| 248 | 12572 VL Sequence | EIVLTQSPATLSLSPGERATLSCRASQSVSSYLAWYQQKPGQAPRLLIYDASNR ATGIPARFSGSGSGTDFTLTISSLEPEDFAVYYCQQGYALPITFGGGTKVEIK |
| 249 | 12572 LCDR1 | RASQSVSSYLA |
| 250 | 12572 LCDR2 | DASNRAT |
| 251 | 12572 LCDR3 | QQGYALPIT |
| 252 | 12576 VH Sequence | QVQLVQSGAEVKKPGSSVKVSCKASGGTFSSYAISWVRQAPGQGLEWMGGIIPI FGTAVYAQKFQGRVTITADESTSTAYMELSSLRSEDTAVYYCARDGPGYSSSWY LDVWGQGTMVTVSS |
| 253 | 12576 HCDR1 | GTFSSYAIS |

| SEQ ID NO | Description | Sequence |
|---|---|---|
| 254 | 12576 HCDR2 | GIIPIFGTAVYAQKFQG |
| 255 | 12576 HCDR3 | ARDGPGYSSSWYLDV |
| 256 | 12576 VL Sequence | EIVLTQSPATLSLSPGERATLSCRASQSVSSYLAWYQQKPGQAPRLLIYDASNR ATGIPARFSGSGSGTDFILTISSLEPEDFAVYYCQQGYALPITFGGGTKVEIK |
| 257 | 12576 LCDR1 | RASQSVSSYLA |
| 258 | 12576 LCDR2 | DASNRAT |
| 259 | 12576 LCDR3 | QQGYALPIT |
| 260 | 12583 VH Sequence | QVQLVQSGAEVKKPGSSVKVSCKASGGTFSSSVISWVRQAPGQGLEWMGGIIPI FGTATYAQKFQGRVTITADESTSTAYMELSSLRSEDTAVYYCARDGPGYSSSWY LDVWGQGTMVTVSS |
| 261 | 12583 HCDR1 | GTFSSSVIS |
| 262 | 12583 HCDR2 | GIIPIFGTATYAQKFQG |
| 263 | 12583 HCDR3 | ARDGPGYSSSWYLDV |
| 264 | 12583 VL Sequence | EIVLTQSPATLSLSPGERATLSCRASQSVSSYLAWYQQKPGQAPRLLIYDASNR ATGIPARFSGSGSGTDFILTISSLEPEDFAVYYCQQGYALPITFGGGTKVEIK |
| 265 | 12583 LCDR1 | RASQSVSSYLA |
| 266 | 12583 LCDR2 | DASNRAT |
| 267 | 12583 LCDR3 | QQGYALPIT |
| 268 | 12584 VH Sequence | QVQLVQSGAEVKKPGASVKVSCKASGGTFDSYVISWVRQAPGQGLEWMGGIIPG FGVANYAQKFQGRVTITADESTSTAYMELSSLRSEDTAVYYCARDGPGYSSSWY LDVWGQGTMVTVSS |
| 269 | 12584 HCDR1 | GTFDSYVIS |
| 270 | 12584 HCDR2 | GIIPGFGVANYAQKFQG |
| 271 | 12584 HCDR3 | ARDGPGYSSSWYLDV |
| 272 | 12584 VL Sequence | EIVLTQSPATLSLSPGERATLSCRASQSVSSYLAWYQQKPGQAPRLLIYDASNR ATGIPARFSGSGSGTDFILTISSLEPEDFAVYYCQQGYALPITFGGGTKVEIK |
| 273 | 12584 LCDR1 | RASQSVSSYLA |
| 274 | 12584 LCDR2 | DASNRAT |
| 275 | 12584 LCDR3 | QQGYALPIT |
| 276 | 11613 VH Sequence | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCAKVYYGMPYWGQ GTLVTVSS |
| 277 | 11613 HCDR1 | FTFSSYAMS |
| 278 | 11613 HCDR2 | AISGSGGSTYYADSVKG |
| 279 | 11613 HCDR3 | AKVYYGMPY |
| 280 | 11613 VL Sequence | DIQMTQSPSSVSASVGDRVTITCRASQGIDSWLAWYQQKPGKAPKLLIYAASSL QSGVPSRFSGSGSGTDFILTISSLQPEDFATYYCQQASDVPWTFGGGTKVEIK |
| 281 | 11613 LCDR1 | RASQGIDSWLA |
| 282 | 11613 LCDR2 | AASSLQS |
| 283 | 11613 LCDR3 | QQASDVPWT |
| 284 | 11645 VH Sequence | QVQLVQSGAEVKKPGSSVKVSCKASGGTFSSYAISWVRQAPGQGLEWMGGIIPI FGTASYAQKFQGRVTITADESTSTAYMELSSLRSEDTAVYYCARDGPGYSSSWY LDVWGQGTMVTVSS |

Table of Sequences

| SEQ ID NO | Description | Sequence |
|---|---|---|
| 285 | 11645 HCDR1 | GTFSSYAIS |
| 286 | 11645 HCDR2 | GIIPIFGTASYAQKFQG |
| 287 | 11645 HCDR3 | ARDGPGYSSSWYLDV |
| 288 | 11645 VL Sequence | EIVLIQSPATLSLSPGERATLSCRASQSVSSYLAWYQQKPGQAPRLLIYDASNR ATGIPARFSGSGSGTDFILTISSLEPEDFAVYYCQQGYALPITFGGGTKVEIK |
| 289 | 11645 LCDR1 | RASQSVSSYLA |
| 290 | 11645 LCDR2 | DASNRAT |
| 291 | 11645 LCDR3 | QQGYALPIT |
| 292 | 11606 VH Sequence | QVQLVQSGAEVKKPGASVKVSCKASGYTFTSYYMHWVRQAPGQGLEWMGIINPS GGSTSYAQKFQGRVIMIRDTSTSTVYMELSSLRSEDTAVYYCARAGGYSYSWGG SNIWGQGTMVTVSS |
| 293 | 11606 HCDR1 | YTFTSYYMH |
| 294 | 11606 HCDR2 | IINPSGGSTSYAQKFQG |
| 295 | 11606 HCDR3 | ARAGGYSYSWGGSNI |
| 296 | 11606 VL Sequence | DIQMTQSPSTLSASVGDRVTITCRASQSISSWLAWYQQKPGKAPKLLIYKASSL ESGVPSRFSGSGSGTEFTLTISSLQPDDFATYYCQQDGSFPYTFGGGTKVEIK |
| 297 | 11606 LCDR1 | RASQSISSWLA |
| 298 | 11606 LCDR2 | KASSLES |
| 299 | 11606 LCDR3 | QQDGSFPYT |
| 300 | 12220 VH Sequence | QVQLVQSGAEVKKPGASVKVSCKASGYTFTSYYMHWVRQAPGQGLEWMGIINPG GGSTSYAQKFQGRVIMIRDTSTSTVYMELSSLRSEDTAVYYCARDPRYTTLIGS YYYGMDVWGQGTIVTVSS |
| 301 | 12220 HCDR1 | YTFTSYYMH |
| 302 | 12220 HCDR2 | IINPGGGSTSYAQKFQG |
| 303 | 12220 HCDR3 | ARDPRYTTLTGSYYYGMDV |
| 304 | 12220 VL Sequence | DIQLTQSPSSVSASVGDRVTITCRASQDISSWLAWYQQKPGKAPKLLIYAASSL QSGVPSRFSGSGSGTDFILTISSLQPEDFATYYCQQAVNFPPITFGGGTKVEIK |
| 305 | 12220 LCDR1 | RASQDISSWLA |
| 306 | 12220 LCDR2 | AASSLQS |
| 307 | 12220 LCDR3 | QQAVNFPPIT |
| 308 | 11624 VH Sequence | QVQLVQSGAEVKKPGASVKVSCKASGYTFTGYYMHWVRQAPGQGLEWMGWINPN SGGTKYAQKFQGRVIMTRDTSISTAYMELSRLRSDDTAVYYCAREASWLPGSLD VWGKGTTVTVSS |
| 309 | 11624 HCDR1 | YTFTGYYMH |
| 310 | 11624 HCDR2 | WINPNSGGTKYAQKFQG |
| 311 | 11624 HCDR3 | AREASWLPGSLDV |
| 312 | 11624 VL Sequence | DIVMTQSPDSLAVSLGERATINCKSSQSVLYSSNNKNYLAWYQQKPGQPPKLLI YWASTRESGVPDRFSGSGSGTDFILTISSLQAEDVAVYYCQQYDNFPITFGGGT KVEIK |
| 313 | 11624 LCDR1 | KSSQSVLYSSNNKNYLA |
| 314 | 11624 LCDR2 | WASTRES |
| 315 | 11624 LCDR3 | QQYDNFPIT |
| 316 | 12190 VH Sequence | QVQLVQSGAEVKKPGASVKVSCKASGYTFTSYYMHWVRQAPGQGLEWMGIINPG GGSTSYAQKFQGRVIMIRDTSTSTVYMELSSLRSEDTAVYYCARDPRYTTLIGS YYYGMDVWGQGTTVTVSS |

-continued

Table of Sequences

| SEQ ID NO | Description | Sequence |
|---|---|---|
| 317 | 12190 HCDR1 | YTFTSYYMH |
| 318 | 12190 HCDR2 | IINPGGGSTSYAQKFQG |
| 319 | 12190 HCDR3 | ARDPRYTTLTGSYYYGMDV |
| 320 | 12190 VL Sequence | DIQMTQSPSSLSASVGDRVTITCRASQSISSYLNWYQQKPGKAPKLLIYAASSL QSGVPSRFSGSGSGTDFILTISSLQPEDFATYYCQQSANTPPWTFGGGTKVEIK |
| 321 | 12190 LCDR1 | RASQSISSYLN |
| 322 | 12190 LCDR2 | AASSLQS |
| 323 | 12190 LCDR3 | QQSANTPPWT |
| 324 | 37A10 heavy chain variable region | EVQLVESGGGLVKPGGSLKLSCAASGF TFSDYWMDWVRQAPGKGLEWVGNIDED GSITEYSPFVKGRFTISRDNVKNTLYL QMNSVKSEDTATYYCTRWGRFGFDSWG QGTLVTVSS |
| 325 | 37A10 light chain variable region | DIVMTQSPSSLAVSAGDRVTINCKSSQ SLLSGSFNYLTWYQQKTGQAPKLLIFY ASTRHTGVPDRFMGSGSGTDFTLTINS FQTEDLGDYYCHHHYNAPPTFGPGTKL ELR |
| 326 | 37A10 VH CDR1 | GFTFSDYWMD |
| 327 | 37A10 VH CDR2 | NIDEDGSITEYSPFVKG |
| 328 | 37A10 VH CDR3 | WGRFGFDS |
| 329 | 37A10 VL CDR1 | KSSQSLLSGSFNYLT |
| 330 | 37A10 VL CDR2 | YASTRHT |
| 331 | 37A10 VL CDR3 | HHHYNAPPT |
| 332 | 37A10S713 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |
| 333 | 37A10S713 light chain variable region | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI K |
| 334 | 37A10S713 VH CDR1 | GFTFSDYWMD |
| 335 | 37A10S713 VH CDR2 | NIDEDGSITEYSPFVKG |
| 336 | 37A10S713 VH CDR3 | WGRFGFDS |
| 337 | 37A10S713 VL CDR1 | KSSQSLLSGSFNYLT |
| 338 | 37A10S713 VL CDR2 | YASTRHT |
| 339 | 37A10S713 VL CDR3 | HHHYNAPPT |
| 340 | 37A10S714 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |

-continued

Table of Sequences

| SEQ ID NO | Description | Sequence |
|---|---|---|
| 341 | 37A10S714 light chain variable region | DIVMTQSPDS LAVSLGERAT INCKSSQSLL SGSFNYLTWY QQKPGQPPKL LIFYASTRET GVPDRFSGSG SGTDFTLTIS SLQAEDVAVY YCHHHYNAPP TFGPGTKVDI K |
| 342 | 37A10S714 VH CDR1 | GFTFSDYWMD |
| 343 | 37A10S714 VH CDR2 | NIDEDGSITEYSPFVKG |
| 344 | 37A10S714 VH CDR3 | WGRFGFDS |
| 345 | 37A10S714 VL CDR1 | KSSQSLLSGSFNYLT |
| 346 | 37A10S714 VL CDR2 | YASTRET |
| 347 | 37A10S714 VL CDR3 | HHHYNAPPT |
| 348 | 37A10S715 heavy chain variable region | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSS |
| 349 | 37A10S715 light chain variable region | DIVMTQSPDS LAVSLGERAT INCKSSQSLL SGSFNYLTWY QQKPGQPPKL LIFYASTRQT GVPDRFSGSG SGTDFTLTIS SLQAEDVAVY YCHHHYNAPP TFGPGTKVDI K |
| 350 | 37A10S715 VH CDR1 | GFTFSDYWMD |
| 351 | 37A10S715 VH CDR2 | NIDEDGSITEYSPFVKG |
| 352 | 37A10S715 VH CDR3 | WGRFGFDS |
| 353 | 37A10S715 VL CDR1 | KSSQSLLSGSFNYLT |
| 354 | 37A10S715 VL CDR2 | YASTRQT |
| 355 | 37A10S715 VL CDR3 | HHHYNAPPT |
| 356 | 37A10S716 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |
| 357 | 37A10S716 light chain variable region | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI K |
| 358 | 37A10S716 VH CDR1 | GFTFSDYWMD |
| 359 | 37A10S716 VH CDR2 | NIDESGSITEYSPFVKG |
| 360 | 37A10S716 VH CDR3 | WGRFGFDS |
| 361 | 37A10S716 VL CDR1 | KSSQSLLSGSFNYLT |
| 362 | 37A10S716 VL CDR2 | YASTRHT |

-continued

Table of Sequences

| SEQ ID NO | Description | Sequence |
|---|---|---|
| 363 | 37A10S716 VL CDR3 | HHHYNAPPT |
| 364 | 37A10S717 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |
| 365 | 37A10S717 light chain variable region | DIVMTQSPDS LAVSLGERAT INCKSSQSLL SGSFNYLTWY QQKPGQPPKL LIFYASTRET GVPDRFSGSG SGTDFTLTIS SLQAEDVAVY YCHHHYNAPP TFGPGTKVDI K |
| 366 | 37A10S717 VH CDR1 | GFTFSDYWMD |
| 367 | 37A10S717 VH CDR2 | NIDESGSITEYSPFVKG |
| 368 | 37A10S717 VH CDR3 | WGRFGFDS |
| 369 | 37A10S717 VL CDR1 | KSSQSLLSGSFNYLT |
| 370 | 37A10S717 VL CDR2 | YASTRET |
| 371 | 37A10S717 VL CDR3 | HHHYNAPPT |
| 372 | 37A10S718 heavy chain variable region | EVQLVESGGG LVQPGGSLRL SCAASGFTFS DYWMDWVRQA PGKGLVWVSN IDESGSITEY SPFVKGRFTI SRDNAKNTLY LQMNSLRAED TAVYYCTRWG RFGFDSWGQG TLVTVSS |
| 373 | 37A10S718 light chain variable region | DIVMTQSPDS LAVSLGERAT INCKSSQSLL SGSFNYLTWY QQKPGQPPKL LIFYASTRQT GVPDRFSGSG SGTDFTLTIS SLQAEDVAVY YCHHHYNAPP TFGPGTKVDI K |
| 374 | 37A10S718 VH CDR1 | GFTFSDYWMD |
| 375 | 37A10S718 VH CDR2 | NIDESGSITEYSPFVKG |
| 376 | 37A10S718 VH CDR3 | WGRFGFDS |
| 377 | 37A10S718 VL CDR1 | KSSQSLLSGSFNYLT |
| 378 | 37A10S718 VL CDR2 | YASTRQT |
| 379 | 37A10S718 VL CDR3 | HHHYNAPPT |
| 380 | 37A10S713 human IgG1 heavy chain | EVQLVESGGG LVQPGGSLRL SCAASGFTFS DYWMDWVRQA PGKGLVWVSN IDEDGSITEY SPFVKGRFTI SRDNAKNTLY LQMNSLRAED TAVYYCTRWG RFGFDSWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKKVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 381 | 37A10S713 human K light chain | DIVMTQSPDS LAVSLGERAT INCKSSQSLL SGSFNYLTWY QQKPGQPPKL LIFYASTRHT GVPDRFSGSG SGTDFTLTIS SLQAEDVAVY YCHHHYNAPP TFGPGTKVDI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

What is claimed is:

1. A method of treating cancer in a human subject comprising administering to the subject an effective amount of an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

2. The method of claim 1, wherein the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC).

3. The method of claim 2, wherein the cancer is selected from melanoma, gastric cancer, head & neck squamous cell cancer (HNSCC), non-small cell lung cancer (NSCLC), and triple negative breast cancer (TNBC).

4. A method of enhancing an immune response in a human subject comprising administering to the subject an effective amount of an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25;

(e) LCDR2 comprising the amino acid sequence of SEQ ID NO: 26; and (f) LCDR3 comprising the amino acid sequence of SEQ ID NO: 27.

5. A method of increasing activation of a T cell in a human subject comprising administering to the subject an effective amount of an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25;

(e) LCDR2 comprising the amino acid sequence of SEQ ID NO: 26; and (f) LCDR3 comprising the amino acid sequence of SEQ ID NO: 27.

6. A method of reducing tumor size in a human subject with cancer comprising administering to the subject an effective amount of an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

7. The method of claim 1, wherein the subject is administered at least one additional therapeutic agent.

8. The method of claim 7, wherein the additional therapeutic agent is administered concurrently or sequentially with the anti-PD-1 antibody.

9. The method of claim 7 wherein the additional therapeutic agent is selected from an anti-ICOS antibody and an anti-CTLA4 antibody.

10. The method of claim 9, wherein the additional therapeutic agent is the anti-ICOS antibody.

11. A method of increasing the level of at least one cytokine selected from IFNγγ and IL-2 in a human subject, comprising administering to the subject an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

12. The method of claim 11, wherein the level of the cytokine is measured 1 hour, 2 hours, 3 hours, 4 hours, 5 hours, 6 hours, 8 hours, 10 hours, 12 hours, 14 hours, 16 hours, 18 hours, 20 hours, 22 hours, 24 hours, 36 hours, or 48 hours after administration of the anti-PD-1 antibody.

13. The method of claim 11, wherein the at least one cytokine is IFNγ.

14. The method of claim 11, wherein the at least one cytokine is IL-2.

15. The method of claim 11, wherein the level of the cytokine is measured 24 hours after administration of the antibody.

16. The method of claim 11, wherein the human subject has cancer.

17. The method of claim 16, wherein the cancer is selected from melanoma, non-small cell lung cancer (NSCLC), renal cell carcinoma (RCC), gastric cancer, bladder cancer, diffuse large B-cell lymphoma (DLBCL), Hodgkin's lymphoma, ovarian cancer, head & neck squamous cell cancer (HNSCC), mesothelioma, and triple negative breast cancer (TNBC).

18. The method of claim 17, wherein the cancer is selected from melanoma, gastric cancer, head & neck squamous cell cancer (HNSCC), non-small cell lung cancer (NSCLC), and triple negative breast cancer (TNBC).

19. The method of claim 11, wherein an immune response is enhanced following administration of the anti-PD-1 antibody.

20. The method of claim 11, wherein activation of T cells is increased following administration of the anti-PD-1 antibody.

21. The method of claim 16, wherein tumor size is decreased following administration of the anti-PD-1 antibody.

22. The method of claim 11, wherein the subject is administered at least one additional therapeutic agent.

23. The method of claim 22, wherein the additional therapeutic agent is administered concurrently or sequentially with the anti-PD-1 antibody.

24. The method of claim 22, wherein the additional therapeutic agent is selected from an anti-ICOS antibody and an anti-CTLA4 antibody.

25. The method of claim 24, wherein the additional therapeutic is the anti-ICOS antibody.

26. The method of claim 1, wherein a sample of the cancer has been determined to express PD-1.

27. The method of claim 26, wherein the sample shows 1+, 2+, or 3+staining of PD-1 by immunohistochemistry (IHC).

28. The method of claim 1, wherein the sample has been determined to have an elevated level of PD-L1.

29. The method of claim 28, wherein PD-L1 levels are determined using IHC.

30. The method of claim 1, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

31. The method of claim 1, wherein the anti-PD-1 antibody comprises a $V_H$ comprising the amino acid sequence of SEQ ID NO: 20 and a $V_L$ comprising the amino acid sequence of SEQ ID NO: 24.

32. The method of claim 1, wherein the anti-PD-1 antibody binds to human PD-1 with an affinity ($K_D$) of less than 5 nM.

33. The method of claim 32, wherein affinity is determined using biolayer interferometry.

34. The method of claim 1, wherein the anti-PD-1 antibody is an antibody fragment selected from a Fab, Fab', Fv, scFv or (Fab')2 fragment.

35. The method of claim 1, wherein the anti-PD-1 antibody is a full length antibody.

36. The method of claim 4, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

37. The method of claim 4, wherein the anti-PD-1 antibody comprises a $V_H$ comprising the amino acid sequence of SEQ ID NO: 20 and a $V_L$ comprising the amino acid sequence of SEQ ID NO: 24.

38. The method of claim 4, wherein the anti-PD-1 antibody binds to human PD-1 with an affinity (KD) of less than 5 nM.

39. The method of claim 38, wherein affinity is determined using biolayer interferometry.

40. The method of claim 4, wherein the anti-PD-1 antibody is an antibody fragment selected from a Fab, Fab', Fv, scFv or (Fab')2 fragment.

41. The method of claim 4, wherein the anti-PD-1 antibody is a full length antibody.

42. The method of claim 5, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

43. The method of claim 5, wherein the anti-PD-1 antibody comprises a $V_H$ comprising the amino acid sequence of SEQ ID NO: 20 and a $V_L$ comprising the amino acid sequence of SEQ ID NO: 24.

44. The method of claim 5, wherein the anti-PD-1 antibody binds to human PD-1 with an affinity (KD) of less than 5 nM.

45. The method of claim 44, wherein affinity is determined using biolayer interferometry.

46. The method of claim 5, wherein the anti-PD-1 antibody is an antibody fragment selected from a Fab, Fab', Fv, scFv or (Fab')2 fragment.

47. The method of claim 5, wherein the anti-PD-1 antibody is a full length antibody.

48. The method of claim 6, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

49. The method of claim 6, wherein the anti-PD-1 antibody comprises a $V_H$ comprising the amino acid sequence of SEQ ID NO: 20 and a $V_L$ comprising the amino acid sequence of SEQ ID NO: 24.

50. The method of claim 6, wherein the anti-PD-1 antibody binds to human PD-1 with an affinity (KD) of less than 5 nM.

51. The method of claim 50, wherein affinity is determined using biolayer interferometry.

52. The method of claim 6, wherein the anti-PD-1 antibody is an antibody fragment selected from a Fab, Fab', Fv, scFv or (Fab')2 fragment.

53. The method of claim 6, wherein the anti-PD-1 antibody is a full length antibody.

54. The method of claim 11, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

55. The method of claim 11, wherein the anti-PD-1 antibody comprises a $V_H$ comprising the amino acid sequence of SEQ ID NO: 20 and a $V_L$ comprising the amino acid sequence of SEQ ID NO: 24.

56. The method of claim 11, wherein the anti-PD-1 antibody binds to human PD-1 with an affinity (KD) of less than 5 nM.

57. The method of claim 56, wherein affinity is determined using biolayer interferometry.

58. The method of claim 11, wherein the anti-PD-1 antibody is an antibody fragment selected from a Fab, Fab', Fv, scFv or (Fab')2 fragment.

59. The method of claim 11, wherein the anti-PD-1 antibody is a full length antibody.

60. A method of stimulating the activity of an immune cell or reducing the downmodulation of an immune cell in a human subject comprising administering to the subject an effective amount of an anti-PD-1 antibody, wherein the anti-PD-1 antibody comprises (a) HCDR1 comprising the amino acid sequence of SEQ ID NO: 21; (b) HCDR2 comprising the amino acid sequence of SEQ ID NO: 22; (c) HCDR3 comprising the amino acid sequence of SEQ ID NO: 23; (d) LCDR1 comprising the amino acid sequence of SEQ ID NO: 25; (e) LCDR2 comprising the amino acid sequence of SEQ ID NO: 26; and (f) LCDR3 comprising the amino acid sequence of SEQ ID NO: 27.

61. The method of claim 60, wherein the anti-PD-1 antibody comprises a heavy chain variable region ($V_H$) that is at least 90% identical to the amino acid sequence of SEQ ID NO: 20 and a light chain variable region ($V_L$) that is at least 90% identical to the amino acid sequence of SEQ ID NO: 24.

62. The method of claim 60, wherein the anti-PD-1 antibody comprises a $V_H$ comprising the amino acid sequence of SEQ ID NO: 20 and a $V_L$ comprising the amino acid sequence of SEQ ID NO: 24.

63. The method of claim 60, wherein the anti-PD-1 antibody binds to human PD-1 with an affinity ($K_D$) of less than 5 nM.

64. The method of claim 63, wherein affinity is determined using biolayer interferometry.

65. The method of claim 60, wherein the anti-PD-1 antibody is an antibody fragment selected from a Fab, Fab', Fv, scFv or (Fab')2 fragment.

66. The method of claim 60, wherein the anti-PD-1 antibody is a full length antibody.

67. The method of claim 31, wherein the anti-PD-1 antibody is a full length antibody.

68. The method of claim 37, wherein the anti-PD-1 antibody is a full length antibody.

69. The method of claim 43, wherein the anti-PD-1 antibody is a full length antibody.

70. The method of claim 49, wherein the anti-PD-1 antibody is a full length antibody.

71. The method of claim 55, wherein the anti-PD-1 antibody is a full length antibody.

72. The method of claim 62, wherein the anti-PD-1 antibody is a full length antibody.

* * * * *

UNITED STATES PATENT AND TRADEMARK OFFICE
CERTIFICATE OF CORRECTION

PATENT NO.        : 11,384,147 B2
APPLICATION NO.   : 16/845805
DATED             : July 12, 2022
INVENTOR(S)       : George Robert Mabry, III and Stephen Sazinsky It is certified that error appears in the above-identified patent and that said Letters Patent is hereby corrected as shown below:

In the Claims

Claim 11, Column 322, Line 44, "IFNγγ" should be --IFNγ--.

Claim 27, Column 323, Line 34, "3+staining" should be --3+ staining--.

Claim 34, Column 323, Line 57, "(Fab')2" should be --(Fab')$_2$--.

Claim 40, Column 324, Line 10, "(Fab')2" should be --(Fab')$_2$--.

Claim 46, Column 324, Line 30, "(Fab')2" should be --(Fab')$_2$--.

Claim 50, Column 324, Line 44, "(KD)" should be --($K_D$)--.

Claim 52, Column 324, Line 50, "(Fab')2" should be --(Fab')$_2$--.

Claim 56, Column 324, Line 64, "(KD)" should be --($K_D$)--.

Claim 58, Column 325, Line 3, "(Fab')2" should be --(Fab')$_2$--.

Claim 65, Column 326, Line 10, "(Fab')2" should be --(Fab')$_2$--.

Signed and Sealed this
First Day of November, 2022

Katherine Kelly Vidal
*Director of the United States Patent and Trademark Office*

SEQUENCE LISTING

<160> NUMBER OF SEQ ID NOS: 406

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 288
<212> TYPE: PRT
<213> ORGANISM: Mus musculus

<400> SEQUENCE: 2

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala

```
                35                  40                  45
Asn Ala Thr Phe Thr Cys Ser Leu Ser Asn Trp Ser Glu Asp Leu Met
 50                  55                  60

Leu Asn Trp Asn Arg Leu Ser Pro Ser Asn Thr Glu Lys Gln Ala
 65                  70                  75                  80

Ala Phe Cys Asn Gly Leu Ser Gln Pro Val Gln Asp Ala Arg Phe Gln
                     85                  90                  95

Ile Ile Gln Leu Pro Asn Arg His Asp Phe His Met Asn Ile Leu Asp
                100                 105                 110

Thr Arg Arg Asn Asp Ser Gly Ile Tyr Leu Cys Gly Ala Ile Ser Leu
                115                 120                 125

His Pro Lys Ala Lys Ile Glu Glu Ser Pro Gly Ala Glu Leu Val Val
                130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
                180                 185                 190

Phe Cys Ser Thr Ser Met Ser Glu Ala Arg Gly Ala Gly Ser Lys Asp
                195                 200                 205

Asp Thr Leu Lys Glu Glu Pro Ser Ala Ala Pro Val Pro Ser Val Ala
210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Gly Ser Ala Asp Gly Leu Gln
                260                 265                 270

Gly Pro Arg Pro Pro Arg His Glu Asp Gly His Cys Ser Trp Pro Leu
                275                 280                 285

<210> SEQ ID NO 3
<211> LENGTH: 288
<212> TYPE: PRT
<213> ORGANISM: Macaca fascicularis

<400> SEQUENCE: 3

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                 20                  25                  30

Asn Pro Pro Thr Phe Ser Pro Ala Leu Leu Val Val Thr Glu Gly Asp
                 35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                     85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125
```

-continued

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 4
<211> LENGTH: 118
<212> TYPE: PRT
<213> ORGANISM: Homo sapiens

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
            100                 105                 110

Leu Val Thr Val Ser Ser
        115

<210> SEQ ID NO 5
<211> LENGTH: 9
<212> TYPE: PRT
<213> ORGANISM: Homo sapiens

<400> SEQUENCE: 5

Tyr Thr Phe Thr Ser Tyr Tyr Met His
1               5

<210> SEQ ID NO 6
<211> LENGTH: 17
<212> TYPE: PRT
<213> ORGANISM: Homo sapiens

```
<400> SEQUENCE: 6

Ile Ile Asn Pro Ser Gly Gly Ser Thr Ser Tyr Ala Gln Lys Phe Gln
1               5                   10                  15

Gly

<210> SEQ ID NO 7
<211> LENGTH: 11
<212> TYPE: PRT
<213> ORGANISM: Homo sapiens

<400> SEQUENCE: 7

Ala Arg Gly Gly Thr Tyr Tyr Asp Tyr Thr Tyr
1               5                   10

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 9
<211> LENGTH: 11
<212> TYPE: PRT
<213> ORGANISM: Homo sapiens

<400> SEQUENCE: 9

Arg Ala Ser Gln Ser Ile Ser Ser Trp Leu Ala
1               5                   10

<210> SEQ ID NO 10
<211> LENGTH: 7
<212> TYPE: PRT
<213> ORGANISM: Homo sapiens

<400> SEQUENCE: 10

Glu Ala Ser Ser Leu Glu Ser
1               5

<210> SEQ ID NO 11
<211> LENGTH: 9
<212> TYPE: PRT
<213> ORGANISM: Homo sapiens

<400> SEQUENCE: 11

Gln Gln Tyr Asn Ser Phe Pro Pro Thr
1               5
```

```
<210> SEQ ID NO 12
<211> LENGTH: 118
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Gln Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ala Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
            100                 105                 110

Leu Val Thr Val Ser Ser
        115

<210> SEQ ID NO 13
<211> LENGTH: 9
<212> TYPE: PRT
<213> ORGANISM: Homo sapiens

<400> SEQUENCE: 13

Tyr Thr Phe Asp Gln Tyr Tyr Met His
1               5

<210> SEQ ID NO 14
<211> LENGTH: 17
<212> TYPE: PRT
<213> ORGANISM: Homo sapiens

<400> SEQUENCE: 14

Ile Ile Asn Pro Ser Gly Gly Ser Thr Ala Tyr Ala Gln Lys Phe Gln
1               5                   10                  15

Gly

<210> SEQ ID NO 15
<211> LENGTH: 11
<212> TYPE: PRT
<213> ORGANISM: Homo sapiens

<400> SEQUENCE: 15

Ala Arg Gly Gly Thr Tyr Tyr Asp Tyr Thr Tyr
1               5                   10

<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Glu Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105
```

<210> SEQ ID NO 17
<211> LENGTH: 11
<212> TYPE: PRT
<213> ORGANISM: Homo sapiens

<400> SEQUENCE: 17

```
Arg Ala Ser Gln Ser Ile Ser Ser Trp Leu Ala
1               5                   10
```

<210> SEQ ID NO 18
<211> LENGTH: 7
<212> TYPE: PRT
<213> ORGANISM: Homo sapiens

<400> SEQUENCE: 18

```
Glu Ala Ser Ser Leu Glu Ser
1               5
```

<210> SEQ ID NO 19
<211> LENGTH: 9
<212> TYPE: PRT
<213> ORGANISM: Homo sapiens

<400> SEQUENCE: 19

```
Gln Gln Tyr Asn Ser Phe Pro Pro Thr
1               5
```

<210> SEQ ID NO 20
<211> LENGTH: 118
<212> TYPE: PRT
<213> ORGANISM: Homo sapiens

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser Tyr
                20                  25                  30

Tyr Met His Trp Val Arg Gln Ala Pro Gly Gln Gly Leu Glu Trp Met
            35                  40                  45

Gly Ile Ile Asn Pro Glu Gly Gly Ser Thr Ala Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
            100                 105                 110
```

Leu Val Thr Val Ser Ser
        115

<210> SEQ ID NO 21
<211> LENGTH: 9
<212> TYPE: PRT
<213> ORGANISM: Homo sapiens

<400> SEQUENCE: 21

Tyr Thr Phe Pro Ser Tyr Tyr Met His
1               5

<210> SEQ ID NO 22
<211> LENGTH: 17
<212> TYPE: PRT
<213> ORGANISM: Homo sapiens

<400> SEQUENCE: 22

Ile Ile Asn Pro Glu Gly Gly Ser Thr Ala Tyr Ala Gln Lys Phe Gln
1               5                   10                  15

Gly

<210> SEQ ID NO 23
<211> LENGTH: 11
<212> TYPE: PRT
<213> ORGANISM: Homo sapiens

<400> SEQUENCE: 23

Ala Arg Gly Gly Thr Tyr Tyr Asp Tyr Thr Tyr
1               5                   10

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 25
<211> LENGTH: 11
<212> TYPE: PRT
<213> ORGANISM: Homo sapiens

<400> SEQUENCE: 25

Arg Ala Ser Gln Ser Ile Ser Ser Trp Leu Ala
1               5                   10

<210> SEQ ID NO 26
<211> LENGTH: 7
<212> TYPE: PRT
<213> ORGANISM: Homo sapiens

<400> SEQUENCE: 26

Glu Ala Ser Ser Leu Glu Ser
1               5

<210> SEQ ID NO 27
<211> LENGTH: 9
<212> TYPE: PRT
<213> ORGANISM: Homo sapiens

<400> SEQUENCE: 27

Gln Gln Tyr Asn Ser Phe Pro Pro Thr
1               5

<210> SEQ ID NO 28
<211> LENGTH: 118
<212> TYPE: PRT
<213> ORGANISM: Homo sapiens

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Val Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
            100                 105                 110

Leu Val Thr Val Ser Ser
        115

<210> SEQ ID NO 29
<211> LENGTH: 9
<212> TYPE: PRT
<213> ORGANISM: Homo sapiens

<400> SEQUENCE: 29

Tyr Thr Phe Ser Asp Tyr Tyr Met His
1               5

<210> SEQ ID NO 30
<211> LENGTH: 17
<212> TYPE: PRT
<213> ORGANISM: Homo sapiens

<400> SEQUENCE: 30

Ile Ile Asn Pro Ser Gly Gly Val Thr Ala Tyr Ala Gln Lys Phe Gln
1               5                   10                  15

Gly

```
<210> SEQ ID NO 31
<211> LENGTH: 11
<212> TYPE: PRT
<213> ORGANISM: Homo sapiens

<400> SEQUENCE: 31

Ala Arg Gly Gly Thr Tyr Tyr Asp Tyr Thr Tyr
1               5                   10

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 33
<211> LENGTH: 11
<212> TYPE: PRT
<213> ORGANISM: Homo sapiens

<400> SEQUENCE: 33

Arg Ala Ser Gln Ser Ile Ser Ser Trp Leu Ala
1               5                   10

<210> SEQ ID NO 34
<211> LENGTH: 7
<212> TYPE: PRT
<213> ORGANISM: Homo sapiens

<400> SEQUENCE: 34

Glu Ala Ser Ser Leu Glu Ser
1               5

<210> SEQ ID NO 35
<211> LENGTH: 9
<212> TYPE: PRT
<213> ORGANISM: Homo sapiens

<400> SEQUENCE: 35

Gln Gln Tyr Asn Ser Phe Pro Pro Thr
1               5

<210> SEQ ID NO 36
<211> LENGTH: 118
<212> TYPE: PRT
<213> ORGANISM: Homo sapiens

<400> SEQUENCE: 36
```

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Glu Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Val Thr Ala Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Tyr Tyr Asp Tyr Thr Tyr Trp Gly Gln Gly Thr
            100                 105                 110

Leu Val Thr Val Ser Ser
        115

<210> SEQ ID NO 37
<211> LENGTH: 9
<212> TYPE: PRT
<213> ORGANISM: Homo sapiens

<400> SEQUENCE: 37

Tyr Thr Phe Glu Ser Tyr Tyr Met His
1               5

<210> SEQ ID NO 38
<211> LENGTH: 17
<212> TYPE: PRT
<213> ORGANISM: Homo sapiens

<400> SEQUENCE: 38

Ile Ile Asn Pro Ser Gly Gly Val Thr Ala Tyr Ala Gln Lys Phe Gln
1               5                   10                  15

Gly

<210> SEQ ID NO 39
<211> LENGTH: 11
<212> TYPE: PRT
<213> ORGANISM: Homo sapiens

<400> SEQUENCE: 39

Ala Arg Gly Gly Thr Tyr Tyr Asp Tyr Thr Tyr
1               5                   10

<210> SEQ ID NO 40
<211> LENGTH: 107
<212> TYPE: PRT
<213> ORGANISM: Homo sapiens

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 41
<211> LENGTH: 11
<212> TYPE: PRT
<213> ORGANISM: Homo sapiens

<400> SEQUENCE: 41

Arg Ala Ser Gln Ser Ile Ser Ser Trp Leu Ala
1               5                   10

<210> SEQ ID NO 42
<211> LENGTH: 7
<212> TYPE: PRT
<213> ORGANISM: Homo sapiens

<400> SEQUENCE: 42

Glu Ala Ser Ser Leu Glu Ser
1               5

<210> SEQ ID NO 43
<211> LENGTH: 9
<212> TYPE: PRT
<213> ORGANISM: Homo sapiens

<400> SEQUENCE: 43

Gln Gln Tyr Asn Ser Phe Pro Pro Thr
1               5

<210> SEQ ID NO 44
<211> LENGTH: 119
<212> TYPE: PRT
<213> ORGANISM: Homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Asp Ala Gly Ser Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Gly His Tyr Tyr Gly Met Gly Val Trp Gly Gln Gly
            100                 105                 110

Thr Thr Val Thr Val Ser Ser
        115

<210> SEQ ID NO 45
<211> LENGTH: 9
<212> TYPE: PRT
```

<213> ORGANISM: Homo sapiens

<400> SEQUENCE: 45

Tyr Thr Phe Thr Ser Tyr Tyr Met His
1               5

<210> SEQ ID NO 46
<211> LENGTH: 17
<212> TYPE: PRT
<213> ORGANISM: Homo sapiens

<400> SEQUENCE: 46

Ile Ile Asn Pro Asp Ala Gly Ser Thr Ala Tyr Ala Gln Lys Phe Gln
1               5                   10                  15

Gly

<210> SEQ ID NO 47
<211> LENGTH: 12
<212> TYPE: PRT
<213> ORGANISM: Homo sapiens

<400> SEQUENCE: 47

Ala Arg Asp Gln Gly His Tyr Tyr Gly Met Gly Val
1               5                   10

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Asn Ser Tyr Pro Pro
                85                  90                  95

Thr Phe Gly Gly Gly Thr Lys Val Glu Ile Lys
            100                 105

<210> SEQ ID NO 49
<211> LENGTH: 11
<212> TYPE: PRT
<213> ORGANISM: Homo sapiens

<400> SEQUENCE: 49

Arg Ala Ser Gln Ser Ile Ser Ser Trp Leu Ala
1               5                   10

<210> SEQ ID NO 50
<211> LENGTH: 7
<212> TYPE: PRT
<213> ORGANISM: Homo sapiens

<400> SEQUENCE: 50

Glu Ala Ser Ser Leu Glu Ser
1               5

<210> SEQ ID NO 51
<211> LENGTH: 9
<212> TYPE: PRT
<213> ORGANISM: Homo sapiens

<400> SEQUENCE: 51

Gln Gln His Asn Ser Tyr Pro Pro Thr
1               5

<210> SEQ ID NO 52
<211> LENGTH: 119
<212> TYPE: PRT
<213> ORGANISM: Homo sapiens

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Glu Tyr
            20                  25                  30

Tyr Met His Trp Val Arg Gln Ala Pro Gly Gln Gly Leu Glu Trp Met
        35                  40                  45

Gly Ile Ile Asn Pro Ser Glu Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Gly His Tyr Tyr Gly Met Gly Val Trp Gly Gln Gly
            100                 105                 110

Thr Thr Val Thr Val Ser Ser
        115

<210> SEQ ID NO 53
<211> LENGTH: 9
<212> TYPE: PRT
<213> ORGANISM: Homo sapiens

<400> SEQUENCE: 53

Tyr Thr Phe Gly Glu Tyr Tyr Met His
1               5

<210> SEQ ID NO 54
<211> LENGTH: 17
<212> TYPE: PRT
<213> ORGANISM: Homo sapiens

<400> SEQUENCE: 54

Ile Ile Asn Pro Ser Glu Gly Ser Thr Gly Tyr Ala Gln Lys Phe Gln
1               5                   10                  15

Gly

<210> SEQ ID NO 55
<211> LENGTH: 12
<212> TYPE: PRT
<213> ORGANISM: Homo sapiens

<400> SEQUENCE: 55

Ala Arg Asp Gln Gly His Tyr Tyr Gly Met Gly Val

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Glu Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln His Asn Ser Tyr Pro Pro
                85                  90                  95
Thr Phe Gly Gly Gly Thr Lys Val Glu Ile Lys
            100                 105

<210> SEQ ID NO 57
<211> LENGTH: 11
<212> TYPE: PRT
<213> ORGANISM: Homo sapiens

<400> SEQUENCE: 57

Arg Ala Ser Gln Ser Ile Ser Ser Trp Leu Ala
1               5                   10

<210> SEQ ID NO 58
<211> LENGTH: 7
<212> TYPE: PRT
<213> ORGANISM: Homo sapiens

<400> SEQUENCE: 58

Glu Ala Ser Ser Leu Glu Ser
1               5

<210> SEQ ID NO 59
<211> LENGTH: 9
<212> TYPE: PRT
<213> ORGANISM: Homo sapiens

<400> SEQUENCE: 59

Gln Gln His Asn Ser Tyr Pro Pro Thr
1               5

<210> SEQ ID NO 60
<211> LENGTH: 119
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ser Asp Tyr
            20                  25                  30
Tyr Met His Trp Val Arg Gln Ala Pro Gly Gln Gly Leu Glu Trp Met

```
                35                  40                  45
Gly Ile Ile Asn Pro Ser Ala Gly Ser Thr Gly Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Asp Gln Gly His Tyr Tyr Gly Met Gly Val Trp Gly Gln Gly
            100                 105                 110

Thr Thr Val Thr Val Ser Ser
            115

<210> SEQ ID NO 61
<211> LENGTH: 9
<212> TYPE: PRT
<213> ORGANISM: Homo sapiens

<400> SEQUENCE: 61

Tyr Thr Phe Ser Asp Tyr Tyr Met His
 1               5

<210> SEQ ID NO 62
<211> LENGTH: 17
<212> TYPE: PRT
<213> ORGANISM: Homo sapiens

<400> SEQUENCE: 62

Ile Ile Asn Pro Ser Ala Gly Ser Thr Gly Tyr Ala Gln Lys Phe Gln
 1               5                  10                  15

Gly

<210> SEQ ID NO 63
<211> LENGTH: 12
<212> TYPE: PRT
<213> ORGANISM: Homo sapiens

<400> SEQUENCE: 63

Ala Arg Asp Gln Gly His Tyr Tyr Gly Met Gly Val
 1               5                  10

<210> SEQ ID NO 64
<211> LENGTH: 107
<212> TYPE: PRT
<213> ORGANISM: Homo sapiens

<400> SEQUENCE: 64

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln His Asn Ser Tyr Pro Pro
                85                  90                  95

Thr Phe Gly Gly Gly Thr Lys Val Glu Ile Lys
```

<210> SEQ ID NO 65
<211> LENGTH: 11
<212> TYPE: PRT
<213> ORGANISM: Homo sapiens

<400> SEQUENCE: 65

Arg Ala Ser Gln Ser Ile Ser Ser Trp Leu Ala
1               5                   10

<210> SEQ ID NO 66
<211> LENGTH: 7
<212> TYPE: PRT
<213> ORGANISM: Homo sapiens

<400> SEQUENCE: 66

Glu Ala Ser Ser Leu Glu Ser
1               5

<210> SEQ ID NO 67
<211> LENGTH: 9
<212> TYPE: PRT
<213> ORGANISM: Homo sapiens

<400> SEQUENCE: 67

Gln Gln His Asn Ser Tyr Pro Pro Thr
1               5

<210> SEQ ID NO 68
<211> LENGTH: 116
<212> TYPE: PRT
<213> ORGANISM: Homo sapiens

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met Ser Trp Val Arg Gln Ala Pro Gly Gln Gly Leu Glu Trp Met
        35                  40                  45

Gly Ile Ile Asp Pro Ser Lys Gly Ser Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Tyr Gly Met Asp Val Trp Gly Gln Gly Thr Thr Val
            100                 105                 110

Thr Val Ser Ser
        115

<210> SEQ ID NO 69
<211> LENGTH: 9
<212> TYPE: PRT
<213> ORGANISM: Homo sapiens

<400> SEQUENCE: 69

Tyr Thr Phe Asn Ser Tyr Tyr Met Ser
1               5

```
<210> SEQ ID NO 70
<211> LENGTH: 17
<212> TYPE: PRT
<213> ORGANISM: Homo sapiens

<400> SEQUENCE: 70

Ile Ile Asp Pro Ser Lys Gly Ser Thr Ala Tyr Ala Gln Lys Phe Gln
1               5                   10                  15

Gly

<210> SEQ ID NO 71
<211> LENGTH: 9
<212> TYPE: PRT
<213> ORGANISM: Homo sapiens

<400> SEQUENCE: 71

Ala Arg His Glu Tyr Gly Met Asp Val
1               5

<210> SEQ ID NO 72
<211> LENGTH: 107
<212> TYPE: PRT
<213> ORGANISM: Homo sapiens

<400> SEQUENCE: 72

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 73
<211> LENGTH: 11
<212> TYPE: PRT
<213> ORGANISM: Homo sapiens

<400> SEQUENCE: 73

Arg Ala Ser Gln Ser Ile Ser Ser Trp Leu Ala
1               5                   10

<210> SEQ ID NO 74
<211> LENGTH: 7
<212> TYPE: PRT
<213> ORGANISM: Homo sapiens

<400> SEQUENCE: 74

Glu Ala Ser Ser Leu Glu Ser
1               5

<210> SEQ ID NO 75
<211> LENGTH: 9
<212> TYPE: PRT
<213> ORGANISM: Homo sapiens
```

<400> SEQUENCE: 75

Gln Gln Tyr Asn Ser Phe Pro Pro Thr
1               5

<210> SEQ ID NO 76
<211> LENGTH: 116
<212> TYPE: PRT
<213> ORGANISM: Homo sapiens

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
                20                  25                  30

Tyr Met Ser Trp Val Arg Gln Ala Pro Gly Gln Gly Leu Glu Trp Met
            35                  40                  45

Gly Met Ile Asn Pro Glu Gly Gly Ser Thr Ala Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Tyr Gly Met Asp Val Trp Gly Gln Gly Thr Thr Val
            100                 105                 110

Thr Val Ser Ser
        115

<210> SEQ ID NO 77
<211> LENGTH: 9
<212> TYPE: PRT
<213> ORGANISM: Homo sapiens

<400> SEQUENCE: 77

Tyr Thr Phe Thr His Tyr Tyr Met Ser
1               5

<210> SEQ ID NO 78
<211> LENGTH: 17
<212> TYPE: PRT
<213> ORGANISM: Homo sapiens

<400> SEQUENCE: 78

Met Ile Asn Pro Glu Gly Gly Ser Thr Ala Tyr Ala Gln Lys Phe Gln
1               5                   10                  15

Gly

<210> SEQ ID NO 79
<211> LENGTH: 9
<212> TYPE: PRT
<213> ORGANISM: Homo sapiens

<400> SEQUENCE: 79

Ala Arg His Glu Tyr Gly Met Asp Val
1               5

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 81
<211> LENGTH: 11
<212> TYPE: PRT
<213> ORGANISM: Homo sapiens

<400> SEQUENCE: 81

Arg Ala Ser Gln Ser Ile Ser Ser Trp Leu Ala
1               5                   10

<210> SEQ ID NO 82
<211> LENGTH: 7
<212> TYPE: PRT
<213> ORGANISM: Homo sapiens

<400> SEQUENCE: 82

Glu Ala Ser Ser Leu Glu Ser
1               5

<210> SEQ ID NO 83
<211> LENGTH: 9
<212> TYPE: PRT
<213> ORGANISM: Homo sapiens

<400> SEQUENCE: 83

Gln Gln Tyr Asn Ser Phe Pro Pro Thr
1               5

<210> SEQ ID NO 84
<211> LENGTH: 116
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Ser Tyr
            20                  25                  30

Tyr Met Ser Trp Val Arg Gln Ala Pro Gly Gln Gly Leu Glu Trp Met
        35                  40                  45

Gly Met Ile Asn Pro Ser Val Gly Ser Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
             85                  90                  95

Ala Arg His Glu Tyr Gly Met Asp Val Trp Gly Gln Gly Thr Thr Val
            100                 105                 110

Thr Val Ser Ser
        115

<210> SEQ ID NO 85
<211> LENGTH: 9
<212> TYPE: PRT
<213> ORGANISM: Homo sapiens

<400> SEQUENCE: 85

Tyr Thr Phe Asp Ser Tyr Tyr Met Ser
1               5

<210> SEQ ID NO 86
<211> LENGTH: 17
<212> TYPE: PRT
<213> ORGANISM: Homo sapiens

<400> SEQUENCE: 86

Met Ile Asn Pro Ser Val Gly Ser Thr Ala Tyr Ala Gln Lys Phe Gln
1               5                   10                  15

Gly

<210> SEQ ID NO 87
<211> LENGTH: 9
<212> TYPE: PRT
<213> ORGANISM: Homo sapiens

<400> SEQUENCE: 87

Ala Arg His Glu Tyr Gly Met Asp Val
1               5

<210> SEQ ID NO 88
<211> LENGTH: 107
<212> TYPE: PRT
<213> ORGANISM: Homo sapiens

<400> SEQUENCE: 88

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 89
<211> LENGTH: 11
<212> TYPE: PRT
<213> ORGANISM: Homo sapiens
```

```
<400> SEQUENCE: 89

Arg Ala Ser Gln Ser Ile Ser Ser Trp Leu Ala
1               5                   10

<210> SEQ ID NO 90
<211> LENGTH: 7
<212> TYPE: PRT
<213> ORGANISM: Homo sapiens

<400> SEQUENCE: 90

Glu Ala Ser Ser Leu Glu Ser
1               5

<210> SEQ ID NO 91
<211> LENGTH: 9
<212> TYPE: PRT
<213> ORGANISM: Homo sapiens

<400> SEQUENCE: 91

Gln Gln Tyr Asn Ser Phe Pro Pro Thr
1               5

<210> SEQ ID NO 92
<211> LENGTH: 116
<212> TYPE: PRT
<213> ORGANISM: Homo sapiens

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
                20                  25                  30

Ala Met Ser Trp Val Arg Gln Ala Pro Gly Gln Gly Leu Glu Trp Met
            35                  40                  45

Gly Ile Ile Phe Pro Gly Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Tyr Gly Met Asp Val Trp Gly Gln Gly Thr Thr Val
            100                 105                 110

Thr Val Ser Ser
        115

<210> SEQ ID NO 93
<211> LENGTH: 9
<212> TYPE: PRT
<213> ORGANISM: Homo sapiens

<400> SEQUENCE: 93

Tyr Thr Phe Ala Ser Tyr Ala Met Ser
1               5

<210> SEQ ID NO 94
<211> LENGTH: 17
<212> TYPE: PRT
<213> ORGANISM: Homo sapiens

<400> SEQUENCE: 94

Ile Ile Phe Pro Gly Gly Gly Ser Thr Ser Tyr Ala Gln Lys Phe Gln
```

<210> SEQ ID NO 95
<211> LENGTH: 9
<212> TYPE: PRT
<213> ORGANISM: Homo sapiens

<400> SEQUENCE: 95

Ala Arg His Glu Tyr Gly Met Asp Val
1               5

<210> SEQ ID NO 96
<211> LENGTH: 107
<212> TYPE: PRT
<213> ORGANISM: Homo sapiens

<400> SEQUENCE: 96

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 97
<211> LENGTH: 11
<212> TYPE: PRT
<213> ORGANISM: Homo sapiens

<400> SEQUENCE: 97

Arg Ala Ser Gln Ser Ile Ser Ser Trp Leu Ala
1               5                   10

<210> SEQ ID NO 98
<211> LENGTH: 7
<212> TYPE: PRT
<213> ORGANISM: Homo sapiens

<400> SEQUENCE: 98

Glu Ala Ser Ser Leu Glu Ser
1               5

<210> SEQ ID NO 99
<211> LENGTH: 9
<212> TYPE: PRT
<213> ORGANISM: Homo sapiens

<400> SEQUENCE: 99

Gln Gln Tyr Asn Ser Phe Pro Pro Thr
1               5

<210> SEQ ID NO 100

```
<211> LENGTH: 116
<212> TYPE: PRT
<213> ORGANISM: Homo sapiens

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ser Tyr
            20                  25                  30

Tyr Met Gly Trp Val Arg Gln Ala Pro Gly Gln Gly Leu Glu Trp Met
        35                  40                  45

Gly Ile Ile Asn Pro Ala Gly Gly Ser Thr Ala Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Tyr Gly Met Asp Val Trp Gly Gln Gly Thr Thr Val
            100                 105                 110

Thr Val Ser Ser
        115

<210> SEQ ID NO 101
<211> LENGTH: 9
<212> TYPE: PRT
<213> ORGANISM: Homo sapiens

<400> SEQUENCE: 101

Tyr Thr Phe Ala Ser Tyr Tyr Met Gly
1               5

<210> SEQ ID NO 102
<211> LENGTH: 17
<212> TYPE: PRT
<213> ORGANISM: Homo sapiens

<400> SEQUENCE: 102

Ile Ile Asn Pro Ala Gly Gly Ser Thr Ala Tyr Ala Gln Lys Phe Gln
1               5                   10                  15

Gly

<210> SEQ ID NO 103
<211> LENGTH: 9
<212> TYPE: PRT
<213> ORGANISM: Homo sapiens

<400> SEQUENCE: 103

Ala Arg His Glu Tyr Gly Met Asp Val
1               5

<210> SEQ ID NO 104
<211> LENGTH: 107
<212> TYPE: PRT
<213> ORGANISM: Homo sapiens

<400> SEQUENCE: 104

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Leu Leu Ile
             35                  40                  45

Tyr Glu Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Phe Pro Pro
                 85                  90                  95

Thr Phe Gly Gly Gly Thr Lys Val Glu Ile Lys
                100                 105
```

<210> SEQ ID NO 105
<211> LENGTH: 11
<212> TYPE: PRT
<213> ORGANISM: Homo sapiens

<400> SEQUENCE: 105

```
Arg Ala Ser Gln Ser Ile Ser Ser Trp Leu Ala
 1               5                  10
```

<210> SEQ ID NO 106
<211> LENGTH: 7
<212> TYPE: PRT
<213> ORGANISM: Homo sapiens

<400> SEQUENCE: 106

```
Glu Ala Ser Ser Leu Glu Ser
 1               5
```

<210> SEQ ID NO 107
<211> LENGTH: 9
<212> TYPE: PRT
<213> ORGANISM: Homo sapiens

<400> SEQUENCE: 107

```
Gln Gln Tyr Asn Ser Phe Pro Pro Thr
 1               5
```

<210> SEQ ID NO 108
<211> LENGTH: 119
<212> TYPE: PRT
<213> ORGANISM: Homo sapiens

<400> SEQUENCE: 108

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Gly Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gln Gly His Tyr Tyr Gly Met Gly Val Trp Gly Gln Gly
                100                 105                 110

Thr Thr Val Thr Val Ser Ser
            115
```

<210> SEQ ID NO 109
<211> LENGTH: 9
<212> TYPE: PRT
<213> ORGANISM: Homo sapiens

<400> SEQUENCE: 109

Tyr Thr Phe Thr Ser Tyr Tyr Met His
1               5

<210> SEQ ID NO 110
<211> LENGTH: 17
<212> TYPE: PRT
<213> ORGANISM: Homo sapiens

<400> SEQUENCE: 110

Ile Ile Asn Pro Gly Gly Gly Ser Thr Ser Tyr Ala Gln Lys Phe Gln
1               5                   10                  15

Gly

<210> SEQ ID NO 111
<211> LENGTH: 12
<212> TYPE: PRT
<213> ORGANISM: Homo sapiens

<400> SEQUENCE: 111

Ala Arg Asp Gln Gly His Tyr Tyr Gly Met Gly Val
1               5                   10

<210> SEQ ID NO 112
<211> LENGTH: 107
<212> TYPE: PRT
<213> ORGANISM: Homo sapiens

<400> SEQUENCE: 112

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Asn Ser Tyr Pro Pro
                85                  90                  95

Thr Phe Gly Gly Gly Thr Lys Val Glu Ile Lys
            100                 105

<210> SEQ ID NO 113
<211> LENGTH: 11
<212> TYPE: PRT
<213> ORGANISM: Homo sapiens

<400> SEQUENCE: 113

Arg Ala Ser Gln Ser Ile Ser Ser Trp Leu Ala
1               5                   10

<210> SEQ ID NO 114
<211> LENGTH: 7

<212> TYPE: PRT
<213> ORGANISM: Homo sapiens

<400> SEQUENCE: 114

Glu Ala Ser Ser Leu Glu Ser
1               5

<210> SEQ ID NO 115
<211> LENGTH: 9
<212> TYPE: PRT
<213> ORGANISM: Homo sapiens

<400> SEQUENCE: 115

Gln Gln His Asn Ser Tyr Pro Pro Thr
1               5

<210> SEQ ID NO 116
<211> LENGTH: 116
<212> TYPE: PRT
<213> ORGANISM: Homo sapiens

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Ser Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Glu Tyr Gly Met Asp Val Trp Gly Gln Gly Thr Thr Val
            100                 105                 110

Thr Val Ser Ser
        115

<210> SEQ ID NO 117
<211> LENGTH: 9
<212> TYPE: PRT
<213> ORGANISM: Homo sapiens

<400> SEQUENCE: 117

Tyr Thr Phe Thr Ser Tyr Tyr Met Ser
1               5

<210> SEQ ID NO 118
<211> LENGTH: 17
<212> TYPE: PRT
<213> ORGANISM: Homo sapiens

<400> SEQUENCE: 118

Ile Ile Asn Pro Ser Gly Gly Ser Thr Ser Tyr Ala Gln Lys Phe Gln
1               5                   10                  15

Gly

<210> SEQ ID NO 119
<211> LENGTH: 9
<212> TYPE: PRT

<213> ORGANISM: Homo sapiens

<400> SEQUENCE: 119

Ala Arg His Glu Tyr Gly Met Asp Val
1               5

<210> SEQ ID NO 120
<211> LENGTH: 107
<212> TYPE: PRT
<213> ORGANISM: Homo sapiens

<400> SEQUENCE: 120

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 121
<211> LENGTH: 11
<212> TYPE: PRT
<213> ORGANISM: Homo sapiens

<400> SEQUENCE: 121

Arg Ala Ser Gln Ser Ile Ser Ser Trp Leu Ala
1               5                   10

<210> SEQ ID NO 122
<211> LENGTH: 7
<212> TYPE: PRT
<213> ORGANISM: Homo sapiens

<400> SEQUENCE: 122

Glu Ala Ser Ser Leu Glu Ser
1               5

<210> SEQ ID NO 123
<211> LENGTH: 9
<212> TYPE: PRT
<213> ORGANISM: Homo sapiens

<400> SEQUENCE: 123

Gln Gln Tyr Asn Ser Phe Pro Pro Thr
1               5

<210> SEQ ID NO 124
<211> LENGTH: 116
<212> TYPE: PRT
<213> ORGANISM: Homo sapiens

<400> SEQUENCE: 124

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser His Tyr
            20                  25                  30

Leu Met Ser Trp Val Arg Gln Ala Pro Gly Lys Gly Leu Glu Trp Val
        35                  40                  45

Ser Ala Ile Ser Gly Ser Gly Lys Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 125
<211> LENGTH: 9
<212> TYPE: PRT
<213> ORGANISM: Homo sapiens

<400> SEQUENCE: 125

Phe Thr Phe Ser His Tyr Leu Met Ser
1               5

<210> SEQ ID NO 126
<211> LENGTH: 17
<212> TYPE: PRT
<213> ORGANISM: Homo sapiens

<400> SEQUENCE: 126

Ala Ile Ser Gly Ser Gly Lys Ser Thr Tyr Tyr Ala Asp Ser Val Lys
1               5                   10                  15

Gly

<210> SEQ ID NO 127
<211> LENGTH: 9
<212> TYPE: PRT
<213> ORGANISM: Homo sapiens

<400> SEQUENCE: 127

Ala Lys Val Tyr Tyr Gly Met Pro Tyr
1               5

<210> SEQ ID NO 128
<211> LENGTH: 107
<212> TYPE: PRT
<213> ORGANISM: Homo sapiens

<400> SEQUENCE: 128

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80
```

Glu Asp Phe Ala Thr Tyr Tyr Cys Gln Gln Ala Ser Asp Val Pro Trp
            85                  90                  95

Thr Phe Gly Gly Gly Thr Lys Val Glu Ile Lys
            100                 105

<210> SEQ ID NO 129
<211> LENGTH: 11
<212> TYPE: PRT
<213> ORGANISM: Homo sapiens

<400> SEQUENCE: 129

Arg Ala Ser Gln Gly Ile Asp Ser Trp Leu Ala
1               5                   10

<210> SEQ ID NO 130
<211> LENGTH: 7
<212> TYPE: PRT
<213> ORGANISM: Homo sapiens

<400> SEQUENCE: 130

Ala Ala Ser Ser Leu Gln Ser
1               5

<210> SEQ ID NO 131
<211> LENGTH: 9
<212> TYPE: PRT
<213> ORGANISM: Homo sapiens

<400> SEQUENCE: 131

Gln Gln Ala Ser Asp Val Pro Trp Thr
1               5

<210> SEQ ID NO 132
<211> LENGTH: 116
<212> TYPE: PRT
<213> ORGANISM: Homo sapiens

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Leu Met Ser Trp Val Arg Gln Ala Pro Gly Lys Gly Leu Glu Trp Val
        35                  40                  45

Ser Ala Ile Gly Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 133
<211> LENGTH: 9
<212> TYPE: PRT
<213> ORGANISM: Homo sapiens

<400> SEQUENCE: 133

```
Phe Thr Phe Ser Gln Tyr Leu Met Ser
1               5

<210> SEQ ID NO 134
<211> LENGTH: 17
<212> TYPE: PRT
<213> ORGANISM: Homo sapiens

<400> SEQUENCE: 134

Ala Ile Gly Gly Ser Gly Ala Ser Thr Tyr Tyr Ala Asp Ser Val Lys
1               5                   10                  15

Gly

<210> SEQ ID NO 135
<211> LENGTH: 9
<212> TYPE: PRT
<213> ORGANISM: Homo sapiens

<400> SEQUENCE: 135

Ala Lys Val Tyr Tyr Gly Met Pro Tyr
1               5

<210> SEQ ID NO 136
<211> LENGTH: 107
<212> TYPE: PRT
<213> ORGANISM: Homo sapiens

<400> SEQUENCE: 136

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105

<210> SEQ ID NO 137
<211> LENGTH: 11
<212> TYPE: PRT
<213> ORGANISM: Homo sapiens

<400> SEQUENCE: 137

Arg Ala Ser Gln Gly Ile Asp Ser Trp Leu Ala
1               5                   10

<210> SEQ ID NO 138
<211> LENGTH: 7
<212> TYPE: PRT
<213> ORGANISM: Homo sapiens

<400> SEQUENCE: 138

Ala Ala Ser Ser Leu Gln Ser
1               5
```

<210> SEQ ID NO 139
<211> LENGTH: 9
<212> TYPE: PRT
<213> ORGANISM: Homo sapiens

<400> SEQUENCE: 139

Gln Gln Ala Ser Asp Val Pro Trp Thr
1               5

<210> SEQ ID NO 140
<211> LENGTH: 116
<212> TYPE: PRT
<213> ORGANISM: Homo sapiens

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Met Met Ser Trp Val Arg Gln Ala Pro Gly Lys Gly Leu Glu Trp Val
        35                  40                  45

Ser Ala Ile Ser Gly Ser Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 141
<211> LENGTH: 9
<212> TYPE: PRT
<213> ORGANISM: Homo sapiens

<400> SEQUENCE: 141

Phe Thr Phe Arg Ser Tyr Met Met Ser
1               5

<210> SEQ ID NO 142
<211> LENGTH: 17
<212> TYPE: PRT
<213> ORGANISM: Homo sapiens

<400> SEQUENCE: 142

Ala Ile Ser Gly Ser Gly Arg Asp Thr Tyr Tyr Ala Asp Ser Val Lys
1               5                   10                  15

Gly

<210> SEQ ID NO 143
<211> LENGTH: 9
<212> TYPE: PRT
<213> ORGANISM: Homo sapiens

<400> SEQUENCE: 143

Ala Lys Val Tyr Tyr Gly Met Pro Tyr
1               5

```
<210> SEQ ID NO 144
<211> LENGTH: 107
<212> TYPE: PRT
<213> ORGANISM: Homo sapiens

<400> SEQUENCE: 144

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105

<210> SEQ ID NO 145
<211> LENGTH: 11
<212> TYPE: PRT
<213> ORGANISM: Homo sapiens

<400> SEQUENCE: 145

Arg Ala Ser Gln Gly Ile Asp Ser Trp Leu Ala
1               5                   10

<210> SEQ ID NO 146
<211> LENGTH: 7
<212> TYPE: PRT
<213> ORGANISM: Homo sapiens

<400> SEQUENCE: 146

Ala Ala Ser Ser Leu Gln Ser
1               5

<210> SEQ ID NO 147
<211> LENGTH: 9
<212> TYPE: PRT
<213> ORGANISM: Homo sapiens

<400> SEQUENCE: 147

Gln Gln Ala Ser Asp Val Pro Trp Thr
1               5

<210> SEQ ID NO 148
<211> LENGTH: 116
<212> TYPE: PRT
<213> ORGANISM: Homo sapiens

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Met Met Ser Trp Val Arg Gln Ala Pro Gly Lys Gly Leu Glu Trp Val
        35                  40                  45

Ser Gly Ile Ser Gly Ser Gly Gly Glu Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Tyr Tyr Gly Met Pro Tyr Trp Gly Gln Gly Thr Leu Val
                100                 105                 110

Thr Val Ser Ser
        115

<210> SEQ ID NO 149
<211> LENGTH: 9
<212> TYPE: PRT
<213> ORGANISM: Homo sapiens

<400> SEQUENCE: 149

Phe Thr Phe Ser Gln Tyr Met Met Ser
 1               5

<210> SEQ ID NO 150
<211> LENGTH: 17
<212> TYPE: PRT
<213> ORGANISM: Homo sapiens

<400> SEQUENCE: 150

Gly Ile Ser Gly Ser Gly Gly Glu Thr Tyr Tyr Ala Asp Ser Val Lys
 1               5                  10                  15

Gly

<210> SEQ ID NO 151
<211> LENGTH: 9
<212> TYPE: PRT
<213> ORGANISM: Homo sapiens

<400> SEQUENCE: 151

Ala Lys Val Tyr Tyr Gly Met Pro Tyr
 1               5

<210> SEQ ID NO 152
<211> LENGTH: 107
<212> TYPE: PRT
<213> ORGANISM: Homo sapiens

<400> SEQUENCE: 152

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Asp Ser Trp
                 20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ser Asp Val Pro Trp
                 85                  90                  95

Thr Phe Gly Gly Gly Thr Lys Val Glu Ile Lys
                100                 105
```

```
<210> SEQ ID NO 153
<211> LENGTH: 11
<212> TYPE: PRT
<213> ORGANISM: Homo sapiens

<400> SEQUENCE: 153

Arg Ala Ser Gln Gly Ile Asp Ser Trp Leu Ala
1               5                   10

<210> SEQ ID NO 154
<211> LENGTH: 7
<212> TYPE: PRT
<213> ORGANISM: Homo sapiens

<400> SEQUENCE: 154

Ala Ala Ser Ser Leu Gln Ser
1               5

<210> SEQ ID NO 155
<211> LENGTH: 9
<212> TYPE: PRT
<213> ORGANISM: Homo sapiens

<400> SEQUENCE: 155

Gln Gln Ala Ser Asp Val Pro Trp Thr
1               5

<210> SEQ ID NO 156
<211> LENGTH: 116
<212> TYPE: PRT
<213> ORGANISM: Homo sapiens

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 157
<211> LENGTH: 9
<212> TYPE: PRT
<213> ORGANISM: Homo sapiens

<400> SEQUENCE: 157

Phe Thr Phe Ser Ser Tyr Leu Met Ser
1               5

<210> SEQ ID NO 158
<211> LENGTH: 17
<212> TYPE: PRT
```

<213> ORGANISM: Homo sapiens

<400> SEQUENCE: 158

Ala Ile Ser Gly Ser Gly Ser Ser Thr Tyr Tyr Ala Asp Ser Val Lys
1               5                   10                  15
Gly

<210> SEQ ID NO 159
<211> LENGTH: 9
<212> TYPE: PRT
<213> ORGANISM: Homo sapiens

<400> SEQUENCE: 159

Ala Lys Val Tyr Tyr Gly Met Pro Tyr
1               5

<210> SEQ ID NO 160
<211> LENGTH: 107
<212> TYPE: PRT
<213> ORGANISM: Homo sapiens

<400> SEQUENCE: 160

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105

<210> SEQ ID NO 161
<211> LENGTH: 11
<212> TYPE: PRT
<213> ORGANISM: Homo sapiens

<400> SEQUENCE: 161

Arg Ala Ser Gln Gly Ile Asp Ser Trp Leu Ala
1               5                   10

<210> SEQ ID NO 162
<211> LENGTH: 7
<212> TYPE: PRT
<213> ORGANISM: Homo sapiens

<400> SEQUENCE: 162

Ala Ala Ser Ser Leu Gln Ser
1               5

<210> SEQ ID NO 163
<211> LENGTH: 9
<212> TYPE: PRT
<213> ORGANISM: Homo sapiens

<400> SEQUENCE: 163

```
Gln Gln Ala Ser Asp Val Pro Trp Thr
1               5

<210> SEQ ID NO 164
<211> LENGTH: 116
<212> TYPE: PRT
<213> ORGANISM: Homo sapiens

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Leu Met Ser Trp Val Arg Gln Ala Pro Gly Lys Gly Leu Glu Trp Val
        35                  40                  45

Ser Ala Ile Ser Gly Ser Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 165
<211> LENGTH: 9
<212> TYPE: PRT
<213> ORGANISM: Homo sapiens

<400> SEQUENCE: 165

Phe Thr Phe Ser His Tyr Leu Met Ser
1               5

<210> SEQ ID NO 166
<211> LENGTH: 17
<212> TYPE: PRT
<213> ORGANISM: Homo sapiens

<400> SEQUENCE: 166

Ala Ile Ser Gly Ser Gly Gly Gln Thr Tyr Tyr Ala Asp Ser Val Lys
1               5                   10                  15

Gly

<210> SEQ ID NO 167
<211> LENGTH: 9
<212> TYPE: PRT
<213> ORGANISM: Homo sapiens

<400> SEQUENCE: 167

Ala Lys Val Tyr Tyr Gly Met Pro Tyr
1               5

<210> SEQ ID NO 168
<211> LENGTH: 107
<212> TYPE: PRT
<213> ORGANISM: Homo sapiens

<400> SEQUENCE: 168

Asp Ile Gln Met Thr Gln Ser Pro Ser Ser Val Ser Ala Ser Val Gly
```

```
            1               5                  10                  15
Asp Arg Val Thr Ile Thr Cys Arg Ala Ser Gln Gly Ile Asp Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
                100                 105

<210> SEQ ID NO 169
<211> LENGTH: 11
<212> TYPE: PRT
<213> ORGANISM: Homo sapiens

<400> SEQUENCE: 169

Arg Ala Ser Gln Gly Ile Asp Ser Trp Leu Ala
1               5                   10

<210> SEQ ID NO 170
<211> LENGTH: 7
<212> TYPE: PRT
<213> ORGANISM: Homo sapiens

<400> SEQUENCE: 170

Ala Ala Ser Ser Leu Gln Ser
1               5

<210> SEQ ID NO 171
<211> LENGTH: 9
<212> TYPE: PRT
<213> ORGANISM: Homo sapiens

<400> SEQUENCE: 171

Gln Gln Ala Ser Asp Val Pro Trp Thr
1               5

<210> SEQ ID NO 172
<211> LENGTH: 116
<212> TYPE: PRT
<213> ORGANISM: Homo sapiens

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Ser Met Ser Trp Val Arg Gln Ala Pro Gly Lys Gly Leu Glu Trp Val
        35                  40                  45

Ser Ala Ile Ser Gly Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Val Tyr Tyr Gly Met Pro Tyr Trp Gly Gln Gly Thr Leu Val
            100                 105                 110
Thr Val Ser Ser
        115

<210> SEQ ID NO 173
<211> LENGTH: 9
<212> TYPE: PRT
<213> ORGANISM: Homo sapiens

<400> SEQUENCE: 173

Phe Thr Phe Ser Gln Tyr Ser Met Ser
1               5

<210> SEQ ID NO 174
<211> LENGTH: 17
<212> TYPE: PRT
<213> ORGANISM: Homo sapiens

<400> SEQUENCE: 174

Ala Ile Ser Gly Gly Gly Gly Gln Thr Tyr Tyr Ala Asp Ser Val Lys
1               5                   10                  15
Gly

<210> SEQ ID NO 175
<211> LENGTH: 9
<212> TYPE: PRT
<213> ORGANISM: Homo sapiens

<400> SEQUENCE: 175

Ala Lys Val Tyr Tyr Gly Met Pro Tyr
1               5

<210> SEQ ID NO 176
<211> LENGTH: 107
<212> TYPE: PRT
<213> ORGANISM: Homo sapiens

<400> SEQUENCE: 176

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105

<210> SEQ ID NO 177
<211> LENGTH: 11
<212> TYPE: PRT
<213> ORGANISM: Homo sapiens

<400> SEQUENCE: 177

Arg Ala Ser Gln Gly Ile Asp Ser Trp Leu Ala
1               5                   10
```

```
<210> SEQ ID NO 178
<211> LENGTH: 7
<212> TYPE: PRT
<213> ORGANISM: Homo sapiens

<400> SEQUENCE: 178

Ala Ala Ser Ser Leu Gln Ser
1               5

<210> SEQ ID NO 179
<211> LENGTH: 9
<212> TYPE: PRT
<213> ORGANISM: Homo sapiens

<400> SEQUENCE: 179

Gln Gln Ala Ser Asp Val Pro Trp Thr
1               5

<210> SEQ ID NO 180
<211> LENGTH: 116
<212> TYPE: PRT
<213> ORGANISM: Homo sapiens

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 181
<211> LENGTH: 9
<212> TYPE: PRT
<213> ORGANISM: Homo sapiens

<400> SEQUENCE: 181

Phe Thr Phe Ser Leu Tyr Ala Met Ser
1               5

<210> SEQ ID NO 182
<211> LENGTH: 17
<212> TYPE: PRT
<213> ORGANISM: Homo sapiens

<400> SEQUENCE: 182

Ala Ile Ser Gly Ser Gly Gly Gln Thr Tyr Tyr Ala Asp Ser Val Lys
1               5                   10                  15

Gly
```

<210> SEQ ID NO 183
<211> LENGTH: 9
<212> TYPE: PRT
<213> ORGANISM: Homo sapiens

<400> SEQUENCE: 183

Ala Lys Val Tyr Tyr Gly Met Pro Tyr
1               5

<210> SEQ ID NO 184
<211> LENGTH: 107
<212> TYPE: PRT
<213> ORGANISM: Homo sapiens

<400> SEQUENCE: 184

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105

<210> SEQ ID NO 185
<211> LENGTH: 11
<212> TYPE: PRT
<213> ORGANISM: Homo sapiens

<400> SEQUENCE: 185

Arg Ala Ser Gln Gly Ile Asp Ser Trp Leu Ala
1               5                   10

<210> SEQ ID NO 186
<211> LENGTH: 7
<212> TYPE: PRT
<213> ORGANISM: Homo sapiens

<400> SEQUENCE: 186

Ala Ala Ser Ser Leu Gln Ser
1               5

<210> SEQ ID NO 187
<211> LENGTH: 9
<212> TYPE: PRT
<213> ORGANISM: Homo sapiens

<400> SEQUENCE: 187

Gln Gln Ala Ser Asp Val Pro Trp Thr
1               5

<210> SEQ ID NO 188
<211> LENGTH: 121
<212> TYPE: PRT
<213> ORGANISM: Homo sapiens

<400> SEQUENCE: 188

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Glu Tyr
            20                  25                  30

Ala Ile Ser Trp Val Arg Gln Ala Pro Gly Gln Gly Leu Glu Trp Met
        35                  40                  45

Gly Leu Ile Ile Pro Ile Phe Gly Thr Ala Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Asp Gly Glu Thr Gly Arg Leu Asp Leu Trp Gly
            100                 105                 110

Arg Gly Thr Leu Val Thr Val Ser Ser
        115                 120

<210> SEQ ID NO 189
<211> LENGTH: 9
<212> TYPE: PRT
<213> ORGANISM: Homo sapiens

<400> SEQUENCE: 189

Gly Thr Phe Gly Glu Tyr Ala Ile Ser
1               5

<210> SEQ ID NO 190
<211> LENGTH: 17
<212> TYPE: PRT
<213> ORGANISM: Homo sapiens

<400> SEQUENCE: 190

Leu Ile Ile Pro Ile Phe Gly Thr Ala Gln Tyr Ala Gln Lys Phe Gln
1               5                   10                  15

Gly

<210> SEQ ID NO 191
<211> LENGTH: 14
<212> TYPE: PRT
<213> ORGANISM: Homo sapiens

<400> SEQUENCE: 191

Ala Arg Gly Ala Ser Asp Gly Glu Thr Gly Arg Leu Asp Leu
1               5                   10

<210> SEQ ID NO 192
<211> LENGTH: 113
<212> TYPE: PRT
<213> ORGANISM: Homo sapiens

<400> SEQUENCE: 192

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Ser Tyr Ser Leu Pro Phe Thr Phe Gly Gly Gly Thr Lys Val Glu Ile
                100                 105                 110

Lys

<210> SEQ ID NO 193
<211> LENGTH: 17
<212> TYPE: PRT
<213> ORGANISM: Homo sapiens

<400> SEQUENCE: 193

Lys Ser Ser Gln Ser Val Leu Tyr Ser Ser Asn Asn Lys Asn Tyr Leu
1               5                   10                  15

Ala

<210> SEQ ID NO 194
<211> LENGTH: 7
<212> TYPE: PRT
<213> ORGANISM: Homo sapiens

<400> SEQUENCE: 194

Trp Ala Ser Thr Arg Glu Ser
1               5

<210> SEQ ID NO 195
<211> LENGTH: 9
<212> TYPE: PRT
<213> ORGANISM: Homo sapiens

<400> SEQUENCE: 195

Gln Gln Ser Tyr Ser Leu Pro Phe Thr
1               5

<210> SEQ ID NO 196
<211> LENGTH: 121
<212> TYPE: PRT
<213> ORGANISM: Homo sapiens

<400> SEQUENCE: 196

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Leu Ile Ile Pro Ala Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Asp Gly Glu Thr Gly Arg Leu Asp Leu Trp Gly
                100                 105                 110

Arg Gly Thr Leu Val Thr Val Ser Ser

```
                115                 120

<210> SEQ ID NO 197
<211> LENGTH: 9
<212> TYPE: PRT
<213> ORGANISM: Homo sapiens

<400> SEQUENCE: 197

Gly Thr Phe Ser Ser Tyr Ala Ile Ser
1               5

<210> SEQ ID NO 198
<211> LENGTH: 17
<212> TYPE: PRT
<213> ORGANISM: Homo sapiens

<400> SEQUENCE: 198

Leu Ile Ile Pro Ala Phe Gly Thr Ala Asn Tyr Ala Gln Lys Phe Gln
1               5                   10                  15

Gly

<210> SEQ ID NO 199
<211> LENGTH: 14
<212> TYPE: PRT
<213> ORGANISM: Homo sapiens

<400> SEQUENCE: 199

Ala Arg Gly Ala Ser Asp Gly Glu Thr Gly Arg Leu Asp Leu
1               5                   10

<210> SEQ ID NO 200
<211> LENGTH: 113
<212> TYPE: PRT
<213> ORGANISM: Homo sapiens

<400> SEQUENCE: 200

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Leu Pro Phe Thr Phe Gly Gly Gly Thr Lys Val Glu Ile
            100                 105                 110

Lys

<210> SEQ ID NO 201
<211> LENGTH: 17
<212> TYPE: PRT
<213> ORGANISM: Homo sapiens

<400> SEQUENCE: 201

Lys Ser Ser Gln Ser Val Leu Tyr Ser Ser Asn Asn Lys Asn Tyr Leu
1               5                   10                  15
```

Ala

<210> SEQ ID NO 202
<211> LENGTH: 7
<212> TYPE: PRT
<213> ORGANISM: Homo sapiens

<400> SEQUENCE: 202

Trp Ala Ser Thr Arg Glu Ser
1               5

<210> SEQ ID NO 203
<211> LENGTH: 9
<212> TYPE: PRT
<213> ORGANISM: Homo sapiens

<400> SEQUENCE: 203

Gln Gln Ser Tyr Ser Leu Pro Phe Thr
1               5

<210> SEQ ID NO 204
<211> LENGTH: 121
<212> TYPE: PRT
<213> ORGANISM: Homo sapiens

<400> SEQUENCE: 204

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Glu Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Asp Gly Glu Thr Gly Arg Leu Asp Leu Trp Gly
            100                 105                 110

Arg Gly Thr Leu Val Thr Val Ser Ser
        115                 120

<210> SEQ ID NO 205
<211> LENGTH: 9
<212> TYPE: PRT
<213> ORGANISM: Homo sapiens

<400> SEQUENCE: 205

Gly Thr Phe Ser Ser Tyr Ala Ile Ser
1               5

<210> SEQ ID NO 206
<211> LENGTH: 17
<212> TYPE: PRT
<213> ORGANISM: Homo sapiens

<400> SEQUENCE: 206

Val Ile Ile Pro Ile Phe Gly Glu Ala Asn Tyr Ala Gln Lys Phe Gln
1               5                   10                  15

Gly

<210> SEQ ID NO 207
<211> LENGTH: 14
<212> TYPE: PRT
<213> ORGANISM: Homo sapiens

<400> SEQUENCE: 207

Ala Arg Gly Ala Ser Asp Gly Glu Thr Gly Arg Leu Asp Leu
1               5                   10

<210> SEQ ID NO 208
<211> LENGTH: 113
<212> TYPE: PRT
<213> ORGANISM: Homo sapiens

<400> SEQUENCE: 208

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Leu Pro Phe Thr Phe Gly Gly Gly Thr Lys Val Glu Ile
            100                 105                 110

Lys

<210> SEQ ID NO 209
<211> LENGTH: 17
<212> TYPE: PRT
<213> ORGANISM: Homo sapiens

<400> SEQUENCE: 209

Lys Ser Ser Gln Ser Val Leu Tyr Ser Ser Asn Asn Lys Asn Tyr Leu
1               5                   10                  15

Ala

<210> SEQ ID NO 210
<211> LENGTH: 7
<212> TYPE: PRT
<213> ORGANISM: Homo sapiens

<400> SEQUENCE: 210

Trp Ala Ser Thr Arg Glu Ser
1               5

<210> SEQ ID NO 211
<211> LENGTH: 9
<212> TYPE: PRT
<213> ORGANISM: Homo sapiens

<400> SEQUENCE: 211

Gln Gln Ser Tyr Ser Leu Pro Phe Thr
1               5

```
<210> SEQ ID NO 212
<211> LENGTH: 121
<212> TYPE: PRT
<213> ORGANISM: Homo sapiens

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Asp Gly Glu Thr Gly Arg Leu Asp Leu Trp Gly
            100                 105                 110

Arg Gly Thr Leu Val Thr Val Ser Ser
        115                 120

<210> SEQ ID NO 213
<211> LENGTH: 9
<212> TYPE: PRT
<213> ORGANISM: Homo sapiens

<400> SEQUENCE: 213

Gly Thr Phe Gly Ser Tyr Ala Ile Ser
1               5

<210> SEQ ID NO 214
<211> LENGTH: 17
<212> TYPE: PRT
<213> ORGANISM: Homo sapiens

<400> SEQUENCE: 214

Val Ile Ile Pro Ile Phe Gly Thr Ala Asn Tyr Ala Gln Lys Phe Gln
1               5                   10                  15

Gly

<210> SEQ ID NO 215
<211> LENGTH: 14
<212> TYPE: PRT
<213> ORGANISM: Homo sapiens

<400> SEQUENCE: 215

Ala Arg Gly Ala Ser Asp Gly Glu Thr Gly Arg Leu Asp Leu
1               5                   10

<210> SEQ ID NO 216
<211> LENGTH: 113
<212> TYPE: PRT
<213> ORGANISM: Homo sapiens

<400> SEQUENCE: 216

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
            85                  90                  95

Ser Tyr Ser Leu Pro Phe Thr Phe Gly Gly Gly Thr Lys Val Glu Ile
            100                 105                 110

Lys

<210> SEQ ID NO 217
<211> LENGTH: 17
<212> TYPE: PRT
<213> ORGANISM: Homo sapiens

<400> SEQUENCE: 217

Lys Ser Ser Gln Ser Val Leu Tyr Ser Ser Asn Asn Lys Asn Tyr Leu
1               5                   10                  15

Ala

<210> SEQ ID NO 218
<211> LENGTH: 7
<212> TYPE: PRT
<213> ORGANISM: Homo sapiens

<400> SEQUENCE: 218

Trp Ala Ser Thr Arg Glu Ser
1               5

<210> SEQ ID NO 219
<211> LENGTH: 9
<212> TYPE: PRT
<213> ORGANISM: Homo sapiens

<400> SEQUENCE: 219

Gln Gln Ser Tyr Ser Leu Pro Phe Thr
1               5

<210> SEQ ID NO 220
<211> LENGTH: 121
<212> TYPE: PRT
<213> ORGANISM: Homo sapiens

<400> SEQUENCE: 220

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Gln Tyr
            20                  25                  30

Ala Ile Ser Trp Val Arg Gln Ala Pro Gly Gln Gly Leu Glu Trp Met
            35                  40                  45

Gly Val Ile Ile Pro Ser Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
            85                  90                  95

```
Ala Arg Gly Ala Ser Asp Gly Glu Thr Gly Arg Leu Asp Leu Trp Gly
            100                 105                 110
Arg Gly Thr Leu Val Thr Val Ser Ser
        115                 120
```

<210> SEQ ID NO 221
<211> LENGTH: 9
<212> TYPE: PRT
<213> ORGANISM: Homo sapiens

<400> SEQUENCE: 221

```
Gly Thr Phe Ser Gln Tyr Ala Ile Ser
1               5
```

<210> SEQ ID NO 222
<211> LENGTH: 17
<212> TYPE: PRT
<213> ORGANISM: Homo sapiens

<400> SEQUENCE: 222

```
Val Ile Ile Pro Ser Phe Gly Thr Ala Asn Tyr Ala Gln Lys Phe Gln
1               5                   10                  15
Gly
```

<210> SEQ ID NO 223
<211> LENGTH: 14
<212> TYPE: PRT
<213> ORGANISM: Homo sapiens

<400> SEQUENCE: 223

```
Ala Arg Gly Ala Ser Asp Gly Glu Thr Gly Arg Leu Asp Leu
1               5                   10
```

<210> SEQ ID NO 224
<211> LENGTH: 113
<212> TYPE: PRT
<213> ORGANISM: Homo sapiens

<400> SEQUENCE: 224

```
Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Ser Tyr Ser Leu Pro Phe Thr Phe Gly Gly Gly Thr Lys Val Glu Ile
            100                 105                 110
Lys
```

<210> SEQ ID NO 225
<211> LENGTH: 17
<212> TYPE: PRT
<213> ORGANISM: Homo sapiens

<400> SEQUENCE: 225

```
Lys Ser Ser Gln Ser Val Leu Tyr Ser Asn Asn Lys Asn Tyr Leu
1               5                   10                  15

Ala

<210> SEQ ID NO 226
<211> LENGTH: 7
<212> TYPE: PRT
<213> ORGANISM: Homo sapiens

<400> SEQUENCE: 226

Trp Ala Ser Thr Arg Glu Ser
1               5

<210> SEQ ID NO 227
<211> LENGTH: 9
<212> TYPE: PRT
<213> ORGANISM: Homo sapiens

<400> SEQUENCE: 227

Gln Gln Ser Tyr Ser Leu Pro Phe Thr
1               5

<210> SEQ ID NO 228
<211> LENGTH: 121
<212> TYPE: PRT
<213> ORGANISM: Homo sapiens

<400> SEQUENCE: 228

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Glu Tyr
            20                  25                  30

Ala Ile Ser Trp Val Arg Gln Ala Pro Gly Gln Gly Leu Glu Trp Met
        35                  40                  45

Gly Leu Ile Ile Pro Ile Phe Gly Thr Ala Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ser Asp Gly Glu Thr Gly Arg Leu Asp Leu Trp Gly
            100                 105                 110

Arg Gly Thr Leu Val Thr Val Ser Ser
        115                 120

<210> SEQ ID NO 229
<211> LENGTH: 9
<212> TYPE: PRT
<213> ORGANISM: Homo sapiens

<400> SEQUENCE: 229

Gly Thr Phe Gly Glu Tyr Ala Ile Ser
1               5

<210> SEQ ID NO 230
<211> LENGTH: 17
<212> TYPE: PRT
<213> ORGANISM: Homo sapiens

<400> SEQUENCE: 230
```

```
Leu Ile Ile Pro Ile Phe Gly Thr Ala Gln Tyr Ala Gln Lys Phe Gln
 1               5                  10                  15

Gly

<210> SEQ ID NO 231
<211> LENGTH: 14
<212> TYPE: PRT
<213> ORGANISM: Homo sapiens

<400> SEQUENCE: 231

Ala Arg Gly Ala Ser Asp Gly Glu Thr Gly Arg Leu Asp Leu
 1               5                  10

<210> SEQ ID NO 232
<211> LENGTH: 113
<212> TYPE: PRT
<213> ORGANISM: Homo sapiens

<400> SEQUENCE: 232

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys Gln Gln
                85                  90                  95

Ser Tyr Ser Leu Pro Phe Thr Phe Gly Gly Gly Thr Lys Val Glu Ile
            100                 105                 110

Lys

<210> SEQ ID NO 233
<211> LENGTH: 17
<212> TYPE: PRT
<213> ORGANISM: Homo sapiens

<400> SEQUENCE: 233

Lys Ser Ser Gln Ser Val Leu Tyr Ser Ser Asn Asn Lys Asn Tyr Leu
 1               5                  10                  15

Ala

<210> SEQ ID NO 234
<211> LENGTH: 7
<212> TYPE: PRT
<213> ORGANISM: Homo sapiens

<400> SEQUENCE: 234

Trp Ala Ser Thr Arg Glu Ser
 1               5

<210> SEQ ID NO 235
<211> LENGTH: 9
<212> TYPE: PRT
<213> ORGANISM: Homo sapiens

<400> SEQUENCE: 235
```

Gln Gln Ser Tyr Ser Leu Pro Phe Thr
1               5

<210> SEQ ID NO 236
<211> LENGTH: 122
<212> TYPE: PRT
<213> ORGANISM: Homo sapiens

<400> SEQUENCE: 236

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Ser
            20                  25                  30

Ala Ile Ser Trp Val Arg Gln Ala Pro Gly Gln Gly Leu Glu Trp Met
        35                  40                  45

Gly Gly Ile Ile Pro Leu Phe Gly Thr Ala Ala Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Gly Tyr Ser Ser Ser Trp Tyr Leu Asp Val Trp
            100                 105                 110

Gly Gln Gly Thr Met Val Thr Val Ser Ser
        115                 120

<210> SEQ ID NO 237
<211> LENGTH: 9
<212> TYPE: PRT
<213> ORGANISM: Homo sapiens

<400> SEQUENCE: 237

Gly Thr Phe Gly Ser Ser Ala Ile Ser
1               5

<210> SEQ ID NO 238
<211> LENGTH: 17
<212> TYPE: PRT
<213> ORGANISM: Homo sapiens

<400> SEQUENCE: 238

Gly Ile Ile Pro Leu Phe Gly Thr Ala Ala Tyr Ala Gln Lys Phe Gln
1               5                   10                  15

Gly

<210> SEQ ID NO 239
<211> LENGTH: 15
<212> TYPE: PRT
<213> ORGANISM: Homo sapiens

<400> SEQUENCE: 239

Ala Arg Asp Gly Pro Gly Tyr Ser Ser Ser Trp Tyr Leu Asp Val
1               5                   10                  15

<210> SEQ ID NO 240
<211> LENGTH: 107
<212> TYPE: PRT
<213> ORGANISM: Homo sapiens

<400> SEQUENCE: 240

Glu Ile Val Leu Thr Gln Ser Pro Ala Thr Leu Ser Leu Ser Pro Gly

```
                1               5                   10                  15
        Glu Arg Ala Thr Leu Ser Cys Arg Ala Ser Gln Ser Val Ser Ser Tyr
                        20                  25                  30

Leu Ala Trp Tyr Gln Gln Lys Pro Gly Gln Ala Pro Arg Leu Leu Ile
                        35                  40                  45

Tyr Asp Ala Ser Asn Arg Ala Thr Gly Ile Pro Ala Arg Phe Ser Gly
                        50                  55                  60

Ser Gly Ser Gly Thr Asp Phe Thr Leu Thr Ile Ser Ser Leu Glu Pro
        65                      70                  75                  80

Glu Asp Phe Ala Val Tyr Tyr Cys Gln Gln Gly Tyr Ala Leu Pro Ile
                        85                  90                  95

Thr Phe Gly Gly Gly Thr Lys Val Glu Ile Lys
                        100                 105
```

<210> SEQ ID NO 241
<211> LENGTH: 11
<212> TYPE: PRT
<213> ORGANISM: Homo sapiens

<400> SEQUENCE: 241

```
Arg Ala Ser Gln Ser Val Ser Ser Tyr Leu Ala
1               5                   10
```

<210> SEQ ID NO 242
<211> LENGTH: 7
<212> TYPE: PRT
<213> ORGANISM: Homo sapiens

<400> SEQUENCE: 242

```
Asp Ala Ser Asn Arg Ala Thr
1               5
```

<210> SEQ ID NO 243
<211> LENGTH: 9
<212> TYPE: PRT
<213> ORGANISM: Homo sapiens

<400> SEQUENCE: 243

```
Gln Gln Gly Tyr Ala Leu Pro Ile Thr
1               5
```

<210> SEQ ID NO 244
<211> LENGTH: 122
<212> TYPE: PRT
<213> ORGANISM: Homo sapiens

<400> SEQUENCE: 244

```
        Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Glu Tyr
                        20                  25                  30

Ala Ile Ser Trp Val Arg Gln Ala Pro Gly Gln Gly Leu Glu Trp Met
                        35                  40                  45

Gly Gly Ile Ile Pro Ile Phe Gly Thr Ala Val Tyr Ala Gln Lys Phe
                        50                  55                  60

Gln Gly Arg Val Thr Ile Thr Ala Asp Glu Ser Thr Ser Thr Ala Tyr
        65                      70                  75                  80

Met Glu Leu Ser Ser Leu Arg Ser Glu Asp Thr Ala Val Tyr Tyr Cys
                        85                  90                  95
```

Ala Arg Asp Gly Pro Gly Tyr Ser Ser Ser Trp Tyr Leu Asp Val Trp
            100                 105                 110

Gly Gln Gly Thr Met Val Thr Val Ser Ser
        115                 120

<210> SEQ ID NO 245
<211> LENGTH: 9
<212> TYPE: PRT
<213> ORGANISM: Homo sapiens

<400> SEQUENCE: 245

Gly Thr Phe Ser Glu Tyr Ala Ile Ser
1               5

<210> SEQ ID NO 246
<211> LENGTH: 17
<212> TYPE: PRT
<213> ORGANISM: Homo sapiens

<400> SEQUENCE: 246

Gly Ile Ile Pro Ile Phe Gly Thr Ala Val Tyr Ala Gln Lys Phe Gln
1               5                   10                  15

Gly

<210> SEQ ID NO 247
<211> LENGTH: 15
<212> TYPE: PRT
<213> ORGANISM: Homo sapiens

<400> SEQUENCE: 247

Ala Arg Asp Gly Pro Gly Tyr Ser Ser Ser Trp Tyr Leu Asp Val
1               5                   10                  15

<210> SEQ ID NO 248
<211> LENGTH: 107
<212> TYPE: PRT
<213> ORGANISM: Homo sapiens

<400> SEQUENCE: 248

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ala Leu Pro Ile
                85                  90                  95

Thr Phe Gly Gly Gly Thr Lys Val Glu Ile Lys
            100                 105

<210> SEQ ID NO 249
<211> LENGTH: 11
<212> TYPE: PRT
<213> ORGANISM: Homo sapiens

<400> SEQUENCE: 249

Arg Ala Ser Gln Ser Val Ser Ser Tyr Leu Ala

<210> SEQ ID NO 250
<211> LENGTH: 7
<212> TYPE: PRT
<213> ORGANISM: Homo sapiens

<400> SEQUENCE: 250

Asp Ala Ser Asn Arg Ala Thr
1               5

<210> SEQ ID NO 251
<211> LENGTH: 9
<212> TYPE: PRT
<213> ORGANISM: Homo sapiens

<400> SEQUENCE: 251

Gln Gln Gly Tyr Ala Leu Pro Ile Thr
1               5

<210> SEQ ID NO 252
<211> LENGTH: 122
<212> TYPE: PRT
<213> ORGANISM: Homo sapiens

<400> SEQUENCE: 252

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Gly Tyr Ser Ser Ser Trp Tyr Leu Asp Val Trp
            100                 105                 110

Gly Gln Gly Thr Met Val Thr Val Ser Ser
        115                 120

<210> SEQ ID NO 253
<211> LENGTH: 9
<212> TYPE: PRT
<213> ORGANISM: Homo sapiens

<400> SEQUENCE: 253

Gly Thr Phe Ser Ser Tyr Ala Ile Ser
1               5

<210> SEQ ID NO 254
<211> LENGTH: 17
<212> TYPE: PRT
<213> ORGANISM: Homo sapiens

<400> SEQUENCE: 254

Gly Ile Ile Pro Ile Phe Gly Thr Ala Val Tyr Ala Gln Lys Phe Gln
1               5                   10                  15

Gly

<210> SEQ ID NO 255
<211> LENGTH: 15
<212> TYPE: PRT
<213> ORGANISM: Homo sapiens

<400> SEQUENCE: 255

Ala Arg Asp Gly Pro Gly Tyr Ser Ser Ser Trp Tyr Leu Asp Val
1               5                   10                  15

<210> SEQ ID NO 256
<211> LENGTH: 107
<212> TYPE: PRT
<213> ORGANISM: Homo sapiens

<400> SEQUENCE: 256

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ala Leu Pro Ile
                85                  90                  95

Thr Phe Gly Gly Gly Thr Lys Val Glu Ile Lys
            100                 105

<210> SEQ ID NO 257
<211> LENGTH: 11
<212> TYPE: PRT
<213> ORGANISM: Homo sapiens

<400> SEQUENCE: 257

Arg Ala Ser Gln Ser Val Ser Ser Tyr Leu Ala
1               5                   10

<210> SEQ ID NO 258
<211> LENGTH: 7
<212> TYPE: PRT
<213> ORGANISM: Homo sapiens

<400> SEQUENCE: 258

Asp Ala Ser Asn Arg Ala Thr
1               5

<210> SEQ ID NO 259
<211> LENGTH: 9
<212> TYPE: PRT
<213> ORGANISM: Homo sapiens

<400> SEQUENCE: 259

Gln Gln Gly Tyr Ala Leu Pro Ile Thr
1               5

<210> SEQ ID NO 260
<211> LENGTH: 122
<212> TYPE: PRT
<213> ORGANISM: Homo sapiens

<400> SEQUENCE: 260

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Ser
            20                  25                  30

Val Ile Ser Trp Val Arg Gln Ala Pro Gly Gln Gly Leu Glu Trp Met
        35                  40                  45

Gly Gly Ile Ile Pro Ile Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Gly Tyr Ser Ser Ser Trp Tyr Leu Asp Val Trp
            100                 105                 110

Gly Gln Gly Thr Met Val Thr Val Ser Ser
        115                 120

<210> SEQ ID NO 261
<211> LENGTH: 9
<212> TYPE: PRT
<213> ORGANISM: Homo sapiens

<400> SEQUENCE: 261

Gly Thr Phe Ser Ser Ser Val Ile Ser
1               5

<210> SEQ ID NO 262
<211> LENGTH: 17
<212> TYPE: PRT
<213> ORGANISM: Homo sapiens

<400> SEQUENCE: 262

Gly Ile Ile Pro Ile Phe Gly Thr Ala Thr Tyr Ala Gln Lys Phe Gln
1               5                   10                  15

Gly

<210> SEQ ID NO 263
<211> LENGTH: 15
<212> TYPE: PRT
<213> ORGANISM: Homo sapiens

<400> SEQUENCE: 263

Ala Arg Asp Gly Pro Gly Tyr Ser Ser Ser Trp Tyr Leu Asp Val
1               5                   10                  15

<210> SEQ ID NO 264
<211> LENGTH: 107
<212> TYPE: PRT
<213> ORGANISM: Homo sapiens

<400> SEQUENCE: 264

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ala Leu Pro Ile
                85                  90                  95

Thr Phe Gly Gly Gly Thr Lys Val Glu Ile Lys
            100                 105

<210> SEQ ID NO 265
<211> LENGTH: 11
<212> TYPE: PRT
<213> ORGANISM: Homo sapiens

<400> SEQUENCE: 265

Arg Ala Ser Gln Ser Val Ser Ser Tyr Leu Ala
1               5                   10

<210> SEQ ID NO 266
<211> LENGTH: 7
<212> TYPE: PRT
<213> ORGANISM: Homo sapiens

<400> SEQUENCE: 266

Asp Ala Ser Asn Arg Ala Thr
1               5

<210> SEQ ID NO 267
<211> LENGTH: 9
<212> TYPE: PRT
<213> ORGANISM: Homo sapiens

<400> SEQUENCE: 267

Gln Gln Gly Tyr Ala Leu Pro Ile Thr
1               5

<210> SEQ ID NO 268
<211> LENGTH: 122
<212> TYPE: PRT
<213> ORGANISM: Homo sapiens

<400> SEQUENCE: 268

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Asp Ser Tyr
                20                  25                  30

Val Ile Ser Trp Val Arg Gln Ala Pro Gly Gln Gly Leu Glu Trp Met
            35                  40                  45

Gly Gly Ile Ile Pro Gly Phe Gly Val Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Gly Tyr Ser Ser Trp Tyr Leu Asp Val Trp
                100                 105                 110

Gly Gln Gly Thr Met Val Thr Val Ser Ser
        115                 120

<210> SEQ ID NO 269

<211> LENGTH: 9
<212> TYPE: PRT
<213> ORGANISM: Homo sapiens

<400> SEQUENCE: 269

Gly Thr Phe Asp Ser Tyr Val Ile Ser
1               5

<210> SEQ ID NO 270
<211> LENGTH: 17
<212> TYPE: PRT
<213> ORGANISM: Homo sapiens

<400> SEQUENCE: 270

Gly Ile Ile Pro Gly Phe Gly Val Ala Asn Tyr Ala Gln Lys Phe Gln
1               5                   10                  15

Gly

<210> SEQ ID NO 271
<211> LENGTH: 15
<212> TYPE: PRT
<213> ORGANISM: Homo sapiens

<400> SEQUENCE: 271

Ala Arg Asp Gly Pro Gly Tyr Ser Ser Ser Trp Tyr Leu Asp Val
1               5                   10                  15

<210> SEQ ID NO 272
<211> LENGTH: 107
<212> TYPE: PRT
<213> ORGANISM: Homo sapiens

<400> SEQUENCE: 272

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ala Leu Pro Ile
                85                  90                  95

Thr Phe Gly Gly Gly Thr Lys Val Glu Ile Lys
            100                 105

<210> SEQ ID NO 273
<211> LENGTH: 11
<212> TYPE: PRT
<213> ORGANISM: Homo sapiens

<400> SEQUENCE: 273

Arg Ala Ser Gln Ser Val Ser Ser Tyr Leu Ala
1               5                   10

<210> SEQ ID NO 274
<211> LENGTH: 7
<212> TYPE: PRT
<213> ORGANISM: Homo sapiens

<400> SEQUENCE: 274

Asp Ala Ser Asn Arg Ala Thr
1               5

<210> SEQ ID NO 275
<211> LENGTH: 9
<212> TYPE: PRT
<213> ORGANISM: Homo sapiens

<400> SEQUENCE: 275

Gln Gln Gly Tyr Ala Leu Pro Ile Thr
1               5

<210> SEQ ID NO 276
<211> LENGTH: 116
<212> TYPE: PRT
<213> ORGANISM: Homo sapiens

<400> SEQUENCE: 276

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Tyr Gly Met Pro Tyr Trp Gly Gln Gly Thr Leu Val
            100                 105                 110

Thr Val Ser Ser
        115

<210> SEQ ID NO 277
<211> LENGTH: 9
<212> TYPE: PRT
<213> ORGANISM: Homo sapiens

<400> SEQUENCE: 277

Phe Thr Phe Ser Ser Tyr Ala Met Ser
1               5

<210> SEQ ID NO 278
<211> LENGTH: 17
<212> TYPE: PRT
<213> ORGANISM: Homo sapiens

<400> SEQUENCE: 278

Ala Ile Ser Gly Ser Gly Gly Ser Thr Tyr Tyr Ala Asp Ser Val Lys
1               5                   10                  15

Gly

<210> SEQ ID NO 279
<211> LENGTH: 9
<212> TYPE: PRT
<213> ORGANISM: Homo sapiens

<400> SEQUENCE: 279

```
Ala Lys Val Tyr Tyr Gly Met Pro Tyr
1               5
```

<210> SEQ ID NO 280
<211> LENGTH: 107
<212> TYPE: PRT
<213> ORGANISM: Homo sapiens

<400> SEQUENCE: 280

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Asp Val Pro Trp
                85                  90                  95

Thr Phe Gly Gly Gly Thr Lys Val Glu Ile Lys
            100                 105
```

<210> SEQ ID NO 281
<211> LENGTH: 11
<212> TYPE: PRT
<213> ORGANISM: Homo sapiens

<400> SEQUENCE: 281

```
Arg Ala Ser Gln Gly Ile Asp Ser Trp Leu Ala
1               5                   10
```

<210> SEQ ID NO 282
<211> LENGTH: 7
<212> TYPE: PRT
<213> ORGANISM: Homo sapiens

<400> SEQUENCE: 282

```
Ala Ala Ser Ser Leu Gln Ser
1               5
```

<210> SEQ ID NO 283
<211> LENGTH: 9
<212> TYPE: PRT
<213> ORGANISM: Homo sapiens

<400> SEQUENCE: 283

```
Gln Gln Ala Ser Asp Val Pro Trp Thr
1               5
```

<210> SEQ ID NO 284
<211> LENGTH: 122
<212> TYPE: PRT
<213> ORGANISM: Homo sapiens

<400> SEQUENCE: 284

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Pro Gly Tyr Ser Ser Ser Trp Tyr Leu Asp Val Trp
            100                 105                 110

Gly Gln Gly Thr Met Val Thr Val Ser Ser
            115                 120

<210> SEQ ID NO 285
<211> LENGTH: 9
<212> TYPE: PRT
<213> ORGANISM: Homo sapiens

<400> SEQUENCE: 285

Gly Thr Phe Ser Ser Tyr Ala Ile Ser
1               5

<210> SEQ ID NO 286
<211> LENGTH: 17
<212> TYPE: PRT
<213> ORGANISM: Homo sapiens

<400> SEQUENCE: 286

Gly Ile Ile Pro Ile Phe Gly Thr Ala Ser Tyr Ala Gln Lys Phe Gln
1               5                   10                  15

Gly

<210> SEQ ID NO 287
<211> LENGTH: 15
<212> TYPE: PRT
<213> ORGANISM: Homo sapiens

<400> SEQUENCE: 287

Ala Arg Asp Gly Pro Gly Tyr Ser Ser Ser Trp Tyr Leu Asp Val
1               5                   10                  15

<210> SEQ ID NO 288
<211> LENGTH: 107
<212> TYPE: PRT
<213> ORGANISM: Homo sapiens

<400> SEQUENCE: 288

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ala Leu Pro Ile
                85                  90                  95
```

```
Thr Phe Gly Gly Gly Thr Lys Val Glu Ile Lys
            100                 105

<210> SEQ ID NO 289
<211> LENGTH: 11
<212> TYPE: PRT
<213> ORGANISM: Homo sapiens

<400> SEQUENCE: 289

Arg Ala Ser Gln Ser Val Ser Ser Tyr Leu Ala
1               5                   10

<210> SEQ ID NO 290
<211> LENGTH: 7
<212> TYPE: PRT
<213> ORGANISM: Homo sapiens

<400> SEQUENCE: 290

Asp Ala Ser Asn Arg Ala Thr
1               5

<210> SEQ ID NO 291
<211> LENGTH: 9
<212> TYPE: PRT
<213> ORGANISM: Homo sapiens

<400> SEQUENCE: 291

Gln Gln Gly Tyr Ala Leu Pro Ile Thr
1               5

<210> SEQ ID NO 292
<211> LENGTH: 122
<212> TYPE: PRT
<213> ORGANISM: Homo sapiens

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Gly Tyr Ser Tyr Ser Trp Gly Gly Ser Asn Ile Trp
            100                 105                 110

Gly Gln Gly Thr Met Val Thr Val Ser Ser
        115                 120

<210> SEQ ID NO 293
<211> LENGTH: 9
<212> TYPE: PRT
<213> ORGANISM: Homo sapiens

<400> SEQUENCE: 293

Tyr Thr Phe Thr Ser Tyr Tyr Met His
1               5
```

<210> SEQ ID NO 294
<211> LENGTH: 17
<212> TYPE: PRT
<213> ORGANISM: Homo sapiens

<400> SEQUENCE: 294

Ile Ile Asn Pro Ser Gly Gly Ser Thr Ser Tyr Ala Gln Lys Phe Gln
1               5                   10                  15
Gly

<210> SEQ ID NO 295
<211> LENGTH: 15
<212> TYPE: PRT
<213> ORGANISM: Homo sapiens

<400> SEQUENCE: 295

Ala Arg Ala Gly Gly Tyr Ser Tyr Ser Trp Gly Gly Ser Asn Ile
1               5                   10                  15

<210> SEQ ID NO 296
<211> LENGTH: 107
<212> TYPE: PRT
<213> ORGANISM: Homo sapiens

<400> SEQUENCE: 296

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asp Gly Ser Phe Pro Tyr
                85                  90                  95

Thr Phe Gly Gly Gly Thr Lys Val Glu Ile Lys
            100                 105

<210> SEQ ID NO 297
<211> LENGTH: 11
<212> TYPE: PRT
<213> ORGANISM: Homo sapiens

<400> SEQUENCE: 297

Arg Ala Ser Gln Ser Ile Ser Ser Trp Leu Ala
1               5                   10

<210> SEQ ID NO 298
<211> LENGTH: 7
<212> TYPE: PRT
<213> ORGANISM: Homo sapiens

<400> SEQUENCE: 298

Lys Ala Ser Ser Leu Glu Ser
1               5

<210> SEQ ID NO 299
<211> LENGTH: 9

<212> TYPE: PRT
<213> ORGANISM: Homo sapiens

<400> SEQUENCE: 299

Gln Gln Asp Gly Ser Phe Pro Tyr Thr
1               5

<210> SEQ ID NO 300
<211> LENGTH: 126
<212> TYPE: PRT
<213> ORGANISM: Homo sapiens

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Arg Tyr Thr Thr Leu Thr Gly Ser Tyr Tyr Tyr Gly
                100                 105                 110

Met Asp Val Trp Gly Gln Gly Thr Thr Val Thr Val Ser Ser
            115                 120                 125

<210> SEQ ID NO 301
<211> LENGTH: 9
<212> TYPE: PRT
<213> ORGANISM: Homo sapiens

<400> SEQUENCE: 301

Tyr Thr Phe Thr Ser Tyr Tyr Met His
1               5

<210> SEQ ID NO 302
<211> LENGTH: 17
<212> TYPE: PRT
<213> ORGANISM: Homo sapiens

<400> SEQUENCE: 302

Ile Ile Asn Pro Gly Gly Gly Ser Thr Ser Tyr Ala Gln Lys Phe Gln
1               5                   10                  15

Gly

<210> SEQ ID NO 303
<211> LENGTH: 19
<212> TYPE: PRT
<213> ORGANISM: Homo sapiens

<400> SEQUENCE: 303

Ala Arg Asp Pro Arg Tyr Thr Thr Leu Thr Gly Ser Tyr Tyr Tyr Gly
1               5                   10                  15

Met Asp Val

<210> SEQ ID NO 304

```
<211> LENGTH: 108
<212> TYPE: PRT
<213> ORGANISM: Homo sapiens

<400> SEQUENCE: 304

Asp Ile Gln Leu Thr Gln Ser Pro Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Val Asn Phe Pro Pro
                85                  90                  95

Ile Thr Phe Gly Gly Gly Thr Lys Val Glu Ile Lys
            100                 105

<210> SEQ ID NO 305
<211> LENGTH: 11
<212> TYPE: PRT
<213> ORGANISM: Homo sapiens

<400> SEQUENCE: 305

Arg Ala Ser Gln Asp Ile Ser Ser Trp Leu Ala
1               5                   10

<210> SEQ ID NO 306
<211> LENGTH: 7
<212> TYPE: PRT
<213> ORGANISM: Homo sapiens

<400> SEQUENCE: 306

Ala Ala Ser Ser Leu Gln Ser
1               5

<210> SEQ ID NO 307
<211> LENGTH: 10
<212> TYPE: PRT
<213> ORGANISM: Homo sapiens

<400> SEQUENCE: 307

Gln Gln Ala Val Asn Phe Pro Pro Ile Thr
1               5                   10

<210> SEQ ID NO 308
<211> LENGTH: 120
<212> TYPE: PRT
<213> ORGANISM: Homo sapiens

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Ala Ser Trp Leu Pro Gly Ser Leu Asp Val Trp Gly Lys
            100                 105                 110

Gly Thr Thr Val Thr Val Ser Ser
            115                 120

<210> SEQ ID NO 309
<211> LENGTH: 9
<212> TYPE: PRT
<213> ORGANISM: Homo sapiens

<400> SEQUENCE: 309

Tyr Thr Phe Thr Gly Tyr Tyr Met His
 1               5

<210> SEQ ID NO 310
<211> LENGTH: 17
<212> TYPE: PRT
<213> ORGANISM: Homo sapiens

<400> SEQUENCE: 310

Trp Ile Asn Pro Asn Ser Gly Gly Thr Lys Tyr Ala Gln Lys Phe Gln
 1               5                  10                  15

Gly

<210> SEQ ID NO 311
<211> LENGTH: 13
<212> TYPE: PRT
<213> ORGANISM: Homo sapiens

<400> SEQUENCE: 311

Ala Arg Glu Ala Ser Trp Leu Pro Gly Ser Leu Asp Val
 1               5                  10

<210> SEQ ID NO 312
<211> LENGTH: 113
<212> TYPE: PRT
<213> ORGANISM: Homo sapiens

<400> SEQUENCE: 312

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Asp Asn Phe Pro Ile Thr Phe Gly Gly Gly Thr Lys Val Glu Ile
            100                 105                 110

Lys
```

<210> SEQ ID NO 313
<211> LENGTH: 17
<212> TYPE: PRT
<213> ORGANISM: Homo sapiens

<400> SEQUENCE: 313

Lys Ser Ser Gln Ser Val Leu Tyr Ser Ser Asn Asn Lys Asn Tyr Leu
1               5                   10                  15

Ala

<210> SEQ ID NO 314
<211> LENGTH: 7
<212> TYPE: PRT
<213> ORGANISM: Homo sapiens

<400> SEQUENCE: 314

Trp Ala Ser Thr Arg Glu Ser
1               5

<210> SEQ ID NO 315
<211> LENGTH: 9
<212> TYPE: PRT
<213> ORGANISM: Homo sapiens

<400> SEQUENCE: 315

Gln Gln Tyr Asp Asn Phe Pro Ile Thr
1               5

<210> SEQ ID NO 316
<211> LENGTH: 126
<212> TYPE: PRT
<213> ORGANISM: Homo sapiens

<400> SEQUENCE: 316

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Arg Tyr Thr Leu Thr Gly Ser Tyr Tyr Tyr Gly
            100                 105                 110

Met Asp Val Trp Gly Gln Gly Thr Thr Val Thr Val Ser Ser
        115                 120                 125

<210> SEQ ID NO 317
<211> LENGTH: 9
<212> TYPE: PRT
<213> ORGANISM: Homo sapiens

<400> SEQUENCE: 317

Tyr Thr Phe Thr Ser Tyr Tyr Met His
1               5

```
<210> SEQ ID NO 318
<211> LENGTH: 17
<212> TYPE: PRT
<213> ORGANISM: Homo sapiens

<400> SEQUENCE: 318

Ile Ile Asn Pro Gly Gly Gly Ser Thr Ser Tyr Ala Gln Lys Phe Gln
1               5                   10                  15

Gly

<210> SEQ ID NO 319
<211> LENGTH: 19
<212> TYPE: PRT
<213> ORGANISM: Homo sapiens

<400> SEQUENCE: 319

Ala Arg Asp Pro Arg Tyr Thr Thr Leu Thr Gly Ser Tyr Tyr Gly
1               5                   10                  15

Met Asp Val

<210> SEQ ID NO 320
<211> LENGTH: 108
<212> TYPE: PRT
<213> ORGANISM: Homo sapiens

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ala Asn Thr Pro Pro
                85                  90                  95

Trp Thr Phe Gly Gly Gly Thr Lys Val Glu Ile Lys
            100                 105

<210> SEQ ID NO 321
<211> LENGTH: 11
<212> TYPE: PRT
<213> ORGANISM: Homo sapiens

<400> SEQUENCE: 321

Arg Ala Ser Gln Ser Ile Ser Ser Tyr Leu Asn
1               5                   10

<210> SEQ ID NO 322
<211> LENGTH: 7
<212> TYPE: PRT
<213> ORGANISM: Homo sapiens

<400> SEQUENCE: 322

Ala Ala Ser Ser Leu Gln Ser
1               5

<210> SEQ ID NO 323
<211> LENGTH: 10
```

```
<212> TYPE: PRT
<213> ORGANISM: Homo sapiens

<400> SEQUENCE: 323

Gln Gln Ser Ala Asn Thr Pro Pro Trp Thr
1               5                   10

<210> SEQ ID NO 324
<211> LENGTH: 117
<212> TYPE: PRT
<213> ORGANISM: Artificial sequence
<220> FEATURE:
<223> OTHER INFORMATION: Humanized antibody

<400> SEQUENCE: 324

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
                20                  25                  30

Trp Met Asp Trp Val Arg Gln Ala Pro Gly Lys Gly Leu Glu Trp Val
            35                  40                  45

Gly Asn Ile Asp Glu Asp Gly Ser Ile Thr Glu Tyr Ser Pro Phe Val
50                  55                  60

Lys Gly Arg Phe Thr Ile Ser Arg Asp Asn Val Lys Asn Thr Leu Tyr
65                  70                  75                  80

Leu Gln Met Asn Ser Val Lys Ser Glu Asp Thr Ala Thr Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 325
<211> LENGTH: 111
<212> TYPE: PRT
<213> ORGANISM: Artificial sequence
<220> FEATURE:
<223> OTHER INFORMATION: Humanized antibody

<400> SEQUENCE: 325

Asp Ile Val Met Thr Gln Ser Pro Ser Ser Leu Ala Val Ser Ala Gly
1               5                   10                  15

Asp Arg Val Thr Ile Asn Cys Lys Ser Ser Gln Ser Leu Leu Ser Gly
                20                  25                  30

Ser Phe Asn Tyr Leu Thr Trp Tyr Gln Gln Lys Thr Gly Gln Ala Pro
            35                  40                  45

Lys Leu Leu Ile Phe Tyr Ala Ser Thr Arg His Thr Gly Val Pro Asp
50                  55                  60

Arg Phe Met Gly Ser Gly Ser Gly Thr Asp Phe Thr Leu Thr Ile Asn
65                  70                  75                  80

Ser Phe Gln Thr Glu Asp Leu Gly Asp Tyr Tyr Cys His His His Tyr
                85                  90                  95

Asn Ala Pro Pro Thr Phe Gly Pro Gly Thr Lys Leu Glu Leu Arg
            100                 105                 110

<210> SEQ ID NO 326
<211> LENGTH: 10
<212> TYPE: PRT
<213> ORGANISM: Artificial sequence
<220> FEATURE:
```

-continued

<223> OTHER INFORMATION: Humanized antibody

<400> SEQUENCE: 326

Gly Phe Thr Phe Ser Asp Tyr Trp Met Asp
1               5                   10

<210> SEQ ID NO 327
<211> LENGTH: 17
<212> TYPE: PRT
<213> ORGANISM: Artificial sequence
<220> FEATURE:
<223> OTHER INFORMATION: Humanized antibody

<400> SEQUENCE: 327

Asn Ile Asp Glu Asp Gly Ser Ile Thr Glu Tyr Ser Pro Phe Val Lys
1               5                   10                  15
Gly

<210> SEQ ID NO 328
<211> LENGTH: 8
<212> TYPE: PRT
<213> ORGANISM: Artificial sequence
<220> FEATURE:
<223> OTHER INFORMATION: Humanized antibody

<400> SEQUENCE: 328

Trp Gly Arg Phe Gly Phe Asp Ser
1               5

<210> SEQ ID NO 329
<211> LENGTH: 15
<212> TYPE: PRT
<213> ORGANISM: Artificial sequence
<220> FEATURE:
<223> OTHER INFORMATION: Humanized antibody

<400> SEQUENCE: 329

Lys Ser Ser Gln Ser Leu Leu Ser Gly Ser Phe Asn Tyr Leu Thr
1               5                   10                  15

<210> SEQ ID NO 330
<211> LENGTH: 7
<212> TYPE: PRT
<213> ORGANISM: Artificial sequence
<220> FEATURE:
<223> OTHER INFORMATION: Humanized antibody

<400> SEQUENCE: 330

Tyr Ala Ser Thr Arg His Thr
1               5

<210> SEQ ID NO 331
<211> LENGTH: 9
<212> TYPE: PRT
<213> ORGANISM: Artificial sequence
<220> FEATURE:
<223> OTHER INFORMATION: Humanized antibody

<400> SEQUENCE: 331

His His His Tyr Asn Ala Pro Pro Thr
1               5

<210> SEQ ID NO 332
<211> LENGTH: 117
<212> TYPE: PRT
<213> ORGANISM: Artificial sequence
<220> FEATURE:
<223> OTHER INFORMATION: Humanized antibody

<400> SEQUENCE: 332

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 333
<211> LENGTH: 111
<212> TYPE: PRT
<213> ORGANISM: Artificial sequence
<220> FEATURE:
<223> OTHER INFORMATION: Humanized antibody

<400> SEQUENCE: 333

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Tyr
                85                  90                  95

Asn Ala Pro Pro Thr Phe Gly Pro Gly Thr Lys Val Asp Ile Lys
            100                 105                 110

<210> SEQ ID NO 334
<211> LENGTH: 10
<212> TYPE: PRT
<213> ORGANISM: Artificial sequence
<220> FEATURE:
<223> OTHER INFORMATION: Humanized antibody

<400> SEQUENCE: 334

Gly Phe Thr Phe Ser Asp Tyr Trp Met Asp
1               5                   10

<210> SEQ ID NO 335
<211> LENGTH: 17
<212> TYPE: PRT
<213> ORGANISM: Artificial sequence
<220> FEATURE:

```
<223> OTHER INFORMATION: Humanized antibody

<400> SEQUENCE: 335

Asn Ile Asp Glu Asp Gly Ser Ile Thr Glu Tyr Ser Pro Phe Val Lys
1               5                   10                  15
Gly

<210> SEQ ID NO 336
<211> LENGTH: 8
<212> TYPE: PRT
<213> ORGANISM: Artificial sequence
<220> FEATURE:
<223> OTHER INFORMATION: Humanized antibody

<400> SEQUENCE: 336

Trp Gly Arg Phe Gly Phe Asp Ser
1               5

<210> SEQ ID NO 337
<211> LENGTH: 15
<212> TYPE: PRT
<213> ORGANISM: Artificial sequence
<220> FEATURE:
<223> OTHER INFORMATION: Humanized antibody

<400> SEQUENCE: 337

Lys Ser Ser Gln Ser Leu Leu Ser Gly Ser Phe Asn Tyr Leu Thr
1               5                   10                  15

<210> SEQ ID NO 338
<211> LENGTH: 7
<212> TYPE: PRT
<213> ORGANISM: Artificial sequence
<220> FEATURE:
<223> OTHER INFORMATION: Humanized antibody

<400> SEQUENCE: 338

Tyr Ala Ser Thr Arg His Thr
1               5

<210> SEQ ID NO 339
<211> LENGTH: 9
<212> TYPE: PRT
<213> ORGANISM: Artificial sequence
<220> FEATURE:
<223> OTHER INFORMATION: Humanized antibody

<400> SEQUENCE: 339

His His His Tyr Asn Ala Pro Pro Thr
1               5

<210> SEQ ID NO 340
<211> LENGTH: 117
<212> TYPE: PRT
<213> ORGANISM: Artificial sequence
<220> FEATURE:
<223> OTHER INFORMATION: Humanized antibody

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45
```

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Trp Gly Arg Phe Gly Phe Asp Ser Trp Gly Gln Gly Thr Leu
            100                 105                 110

Val Thr Val Ser Ser
            115

<210> SEQ ID NO 341
<211> LENGTH: 111
<212> TYPE: PRT
<213> ORGANISM: Artificial sequence
<220> FEATURE:
<223> OTHER INFORMATION: Humanized antibody

<400> SEQUENCE: 341

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ser Gly
                 20                  25                  30

Ser Phe Asn Tyr Leu Thr Trp Tyr Gln Gln Lys Pro Gly Gln Pro Pro
             35                  40                  45

Lys Leu Leu Ile Phe Tyr Ala Ser Thr Arg Glu Thr Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys His His His Tyr
                 85                  90                  95

Asn Ala Pro Pro Thr Phe Gly Pro Gly Thr Lys Val Asp Ile Lys
            100                 105                 110

<210> SEQ ID NO 342
<211> LENGTH: 10
<212> TYPE: PRT
<213> ORGANISM: Artificial sequence
<220> FEATURE:
<223> OTHER INFORMATION: Humanized antibody

<400> SEQUENCE: 342

Gly Phe Thr Phe Ser Asp Tyr Trp Met Asp
 1               5                  10

<210> SEQ ID NO 343
<211> LENGTH: 17
<212> TYPE: PRT
<213> ORGANISM: Artificial sequence
<220> FEATURE:
<223> OTHER INFORMATION: Humanized antibody

<400> SEQUENCE: 343

Asn Ile Asp Glu Asp Gly Ser Ile Thr Glu Tyr Ser Pro Phe Val Lys
 1               5                  10                  15

Gly

<210> SEQ ID NO 344
<211> LENGTH: 8
<212> TYPE: PRT

```
<213> ORGANISM: Artificial sequence
<220> FEATURE:
<223> OTHER INFORMATION: Humanized antibody

<400> SEQUENCE: 344

Trp Gly Arg Phe Gly Phe Asp Ser
1               5

<210> SEQ ID NO 345
<211> LENGTH: 15
<212> TYPE: PRT
<213> ORGANISM: Artificial sequence
<220> FEATURE:
<223> OTHER INFORMATION: Humanized antibody

<400> SEQUENCE: 345

Lys Ser Ser Gln Ser Leu Leu Ser Gly Ser Phe Asn Tyr Leu Thr
1               5                   10                  15

<210> SEQ ID NO 346
<211> LENGTH: 7
<212> TYPE: PRT
<213> ORGANISM: Artificial sequence
<220> FEATURE:
<223> OTHER INFORMATION: Humanized antibody

<400> SEQUENCE: 346

Tyr Ala Ser Thr Arg Glu Thr
1               5

<210> SEQ ID NO 347
<211> LENGTH: 9
<212> TYPE: PRT
<213> ORGANISM: Artificial sequence
<220> FEATURE:
<223> OTHER INFORMATION: Humanized antibody

<400> SEQUENCE: 347

His His His Tyr Asn Ala Pro Pro Thr
1               5

<210> SEQ ID NO 348
<211> LENGTH: 117
<212> TYPE: PRT
<213> ORGANISM: Artificial sequence
<220> FEATURE:
<223> OTHER INFORMATION: Humanized antibody

<400> SEQUENCE: 348

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110
```

```
Val Thr Val Ser Ser
        115

<210> SEQ ID NO 349
<211> LENGTH: 111
<212> TYPE: PRT
<213> ORGANISM: Artificial sequence
<220> FEATURE:
<223> OTHER INFORMATION: Humanized antibody

<400> SEQUENCE: 349

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 350
<211> LENGTH: 10
<212> TYPE: PRT
<213> ORGANISM: Artificial sequence
<220> FEATURE:
<223> OTHER INFORMATION: Humanized antibody

<400> SEQUENCE: 350

Gly Phe Thr Phe Ser Asp Tyr Trp Met Asp
1               5                   10

<210> SEQ ID NO 351
<211> LENGTH: 17
<212> TYPE: PRT
<213> ORGANISM: Artificial sequence
<220> FEATURE:
<223> OTHER INFORMATION: Humanized antibody

<400> SEQUENCE: 351

Asn Ile Asp Glu Asp Gly Ser Ile Thr Glu Tyr Ser Pro Phe Val Lys
1               5                   10                  15

Gly

<210> SEQ ID NO 352
<211> LENGTH: 8
<212> TYPE: PRT
<213> ORGANISM: Artificial sequence
<220> FEATURE:
<223> OTHER INFORMATION: Humanized antibody

<400> SEQUENCE: 352

Trp Gly Arg Phe Gly Phe Asp Ser
1               5

<210> SEQ ID NO 353
<211> LENGTH: 15
<212> TYPE: PRT
```

<213> ORGANISM: Artificial sequence
<220> FEATURE:
<223> OTHER INFORMATION: Humanized antibody

<400> SEQUENCE: 353

Lys Ser Ser Gln Ser Leu Leu Ser Gly Ser Phe Asn Tyr Leu Thr
1               5                   10                  15

<210> SEQ ID NO 354
<211> LENGTH: 7
<212> TYPE: PRT
<213> ORGANISM: Artificial sequence
<220> FEATURE:
<223> OTHER INFORMATION: Humanized antibody

<400> SEQUENCE: 354

Tyr Ala Ser Thr Arg Gln Thr
1               5

<210> SEQ ID NO 355
<211> LENGTH: 9
<212> TYPE: PRT
<213> ORGANISM: Artificial sequence
<220> FEATURE:
<223> OTHER INFORMATION: Humanized antibody

<400> SEQUENCE: 355

His His His Tyr Asn Ala Pro Pro Thr
1               5

<210> SEQ ID NO 356
<211> LENGTH: 117
<212> TYPE: PRT
<213> ORGANISM: Artificial sequence
<220> FEATURE:
<223> OTHER INFORMATION: Humanized antibody

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 357
<211> LENGTH: 111
<212> TYPE: PRT
<213> ORGANISM: Artificial sequence
<220> FEATURE:
<223> OTHER INFORMATION: Humanized antibody

<400> SEQUENCE: 357

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 358
<211> LENGTH: 10
<212> TYPE: PRT
<213> ORGANISM: Artificial sequence
<220> FEATURE:
<223> OTHER INFORMATION: Humanized antibody

<400> SEQUENCE: 358

Gly Phe Thr Phe Ser Asp Tyr Trp Met Asp
1               5                   10

<210> SEQ ID NO 359
<211> LENGTH: 17
<212> TYPE: PRT
<213> ORGANISM: Artificial sequence
<220> FEATURE:
<223> OTHER INFORMATION: Humanized antibody

<400> SEQUENCE: 359

Asn Ile Asp Glu Ser Gly Ser Ile Thr Glu Tyr Ser Pro Phe Val Lys
1               5                   10                  15

Gly

<210> SEQ ID NO 360
<211> LENGTH: 8
<212> TYPE: PRT
<213> ORGANISM: Artificial sequence
<220> FEATURE:
<223> OTHER INFORMATION: Humanized antibody

<400> SEQUENCE: 360

Trp Gly Arg Phe Gly Phe Asp Ser
1               5

<210> SEQ ID NO 361
<211> LENGTH: 15
<212> TYPE: PRT
<213> ORGANISM: Artificial sequence
<220> FEATURE:
<223> OTHER INFORMATION: Humanized antibody

<400> SEQUENCE: 361

Lys Ser Ser Gln Ser Leu Leu Ser Gly Ser Phe Asn Tyr Leu Thr
1               5                   10                  15

<210> SEQ ID NO 362
<211> LENGTH: 7
<212> TYPE: PRT

```
<213> ORGANISM: Artificial sequence
<220> FEATURE:
<223> OTHER INFORMATION: Humanized antibody

<400> SEQUENCE: 362

Tyr Ala Ser Thr Arg His Thr
1               5

<210> SEQ ID NO 363
<211> LENGTH: 9
<212> TYPE: PRT
<213> ORGANISM: Artificial sequence
<220> FEATURE:
<223> OTHER INFORMATION: Humanized antibody

<400> SEQUENCE: 363

His His His Tyr Asn Ala Pro Pro Thr
1               5

<210> SEQ ID NO 364
<211> LENGTH: 117
<212> TYPE: PRT
<213> ORGANISM: Artificial sequence
<220> FEATURE:
<223> OTHER INFORMATION: Humanized antibody

<400> SEQUENCE: 364

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 365
<211> LENGTH: 111
<212> TYPE: PRT
<213> ORGANISM: Artificial sequence
<220> FEATURE:
<223> OTHER INFORMATION: Humanized antibody

<400> SEQUENCE: 365

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Glu Thr Gly Val Pro Asp
    50                  55                  60

Arg Phe Ser Gly Ser Gly Ser Gly Thr Asp Phe Thr Leu Thr Ile Ser
```

```
                65                   70                   75                   80
Ser Leu Gln Ala Glu Asp Val Ala Val Tyr Tyr Cys His His Tyr
                    85                   90                   95

Asn Ala Pro Pro Thr Phe Gly Pro Gly Thr Lys Val Asp Ile Lys
                    100                  105                  110
```

<210> SEQ ID NO 366
<211> LENGTH: 10
<212> TYPE: PRT
<213> ORGANISM: Artificial sequence
<220> FEATURE:
<223> OTHER INFORMATION: Humanized antibody

<400> SEQUENCE: 366

```
Gly Phe Thr Phe Ser Asp Tyr Trp Met Asp
1               5                   10
```

<210> SEQ ID NO 367
<211> LENGTH: 17
<212> TYPE: PRT
<213> ORGANISM: Artificial sequence
<220> FEATURE:
<223> OTHER INFORMATION: Humanized antibody

<400> SEQUENCE: 367

```
Asn Ile Asp Glu Ser Gly Ser Ile Thr Glu Tyr Ser Pro Phe Val Lys
1               5                   10                  15

Gly
```

<210> SEQ ID NO 368
<211> LENGTH: 8
<212> TYPE: PRT
<213> ORGANISM: Artificial sequence
<220> FEATURE:
<223> OTHER INFORMATION: Humanized antibody

<400> SEQUENCE: 368

```
Trp Gly Arg Phe Gly Phe Asp Ser
1               5
```

<210> SEQ ID NO 369
<211> LENGTH: 15
<212> TYPE: PRT
<213> ORGANISM: Artificial sequence
<220> FEATURE:
<223> OTHER INFORMATION: Humanized antibody

<400> SEQUENCE: 369

```
Lys Ser Ser Gln Ser Leu Leu Ser Gly Ser Phe Asn Tyr Leu Thr
1               5                   10                  15
```

<210> SEQ ID NO 370
<211> LENGTH: 7
<212> TYPE: PRT
<213> ORGANISM: Artificial sequence
<220> FEATURE:
<223> OTHER INFORMATION: Humanized antibody

<400> SEQUENCE: 370

```
Tyr Ala Ser Thr Arg Glu Thr
1               5
```

<210> SEQ ID NO 371
<211> LENGTH: 9
<212> TYPE: PRT

<213> ORGANISM: Artificial sequence
<220> FEATURE:
<223> OTHER INFORMATION: Humanized antibody

<400> SEQUENCE: 371

His His His Tyr Asn Ala Pro Pro Thr
1               5

<210> SEQ ID NO 372
<211> LENGTH: 117
<212> TYPE: PRT
<213> ORGANISM: Artificial sequence
<220> FEATURE:
<223> OTHER INFORMATION: Humanized antibody

<400> SEQUENCE: 372

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Ser Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser
        115

<210> SEQ ID NO 373
<211> LENGTH: 111
<212> TYPE: PRT
<213> ORGANISM: Artificial sequence
<220> FEATURE:
<223> OTHER INFORMATION: Humanized antibody

<400> SEQUENCE: 373

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg Gln Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His His Tyr
                85                  90                  95

Asn Ala Pro Pro Thr Phe Gly Pro Gly Thr Lys Val Asp Ile Lys
            100                 105                 110

<210> SEQ ID NO 374
<211> LENGTH: 10
<212> TYPE: PRT
<213> ORGANISM: Artificial sequence

```
<220> FEATURE:
<223> OTHER INFORMATION: Humanized antibody

<400> SEQUENCE: 374

Gly Phe Thr Phe Ser Asp Tyr Trp Met Asp
1               5                   10

<210> SEQ ID NO 375
<211> LENGTH: 17
<212> TYPE: PRT
<213> ORGANISM: Artificial sequence
<220> FEATURE:
<223> OTHER INFORMATION: Humanized antibody

<400> SEQUENCE: 375

Asn Ile Asp Glu Ser Gly Ser Ile Thr Glu Tyr Ser Pro Phe Val Lys
1               5                   10                  15

Gly

<210> SEQ ID NO 376
<211> LENGTH: 8
<212> TYPE: PRT
<213> ORGANISM: Artificial sequence
<220> FEATURE:
<223> OTHER INFORMATION: Humanized antibody

<400> SEQUENCE: 376

Trp Gly Arg Phe Gly Phe Asp Ser
1               5

<210> SEQ ID NO 377
<211> LENGTH: 15
<212> TYPE: PRT
<213> ORGANISM: Artificial sequence
<220> FEATURE:
<223> OTHER INFORMATION: Humanized antibody

<400> SEQUENCE: 377

Lys Ser Ser Gln Ser Leu Leu Ser Gly Ser Phe Asn Tyr Leu Thr
1               5                   10                  15

<210> SEQ ID NO 378
<211> LENGTH: 7
<212> TYPE: PRT
<213> ORGANISM: Artificial sequence
<220> FEATURE:
<223> OTHER INFORMATION: Humanized antibody

<400> SEQUENCE: 378

Tyr Ala Ser Thr Arg Gln Thr
1               5

<210> SEQ ID NO 379
<211> LENGTH: 9
<212> TYPE: PRT
<213> ORGANISM: Artificial sequence
<220> FEATURE:
<223> OTHER INFORMATION: Humanized antibody

<400> SEQUENCE: 379

His His His Tyr Asn Ala Pro Pro Thr
1               5

<210> SEQ ID NO 380
<211> LENGTH: 447
<212> TYPE: PRT
```

<213> ORGANISM: Artificial sequence
<220> FEATURE:
<223> OTHER INFORMATION: Humanized antibody

<400> SEQUENCE: 380

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asp Trp Val Arg Gln Ala Pro Gly Lys Gly Leu Val Trp Val
        35                  40                  45

Ser Asn Ile Asp Glu Asp Gly Ser Ile Thr Glu Tyr Ser Pro Phe Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Trp Gly Arg Phe Gly Phe Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
```

```
                385                 390                 395                 400
Asp Gly Ser Phe Phe Leu Tyr Ser Lys Leu Thr Val Asp Lys Ser Arg
                        405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 381
<211> LENGTH: 218
<212> TYPE: PRT
<213> ORGANISM: Artificial sequence
<220> FEATURE:
<223> OTHER INFORMATION: Humanized antibody

<400> SEQUENCE: 381

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Gly
            20                  25                  30

Ser Phe Asn Tyr Leu Thr Trp Tyr Gln Gln Lys Pro Gly Gln Pro Pro
        35                  40                  45

Lys Leu Leu Ile Phe Tyr Ala Ser Thr Arg His Thr Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Tyr
                85                  90                  95

Asn Ala Pro Pro Thr Phe Gly Pro Gly Thr Lys Val Asp Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 382
<211> LENGTH: 268
<212> TYPE: PRT
<213> ORGANISM: Homo sapiens

<400> SEQUENCE: 382

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45
```

```
Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
            195                 200                 205

Gln Trp Arg Glu Lys Thr Pro Glu Pro Pro Val Pro Cys Val Pro Glu
        210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
                260                 265

<210> SEQ ID NO 383
<211> LENGTH: 268
<212> TYPE: PRT
<213> ORGANISM: Mus musculus

<400> SEQUENCE: 383

Ser Gly Trp Leu Leu Glu Val Pro Asn Gly Pro Trp Arg Ser Leu Thr
1               5                   10                  15

Phe Tyr Pro Ala Trp Leu Thr Val Ser Glu Gly Ala Asn Ala Thr Phe
                20                  25                  30

Thr Cys Ser Leu Ser Asn Trp Ser Glu Asp Leu Met Leu Asn Trp Asn
            35                  40                  45

Arg Leu Ser Pro Ser Asn Gln Thr Glu Lys Gln Ala Ala Phe Cys Asn
    50                  55                  60

Gly Leu Ser Gln Pro Val Gln Asp Ala Arg Phe Gln Ile Ile Gln Leu
65                  70                  75                  80

Pro Asn Arg His Asp Phe His Met Asn Ile Leu Asp Thr Arg Arg Asn
                85                  90                  95

Asp Ser Gly Ile Tyr Leu Cys Gly Ala Ile Ser Leu His Pro Lys Ala
                100                 105                 110

Lys Ile Glu Glu Ser Pro Gly Ala Glu Leu Val Val Thr Glu Arg Ile
            115                 120                 125

Leu Glu Thr Ser Thr Arg Tyr Pro Ser Pro Ser Pro Lys Pro Glu Gly
        130                 135                 140

Arg Phe Gln Gly Met Val Ile Gly Ile Met Ser Ala Leu Val Gly Ile
```

```
145                 150                 155                 160

Pro Val Leu Leu Leu Ala Trp Ala Leu Ala Val Phe Cys Ser Thr
                165                 170                 175

Ser Met Ser Glu Ala Arg Gly Ala Gly Ser Lys Asp Asp Thr Leu Lys
            180                 185                 190

Glu Glu Pro Ser Ala Ala Pro Val Pro Ser Val Ala Tyr Glu Glu Leu
                195                 200                 205

Asp Phe Gln Gly Arg Glu Lys Thr Pro Glu Leu Pro Thr Ala Cys Val
210                 215                 220

His Thr Glu Tyr Ala Thr Ile Val Phe Thr Glu Gly Leu Gly Ala Ser
225                 230                 235                 240

Ala Met Gly Arg Arg Gly Ser Ala Asp Gly Leu Gln Gly Pro Arg Pro
                245                 250                 255

Pro Arg His Glu Asp Gly His Cys Ser Trp Pro Leu
                260                 265

<210> SEQ ID NO 384
<211> LENGTH: 268
<212> TYPE: PRT
<213> ORGANISM: Macaca fascicularis

<400> SEQUENCE: 384

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255
```

```
Leu Arg Pro Glu Asp Gly His Cys Ser Trp Pro Leu
            260                 265
```

```
<210> SEQ ID NO 385
<211> LENGTH: 386
<212> TYPE: PRT
<213> ORGANISM: Artificial sequence
<220> FEATURE:
<223> OTHER INFORMATION: Human PD-1 D85G ECD-Fc-His6

<400> SEQUENCE: 385

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Gly Arg Ser Gln Pro
        50                  55                  60

Gly Gln Asp Cys Arg Phe Arg Val Thr Gln Leu Pro Asn Gly Arg Asp
65              70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Pro Thr
            115                 120                 125

Ala His Pro Ser Pro Ser Pro Arg Pro Ala Gly Gln Phe Gln Thr Leu
        130                 135                 140

Val Gly Ser Gly Gly Asp Lys Thr His Thr Cys Pro Pro Cys Pro
145             150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350
```

Phe Ser Cys Ser Val Met His Glu Ala Leu His Asn His Tyr Thr Gln
            355                 360                 365
Lys Ser Leu Ser Leu Ser Pro Gly Lys Gly Ser Gly His His His His
    370                 375                 380
His His
385

<210> SEQ ID NO 386
<211> LENGTH: 386
<212> TYPE: PRT
<213> ORGANISM: Artificial sequence
<220> FEATURE:
<223> OTHER INFORMATION: Human PD-1 R86L ECD-Fc-His6

<400> SEQUENCE: 386

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Leu Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140

Val Gly Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

```
Tyr Lys Thr Thr Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
        340                 345                 350

Phe Ser Cys Ser Val Met His Glu Ala Leu His Asn His Tyr Thr Gln
        355                 360                 365

Lys Ser Leu Ser Leu Ser Pro Gly Lys Gly Ser Gly His His His
370                 375                 380

His His
385

<210> SEQ ID NO 387
<211> LENGTH: 376
<212> TYPE: PRT
<213> ORGANISM: Artificial sequence
<220> FEATURE:
<223> OTHER INFORMATION: Human PD-1 N33-Q167 ECD-Fc-His6

<400> SEQUENCE: 387

Asn Pro Pro Thr Phe Ser Pro Ala Leu Leu Val Val Thr Glu Gly Asp
1               5                   10                  15

Asn Ala Thr Phe Thr Cys Ser Phe Ser Asn Thr Ser Glu Ser Phe Val
            20                  25                  30

Leu Asn Trp Tyr Arg Met Ser Pro Ser Asn Gln Thr Asp Lys Leu Ala
        35                  40                  45

Ala Phe Pro Glu Asp Arg Ser Gln Pro Gly Gln Asp Cys Arg Phe Arg
    50                  55                  60

Val Thr Gln Leu Pro Asn Gly Arg Asp Phe His Met Ser Val Val Arg
65                  70                  75                  80

Ala Arg Arg Asn Asp Ser Gly Thr Tyr Leu Cys Gly Ala Ile Ser Leu
                85                  90                  95

Ala Pro Lys Ala Gln Ile Lys Glu Ser Leu Arg Ala Glu Leu Arg Val
            100                 105                 110

Thr Glu Arg Arg Ala Glu Val Pro Thr Ala His Pro Ser Pro Ser Pro
        115                 120                 125

Arg Pro Ala Gly Gln Phe Gln Gly Gly Ser Gly Gly Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Glu Glu Met Thr Lys Asn Gln Val Ser Leu Thr Cys Leu
        275                 280                 285
```

-continued

```
Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
                340                 345                 350

His Asn His Tyr Thr Gln Lys Ser Leu Ser Leu Ser Pro Gly Lys Gly
            355                 360                 365

Ser Gly His His His His His His
    370                 375

<210> SEQ ID NO 388
<211> LENGTH: 386
<212> TYPE: PRT
<213> ORGANISM: Artificial sequence
<220> FEATURE:
<223> OTHER INFORMATION: Human PD-1 K78A ECD-Fc-His6

<400> SEQUENCE: 388

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Ala Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140

Val Gly Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270
```

```
Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Pro Gly Lys Gly Ser Gly His His His His
            370                 375                 380

His His
385

<210> SEQ ID NO 389
<211> LENGTH: 386
<212> TYPE: PRT
<213> ORGANISM: Artificial sequence
<220> FEATURE:
<223> OTHER INFORMATION: Human PD-1 I126A ECD-Fc-His6

<400> SEQUENCE: 389

Asp Ser Pro Asp Arg Pro Trp Asn Pro Thr Phe Ser Pro Ala Leu
1                5                  10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
            85                  90                  95

Leu Cys Gly Ala Ala Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
            115                 120                 125

Ala His Pro Ser Pro Ser Pro Arg Pro Ala Gly Gln Phe Gln Thr Leu
            130                 135                 140

Val Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
            195                 200                 205

Val Asp Gly Val Glu Val His Asn Ala Lys Thr Lys Pro Arg Glu Glu
            210                 215                 220

Gln Tyr Asn Ser Thr Tyr Arg Val Val Ser Val Leu Thr Val Leu His
225                 230                 235                 240
```

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Ala Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Lys Leu Thr Val Asp Lys Ser Arg Trp Gln Gln Gly Asn Val
        340                 345                 350

Phe Ser Cys Ser Val Met His Glu Ala Leu His Asn His Tyr Thr Gln
    355                 360                 365

Lys Ser Leu Ser Leu Ser Pro Gly Lys Gly Ser Gly His His His His
370                 375                 380

His His
385

<210> SEQ ID NO 390
<211> LENGTH: 386
<212> TYPE: PRT
<213> ORGANISM: Artificial sequence
<220> FEATURE:
<223> OTHER INFORMATION: Human PD-1 L128A ECD-Fc-His6

<400> SEQUENCE: 390

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Ala Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140

Val Gly Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

```
Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
            355                 360                 365

Lys Ser Leu Ser Leu Ser Pro Gly Lys Gly Ser Gly His His His His
370                 375                 380

His His
385
```

<210> SEQ ID NO 391
<211> LENGTH: 386
<212> TYPE: PRT
<213> ORGANISM: Artificial sequence
<220> FEATURE:
<223> OTHER INFORMATION: Human PD-1 A132L ECD-Fc-His6

<400> SEQUENCE: 391

```
Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Leu Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140

Val Gly Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175
```

```
Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys Gly Ser Gly His His His His
    370                 375                 380

His His
385

<210> SEQ ID NO 392
<211> LENGTH: 386
<212> TYPE: PRT
<213> ORGANISM: Artificial sequence
<220> FEATURE:
<223> OTHER INFORMATION: Human PD-1 I134A ECD-Fc-His6

<400> SEQUENCE: 392

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ala Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140
```

Val Gly Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350

Phe Ser Cys Ser Val Met His Glu Ala Leu His Asn His Tyr Thr Gln
        355                 360                 365

Lys Ser Leu Ser Leu Ser Pro Gly Lys Gly Ser Gly His His His His
    370                 375                 380

His His
385

<210> SEQ ID NO 393
<211> LENGTH: 390
<212> TYPE: PRT
<213> ORGANISM: Artificial sequence
<220> FEATURE:
<223> OTHER INFORMATION: Human PD-1 E136A ECD-Fc-His6

<400> SEQUENCE: 393

Asp Thr Thr Gly Asp Ser Pro Asp Arg Pro Trp Asn Pro Thr Phe
1               5                   10                  15

Ser Pro Ala Leu Leu Val Val Thr Glu Gly Asp Asn Ala Thr Phe Thr
                20                  25                  30

Cys Ser Phe Ser Asn Thr Ser Glu Ser Phe Val Leu Asn Trp Tyr Arg
            35                  40                  45

Met Ser Pro Ser Asn Gln Thr Asp Lys Leu Ala Ala Phe Pro Glu Asp
        50                  55                  60

Arg Ser Gln Pro Gly Gln Asp Cys Arg Phe Arg Val Thr Gln Leu Pro
65                  70                  75                  80

Asn Gly Arg Asp Phe His Met Ser Val Val Arg Ala Arg Arg Asn Asp
                85                  90                  95

Ser Gly Thr Tyr Leu Cys Gly Ala Ile Ser Leu Ala Pro Lys Ala Gln
            100                 105                 110

```
Ile Lys Ala Ser Leu Arg Ala Glu Leu Arg Val Thr Glu Arg Arg Ala
            115                 120                 125

Glu Val Pro Thr Ala His Pro Ser Pro Ser Pro Arg Pro Ala Gly Gln
130                 135                 140

Phe Gln Thr Leu Val Gly Gly Ser Gly Gly Asp Lys Thr His Thr Cys
145                 150                 155                 160

Pro Pro Cys Pro Ala Pro Glu Leu Leu Gly Gly Pro Ser Val Phe Leu
                165                 170                 175

Phe Pro Pro Lys Pro Lys Asp Thr Leu Met Ile Ser Arg Thr Pro Glu
            180                 185                 190

Val Thr Cys Val Val Val Asp Val Ser His Glu Asp Pro Glu Val Lys
        195                 200                 205

Phe Asn Trp Tyr Val Asp Gly Val Glu Val His Asn Ala Lys Thr Lys
    210                 215                 220

Pro Arg Glu Glu Gln Tyr Asn Ser Thr Tyr Arg Val Val Ser Val Leu
225                 230                 235                 240

Thr Val Leu His Gln Asp Trp Leu Asn Gly Lys Glu Tyr Lys Cys Lys
                245                 250                 255

Val Ser Asn Lys Ala Leu Pro Ala Pro Ile Glu Lys Thr Ile Ser Lys
            260                 265                 270

Ala Lys Gly Gln Pro Arg Glu Pro Gln Val Tyr Thr Leu Pro Pro Ser
        275                 280                 285

Arg Glu Glu Met Thr Lys Asn Gln Val Ser Leu Thr Cys Leu Val Lys
    290                 295                 300

Gly Phe Tyr Pro Ser Asp Ile Ala Val Glu Trp Glu Ser Asn Gly Gln
305                 310                 315                 320

Pro Glu Asn Asn Tyr Lys Thr Thr Pro Pro Val Leu Asp Ser Asp Gly
                325                 330                 335

Ser Phe Phe Leu Tyr Ser Lys Leu Thr Val Asp Lys Ser Arg Trp Gln
            340                 345                 350

Gln Gly Asn Val Phe Ser Cys Ser Val Met His Glu Ala Leu His Asn
        355                 360                 365

His Tyr Thr Gln Lys Ser Leu Ser Leu Ser Pro Gly Lys Gly Ser Gly
    370                 375                 380

His His His His His His
385                 390

<210> SEQ ID NO 394
<211> LENGTH: 384
<212> TYPE: PRT
<213> ORGANISM: Artificial sequence
<220> FEATURE:
<223> OTHER INFORMATION: Mouse H129P PD-1 ECD-Fc-His6

<400> SEQUENCE: 394

Leu Glu Val Pro Asn Gly Pro Trp Arg Ser Leu Thr Phe Tyr Pro Ala
1               5                   10                  15

Trp Leu Thr Val Ser Glu Gly Ala Asn Ala Thr Phe Thr Cys Ser Leu
                20                  25                  30

Ser Asn Trp Ser Glu Asp Leu Met Leu Asn Trp Asn Arg Leu Ser Pro
            35                  40                  45

Ser Asn Gln Thr Glu Lys Gln Ala Ala Phe Cys Asn Gly Leu Ser Gln
        50                  55                  60

Pro Val Gln Asp Ala Arg Phe Gln Ile Ile Gln Leu Pro Asn Arg His
65                  70                  75                  80
```

-continued

Asp Phe His Met Asn Ile Leu Asp Thr Arg Arg Asn Asp Ser Gly Ile
                85                  90                  95

Tyr Leu Cys Gly Ala Ile Ser Leu Pro Pro Lys Ala Lys Ile Glu Glu
            100                 105                 110

Ser Pro Gly Ala Glu Leu Val Val Thr Glu Arg Ile Leu Glu Thr Ser
        115                 120                 125

Thr Arg Tyr Pro Ser Pro Ser Pro Lys Pro Glu Gly Arg Phe Gln Gly
    130                 135                 140

Gly Ser Gly Gly Asp Lys Thr His Thr Cys Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys Gly Ser Gly His His His His His
    370                 375                 380

<210> SEQ ID NO 395
<211> LENGTH: 287
<212> TYPE: PRT
<213> ORGANISM: Rattus norvegicus

<400> SEQUENCE: 395

Met Trp Val Gln Gln Val Pro Trp Ser Phe Thr Trp Ala Val Leu Gln
1               5                   10                  15

Leu Ser Trp Gln Ser Gly Trp Leu Leu Glu Val Leu Asn Lys Pro Trp
            20                  25                  30

Arg Pro Leu Thr Phe Ser Pro Thr Trp Leu Thr Val Ser Glu Gly Ala
        35                  40                  45

Asn Ala Thr Phe Thr Cys Ser Phe Ser Asn Trp Ser Glu Asp Leu Lys
    50                  55                  60

Leu Asn Trp Tyr Arg Leu Ser Pro Ser Asn Gln Thr Glu Lys Gln Ala
65                  70                  75                  80

Ala Phe Cys Asn Gly Tyr Ser Gln Pro Val Arg Asp Ala Arg Phe Gln
            85                  90                  95

Ile Val Gln Leu Pro Asn Gly His Asp Phe His Met Asn Ile Leu Asp
            100                 105                 110

Ala Arg Arg Asn Asp Ser Gly Ile Tyr Leu Cys Gly Ala Ile Ser Leu
            115                 120                 125

Pro Pro Lys Ala Gln Ile Lys Glu Ser Pro Gly Ala Glu Leu Val Val
        130                 135                 140

Thr Glu Arg Ile Leu Glu Thr Pro Thr Arg Tyr Pro Arg Pro Ser Pro
145                 150                 155                 160

Lys Pro Glu Gly Gln Phe Gln Gly Leu Val Ile Val Ile Met Ser Val
                165                 170                 175

Leu Val Gly Ile Pro Val Leu Leu Leu Leu Ala Trp Ala Leu Ala Ala
            180                 185                 190

Phe Cys Ser Thr Gly Met Ser Glu Ala Arg Glu Ala Gly Arg Lys Glu
            195                 200                 205

Asp Pro Pro Lys Glu Ala His Ala Ala Ala Pro Val Pro Ser Val Ala
        210                 215                 220

Tyr Glu Glu Leu Asp Phe Gln Gly Arg Glu Lys Thr Pro Glu Pro Ala
225                 230                 235                 240

Pro Cys Val His Thr Glu Tyr Ala Thr Ile Val Phe Thr Glu Gly Leu
                245                 250                 255

Asp Ala Ser Ala Ile Gly Arg Arg Gly Ser Ala Asp Gly Pro Gln Gly
            260                 265                 270

Pro Arg Pro Pro Arg His Glu Asp Gly His Cys Ser Trp Pro Leu
        275                 280                 285

<210> SEQ ID NO 396
<211> LENGTH: 263
<212> TYPE: PRT
<213> ORGANISM: Rattus norvegicus

<400> SEQUENCE: 396

Leu Glu Val Leu Asn Lys Pro Trp Arg Pro Leu Thr Phe Ser Pro Thr
1               5                   10                  15

Trp Leu Thr Val Ser Glu Gly Ala Asn Ala Thr Phe Thr Cys Ser Phe
            20                  25                  30

Ser Asn Trp Ser Glu Asp Leu Lys Leu Asn Trp Tyr Arg Leu Ser Pro
        35                  40                  45

Ser Asn Gln Thr Glu Lys Gln Ala Ala Phe Cys Asn Gly Tyr Ser Gln
    50                  55                  60

Pro Val Arg Asp Ala Arg Phe Gln Ile Val Gln Leu Pro Asn Gly His
65                  70                  75                  80

Asp Phe His Met Asn Ile Leu Asp Ala Arg Arg Asn Asp Ser Gly Ile
            85                  90                  95

Tyr Leu Cys Gly Ala Ile Ser Leu Pro Pro Lys Ala Gln Ile Lys Glu
            100                 105                 110

Ser Pro Gly Ala Glu Leu Val Val Thr Glu Arg Ile Leu Glu Thr Pro
            115                 120                 125

Thr Arg Tyr Pro Arg Pro Ser Pro Lys Pro Glu Gly Gln Phe Gln Gly
        130                 135                 140

Leu Val Ile Val Ile Met Ser Val Leu Val Gly Ile Pro Val Leu Leu
145                 150                 155                 160

Leu Leu Ala Trp Ala Leu Ala Ala Phe Cys Ser Thr Gly Met Ser Glu

Ala Arg Glu Ala Gly Arg Lys Glu Asp Pro Lys Glu Ala His Ala
            180                 185                 190

Ala Ala Pro Val Pro Ser Val Ala Tyr Glu Glu Leu Asp Phe Gln Gly
        195                 200                 205

Arg Glu Lys Thr Pro Glu Pro Ala Pro Cys Val His Thr Glu Tyr Ala
    210                 215                 220

Thr Ile Val Phe Thr Glu Gly Leu Asp Ala Ser Ala Ile Gly Arg Arg
225                 230                 235                 240

Gly Ser Ala Asp Gly Pro Gln Gly Pro Arg Pro Arg His Glu Asp
                245                 250                 255

Gly His Cys Ser Trp Pro Leu
            260

<210> SEQ ID NO 397
<211> LENGTH: 384
<212> TYPE: PRT
<213> ORGANISM: Artificial sequence
<220> FEATURE:
<223> OTHER INFORMATION: Rat P129H PD-1 ECD-Fc-His6

<400> SEQUENCE: 397

Leu Glu Val Leu Asn Lys Pro Trp Arg Pro Leu Thr Phe Ser Pro Thr
1               5                   10                  15

Trp Leu Thr Val Ser Glu Gly Ala Asn Ala Thr Phe Thr Cys Ser Phe
            20                  25                  30

Ser Asn Trp Ser Glu Asp Leu Lys Leu Asn Trp Tyr Arg Leu Ser Pro
        35                  40                  45

Ser Asn Gln Thr Glu Lys Gln Ala Ala Phe Cys Asn Gly Tyr Ser Gln
    50                  55                  60

Pro Val Arg Asp Ala Arg Phe Gln Ile Val Gln Leu Pro Asn Gly His
65                  70                  75                  80

Asp Phe His Met Asn Ile Leu Asp Ala Arg Arg Asn Asp Ser Gly Ile
                85                  90                  95

Tyr Leu Cys Gly Ala Ile Ser Leu His Pro Lys Ala Gln Ile Lys Glu
            100                 105                 110

Ser Pro Gly Ala Glu Leu Val Val Thr Glu Arg Ile Leu Glu Thr Pro
        115                 120                 125

Thr Arg Tyr Pro Arg Pro Ser Pro Lys Pro Glu Gly Gln Phe Gln Gly
    130                 135                 140

Gly Ser Gly Gly Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg

```
            260                 265                 270
Glu Pro Gln Val Tyr Thr Leu Pro Pro Ser Arg Glu Glu Met Thr Lys
                275                 280                 285

Asn Gln Val Ser Leu Thr Cys Leu Val Lys Gly Phe Tyr Pro Ser Asp
            290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys Gly Ser Gly His His His His His His
            370                 375                 380

<210> SEQ ID NO 398
<211> LENGTH: 288
<212> TYPE: PRT
<213> ORGANISM: Canis lupus familiaris

<400> SEQUENCE: 398

Met Gly Ser Arg Arg Gly Pro Trp Pro Leu Val Trp Ala Val Leu Gln
1                   5                   10                  15

Leu Gly Trp Trp Pro Gly Trp Leu Leu Asp Ser Pro Asp Arg Pro Trp
                20                  25                  30

Ser Pro Leu Thr Phe Ser Pro Ala Gln Leu Thr Val Gln Glu Gly Glu
            35                  40                  45

Asn Ala Thr Phe Thr Cys Ser Leu Ala Asp Ile Pro Asp Ser Phe Val
        50                  55                  60

Leu Asn Trp Tyr Arg Leu Ser Pro Arg Asn Gln Thr Asp Lys Leu Ala
65                  70                  75                  80

Ala Phe Gln Glu Asp Arg Ile Glu Pro Gly Arg Asp Arg Arg Phe Arg
                85                  90                  95

Val Thr Arg Leu Pro Asn Gly Arg Asp Phe His Met Ser Ile Val Ala
            100                 105                 110

Ala Arg Leu Asn Asp Ser Gly Ile Tyr Leu Cys Gly Ala Ile Tyr Leu
        115                 120                 125

Pro Pro Asn Thr Gln Ile Asn Glu Ser Pro Arg Ala Glu Leu Ser Val
130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
            180                 185                 190

Val Phe Pro Arg Ala Thr Arg Gly Ala Cys Val Cys Gly Ser Glu Asp
        195                 200                 205

Glu Pro Leu Lys Glu Gly Pro Asp Ala Ala Pro Val Phe Thr Leu Asp
    210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255
```

```
Gly Arg Pro Ala Ser Pro Gly Arg Arg Ala Ser Ala Ser Ser Leu Gln
            260                 265                 270

Gly Ala Gln Pro Pro Ser Pro Glu Asp Gly Pro Gly Leu Trp Pro Pro
        275                 280                 285

<210> SEQ ID NO 399
<211> LENGTH: 264
<212> TYPE: PRT
<213> ORGANISM: Canis lupus familiaris

<400> SEQUENCE: 399

Leu Asp Ser Pro Asp Arg Pro Trp Ser Pro Leu Thr Phe Ser Pro Ala
1               5                   10                  15

Gln Leu Thr Val Gln Glu Gly Glu Asn Ala Thr Phe Thr Cys Ser Leu
            20                  25                  30

Ala Asp Ile Pro Asp Ser Phe Val Leu Asn Trp Tyr Arg Leu Ser Pro
        35                  40                  45

Arg Asn Gln Thr Asp Lys Leu Ala Ala Phe Gln Glu Asp Arg Ile Glu
    50                  55                  60

Pro Gly Arg Asp Arg Arg Phe Arg Val Thr Arg Leu Pro Asn Gly Arg
65                  70                  75                  80

Asp Phe His Met Ser Ile Val Ala Ala Arg Leu Asn Asp Ser Gly Ile
                85                  90                  95

Tyr Leu Cys Gly Ala Ile Tyr Leu Pro Pro Asn Thr Gln Ile Asn Glu
            100                 105                 110

Ser Pro Arg Ala Glu Leu Ser Val Thr Glu Arg Thr Leu Glu Pro Pro
        115                 120                 125

Thr Gln Ser Pro Ser Pro Pro Arg Leu Ser Gly Gln Leu Gln Gly
    130                 135                 140

Leu Val Ile Gly Val Thr Ser Val Leu Val Gly Val Leu Leu Leu Leu
145                 150                 155                 160

Leu Leu Thr Trp Val Leu Ala Ala Val Phe Pro Arg Ala Thr Arg Gly
                165                 170                 175

Ala Cys Val Cys Gly Ser Glu Asp Glu Pro Leu Lys Glu Gly Pro Asp
            180                 185                 190

Ala Ala Pro Val Phe Thr Leu Asp Tyr Gly Glu Leu Asp Phe Gln Trp
        195                 200                 205

Arg Glu Lys Thr Pro Glu Pro Pro Ala Pro Cys Ala Pro Glu Gln Thr
    210                 215                 220

Glu Tyr Ala Thr Ile Val Phe Pro Gly Arg Pro Ala Ser Pro Gly Arg
225                 230                 235                 240

Arg Ala Ser Ala Ser Ser Leu Gln Gly Ala Gln Pro Pro Ser Pro Glu
                245                 250                 255

Asp Gly Pro Gly Leu Trp Pro Pro
            260

<210> SEQ ID NO 400
<211> LENGTH: 20
<212> TYPE: PRT
<213> ORGANISM: Homo sapiens

<400> SEQUENCE: 400

Met Gly Thr Pro Ala Gln Leu Leu Phe Leu Leu Leu Leu Trp Leu Pro
1               5                   10                  15

Asp Thr Thr Gly
            20
```

<210> SEQ ID NO 401
<211> LENGTH: 384
<212> TYPE: PRT
<213> ORGANISM: Artificial sequence
<220> FEATURE:
<223> OTHER INFORMATION: Human PD-1 extracellular domain (ECD)-Fc-His6

<400> SEQUENCE: 401

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Gly Ser Gly Gly Asp Lys Thr His Thr Cys Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365
```

```
Leu Ser Leu Ser Pro Gly Lys Gly Ser Gly His His His His His
        370             375             380
```

<210> SEQ ID NO 402
<211> LENGTH: 386
<212> TYPE: PRT
<213> ORGANISM: Artificial sequence
<220> FEATURE:
<223> OTHER INFORMATION: Human PD-1 D85G/R86L ECD-Fc-His6

<400> SEQUENCE: 402

```
Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Gly Leu Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Phe Gln Thr Leu
    130                 135                 140

Val Gly Ser Gly Gly Asp Lys Thr His Thr Cys Pro Pro Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Lys Phe Asn Trp Tyr
        195                 200                 205

Val Asp Gly Val Glu Val His Asn Ala Lys Thr Lys Pro Arg Glu Glu
    210                 215                 220

Gln Tyr Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Lys Leu Thr Val Asp Lys Ser Arg Trp Gln Gln Gly Asn Val
            340                 345                 350
```

Phe Ser Cys Ser Val Met His Glu Ala Leu His Asn His Tyr Thr Gln
            355                 360                 365

Lys Ser Leu Ser Leu Ser Pro Gly Lys Gly Ser Gly His His His His
370                 375                 380

His His
385

<210> SEQ ID NO 403
<211> LENGTH: 384
<212> TYPE: PRT
<213> ORGANISM: Artificial sequence
<220> FEATURE:
<223> OTHER INFORMATION: Mouse PD-1 ECD-Fc-His6

<400> SEQUENCE: 403

Leu Glu Val Pro Asn Gly Pro Trp Arg Ser Leu Thr Phe Tyr Pro Ala
1               5                   10                  15

Trp Leu Thr Val Ser Glu Gly Ala Asn Ala Thr Phe Thr Cys Ser Leu
            20                  25                  30

Ser Asn Trp Ser Glu Asp Leu Met Leu Asn Trp Asn Arg Leu Ser Pro
        35                  40                  45

Ser Asn Gln Thr Glu Lys Gln Ala Ala Phe Cys Asn Gly Leu Ser Gln
    50                  55                  60

Pro Val Gln Asp Ala Arg Phe Gln Ile Ile Gln Leu Pro Asn Arg His
65                  70                  75                  80

Asp Phe His Met Asn Ile Leu Asp Thr Arg Arg Asn Asp Ser Gly Ile
                85                  90                  95

Tyr Leu Cys Gly Ala Ile Ser Leu His Pro Lys Ala Lys Ile Glu Glu
            100                 105                 110

Ser Pro Gly Ala Glu Leu Val Val Thr Glu Arg Ile Leu Glu Thr Ser
        115                 120                 125

Thr Arg Tyr Pro Ser Pro Ser Pro Lys Pro Glu Gly Arg Phe Gln Gly
    130                 135                 140

Gly Ser Gly Gly Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

```
Thr Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys Gly Ser Gly His His His His His His
        370                 375                 380
```

<210> SEQ ID NO 404
<211> LENGTH: 384
<212> TYPE: PRT
<213> ORGANISM: Artificial sequence
<220> FEATURE:
<223> OTHER INFORMATION: Cynomolgus monkey PD-1 ECD-Fc-His6

<400> SEQUENCE: 404

```
Leu Glu Ser Pro Asp Arg Pro Trp Asn Ala Pro Thr Phe Ser Pro Ala
1               5                   10                  15

Leu Leu Leu Val Thr Glu Gly Asp Asn Ala Thr Phe Thr Cys Ser Phe
            20                  25                  30

Ser Asn Ala Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Arg Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
    130                 135                 140

Gly Ser Gly Gly Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300
```

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
            325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
            355                 360                 365

Leu Ser Leu Ser Pro Gly Lys Gly Ser Gly His His His His His His
370                 375                 380

<210> SEQ ID NO 405
<211> LENGTH: 384
<212> TYPE: PRT
<213> ORGANISM: Artificial sequence
<220> FEATURE:
<223> OTHER INFORMATION: Rat PD-1 ECD-Fc-His6

<400> SEQUENCE: 405

Leu Glu Val Leu Asn Lys Pro Trp Arg Pro Leu Thr Phe Ser Pro Thr
1               5                   10                  15

Trp Leu Thr Val Ser Glu Gly Ala Asn Ala Thr Phe Thr Cys Ser Phe
            20                  25                  30

Ser Asn Trp Ser Glu Asp Leu Lys Leu Asn Trp Tyr Arg Leu Ser Pro
        35                  40                  45

Ser Asn Gln Thr Glu Lys Gln Ala Ala Phe Cys Asn Gly Tyr Ser Gln
    50                  55                  60

Pro Val Arg Asp Ala Arg Phe Gln Ile Val Gln Leu Pro Asn Gly His
65                  70                  75                  80

Asp Phe His Met Asn Ile Leu Asp Ala Arg Arg Asn Asp Ser Gly Ile
                85                  90                  95

Tyr Leu Cys Gly Ala Ile Ser Leu Pro Pro Lys Ala Gln Ile Lys Glu
            100                 105                 110

Ser Pro Gly Ala Glu Leu Val Val Thr Glu Arg Ile Leu Glu Thr Pro
        115                 120                 125

Thr Arg Tyr Pro Arg Pro Ser Pro Lys Pro Glu Gly Gln Phe Gln Gly
    130                 135                 140

Gly Ser Gly Gly Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

```
Asn Gln Val Ser Leu Thr Cys Leu Val Lys Gly Phe Tyr Pro Ser Asp
    290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
                340                 345                 350
Cys Ser Val Met His Glu Ala Leu His Asn His Tyr Thr Gln Lys Ser
                355                 360                 365
Leu Ser Leu Ser Pro Gly Lys Gly Ser Gly His His His His His His
                370                 375                 380
```

<210> SEQ ID NO 406
<211> LENGTH: 384
<212> TYPE: PRT
<213> ORGANISM: Artificial sequence
<220> FEATURE:
<223> OTHER INFORMATION: Dog PD-1 ECD-Fc-His6

<400> SEQUENCE: 406

```
Leu Asp Ser Pro Asp Arg Pro Trp Ser Pro Leu Thr Phe Ser Pro Ala
1               5                   10                  15
Gln Leu Thr Val Gln Glu Gly Glu Asn Ala Thr Phe Thr Cys Ser Leu
                20                  25                  30
Ala Asp Ile Pro Asp Ser Phe Val Leu Asn Trp Tyr Arg Leu Ser Pro
                35                  40                  45
Arg Asn Gln Thr Asp Lys Leu Ala Ala Phe Gln Glu Asp Arg Ile Glu
    50                  55                  60
Pro Gly Arg Asp Arg Arg Phe Arg Val Thr Arg Leu Pro Asn Gly Arg
65                  70                  75                  80
Asp Phe His Met Ser Ile Val Ala Ala Arg Leu Asn Asp Ser Gly Ile
                85                  90                  95
Tyr Leu Cys Gly Ala Ile Tyr Leu Pro Pro Asn Thr Gln Ile Asn Glu
                100                 105                 110
Ser Pro Arg Ala Glu Leu Ser Val Thr Glu Arg Thr Leu Glu Pro Pro
                115                 120                 125
Thr Gln Ser Pro Ser Pro Pro Arg Leu Ser Gly Gln Leu Gln Gly
                130                 135                 140
Gly Ser Gly Gly Asp Lys Thr His Thr Cys Pro Pro Cys Pro Ala Pro
145                 150                 155                 160
Glu Leu Leu Gly Gly Pro Ser Val Phe Leu Phe Pro Pro Lys Pro Lys
                165                 170                 175
Asp Thr Leu Met Ile Ser Arg Thr Pro Glu Val Thr Cys Val Val Val
                180                 185                 190
Asp Val Ser His Glu Asp Pro Glu Val Lys Phe Asn Trp Tyr Val Asp
                195                 200                 205
Gly Val Glu Val His Asn Ala Lys Thr Lys Pro Arg Glu Glu Gln Tyr
                210                 215                 220
Asn Ser Thr Tyr Arg Val Val Ser Val Leu Thr Val Leu His Gln Asp
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
                260                 265                 270
```

-continued

```
Glu Pro Gln Val Tyr Thr Leu Pro Pro Ser Arg Glu Met Thr Lys
    275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
                340                 345                 350

Cys Ser Val Met His Glu Ala Leu His Asn His Tyr Thr Gln Lys Ser
        355                 360                 365

Leu Ser Leu Ser Pro Gly Lys Gly Ser Gly His His His His His His
    370                 375                 380
```